(12) United States Patent
Biderman et al.

(10) Patent No.: US 9,884,548 B2
(45) Date of Patent: Feb. 6, 2018

(54) TORQUE ARM ASSEMBLY FOR A MOTORIZED WHEEL

(71) Applicant: Superpedestrian, Inc., Hamilton, MA (US)

(72) Inventors: Assaf Biderman, Boston, MA (US); Robert Paul Roy, Dracut, MA (US); Jeffrey Jay Weinstein, Mansfield, MA (US)

(73) Assignee: Superpedestrian, Inc., Cambridge, MA (US)

( * ) Notice: Subject to any disclaimer, the term of this patent is extended or adjusted under 35 U.S.C. 154(b) by 25 days.

(21) Appl. No.: 14/951,165

(22) Filed: Nov. 24, 2015

(65) Prior Publication Data
US 2016/0243927 A1 Aug. 25, 2016

Related U.S. Application Data

(63) Continuation-in-part of application No. 14/678,855, filed on Apr. 3, 2015.
(Continued)

(51) Int. Cl.
*B60K 7/00* (2006.01)
*A61B 5/00* (2006.01)
(Continued)

(52) U.S. Cl.
CPC .......... *B60K 7/0007* (2013.01); *A61B 5/0002* (2013.01); *A61B 5/11* (2013.01); *A61B 5/6893* (2013.01); *A61B 5/7275* (2013.01); *A61B 5/7282* (2013.01); *A61G 5/04* (2013.01); *A61G 5/048* (2016.11); *B60K 7/00* (2013.01); *B60L 3/0061* (2013.01); *B60L 3/12* (2013.01); *B60L 7/12* (2013.01); *B60L 11/007* (2013.01); *B60L 11/1803* (2013.01); *B60L 11/1816* (2013.01); *B60L 11/1861* (2013.01); *B60L 11/1864* (2013.01); *B60L 15/20* (2013.01); *B60L 15/2009* (2013.01); *B60L 15/2036* (2013.01); *B60Q 5/005* (2013.01); *B60Q 9/00* (2013.01); *B60W 50/085* (2013.01); *B62B 3/00* (2013.01); *B62B 5/004* (2013.01); *B62M 6/45* (2013.01); *G01C 21/3632* (2013.01); *G01C 21/3664* (2013.01); *G06F 8/65* (2013.01); *G07C 5/006* (2013.01); *G07C 5/008* (2013.01); *G07C 5/02* (2013.01); *G07C 5/0808* (2013.01); *G07C 9/00007* (2013.01); *G07C 9/00309* (2013.01); *H04M 1/7253* (2013.01); *H04W 4/00* (2013.01); *B60K 2007/0038* (2013.01); *B60K 2007/0092* (2013.01); *B60L 2200/12* (2013.01);
(Continued)

(58) Field of Classification Search
CPC ................................ B60K 7/007; A61G 5/045
See application file for complete search history.

(56) References Cited

U.S. PATENT DOCUMENTS 5,829,546 A * 11/1998 Tseng ........................ B62M 6/55
180/206.3
7,458,443 B2 * 12/2008 Givonetti .................. B62L 5/00
188/24.11

* cited by examiner

*Primary Examiner* — John Walters
*Assistant Examiner* — James Triggs
(74) *Attorney, Agent, or Firm* — GTC Law Group PC & Affiliates

(57) ABSTRACT

A support block for a torque arm on a vehicle can include a first indentation and a second indentation each having an opening adapted to accept a portion of a torque arm, the first indentation and the second indentation each having a relief cut opposite the opening into which a portion of a torque arm can fit.

20 Claims, 67 Drawing Sheets

Related U.S. Application Data

(60) Provisional application No. 61/975,658, filed on Apr. 4, 2014, provisional application No. 62/083,851, filed on Nov. 24, 2014, provisional application No. 62/092,243, filed on Dec. 15, 2014.

(51) Int. Cl.

| | | |
|---|---|---|
| *A61G 5/04* | (2013.01) | |
| *A61B 5/11* | (2006.01) | |
| *B60W 50/08* | (2012.01) | |
| *B62M 6/45* | (2010.01) | |
| *B60L 3/00* | (2006.01) | |
| *B60L 3/12* | (2006.01) | |
| *B60L 7/12* | (2006.01) | |
| *B60L 11/00* | (2006.01) | |
| *B60Q 5/00* | (2006.01) | |
| *B60Q 9/00* | (2006.01) | |
| *B60L 11/18* | (2006.01) | |
| *B60L 15/20* | (2006.01) | |
| *B62B 3/00* | (2006.01) | |
| *G01C 21/36* | (2006.01) | |
| *G06F 9/445* | (2006.01) | |
| *G07C 5/00* | (2006.01) | |
| *G07C 5/02* | (2006.01) | |
| *G07C 5/08* | (2006.01) | |
| *G07C 9/00* | (2006.01) | |
| *H04M 1/725* | (2006.01) | |
| *B62B 5/00* | (2006.01) | |
| *H04W 4/00* | (2009.01) | |
| *B62M 6/80* | (2010.01) | |
| *B60W 50/00* | (2006.01) | |
| *H04W 4/02* | (2009.01) | |
| *H04W 4/04* | (2009.01) | |

(52) U.S. Cl.
CPC ....... *B60L 2200/34* (2013.01); *B60L 2200/36* (2013.01); *B60L 2200/40* (2013.01); *B60L 2220/44* (2013.01); *B60L 2220/50* (2013.01); *B60L 2240/12* (2013.01); *B60L 2240/36* (2013.01); *B60L 2240/421* (2013.01); *B60L 2240/423* (2013.01); *B60L 2240/425* (2013.01); *B60L 2240/461* (2013.01); *B60L 2240/463* (2013.01); *B60L 2240/545* (2013.01); *B60L 2240/547* (2013.01); *B60L 2240/549* (2013.01); *B60L 2240/622* (2013.01); *B60L 2240/642* (2013.01); *B60L 2240/68* (2013.01); *B60L 2240/70* (2013.01); *B60L 2250/16* (2013.01); *B60L 2250/24* (2013.01); *B60L 2250/26* (2013.01); *B60L 2260/44* (2013.01); *B60W 2050/0014* (2013.01); *B60W 2050/0089* (2013.01); *B60Y 2200/13* (2013.01); *B60Y 2200/84* (2013.01); *B60Y 2300/18* (2013.01); *B60Y 2300/1884* (2013.01); *B60Y 2410/113* (2013.01); *B62K 2204/00* (2013.01); *B62M 6/80* (2013.01); *G07C 2009/00769* (2013.01); *H04W 4/005* (2013.01); *H04W 4/008* (2013.01); *H04W 4/02* (2013.01); *H04W 4/023* (2013.01); *H04W 4/046* (2013.01); *Y02P 90/60* (2015.11); *Y02T 10/641* (2013.01); *Y02T 10/645* (2013.01); *Y02T 10/7005* (2013.01); *Y02T 10/7044* (2013.01); *Y02T 10/7061* (2013.01); *Y02T 10/7072* (2013.01); *Y02T 10/72* (2013.01); *Y02T 10/7275* (2013.01); *Y02T 10/7291* (2013.01); *Y02T 90/14* (2013.01); *Y02T 90/16* (2013.01); *Y02T 90/161* (2013.01); *Y02T 90/162* (2013.01)

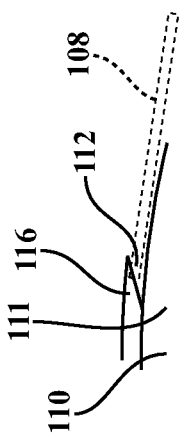
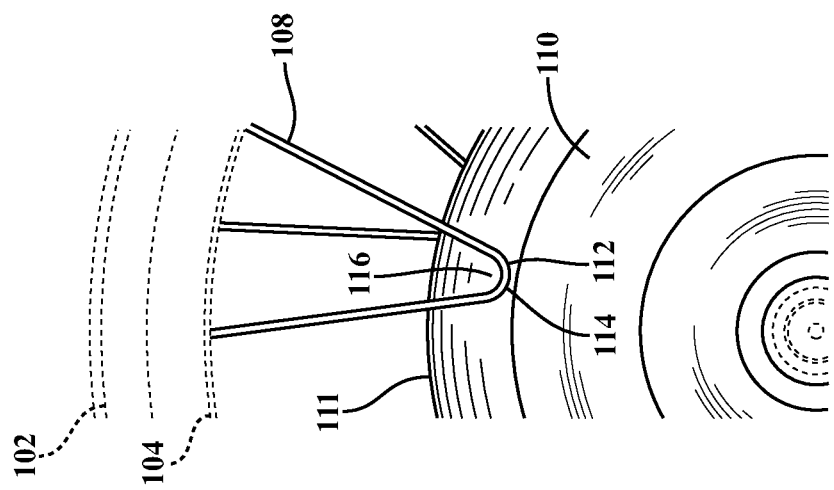
FIG. 1E
FIG. 1D

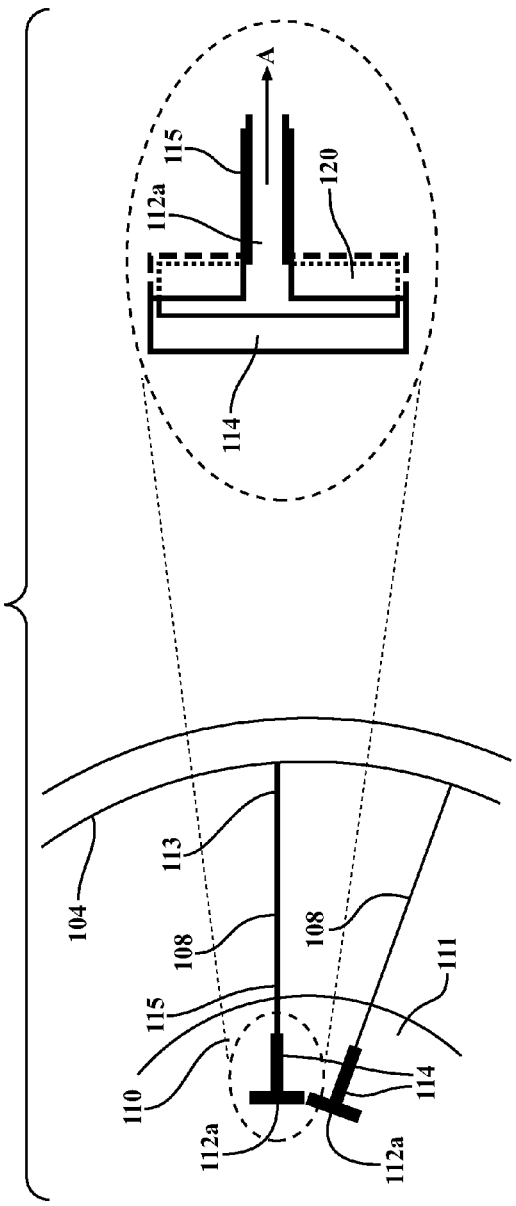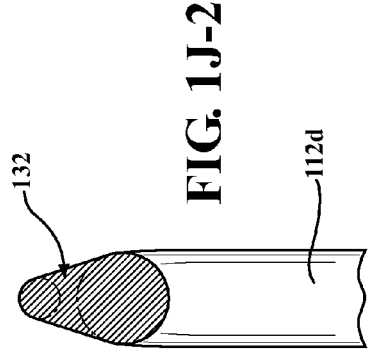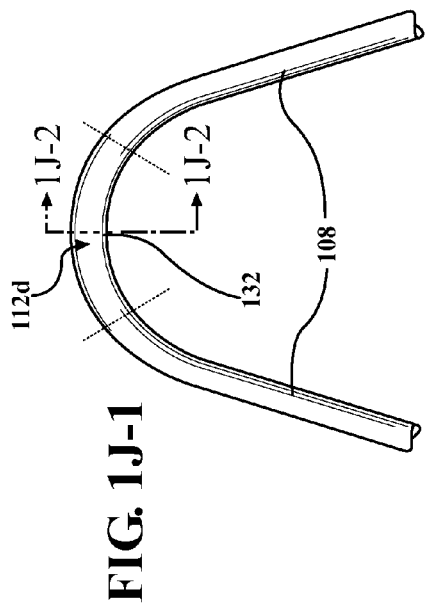

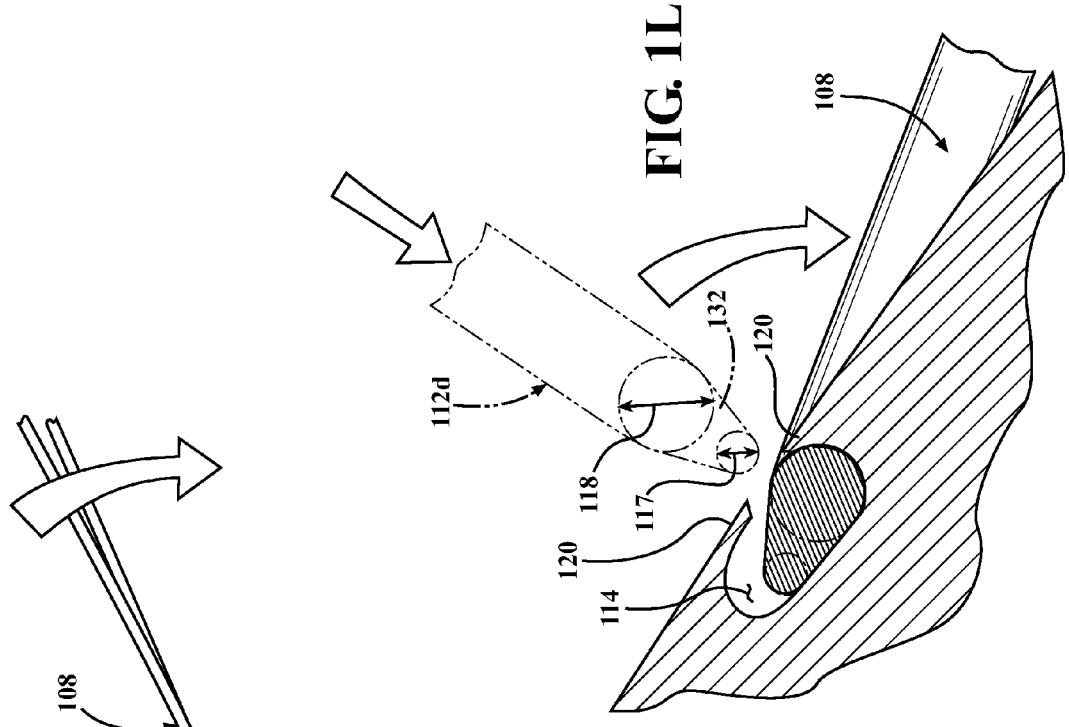
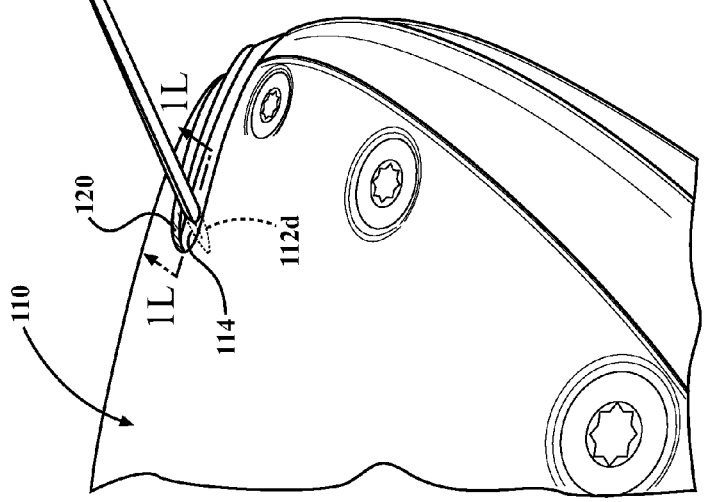

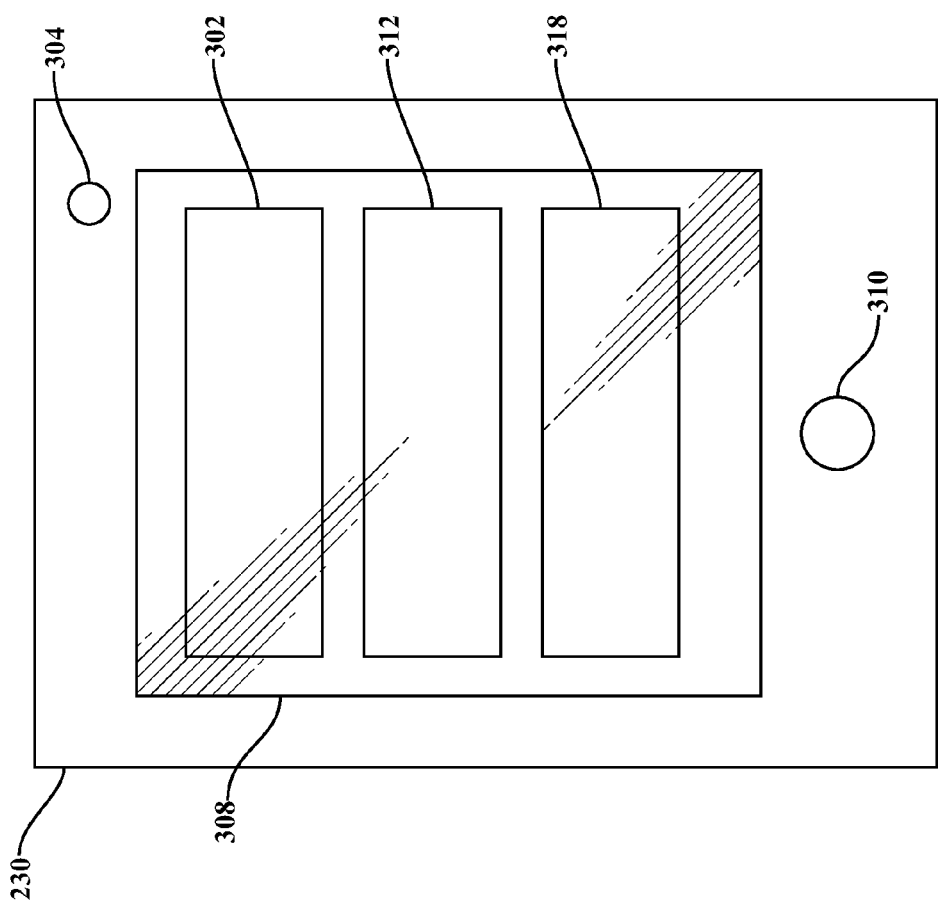

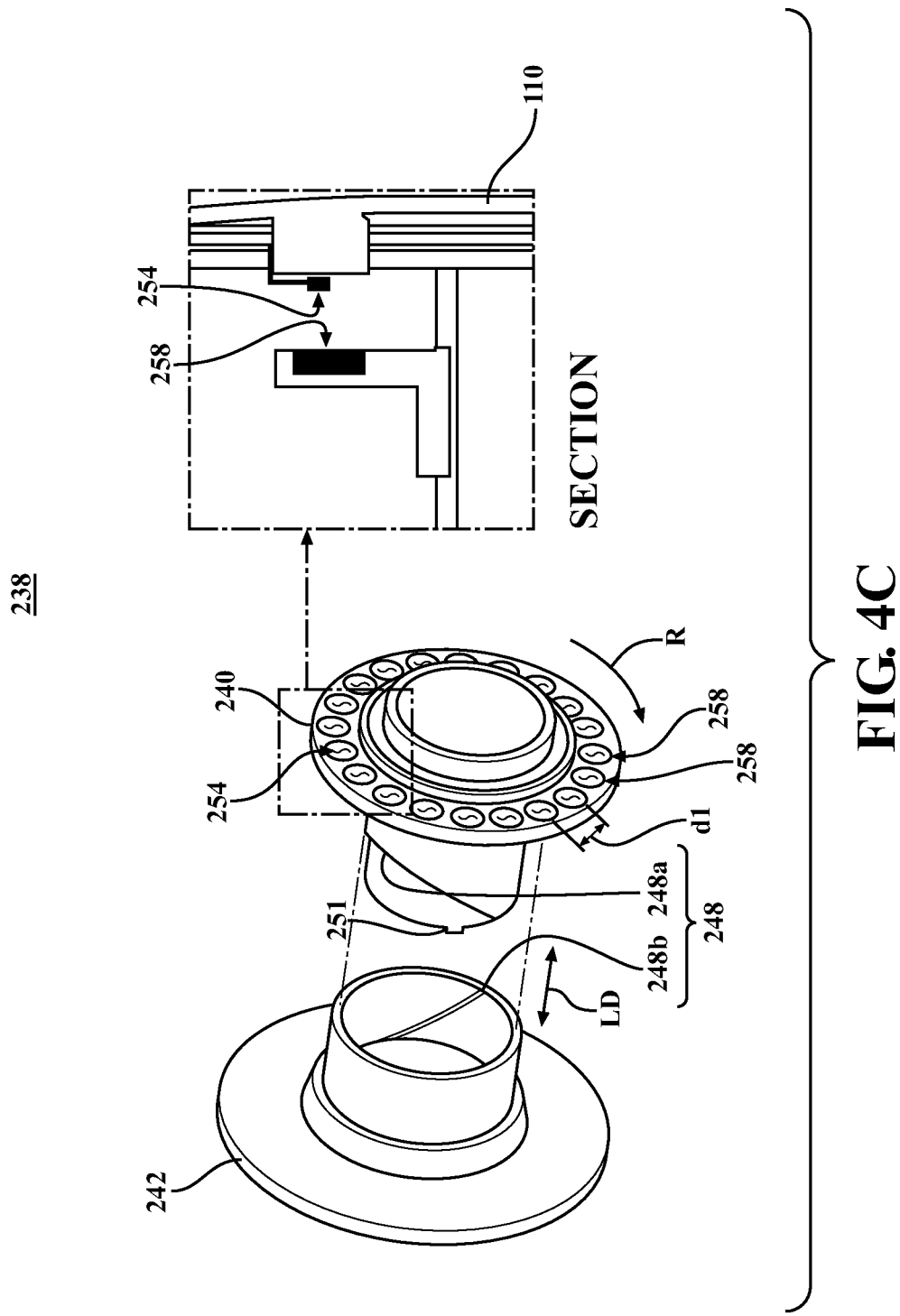

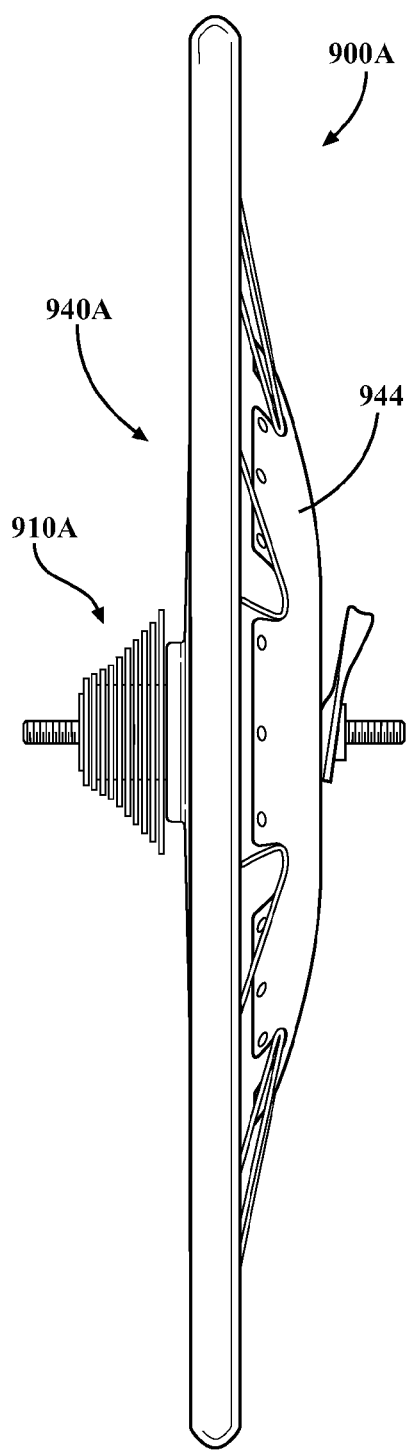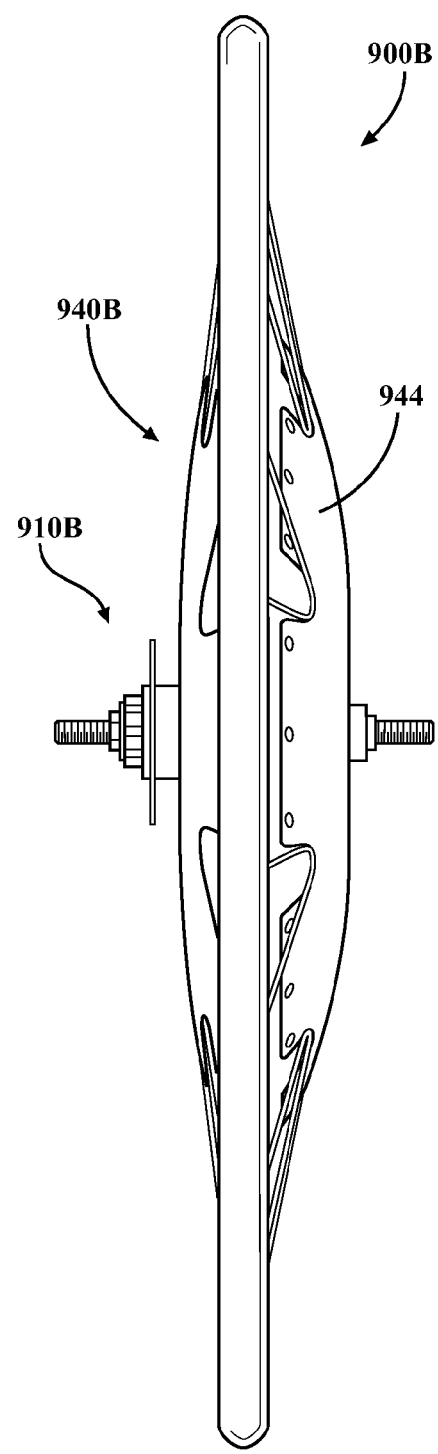
FIG. 10A  FIG. 10B

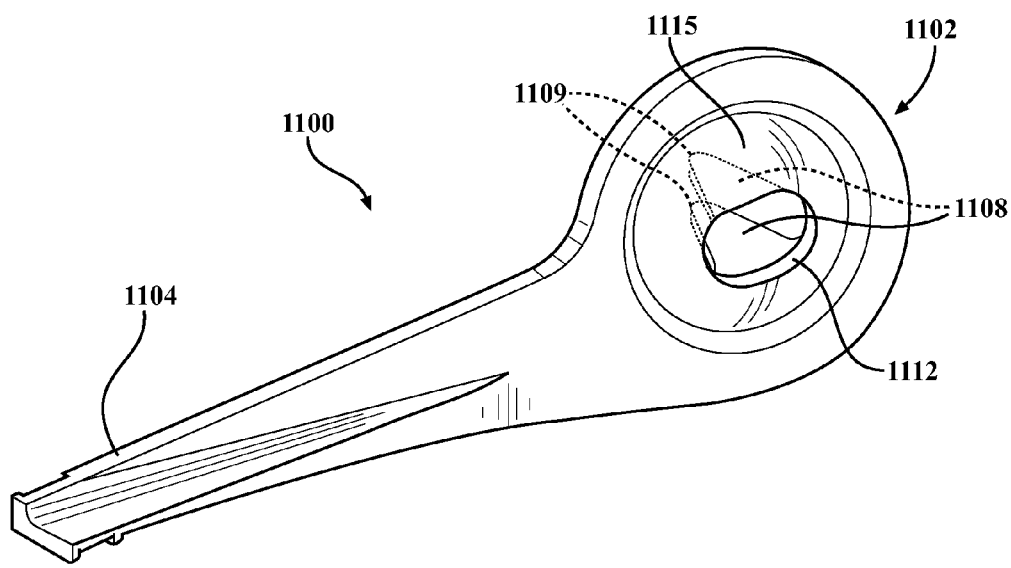
FIG. 11C
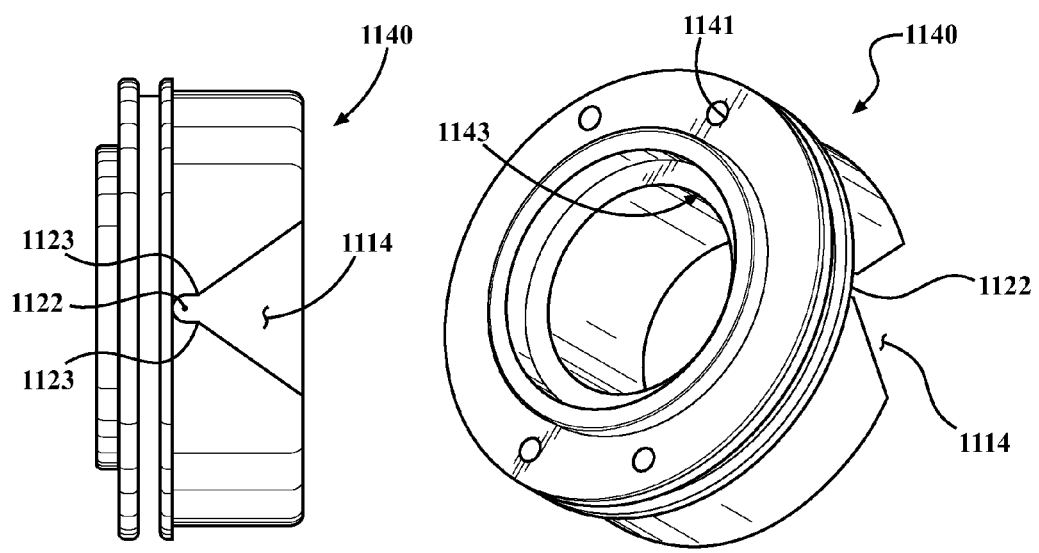
FIG. 11D-1　　FIG. 11D-2

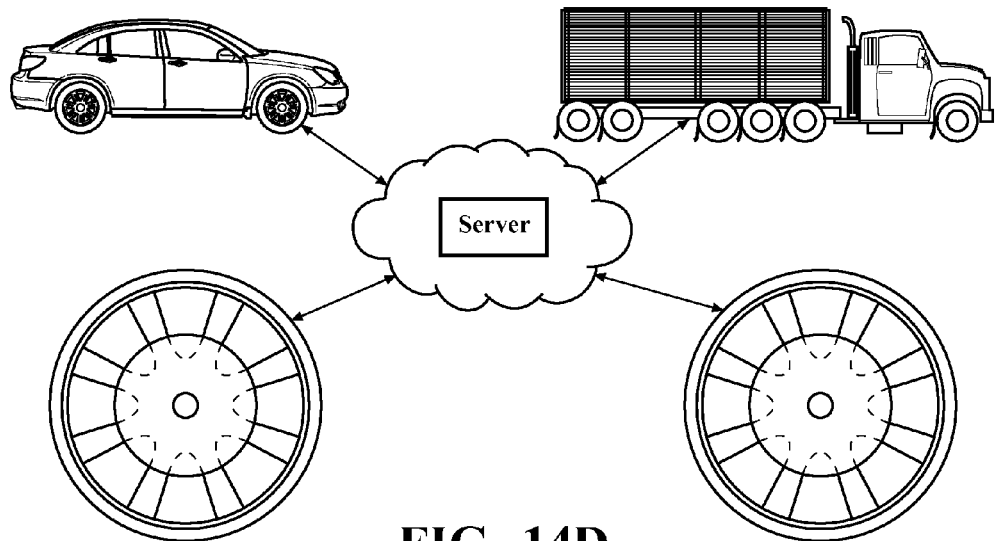
FIG. 14D
FIG. 15A
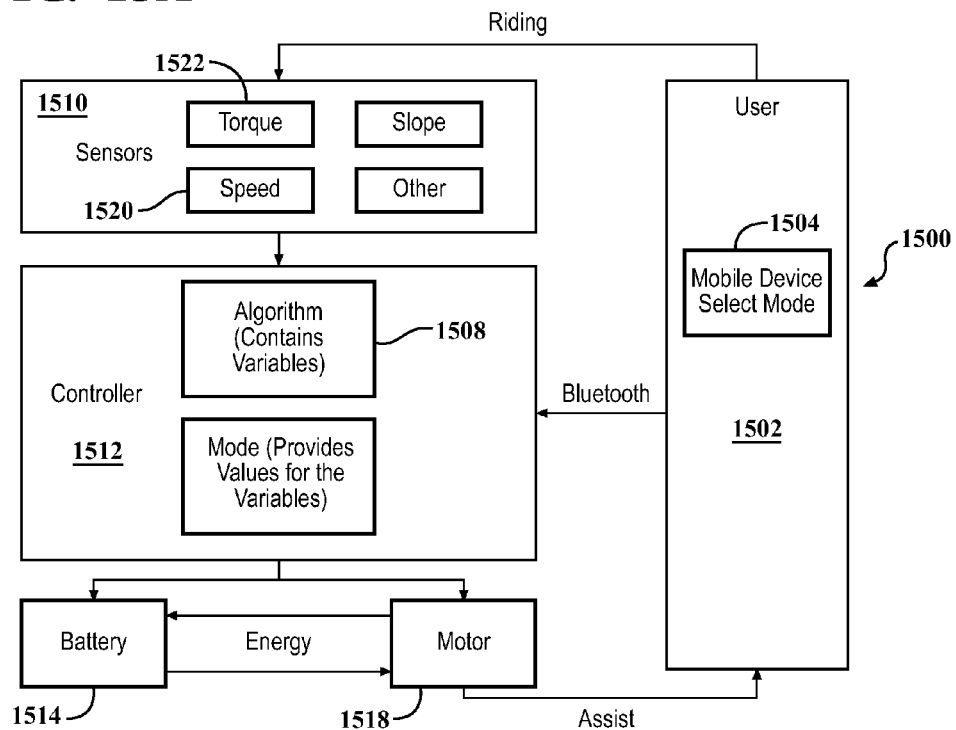

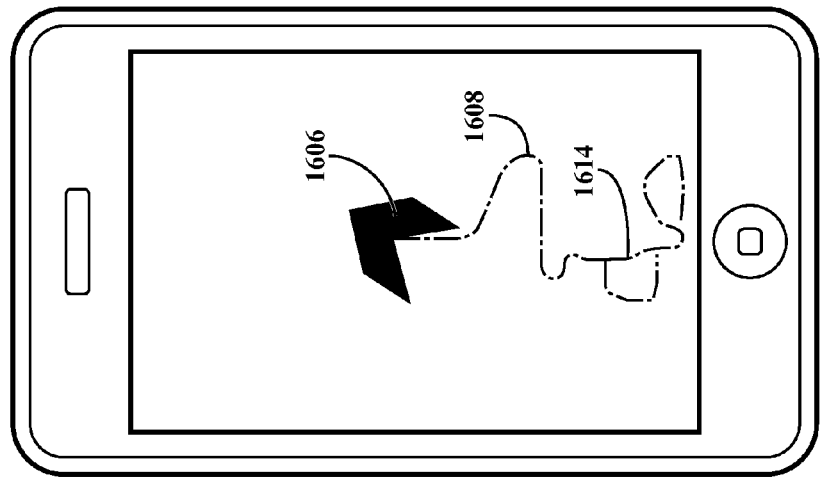
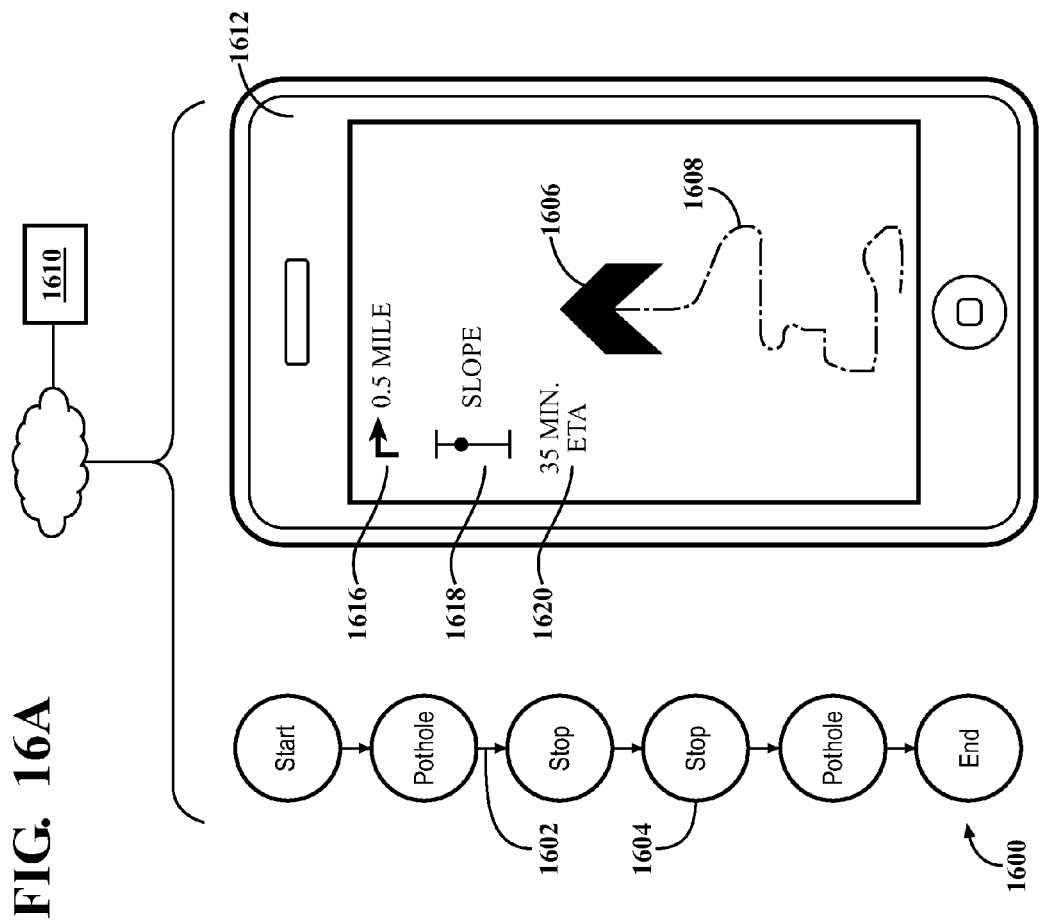
FIG. 16A
FIG. 16B

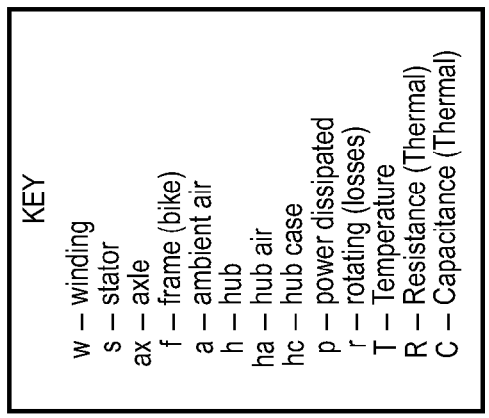
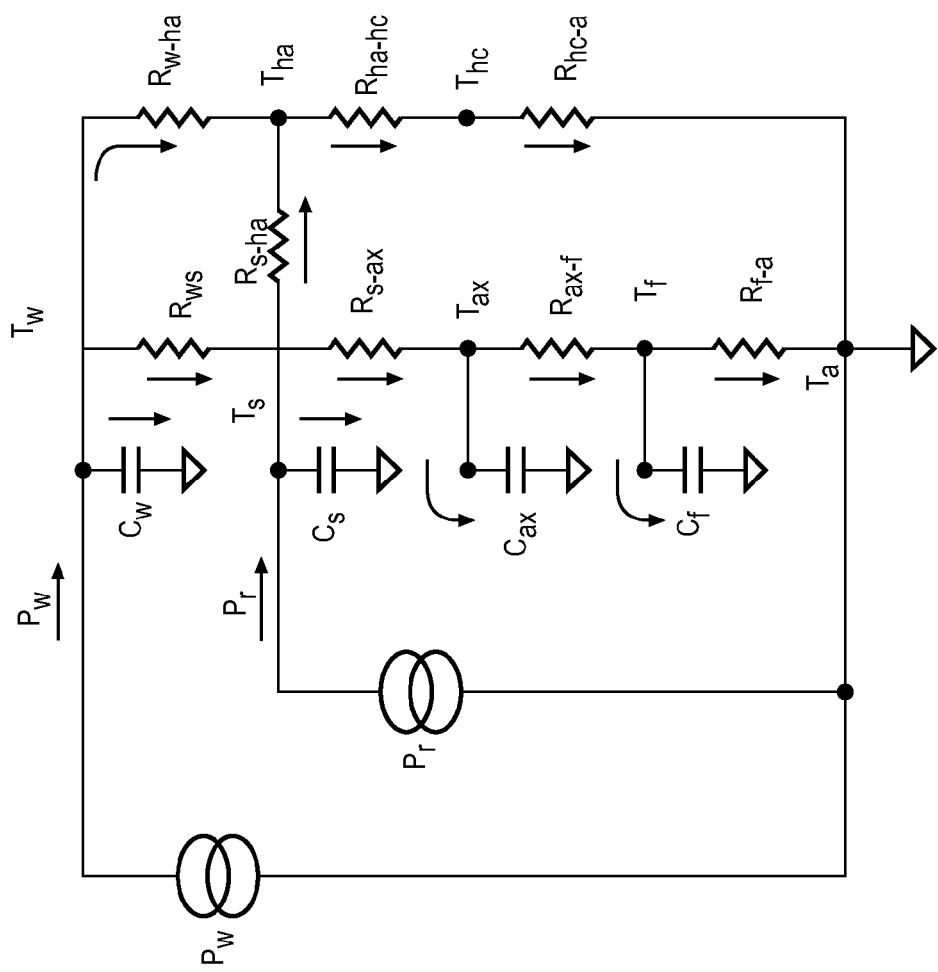
FIG. 23D

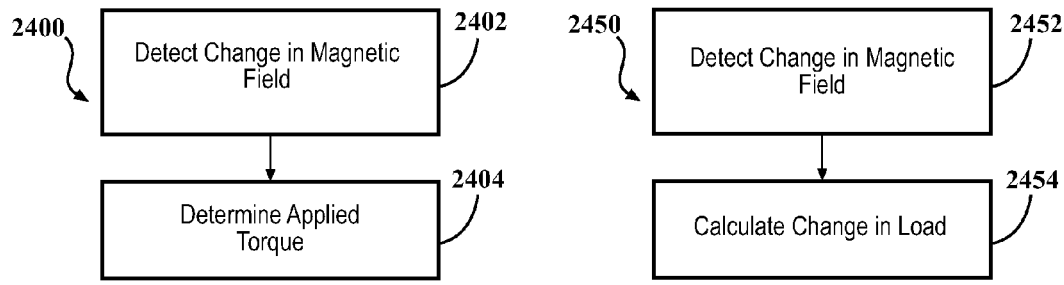
FIG. 24A    FIG. 24B
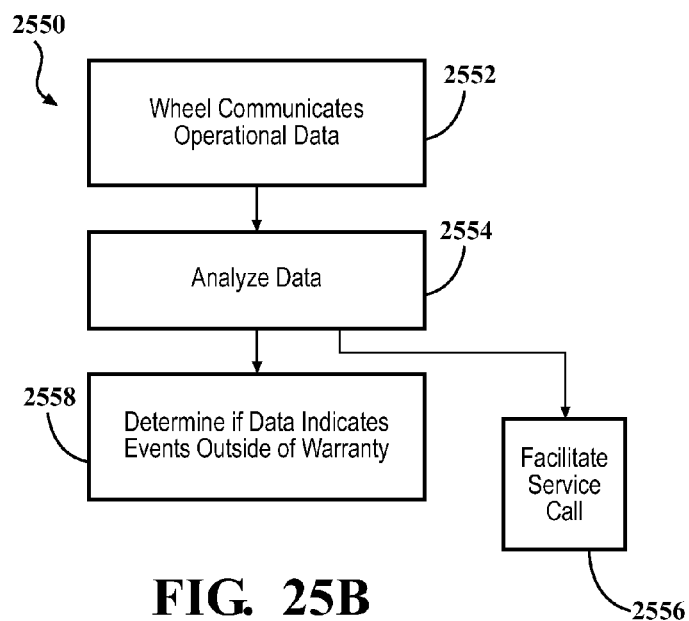
FIG. 25B

TORQUE ARM ASSEMBLY FOR A MOTORIZED WHEEL

This application is a continuation-in-part of U.S. patent application Ser. No. 14/678,855 filed Apr. 3, 2015 which claims priority to: U.S. Provisional Patent Application Ser. No. 61/975,658 filed Apr. 4, 2014; U.S. Provisional Patent Application Ser. No. 62/083,851 filed Nov. 24, 2014; and U.S. Provisional Patent Application Ser. No. 62/092,243 filed Dec. 15, 2014.

This application claims priority to U.S. Provisional Patent Application Ser. No. 62/083,851 filed Nov. 24, 2014 and U.S. Provisional Patent Application Ser. No. 62/092,243 filed Dec. 15, 2014.

Each of the above applications is hereby incorporated by reference in its entirety.

BACKGROUND

The disclosure relates to electrically motorized wheels, and more particularly to an electrically motorized wheel to convert a non-motorized wheeled vehicle to an electrically motorized wheeled vehicle via installation of the wheel on the vehicle.

There are many wheeled vehicles driven or moved by human power, such as bicycles, wheelchairs, wagons, trailers, carts, rolling tables, push lawnmowers, wheelbarrows, etc. Current electric conversion kits for vehicles such as bicycles generally include a relatively large, bulky battery pack, a control system, and an electric motor that are separately mounted on different parts of the bicycle, such as the frame, the handlebars, and the forks. As the components are separated, a wiring harness provides electrical power from the battery pack to the electric motor and operates as a conduit for signals from the control systems. Installation of such systems may be complex and time consuming, typically requiring a variety of tools and a multi-step process.

SUMMARY

The present disclosure describes a method of a system for battery maintenance for an electrically motorized wheel, the method according to one disclosed non-limiting embodiment of the present disclosure can include, accessing a contoured battery within the electrically motorized wheel while each of a multiple of spokes of the electrically motorized wheel remains laced.

A further embodiment of any of the foregoing embodiments of the present disclosure may include situations wherein the method further comprises accessing the contoured battery via a removable access door, the removable access door removably attachable to a non-drive side ring mounted to a drive side shell.

A further embodiment of any of the foregoing embodiments of the present disclosure may include situations wherein the method further comprises removing a cover plate mounted to the drive side shell prior to accessing the contoured battery via the removable access door.

A further embodiment of any of the foregoing embodiments of the present disclosure may include situations wherein the method further comprises accessing the contoured battery from around a panel subsequent to removal of the cover plate.

A further embodiment of any of the foregoing embodiments of the present disclosure may include situations wherein the method further comprises accessing the contoured battery without removal of a bearing mounted to the panel.

A further embodiment of any of the foregoing embodiments of the present disclosure may include situations wherein the method further comprises accessing the contoured battery without disassembly of an electric motor and a control system therefor.

The present disclosure describes a hub casing assembly of an electrically motorized wheel, the hub casing assembly according to one disclosed non-limiting embodiment of the present disclosure can include a drive side casing defined about an axis; a non-drive side ring mounted to the drive side casing, the non-drive side ring defines a non-circular contour; and a contoured battery housing that is passable through the non-circular contour of the non-drive side ring.

A further embodiment of any of the foregoing embodiments of the present disclosure may include situations wherein the hub casing assembly further comprises a removable access door removably attachable to the non-drive side ring.

A further embodiment of any of the foregoing embodiments of the present disclosure may include situations wherein the non-circular contour includes a multiple of arcuate sections.

A further embodiment of any of the foregoing embodiments of the present disclosure may include situations wherein the non-circular contour is scalloped.

A further embodiment of any of the foregoing embodiments of the present disclosure may include situations wherein the contoured battery housing contains a multiple of groups of batteries of a battery system.

A further embodiment of any of the foregoing embodiments of the present disclosure may include situations wherein at least one of the multiple of groups of batteries includes a 2-battery cluster.

A further embodiment of any of the foregoing embodiments of the present disclosure may include situations wherein at least one of the multiple of groups of batteries includes a 4-battery cluster.

A further embodiment of any of the foregoing embodiments of the present disclosure may include situations wherein the 4-battery cluster is arranged in an L-configuration.

A further embodiment of any of the foregoing embodiments of the present disclosure may include situations wherein the hub casing assembly further comprises a cover plate mounted to the drive side casing, the cover plate removable prior to accessing the contoured battery via the removable access door.

A further embodiment of any of the foregoing embodiments of the present disclosure may include situations wherein the contoured battery is contoured to permit removal/replacement from around a panel subsequent to removal of the cover plate.

A further embodiment of any of the foregoing embodiments of the present disclosure may include situations wherein the hub casing assembly further comprises a multiple of spokes mounted to the non-drive side ring and the drive side casing such that a removable access door is removable from the non-drive side ring without delacing any of the multiple of spokes.

The present disclosure describes an electrically motorized wheel, the electrically motorized wheel according to one disclosed non-limiting embodiment of the present disclosure can include a drive side shell defined about an axis; a non-drive side ring mounted to the drive side shell; a removable access door removably attachable to the non-drive side ring; and a multiple of spokes mounted to the non-drive side ring and the drive side casing such that a removable access door is removable from the non-drive side ring without delacing any of the multiple of spokes.

A further embodiment of any of the foregoing embodiments of the present disclosure may include situations wherein the electrically motorized wheel further comprises a contoured battery housing that is passable through a non-circular contour of the non-drive side ring.

The present disclosure describes a spoke for a wheel, the spoke according to one disclosed non-limiting embodiment of the present disclosure can include, a first end, a second end, and an attachment section therebetween, the first end and the second end extend at an acute angle with respect to each other, the attachment section including a non-circular portion in cross-section.

A further embodiment of any of the foregoing embodiments of the present disclosure may include situations wherein the non-circular portion includes a flat section.

A further embodiment of any of the foregoing embodiments of the present disclosure may include situations wherein the non-circular portion includes a triangular section A further embodiment of any of the foregoing embodiments of the present disclosure may include situations wherein the non-circular portion includes a wedge section.

A further embodiment of any of the foregoing embodiments of the present disclosure may include situations wherein the non-circular portion includes a flat section that defines a plane that does not contain the first end and the second end.

A further embodiment of any of the foregoing embodiments of the present disclosure may include situations wherein the acute angle of the plurality of wheel spokes ranges between about 20 degrees and about 60 degrees.

A further embodiment of any of the foregoing embodiments of the present disclosure may include situations wherein the acute angle of the plurality of wheel spokes is about 40 degrees.

The present disclosure describes a wheel, the wheel according to one disclosed non-limiting embodiment of the present disclosure can include, a wheel rim; a wheel hub having a first and second side; and a plurality of wheel spokes connecting the wheel rim to the wheel hub, each of the plurality of wheel spokes has a first end, a second end, and an attachment section therebetween, the ends extend at an acute angle with respect to each other and attach to the rim, the attachment section attached to an attachment pocket in the wheel hub, the attachment section including a non-circular portion in cross-section.

A further embodiment of any of the foregoing embodiments of the present disclosure may include situations wherein the non-circular portion is receivable within the attachment pocket along a first direction, and is locked within the attachment pocket in response to a movement different than the first direction.

A further embodiment of any of the foregoing embodiments of the present disclosure may include situations wherein the movement different than the first direction includes a second direction different than the first direction.

A further embodiment of any of the foregoing embodiments of the present disclosure may include situations wherein the movement different than the first direction includes a rotation.

A further embodiment of any of the foregoing embodiments of the present disclosure may include situations wherein at least one side of the wheel hub has at least one attachment pocket shaped to retain and secure the attachment section of one wheel spoke.

A further embodiment of any of the foregoing embodiments of the present disclosure may include situations wherein the attachment pocket has a shape that is one of: a curved shape, an angled shape.

A further embodiment of any of the foregoing embodiments of the present disclosure may include situations wherein the acute angle of the plurality of wheel spokes ranges between about 20 degrees and about 60 degrees.

A further embodiment of any of the foregoing embodiments of the present disclosure may include situations wherein the acute angle of the plurality of wheel spokes is about 40 degrees.

A further embodiment of any of the foregoing embodiments of the present disclosure may include situations wherein the wheel is an electrically motorized wheel to convert a non-motorized wheeled vehicle to an electrically motorized wheeled vehicle.

The present disclosure describes a method of assembling a spoked wheel, the method according to one disclosed non-limiting embodiment of the present disclosure can include inserting an attachment section of a wheel spoke into an attachment pocket in a wheel hub, the spoke including a first end, a second end, and the attachment section therebetween, the ends extend at an acute angle with respect to each other; and rotating the wheel spoke to lock the attachment section into the attachment pocket.

A further embodiment of any of the foregoing embodiments of the present disclosure may include situations wherein the method further comprises securing the ends of each of the multiple of spokes to a rim.

A further embodiment of any of the foregoing embodiments of the present disclosure may include situations wherein the attachment section includes a non-circular portion in cross-section.

The present disclosure describes a method of thermal management for an electrically motorized wheel, the method according to one disclosed non-limiting embodiment of the present disclosure can include defining a thermally conductive path from at least one component, said at least one component becoming heated during operation of the electrically motorized wheel, providing the path with a thermally conductive material and further defining the path such that the path contacts the at least one component, further defining the path such that the path contacts a hub shell assembly of the electrically motorized wheel thereby conducting heat from the at least one component to the hub shell assembly.

A further embodiment of any of the foregoing embodiments of the present disclosure may include arranging the hub shell assembly in proximity to the at least one component to facilitate a short thermally conductive path therebetween.

A further embodiment of any of the foregoing embodiments of the present disclosure may include locating a plurality of fins on the hub shell assembly that extend from the hub shell assembly.

A further embodiment of any of the foregoing embodiments of the present disclosure may include defining the thermally conductive path from the at least one component to a shaft of the electrically motorized wheel.

A further embodiment of any of the foregoing embodiments of the present disclosure may include further defining the thermally conductive path from the at least one component through the shaft of the electrically motorized wheel to a frame of a wheeled vehicle upon which the electrically motorized wheel is installed.

A further embodiment of any of the foregoing embodiments of the present disclosure may include defining the thermally conductive path through the hub shell assembly by selecting a thickness of the hub shell assembly wherein the thickness is between about 2-4 mm.

A further embodiment of any of the foregoing embodiments of the present disclosure may include defining the thermally conductive path through the hub shell assembly by selecting a material of the hub shell assembly from one of an aluminum, magnesium, steel and titanium alloy.

A further embodiment of any of the foregoing embodiments of the present disclosure may include defining the thermally conductive path through a plurality of fins of the hub shell assembly.

A further embodiment of any of the foregoing embodiments of the present disclosure may include agitating airflow within the hub shell assembly with the plurality of fins.

A further embodiment of any of the foregoing embodiments of the present disclosure may include defining the thermally conductive path from the at least one component through the shaft of the electrically motorized wheel to a frame of a wheeled vehicle upon which the electrically motorized wheel is installed.

A further embodiment of any of the foregoing embodiments of the present disclosure may include, wherein the hub shell assembly in proximity to the at least one component to facilitate a short thermally conductive path therebetween.

A further embodiment of any of the foregoing embodiments of the present disclosure may include a plurality of fins extending from the hub shell assembly.

The present disclosure describes a method of thermal management for an electrically motorized wheel having a hub shell assembly containing at least one component that becomes heated during operation of the electrically motorized wheel, the method according to one disclosed non-limiting embodiment of the present disclosure can include agitating airflow within the hub shell assembly via a plurality of fins that extend within the hub shell assembly; and forming a thermal path from the at least one component that becomes heated during operation of the electrically motorized wheel to the hub shell assembly.

A further embodiment of any of the foregoing embodiments of the present disclosure may include defining the thermal path through the hub shell assembly by selecting a thickness of the hub shell assembly wherein the thickness is between about 2-4 mm.

A further embodiment of any of the foregoing embodiments of the present disclosure may include defining the thermal path through the hub shell assembly by selecting a material of the hub shell assembly from one of an aluminum, magnesium, steel and titanium alloy.

A further embodiment of any of the foregoing embodiments of the present disclosure may include defining the thermal path from the hub shell assembly to a shaft of the electrically motorized wheel.

A further embodiment of any of the foregoing embodiments of the present disclosure may include defining the thermal path from the at least one component that becomes heated through the shaft of the electrically motorized wheel to a frame of a non-motorized wheeled vehicle upon which the electrically motorized wheel is installed.

The present disclosure describes a hub shell assembly for an electrically motorized wheel, the hub shell assembly according to one disclosed non-limiting embodiment of the present disclosure can include a drive side shell defined about an axis; a non-drive side ring mounted to the drive side shell; and a removable access door removably attachable to the non-drive side ring, wherein at least one of the drive side shell, the non-drive side ring and the removable access door forms a portion of a thermal path defined from at least one component that becomes heated during operation of the electrically motorized wheel.

A further embodiment of any of the foregoing embodiments of the present disclosure may include, wherein at least one of the drive side shell, the non-drive side ring and the removable access door includes at least one fin to agitate an airflow within the hub shell assembly.

A further embodiment of any of the foregoing embodiments of the present disclosure may include, wherein at least one of the drive side shell, the non-drive side ring and the removable access door is about 2-4 mm thick.

A further embodiment of any of the foregoing embodiments of the present disclosure may include, wherein at least one of the drive side shell, the non-drive side ring and the removable access door is manufactured of at least one of an aluminum, magnesium, or titanium alloy.

A further embodiment of any of the foregoing embodiments of the present disclosure may include, wherein at least one of the drive side shell, the non-drive side ring and the removable access door is manufactured of a material for heat transfer without air exchange.

The present disclosure describes a device of an electrically motorized wheel to convert a non-motorized wheeled vehicle to an electrically motorized wheeled vehicle via installation of the device to a wheel of the non-motorized wheeled vehicle, the device according to one disclosed non-limiting embodiment of the present disclosure can include a static unit and a rotating unit around a rotor shaft that defines an axis of rotation, the static unit coupled to the non-motorized wheeled vehicle; an electric motor selectively operable to rotate the rotating unit relative to the static unit; a mechanical drive unit operable to rotate the rotational unit in response to a input from the user; a sensing system adapted to identify parameters indicative of input; and a control unit mounted to the electrically motorized wheel, the control unit in communication with the sensing system to continuously control the electric motor in response to input; and wherein at least one component of the electrically motorized wheel becomes heated during operation of the electrically motorized wheel and the at least one component is positioned on a conductive thermal path from the at least one component to the shaft of the wheel.

A further embodiment of any of the foregoing embodiments of the present disclosure may include, wherein the input is mechanical.

A further embodiment of any of the foregoing embodiments of the present disclosure may include, wherein the input is electrical.

A further embodiment of any of the foregoing embodiments of the present disclosure may include, wherein the electric motor is at least partially enclosed in a hub shell assembly.

A further embodiment of any of the foregoing embodiments of the present disclosure may include, wherein the hub shell assembly comprises: a drive side shell defined about an axis; a non-drive side ring mounted to the drive side shell; and a removable access door removably attachable to the non-drive side ring.

A further embodiment of any of the foregoing embodiments of the present disclosure may include, wherein at least one of the drive side shell, the non-drive side ring, and the removable access door includes at least one fin.

A further embodiment of any of the foregoing embodiments of the present disclosure may include, wherein at least one of the drive side shell, the non-drive side ring, and the removable access door is manufactured of magnesium.

A further embodiment of any of the foregoing embodiments of the present disclosure may include, wherein at least one of the drive side shell, the non-drive side ring, and the removable access door is between about 2-4 mm thick.

A further embodiment of any of the foregoing embodiments of the present disclosure may include, defining the thermal path from the at least one component to a shaft of the electrically motorized wheel.

The present disclosure describes a thermal management system for an electrically motorized wheel, the system according to one disclosed non-limiting embodiment of the present disclosure can include a thermally conductive path from at least one component, the at least one component becoming heated during operation of the electrically motorized wheel, wherein the path comprises thermally conductive material and contacts at least one component; and a hub shell assembly of the electrically motorized wheel in contact with the path.

The present disclosure describes a support block for a torque arm on a vehicle according to one disclosed non-limiting embodiment of the present disclosure can include a first indentation and a second indentation each having an opening adapted to accept a portion of a torque arm, the first indentation and the second indentation each having a relief cut opposite the opening into which a portion of a torque arm can fit.

A further embodiment of any of the foregoing embodiments of the present disclosure may include situations, wherein the first indentation and the second indentation are each V-shaped.

A further embodiment of any of the foregoing embodiments of the present disclosure may include situations, wherein the relief cut is located at the apex of the V-shape.

A further embodiment of any of the foregoing embodiments of the present disclosure may include situations, wherein the first indentation and the second indentation are located through a sidewall of the block.

A further embodiment of any of the foregoing embodiments of the present disclosure may include situations, wherein the block has a substantially circular cross section.

A further embodiment of any of the foregoing embodiments of the present disclosure may include situations, wherein the block includes an aperture to receive a shaft.

A further embodiment of any of the foregoing embodiments of the present disclosure may include situations, wherein the block includes a multiple of fastener apertures therethrough.

The present disclosure describes a torque arm assembly for a wheel of a vehicle, the torque arm assembly according to one disclosed non-limiting embodiment of the present disclosure can include a block with a first indentation and a second indentation, the first indentation including a relief cut and the second indentation including a relief cut; and a torque arm with a first hinge portion engageable with the first indentation and extending partially into the relief cut on the first indentation, and a second hinge portion engageable with the second indentation and extending partially into the relief cut on the second hinge portion.

A further embodiment of any of the foregoing embodiments of the present disclosure may include situations, wherein the torque arm includes a non-circular opening.

A further embodiment of any of the foregoing embodiments of the present disclosure may include situations, wherein the non-circular opening rotationally keys the torque arm to a shaft.

A further embodiment of any of the foregoing embodiments of the present disclosure may include situations, wherein the non-circular opening permits the torque arm to pivot about a hinge that defines a pivot for the torque arm such that an arm portion may interface with a frame member of the vehicle.

A further embodiment of any of the foregoing embodiments of the present disclosure may include situations, wherein the arm portion interfaces below a frame member to transfer torque to the frame member of the vehicle.

A further embodiment of any of the foregoing embodiments of the present disclosure may include situations, wherein the hinge portions are substantially V-shaped.

A further embodiment of any of the foregoing embodiments of the present disclosure may include situations, wherein an apex of each of the two hinge portions interface with a respective relief cut to provide a two line contacts for each of the respective first indentation and the second indentation.

A further embodiment of any of the foregoing embodiments of the present disclosure may include situations, wherein an apex of each of the two hinge portions is arcuate.

A further embodiment of any of the foregoing embodiments of the present disclosure may include situations a clamp to retain the arm portion below a frame member.

A further embodiment of any of the foregoing embodiments of the present disclosure may include situations, wherein the torque arm comprises a substantially semi-spherical surface comprising the non-circular opening.

A further embodiment of any of the foregoing embodiments of the present disclosure may include situations a lock nut that interfaces with the semi-spherical portion.

A further embodiment of any of the foregoing embodiments of the present disclosure may include situations, wherein the lock nut includes a non-planar interface that interfaces with the semi-spherical portion.

A further embodiment of any of the foregoing embodiments of the present disclosure may include situations, wherein the lock nut mounts to the shaft to lock the torque arm at a desired angle to accommodate a multiple of vehicle frame arrangements.

The present disclosure describes a user interface for an electrically motorized wheel with a hub shell assembly, the user interface, according to one disclosed non-limiting embodiment of the present disclosure can include, a user interface cover plate for a user interface panel that provides for operation of the electrically motorized wheel, the user interface cover plate rotationally stationary relative to a rotatable portion of the hub shell assembly, the user interface cover plate including an antenna aperture for an antenna of a wireless system.

A further embodiment of any of the foregoing embodiments of the present disclosure may include situations wherein the hub shell assembly comprises: a drive side shell defined about an axis; a non-drive side ring mounted to the drive side shell; and a removable access door removably attachable to the non-drive side ring, the user interface cover plate is generally circular and rotationally fixed within the rotatable removable access door.

A further embodiment of any of the foregoing embodiments of the present disclosure may include a user interface further comprising a switch aperture within the user interface cover plate for an on/off switch mounted to the user interface panel to operate the electrically motorized wheel.

A further embodiment of any of the foregoing embodiments of the present disclosure may include a user interface further comprising a user interface wherein the switch aperture is circular.

A further embodiment of any of the foregoing embodiments of the present disclosure may include situations wherein the switch is low profile.

A further embodiment of any of the foregoing embodiments of the present disclosure further comprising a port aperture within the user interface cover plate for a port mounted to the user interface panel to provide communication with the electrically motorized wheel.

A further embodiment of any of the foregoing embodiments of the present disclosure further comprising a port aperture within the user interface cover plate for a power port to charge the electrically motorized wheel the power port mounted to the user interface panel.

A further embodiment of any of the foregoing embodiments of the present disclosure further comprising a removable cover mountable over the port aperture.

A further embodiment of any of the foregoing embodiments of the present disclosure further comprising an arrangement of status lights to at least partially surround the port.

A further embodiment of any of the foregoing embodiments of the present disclosure may include situations wherein the wireless system is located behind and protected by the user interface cover plate.

A further embodiment of any of the foregoing embodiments of the present disclosure may include situations wherein the antenna of the wireless system is flush with the user interface cover plate.

A further embodiment of any of the foregoing embodiments of the present disclosure may include situations wherein the user interface cover plate includes a central shaft aperture.

A further embodiment of any of the foregoing embodiments of the present disclosure may include situations wherein the central shaft aperture is rectilinear.

The present disclosure describes a method of mounting an antenna to an electrically motorized wheel with a hub shell assembly, the method, according to one disclosed non-limiting embodiment of the present disclosure can include locating an antenna aperture for an antenna of a wireless system in a user interface cover plate for a user interface panel that provides for operation of the electrically motorized wheel, the wireless system mounted to the user interface panel, the user interface cover plate and the user interface panel rotationally stationary relative to a rotatable portion of the hub shell assembly.

A further embodiment of any of the foregoing embodiments of the present disclosure may include mounting the antenna to be flush with the user interface cover plate.

A further embodiment of any of the foregoing embodiments of the present disclosure may include mounting the antenna to the user interface panel behind and protected by the user interface cover plate.

A further embodiment of any of the foregoing embodiments of the present disclosure may include mounting the antenna to the user interface panel to avoid formation of a Faraday cage.

The present disclosure describes a user interface for an electrically motorized wheel, the user interface, according to one disclosed non-limiting embodiment of the present disclosure the user interface can include a user interface cover plate for a user interface panel that provides for operation of the electrically motorized wheel, the user interface cover plate rotationally stationary relative to a rotatable portion of a hub shell assembly, the user interface cover plate including a port aperture within the user interface cover plate for communication access with the user interface panel of the electrically motorized wheel.

A further embodiment of any of the foregoing embodiments of the present disclosure wherein the user interface cover plate is mounted to the user interface panel and the user interface cover plate and the user interface panel are generally circular and form a stationary portion of a hub shell assembly.

A further embodiment of any of the foregoing embodiments of the present disclosure wherein the user interface further comprises a switch aperture within the user interface cover plate for an on/off switch to operate the electrically motorized wheel.

A further embodiment of any of the foregoing embodiments of the present disclosure may include situations wherein the switch aperture is circular.

A further embodiment of any of the foregoing embodiments of the present disclosure may include situations wherein the switch is low profile.

A further embodiment of any of the foregoing embodiments of the present disclosure may include situations wherein the port provides access to a power port to charge the electrically motorized wheel, the power port mounted to the user interface panel.

A further embodiment of any of the foregoing embodiments of the present disclosure may include situations wherein the user interface further comprises a removable cover mountable over the port aperture.

The present disclosure describes a user interface for an electrically motorized wheel, according to one disclosed non-limiting embodiment of the present disclosure the user interface can include a user interface cover plate for a user interface panel that provides for operation of the electrically motorized wheel, the user interface cover plate rotationally stationary relative to a rotatable portion of the hub shell assembly, the user interface cover plate including a switch aperture within the user interface cover plate for an on/off switch mounted to the user interface panel to operate the electrically motorized wheel.

A further embodiment of any of the foregoing embodiments of the present disclosure may include situations wherein the user interface cover plate is generally circular.

A further embodiment of any of the foregoing embodiments of the present disclosure may include situations wherein the switch aperture is circular.

A further embodiment of any of the foregoing embodiments of the present disclosure may include situations wherein the switch is low profile.

These and other systems, methods, objects, features, and advantages of the present disclosure will be apparent to those skilled in the art from the following detailed description of the other embodiment and the drawings. All documents mentioned herein are hereby incorporated in their entirety by reference.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE FIGURES

Various features will become apparent to those skilled in the art from the following detailed description of the disclosed non-limiting embodiment. The drawings that accompany the detailed description can be briefly described as follows:

FIG. 1D schematically represents a side view of a hub and spoke interface.

FIG. 1E schematically represents a sectional view of a hub and spoke interface.

FIG. 1I schematically represents an enlarged plan view of embodiments of an attachment end of a spoke, showing how the attachment end seats into the pocket.

FIG. 1J-1 schematically represents an enlarged cross sectional view of an attachment portion of a spoke.

FIG. 1J-2 schematically represents a cross-section of the attachment portion of FIG. 1J-1.

FIGS. 1K-1L schematically represent the insertion of an attachment portion of a spoke into a hub.

FIG. 3 is a simplified schematic of the mobile device.

FIG. 4C schematically represents details of embodiments of a torque sensor system.

FIG. 10A is a sectional view of a multiple speed electrically motorized wheel.

FIG. 10B is a sectional view of a single speed electrically motorized wheel.

FIG. 11C is a perspective view of a torque arm for the electrically motorized wheel.

FIG. 11D-1 is a side view of a torque arm support block.

FIG. 11D-2 is a perspective view of a support block.

FIG. 13C-1 is an outer side view for a thermal path within the electrically motorized wheel.

FIG. 13C-2 is a perspective view of a thermal path on the interior of the removable access door.

FIG. 14D is a schematic view of a global traffic net system for the electrically motorized vehicle.

FIG. 15A is a schematic view of a system for the electrically motorized vehicle.

FIG. 16A is a schematic view of a system for the electrically motorized vehicle.

FIG. 16B is a mobile device page of a system for the electrically motorized vehicle.

FIG. 23D is an electrical schematic representative of a thermal model for the electrically motorized vehicle.

FIG. 24A is an algorithm for operation of the electrically motorized vehicle.

FIG. 24B is an algorithm for operation of the electrically motorized vehicle.

FIG. 25B is an algorithm for operation of the electrically motorized vehicle.

DETAILED DESCRIPTION

Figure 1A:
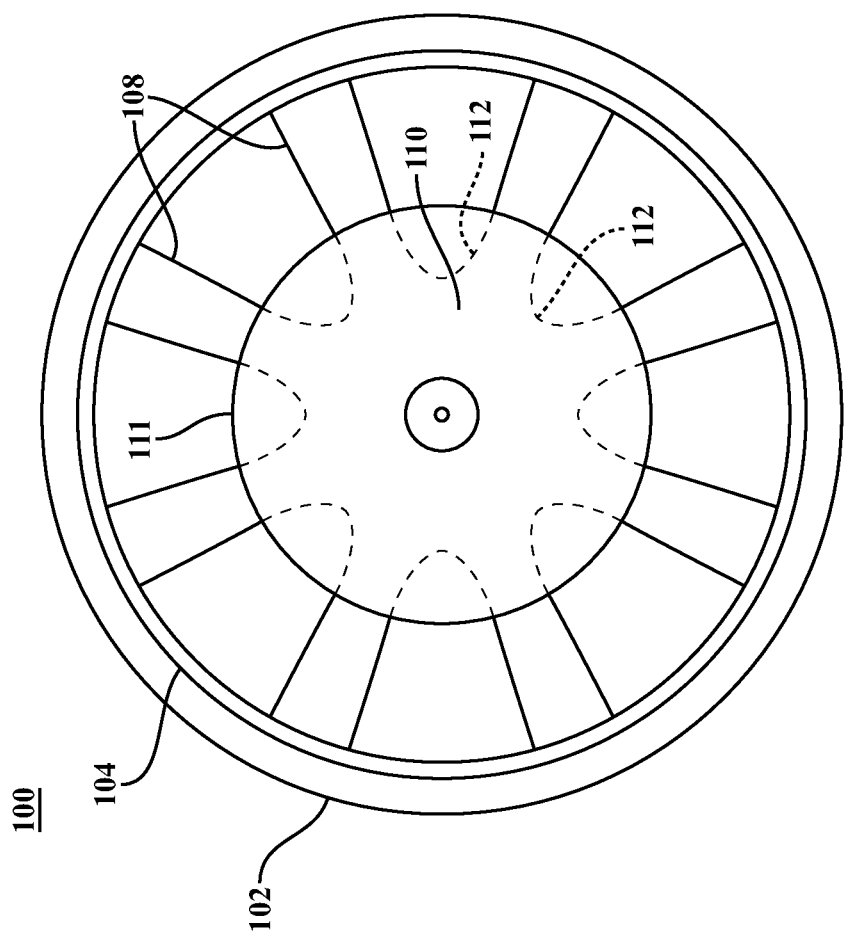
FIG. 1A schematically represents a side view of an electrically motorized wheel.

FIG. 1A schematically illustrates an electrically motorized wheel 100 to convert a non-motorized vehicle, such as a bicycle, into a motorized vehicle, by installation of the electrically motorized wheel onto the vehicle. Disclosure that is not specifically limited to bicycles should be understood to apply to other wheeled vehicles except where context precludes such application. It should be further understood that although particular systems are separately defined, each or any of the systems can be otherwise combined or separated via hardware and/or software.

While many of the components, modules, systems, sub-systems, uses, methods and applications disclosed herein are described in connection with embodiments of an electrically motorized wheel, or a device of an electrically motorized wheel, it should be understood that many of the descriptions herein in connection with an electrically motorized wheel are exemplary and that many of the inventive concepts may be applied more generally (that is not necessarily in connection with a wheel), such as to electrically motorized vehicles generally, electrically motorized bikes, electric bikes, e-bikes, pedelec bikes, electric assist bikes, scooters, battery powered vehicles, wheelchairs, and other vehicles that are powered by mechanisms other than an electrically motorized wheel or device thereof. For example, inventive concepts relating to data collection by or control of an electrically motorized wheel (including involving an associated user device like a smart phone) may apply in the context of another vehicle, such as an electrically motorized or hybrid vehicle, or to a sub-system or component thereof, such as a battery management system, any energy storage and delivery system, any drive system, or the like. Similarly, inventive concepts being described in connection to an electrically motorized wheel, or device thereof, as a platform having various interfaces, including accessory interfaces for connection to and interfacing with a wide range of other devices and systems, may in many cases apply to other vehicles, or components or sub-systems thereof, that do not use an electrically motorized wheel. Further, concepts relating to mechanical and thermal structures may apply more generally, such as to components of other vehicles, to motor systems, and the like. Further, skilled artisans will appreciate, where applicable, that embodiments described herein in connection with the mounting to or otherwise containment on a wheel or device of a wheel may be applied to a vehicle in other spatial arrangements or configurations outside of or off (either partially or wholly), a wheel or device on/of a wheel. Except where otherwise indicated, the disclosure herein is not intended to be limited to an electrically motorized wheel, and various other such embodiments as disclosed throughout this disclosure are intended to be encompassed, as limited only by the claims.

The electrically motorized wheel 100 can include a tire 102, a wheel rim 104, a plurality of spokes 108, and a motorized wheel hub 110. References in this disclosure to a device of an electrically motorized wheel should be understood to encompass any of these elements, as well as components or sub-systems of any of them, except where context indicates otherwise. Also, references throughout this disclosure to the electrically motorized wheel 100 should be understood to encompass any such devices of the wheel, components, or sub-systems, except where context indicates otherwise. For example, a reference to a use of an electrically motorized wheel 100 (such as for data collection, as a platform for connection of accessories, or the like) and/or a reference to an input, operational state, control parameter, or the like of an electrically motorized wheel 100 should be understood to include and apply to uses, inputs, operational states, control parameters, and the like of a device, component or sub-system of the wheel (e.g., using or controlling the motorized wheel hub 110 or some other sub-system inside the hub 110), whether or not the entire set of components is present (e.g., spokes, rim, tire, etc.) in a particular embodiment. The descriptions and corresponding figures are intended to be illustrative only and are in no way to limit the type of vehicles, or the specific details of how a user input is transmitted to and interpreted by the electrically motorized wheel 100.

The motorized wheel hub 110 can include a hub shell assembly 111 that completely encloses components and systems to power the wheel 100, including inducing or resisting movements such as rotation, of the rim 104, spokes 108 and tire 102. The enclosed components and systems may include various modules, components, and sub-systems and may be referred to as a modular systems package. That is, the modular systems package describes the various elements that are contained within the hub shell assembly 111. In embodiments, the wheel rim 104 is connected to the self-contained motorized wheel hub 110 via a plurality of spokes 108 that are under tension. Further, although this embodiment has specific illustrated components in a bicycle embodiment, the embodiments of this disclosure are not limited to those particular combinations and it is possible to use some of the components or features from any of the embodiments in combination with features or components from any of the other embodiments.

In embodiments, each of the plurality of spokes 108 that connect the wheel rim 104 to the motorized wheel hub 110 may have a first end and a second end that extend at an angle to each other, and an intermediate attachment portion 112 formed such that the first and second ends extend at an acute angle with respect to each other such that the first and second ends attach to the wheel rim 104. In one example the acute angle of the plurality of wheel spokes ranges between about 20 degrees and about 60 degrees and may more specifically be formed at about 40 degrees.

Figure 1C:
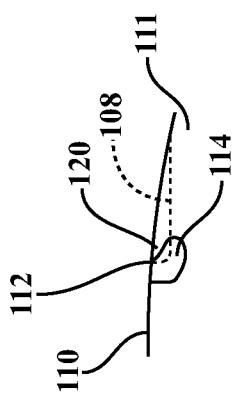
FIG. 1C schematically represents a sectional view of a hub and spoke interface.
Figure 1B:
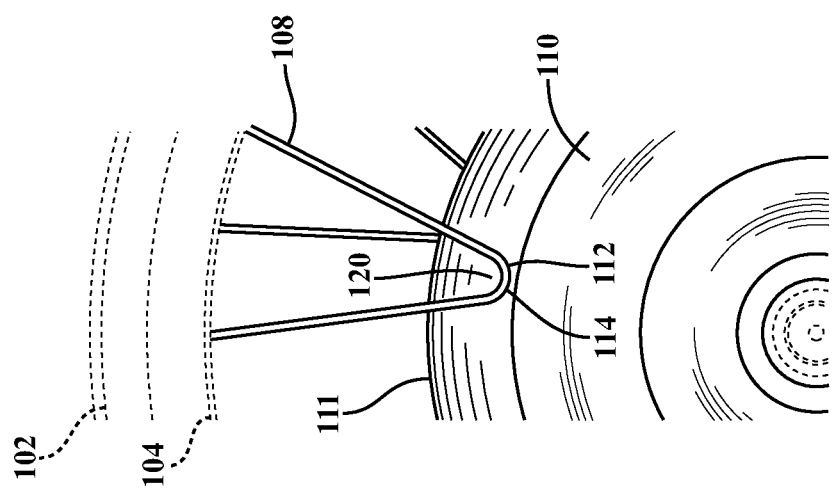
FIG. 1B schematically represents a side view of a hub and spoke interface.

FIGS. 1B-1C illustrate embodiments in which the attachment portion 112 may fit into an attachment pocket 114 in the surface of the motorized wheel hub 110 to secure the motorized wheel hub 110 to the attachment portions 112 of the plurality of spokes 108. The attachment pocket 114 may have a shape to receive and secure a curved or angled attachment portion 112. The internal portion of the attachment pocket 114 extends slightly closer to the wheel rim 104 in a radial direction to form a lip 120. As the spoke 108 is tightened, it pulls attachment portion 112 radially toward electrically motorized wheel rim. This causes the attachment portion to slide along the lip 120 and into the pocket 114. The attachment portion 112 becomes trapped in the attachment pocket 114 thereby securing the spoke attachment portion 112 to the motorized wheel hub 110.

With reference to FIGS. 1D and 1E, the attachment portion 112 is secured at least partially under an overhang 116 in the surface of the motorized wheel hub 110 to thereby secure the motorized wheel hub 110 between the attachment portions 112 of the plurality of spokes 108. The overhang 116 may be shaped to receive and secure under compression the attachment portion 112 of the respective wheel spoke 108. The attachment portion 112 may also be directionally oriented such that the attachment portion 112 is inserted at a particular angle then rotated to be locked into the pocket 114. The attachment portion 112 thereby remains secured within the attachment pocket 114 even if the proper tension no longer remains on the spoke 108.

Figure 1H:
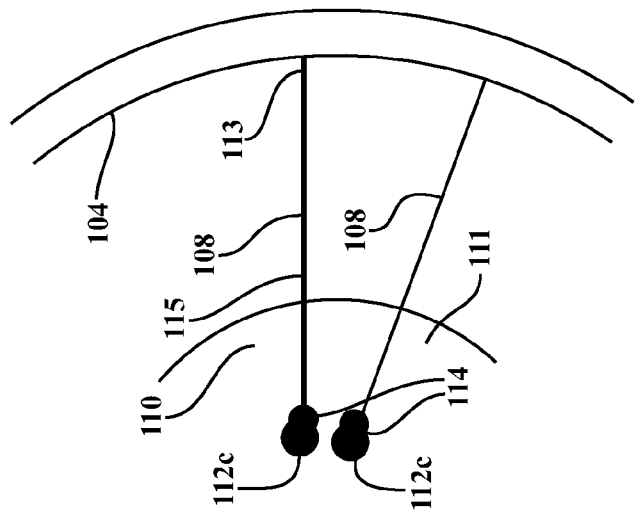
FIG. 1H schematically represents a side view showing a hub and spoke interface.
Figure 1G:
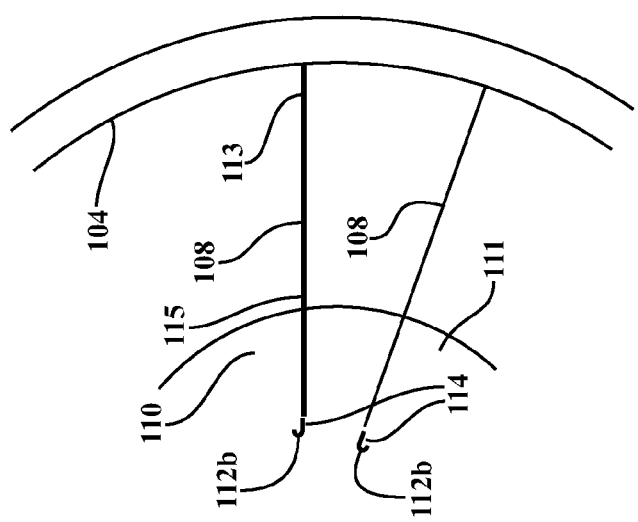
FIG. 1G schematically represents a side view showing a hub and spoke interface.
Figure 1F:
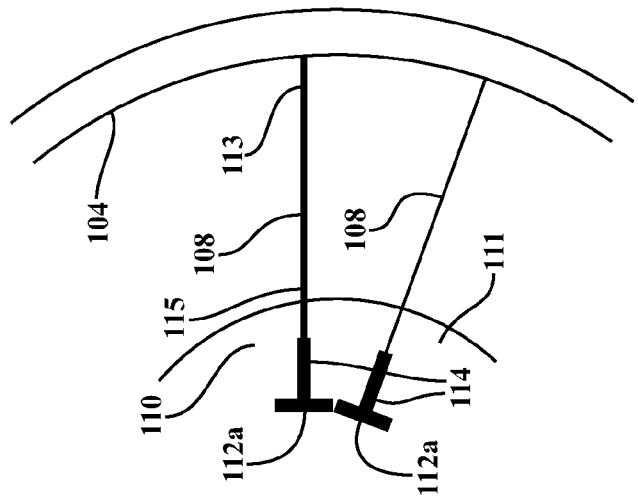
FIG. 1F schematically represents a side view of a hub and spoke interface.

With reference to FIGS. 1F-1H alternative embodiments of connections between the wheel rim 104 and the motorized wheel hub 110 are schematically illustrated. The spokes 108 may have first ends, referred to as the rim ends 113, that extend from the wheel rim 104, and the second ends that attach to the motorized hub 110, being an attachment portion 112*a*, 112*b*, 112*c*. The attachment portions 112*a*, 112*b*, 112*c* may be shaped in the form of a 'T' (FIG. 1F), 'J' (FIG. 1G), 'L', rounded, or otherwise enlarged head shape (FIG. 1H), relative to the diameter of a neck 115 of the spoke.

The attachment portions 112*a*, 112*b*, 112*c* fit into an attachment pocket 114 in the surface of the motorized wheel hub 110 wherein the attachment pocket 114 has the complementary shape to receive the respective attachment portions, to thereby secure the motorized wheel hub 110 to the plurality of spokes 108. The internal portion of each attachment pocket 114 extends toward the wheel rim 104 in a radial direction, to thereby form a lip 120. The lip 120 and the attachment pocket 114 trap and secure the respective attachment portions 112*a*, 112*b*, 112*c* in the attachment pocket 114 as the plurality of spokes 108, under tension, are pulled toward the wheel rim 104.

With reference to FIG. 1I, other embodiments of an attachment portion 112 of the spoke being seated in a respective pocket 114. The attachment portion 112*a* is received into the "T-shaped" attachment pocket 114—generally downward into the plane of the page. After fitting into the pocket 114, the spoke is tightened and the neck 115 is pulled toward the rim (indicated schematically by arrow "A".) This results in the attachment portion being seated within the deepest portion of pocket 114.

Illustrative Clauses

In some implementations, angled spokes may include attachment portions with a non-circular cross-section for improved retention as described in the following clauses and illustrated in FIGS. 1J-1L.

1. A spoke for a wheel, comprising:
a first end, a second end, and an attachment section therebetween, the first end and the second end extend at an acute angle with respect to each other, the attachment section including a non-circular portion in cross-section.

2. The spoke as recited in clause 1, wherein the non-circular portion includes a flat section.

3. The spoke as recited in clause 1, wherein the non-circular portion includes a triangular section.

4. The spoke as recited in clause 1, wherein the non-circular portion includes a wedge section.

5. The spoke as recited in clause 1, wherein the non-circular portion includes a flat section that defines a plane that does not contain the first end and the second end.

6. The spoke as recited in clause 1, wherein the acute angle of the plurality of wheel spokes ranges between about 20 degrees and about 60 degrees.

7. The spoke as recited in clause 1, wherein the acute angle of the plurality of wheel spokes is about 40 degrees.

8. A wheel comprising:
a wheel rim;
a wheel hub having a first and second side; and
a plurality of wheel spokes connecting the wheel rim to the wheel hub, each of the plurality of wheel spokes has a first end, a second end, and an attachment section therebetween, the ends extend at an acute angle with respect to each other and attach to the rim, the attachment section attached to an attachment pocket in the wheel hub, the attachment section including a non-circular portion in cross-section.

9. The wheel as recited in clause 8, wherein the non-circular portion is receivable within the attachment pocket along a first direction, and is locked within the attachment pocket in response to a movement different than the first direction.

10. The wheel as recited in clause 9, wherein the movement different than the first direction includes a second direction different than the first direction.

11. The wheel as recited in clause 9, wherein the movement different than the first direction includes a rotation.

12. The wheel as recited in clause 9, wherein at least one side of the wheel hub has at least one attachment pocket shaped to retain and secure the attachment section of one wheel spoke.

13. The wheel as recited in clause 9, wherein the attachment pocket has a shape that is one of: a curved shape, an angled shape.

14. The wheel as recited in clause 9, wherein the acute angle of the plurality of wheel spokes ranges between about 20 degrees and about 60 degrees.

15. The wheel as recited in clause 9, wherein the acute angle of the plurality of wheel spokes is about 40 degrees.

16. The wheel as recited in clause 9, wherein the wheel is an electrically motorized wheel to convert a non-motorized wheeled vehicle to an electrically motorized wheeled vehicle.

17. A method of assembling a spoked wheel comprising:
 inserting an attachment section of a wheel spoke into an attachment pocket in a wheel hub, the spoke including a first end, a second end, and the attachment section therebetween, the ends extend at an acute angle with respect to each other; and
 rotating the wheel spoke to lock the attachment section into the attachment pocket.

18. The method of clause 17, further comprising securing the ends of each of the multiple of spokes to a rim.

19. The method of clause 17, wherein the attachment section includes a non-circular portion in cross-section.

In other embodiments, angled spokes such as those described previously in regards to FIGS. 1B-1C, may include attachment portions 112d with a non-circular cross-section 132 (FIG. 1J). The non-circular cross-section 132 may be manufactured by swaging, punching, or otherwise deforming the attachment portion 112d. The segments of the spokes 108 outside of the attachment portion 112 may have a circular cross-section, or may be shaped in any other suitable manner (e.g., with an aerodynamic cross section).

With reference to FIGS. 1K and 1L, the spokes 108 may be inserted into a respective attachment pocket 114 then rotated until the attachment portions 112d are retained beneath lips 120. The attachment pocket 114 may be sized to a depth that permits insertion of the attachment portion 112d substantially transverse to the surface of the motorized wheel hub 110 and the lips 120 may be arranged to correspond with a first cross-sectional diameter 118 of the attachment portions 112d that is reduced to a second cross-sectional diameter 117 smaller than the first cross-sectional diameter 118 with generally flat sections therebeween that defines a plane that does not contain the first end and the second end of the spokes 108. That is, the attachment portions 112d may form a generally pointed triangular, wedge, or other generally pointed shape in cross-section that facilitates insertion, rotation, then engagement within the pocket 114.

For example, the attachment pocket 114 may be racetrack shaped, curved, angled or of another shape to permit insertion of the attachment portion 112d, for example, substantially transverse to the surface of the motorized wheel hub 110 (shown in phantom in FIG. 1L) and subsequent rotation. The spokes 108 may then be rotated (e.g., about an axis substantially perpendicular to the axis of rotation of the motorized wheel hub 110; shown solid in FIG. 1L) into their respective final position such that the first and second ends of the spokes 108 can then be attached to the wheel rim 104.

In another example, the first or second end of each of the spokes 108 may be inserted into attachment pockets 114 such that the attachment portions 112d are not initially within the attachment pockets 114. The spokes 108 may then be fed or otherwise threaded through the respective attachment pockets 114 until the attachment portions 112d are retained under lips 120. In these processes, the final position of the spokes 108 may depend on the interface with the rim 104. Each attachment portion 112d may be deformed such that its widest cross section is wider than the aperture of attachment pocket 114 once rotated to the installed position. If the attachment portions 112d are widest in the plane of their respective spoke 108, the spokes 108 are readily retained within the attachment pockets 114 in a direction transverse to the motorized wheel hub 110, even should spoke tension be reduced. For example, under normal use conditions, the tension of the portion of the plurality of spokes 108 immediately adjacent to the ground will be lower than that of the remainder of the spokes due to the compressive force from the weight of the vehicle. Certain actions, such as driving the electrically motorized wheel 100 over a bump, will further reduce that lowered spoke tension. The attachment portions 112d described above facilitate the physical integrity and security of the electrically motorized wheel 100 while in motion even if the tension of the spokes 108 is not well maintained.

The plurality of spokes 108 may include a first set of spokes and a second set of spokes. The attachment sections of the first set of spokes 108 connect to a first side of the motorized wheel hub 110 and the attachment sections of the second set of spokes 108 connect to the surface of a second side of the motorized wheel hub 110. The ends of the plurality of spokes 108 of the first set may be interleaved with the ends of the plurality of spokes 108 of the second set and the interleaved sets alternately connected around an inner circumference of the wheel rim 104 such that the spokes are interlaced, i.e., woven around each other.

In embodiments, the motorized wheel hub 110 is connected to the wheel rim 104 via a mesh material.

In embodiments, the motorized wheel hub 110 is connected to the wheel rim 104 via a disk, or other solid structure.

In embodiments, the wheel rim 104 and motorized wheel hub 110 can alternately be connected according to conventional straight wheel spoking parameters.

Figure 2A:
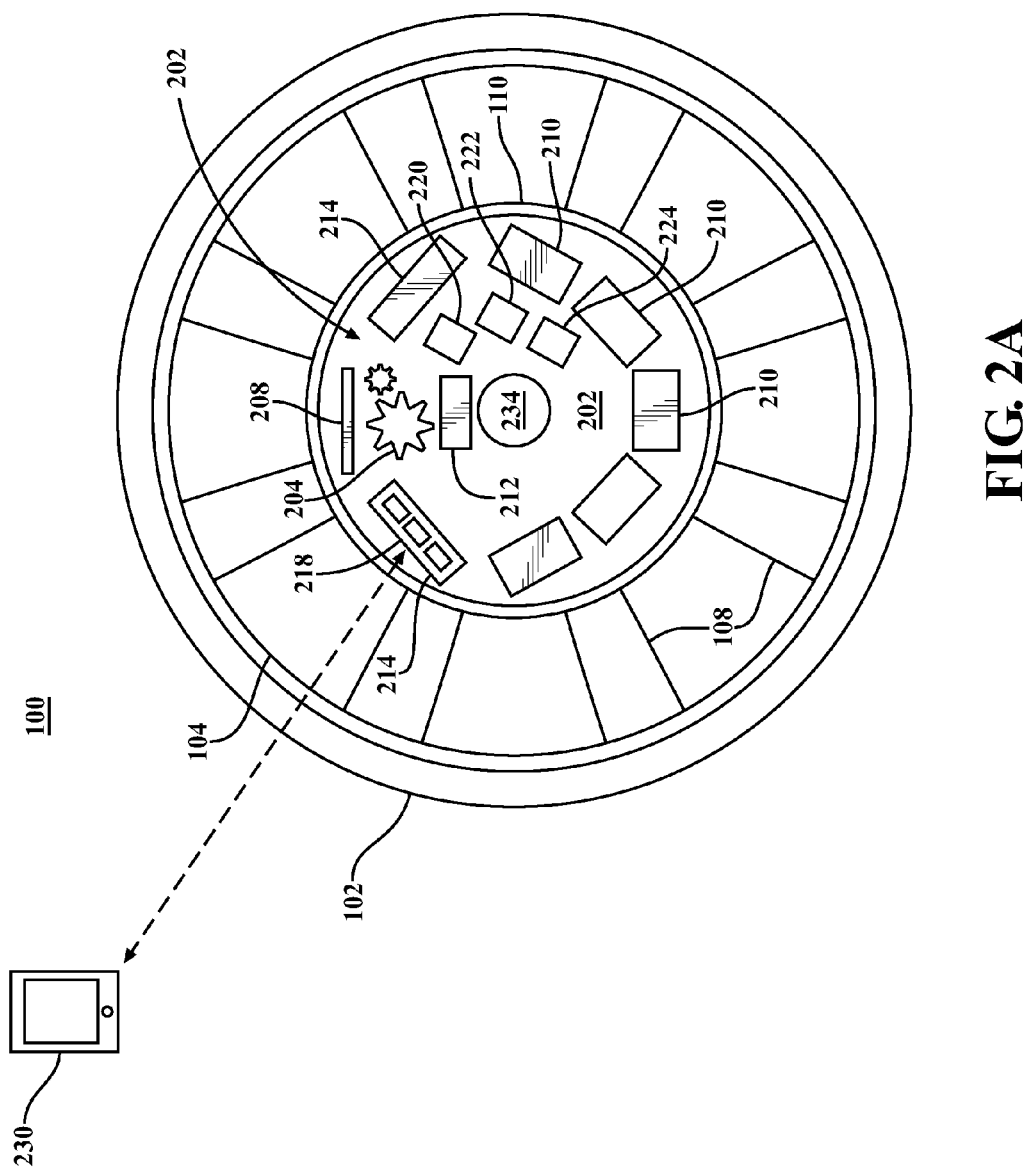
FIG. 2A is a side view of electrically motorized wheel of FIG. 1A with its side cover removed showing internal elements.

With reference to FIG. 2A, the motorized wheel hub 110 can include a modular systems package 202 packaged within a hub shell assembly 111 (FIG. 1A) to enclose elements of the electrically motorized wheel 100. As such, the modular systems package 202 may be completely contained within the hub shell assembly 111 and protected from external environmental conditions. In embodiments, components of the modular systems package may include sub-assemblies, sub-systems, components, modules and the like that may be adapted to be removed and replaced, while other sub-systems, components and modules remain in place. For example, interfaces between the various elements may be adapted to facilitate ease of connection and disconnection of the elements during assembly of the modular systems package 202 or in the field. These interfaces may include various conventional electrical, mechanical and data connectors, ports, adaptors, gateways, buses, conduits, cables, and the like. References in this disclosure to the components of the modular systems package 202 should be understood to include any of the referenced items, except where context indicates otherwise.

In embodiments, a coating material may be applied to the modular systems package 202 and/or its components to protect against environmental conditions, such as moisture, dust, dirt and debris that may penetrate the hub shell assembly 111. The coating material may conform to the hub shell assembly and/or to individual components to encase or otherwise coat the coated components. The coating material may also protect the internal components from impact.

The modular system package 202 may include a motor 204, a motor control system 208, an electrical storage system, such as a battery system 210, a mechanical drive system 212, a control system 214, and accessory port 218, which may include a hardware interface 232, such as a port (e.g., a USB port) to provide support for an accessory device, such as providing electrical power and/or a data connection to the accessory device. The accessory port 218 may be in communication with the battery system 210 to receive power and be in communication with the control system 214. The accessory port 218 may include a short-range wireless communications system 220, a telecommunications system 222, a global positioning system 224, an interface for a removable data storage device 228 (such as a USB storage device), and/or other components.

The mechanical drive system 212 may include a pulley, chain, drive shaft or other interface to transmit a transmit an input by a user such as a rotational or linear force. It should be understood that various interfaces may be provided. If the electrically motorized wheeled vehicle is a bicycle, it may also include a wheel hub gear system 234, or sprocket, connected to the motor 204.

The control system 214 may include one or more processing systems such as micro-processors, CPUs, application specific integrated circuits, field programmable gate arrays, computers (including operating system, CPU, storage and other components, possibly include a hypervisor or other component for virtualization of functions. The processing systems may be configured to communicate with and control the motor control system 208 and the battery system 210, as described in detail elsewhere herein, such as to implement various operational modes, features and the like. The control system 214, may be referred to in some cases as a computing system or as a control system, may further be configured to provide and manage various communications and networking functions communicate with and control the telecommunications system 222, the short-range wireless communications system 220, the global positioning system 224, the removable data storage device 228, various networking systems (e.g., cellular, satellite and internet protocol-based networks) and others.

The telecommunications system 222 and the global positioning system 224 may include a global positioning system (GPS) unit 224 or other location positioning technologies (e.g., using triangulation by cellular tower locations, accessing a database of locations of installed devices, such as wireless access points or infrastructure elements 252 (e.g., call boxes and traffic lights), or the like) that provide location and time data. The telecommunications system 222 can provide access to mobile, cellular, Wi-Fi data networks and others. In embodiments, the telecommunications system 222 includes a general packet radio service (GPRS) unit or other wireless technology that can provide access to 2G, 3G, LTE and other cellular communications systems or other modes of wireless communications. In embodiments, the telecommunications system 222 and the global positioning system 224 may be integrated within the control system 214.

The control system 214 may include processing capabilities for handling the collection of data from various sources, such as sensors, external data sources, external systems (e.g., traffic, weather, and other systems that provide data about the environment of the user and systems that provide data about other wheels, such as fleet management or other aggregate-based information), user input to user interfaces, and others. Processing data may include receiving, translating, transforming, storing, extracting, loading, and otherwise performing operations on the data. Processing may include performing computations and calculations, executing algorithms based on inputs, and providing results, such as to other processing elements of the wheel, to users, to external systems, and the like. Processing may include modules for handling storage systems that are local to the wheel or that are remote, such as cloud storage or storage on a mobile device. Processing may also include handling various interfaces, including managing data and electrical interfaces, such as interfaces with a user interface on the wheel, a user interface of a device, such as a mobile device, that is used to control the wheel, interfaces to storage systems, interfaces to databases, and interfaces to external systems. The interfaces may include application-programming interfaces, including ones that enable machine-to-machine connections to external systems, to control devices, and to other wheels.

The battery system 210 can include one or more rechargeable batteries, one or more bulk capacitors (optionally including one or more super-capacitors), and/or a combination thereof. The battery system 210 can be configured as a single, removable contoured battery 1016. The battery system 210 may have, or be associated with, a battery management system 254, which may be part of, or in data communication with, the control system 214, to collect data related to the operating state of the battery system 210 (e.g., temperature, state of charge, voltage levels, current levels and the like) and to enable management of the wheel, including operating modes of the battery system 210. The battery system 210 may be configured as multiple, removable battery assemblies, which can be controlled from individual battery management systems, or a central battery management system. It should be understood that the battery system 210 may be of various forms such as fuel cells, capacitors, etc.

The accessory port 218 may include various hardware interfaces 232, such as ports that support devices that use such protocols as USB, USB 2.0, Thunderbolt, Dicom, PCI Express, NVMe, NFC, Bluetooth, Wi-Fi, etc. Software, firmware, or the like may be handled by the control system 214 to enable communication according to such protocols. A plurality of accessory ports 218 may, for example, accommodate a respective plurality of sensors. In various embodiments the sensors may be in direct data and/or electrical communication with the control system 214 or may be connected through a facility such as a gateway (such as enabled by a mobile device), network interface, switch, router, or other communications network facility. That is, sensors may be local to the wheel 100, vehicle or may be remote sensors in data communication with the wheel, such as associated with a mobile device that is used to control the wheel or an entirely external system.

The plurality of sensors may include environmental sensors 246 that are operable to measure environmental attributes such as temperature, humidity, wind speed and direction, barometric pressure, elevation, air quality (including particulate levels and levels of specific pollutants, among others), the presence of chemicals, molecules, compounds, and the like (such as carbon dioxide, nitrogen, ozone, oxygen, sulfur and others), radiation levels, noise levels, signal levels (e.g., GPS signal strength, wireless network signal levels, radio frequency signals, and the like), and many others. Sensors may thus sense various physical, chemical, electrical, and other parameters.

The plurality of sensors may also include sensors operable to measure various properties and parameters related to the wheel and elements of the wheel, such as wheel rotation velocity, angular momentum, speed and direction (forward and backward), acceleration, sensors to measure force applied to mechanical components and structures of the vehicle (such as handles, pedals, the frame, the handlebars, the fork, the seat), such as to sense forces, weight, strain, stress, sources and direction of force, increases and reductions in force, and others.

In embodiments, forces are sensed with respect to user input, such as the strength and direction of pedaling or braking by a bicycle user, using a hand brake or throttle on various kinds of vehicle, pushing one or more ring handles of a wheelchair, pushing on handles of a wheelbarrow, pulling on a handle of a wagon, or the like. For example, a torque sensor 238 may sense torque such as from pedaling input by a bicycle user or rotation of a ring handle by a wheelchair user, data from which may be related to the control system 214, which may control the motor control system 208 of the wheel, such as moving the wheel faster as the user pedals faster. The plurality of sensors can include sensors for sensing fields and signals, such as radio frequency (RF), RADAR, SONAR, IR, Bluetooth, RFID, cellular, Wi-Fi, electrical fields, magnetic fields, and others. For example, such sensors can provide functions to a vehicle that is provided with a sensor-enabled wheel 100, such as RADAR detection, communications detection, proximity detection, object detection, collision detection, detection of humans or animals, and others. The accessory port 218 may also support supplemental hardware such as one or more accessory devices to include but not be limited to a gyroscope, lighting systems (including headlights, taillights, brake lights, and the like), audio systems (e.g., with speakers), supplemental memory systems, USB-based accessories (e.g., charging systems for mobile devices), security or anti-theft devices, and many others.

Figure 2B:
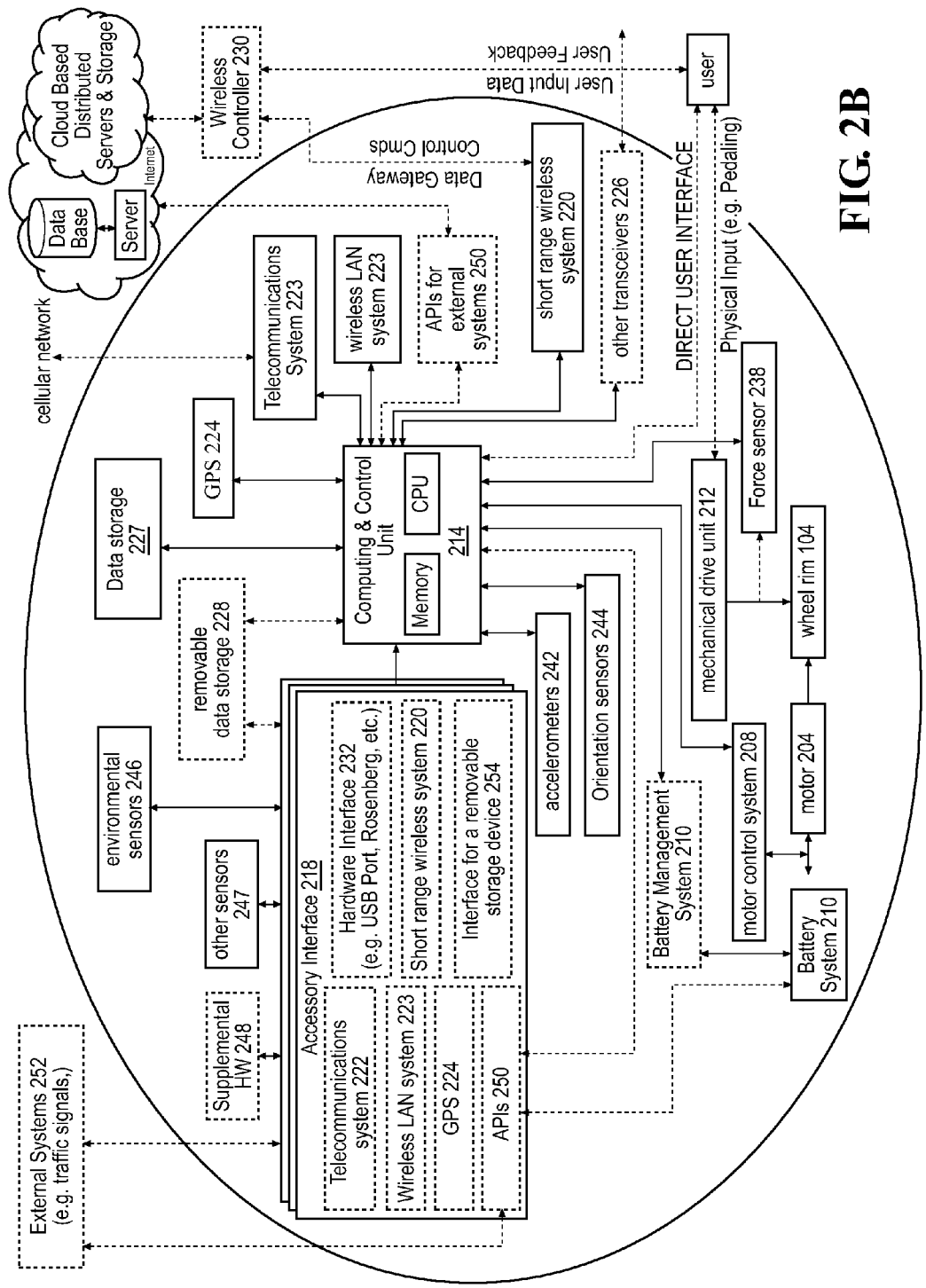
FIG. 2B is a schematic diagram of an embodiments of the electrically motorized vehicle including the electrically motorized wheel of FIG. 1A.

With reference to FIG. 2B, a schematic of embodiments of the motorized vehicle, in embodiments, includes elements of the motorized wheel hub 110 enclosed in the hub shell assembly 111. In operation, a user provides an input force delivered to a physical interface of the mechanical drive system 212 (such as a pedal, handle, or the like). In a bicycle type vehicle environment, a pedal and chain or belt drive the mechanical drive system 212. Other embodiments are described in connection with FIGS. 6-8.

The sensor system may include a force sensor 238, such as a torque sensor, that senses a force, such as the torque applied by the user to the mechanical drive system 212 for subsequent communication to the control system 214. As described later, this torque or other force may be sensed in other connected structures. The control system 214 may be or include a microprocessor, CPU, general computing device, or any other device that is capable of executing instructions on a computer readable medium.

The control system 214 may also receive data from other sources, such as an accelerometer, an orientation sensor 244 and/or other such sensors, either directly (such as through a direct connection to a sensor), or through a network connection or gateway, an API, or through an accessory port 218 (such as enabling access to the sensors of accessories, peripherals or external systems that connect to the wheel through the accessory port 218). Based on the calculation of, for example, sensed torque, acceleration, motion, orientation, etc., the control system 214 determines if power should be applied to a motor 204 through a motor control system 208 to cause acceleration or deceleration of the wheel rim 104. Deceleration may be effectuated by application of power to the motor to generate a rotational force opposite that of the current rotation, or by reducing the level of rotational force in the same direction, such as in cases where the effects of gravity, friction, wind resistance, or the like are enough to induce deceleration on the vehicle in the absence of continued levels of rotational force.

The control system 214 may include one or more accessory devices, peripherals, or external systems in communication therewith. Such accessory devices may include, various sensors, such as environmental sensors 246, and other sensors 247 which may sense various physical parameters of the environment, in connection with the description of supplemental hardware 248 and infrastructure elements 252. The control system 214 may process data collected and received from the various sources and channels described throughout this disclosure, such as from the environmental sensors 246, other sensors 247, external devices, a mobile device, a supplemental hardware device 248, one or more APIs for external systems 250, through various networking channels, such as from servers, distributed storage systems, and the cloud, from force sensors, from user interface elements on the wheel, etc. The control system 214 may store data, such as in local memory associated with the CPU of the control system 214, a separate data storage system, a removable data storage device 228, a server-based data storage system, and a cloud-based storage system. The control system 214 may communicate the data as required to the motor controller, and to the various other systems with respect to which it is in data communication as noted above (e.g., the accessories, sensors, peripherals, servers, storage systems, mobile devices and the like). In embodiments, and as described in more detail below, this may include communication of messages to the user through tactile input, such as a vibration, resistance, or the like, delivered to the user via the mechanical drive system 212. Data may include location data, such as from a GPS unit 224.

The motorized wheel hub 110 may also communicate wirelessly with other elements outside of the hub shell assembly 111 via a communication system such as a telecommunication system 222, a wireless LAN system 223, and/or a short-range wireless system 1221 (FIG. 12B) that, for example, may be a Bluetooth system, an RFID system, an IR system, or the like. Also, other transceivers 226 may be used to communicate with any elements outside of hub shell assembly 111. Communications may be undertaken using various networking protocols (e.g., IP, TCP/IP, and the like), by application programming interfaces, by machine-to-machine interfaces, and the like.

The telecommunication system 222 may be a cellular mobile communication transceiver, which can communicate with mobile devices, servers, or other processing devices that communicate via a cellular network.

The wireless LAN transceiver 223 can communicate with various hosts, servers and other processing equipment through the Internet, such as to servers and cloud computing resources, such as when the motorized wheel hub 110 is within a wireless LAN area, such as near an access point, switch, router, base station, Wi-Fi hot spot, or the like. This may facilitate the upload and download of data, such as new software or firmware to any of the modular components to update the various capabilities of the wheel.

The short-range wireless system 1221 may facilitate communication of the motorized wheel hub 110 either directly to an external system, a server, a cloud resource, or the like, or may facilitate communication via a mobile device 230 not mounted to the motorized wheel hub 110, which may serve as a gateway or bridge for communications between the motorized wheel hub 110 and such external systems, servers, cloud resources, or the like. The mobile device 230 may comprise any element or system external to the motorized wheel hub 110 that can include a data communication interface to the motorized wheel hub 110, such as a smart mobile device, tablet, wireless appliance or the like. The mobile device 230 may include an application, menu, user interface, or the like that is adapted to control the wheel, or one or more functions or features of the wheel, such as displaying data from the wheel, data from sensors, or the like, selecting modes of control or operation of the wheel, providing navigation and other instructions in connection with use of the wheel, and many other capabilities described in more detail throughout this disclosure.

With reference to FIG. 3, the electrically motorized wheel 100 may be configured and/or controlled via the mobile device 230 which may include a microprocessor 302 a low battery light 304, a display 308 which may include a touchscreen, a physical button 310, a short-range wireless communications system 312 such as wireless USB, Bluetooth, IEEE 802.11 and others, and a connection status light 314, a telecommunications system unit 318 such as a general packet radio service (GPRS) unit that can provide access to 2G and 3G cellular communications systems or other types of 2G, 3G and 4G telecommunications systems, an audio speaker 320, an warning light 322 and others.

The mobile device 230 is operable to wirelessly communicate with the electrically motorized wheel 100, such as via the short-range wireless communications systems 312, 220. The mobile device 230 may be operable to access, receive and display various types of data collected by sensors such as delivered through the accessory port 218 of the electrically motorized wheel 100 or by other data collection capabilities described herein, and in embodiments may be used to configure the data collection processes. For example, the mobile device 230 can be utilized to remotely configure the control system 214 and sensor systems of the electrically motorized wheel 100 to collect various types of data, such as environmental, location and wheel status data.

The mobile device 230 can also be utilized as an authentication key to unlock at least one feature of the wheel. For instance, as an owner of the wheel, the mobile device can be authenticated with the owner certificate of the wheel, which would enable that owner to modify wheel settings. Mobile devices owned by non-owners can be used to unlock the same, or different features of the wheel. That is, a non-owner may be restricted from certain features.

The mobile device 230 can also be utilized to select and/or control operational modes of the electrically motorized wheel 100. For example, a user can remotely configure the electrically motorized wheel 100 via the mobile device 230 to operate according to one of a multiple of predefined modes. Alternatively, or in addition thereto, the mobile device 230 may be utilized as an interface to set or modify operational parameters of a control algorithm during operation of the electrically motorized wheel 100, thereby creating "new," e.g., user tailored operational modes.

The mobile device 230 may also be configured to download new operational modes, applications and behaviors to control the electrically motorized wheel 100. The mobile device 230 may also be configured as a game console for gaming applications, provide a display for data updates from the electrically motorized wheel 100, operate as an interface to a fleet management system, and others.

In embodiments the electrically motorized wheel may have a sensor system to sense applied force, vehicle movement, and other data. Sensors may include ones for sensing torque applied to electrically motorized wheel, sensors for measuring wheel rotation velocity, speed and direction (forward or backward), sensors to measure force applied to vehicle handles, sensors on wheel fork to sense source/direction of force reduction, and others. The detected forces and torque may be used to manage energy generation, capture, storage and delivery based on forces and torque detected. User input may be applied to the electrically motorized wheel using pedals on a bicycle or tricycle or a ring handle or push handle for a wheelchair.

Figure 4A:
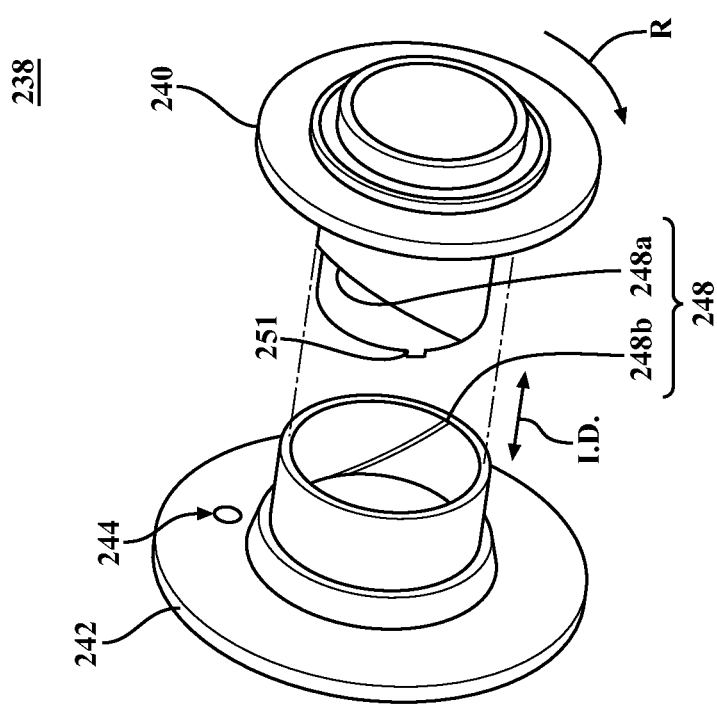
FIG. 4A schematically represents details of an embodiment of a torque sensor system.

With reference to FIG. 4A, a torque sensor system 238 for an electrically motorized wheel 100 is constructed and arranged to measure a user torque applied to electrically motorized wheel hub gear system 234. In embodiments, the torque sensor system 238 is constructed and arranged to measure a rotational velocity of electrically motorized wheel hub gear system 234. The torque sensor system 238 includes an inner sleeve secured to electrically motorized wheel hub gear system such as via welding such that the inner sleeve 240 rotates with the electrically motorized wheel hub gear system 234.

In embodiments, the torque sensor system 234 further includes a proximity sensor 244 on the inner or outer sleeve 240, 242 so that the lateral displacement LD between the inner and outer sleeve 240, 242 can be measured.

In embodiments, an interaction between the inner sleeve 240 and the outer sleeve 242 results in a lateral displacement of the inner sleeve 240 with respect to the outer sleeve 242 such that a torque applied by a user is obtained from the lateral displacement such as via a proximity sensor 244. In other embodiments, the torque sensor system 238 includes a displacement sensor with a spring/elastomer and a pressure sensor located on the outer sleeve 242.

In embodiments, the rotation of the inner sleeve 240 causes a ramp of the inner sleeve to ride up or down a ramp of the outer sleeve 242. The inner and outer sleeves 240, 242 include opposing ramps 248a, 248b, which can affect a lateral displacement ("LD") between the inner sleeve 240 and the outer sleeve 242. For example, when a torque is applied to one of the inner sleeve 240 and outer sleeve 242, the inner sleeve 240 can rotate R in a clockwise or counterclockwise direction with respect to the outer sleeve 242. The rotation R of the inner sleeve 240 causes the ramp 248a of the inner sleeve 240 to ride up or down the ramp 248b of the outer sleeve 240. Accordingly, the rotation R of the inner sleeve 240 can affect the lateral displacement LD between the inner sleeve 240 and the outer sleeve 242. That is, as the ramp 248a of the inner sleeve 240 rides up the ramp 242b of the outer sleeve 242, the lateral displacement LD between the inner and outer sleeves 240, 242 increases, and as the ramp 248a of the inner sleeve 240 rides down the ramp 248b of the outer sleeve 242, the lateral displacement LD between the inner and outer sleeves 240, 242 decreases.

In other embodiments a velocity sensor 250 includes a plurality of magnets provided in an alternating magnetic pole configuration on an outer surface of the inner sleeve 240 and a Hall Effect sensor. In embodiments, the spring/elastomer mechanism being provided in a cylindrical housing of the outer sleeve 242, and configured to provide a gap region so that a notch of the inner sleeve 240 can be positioned in the gap region.

Figure 4B:
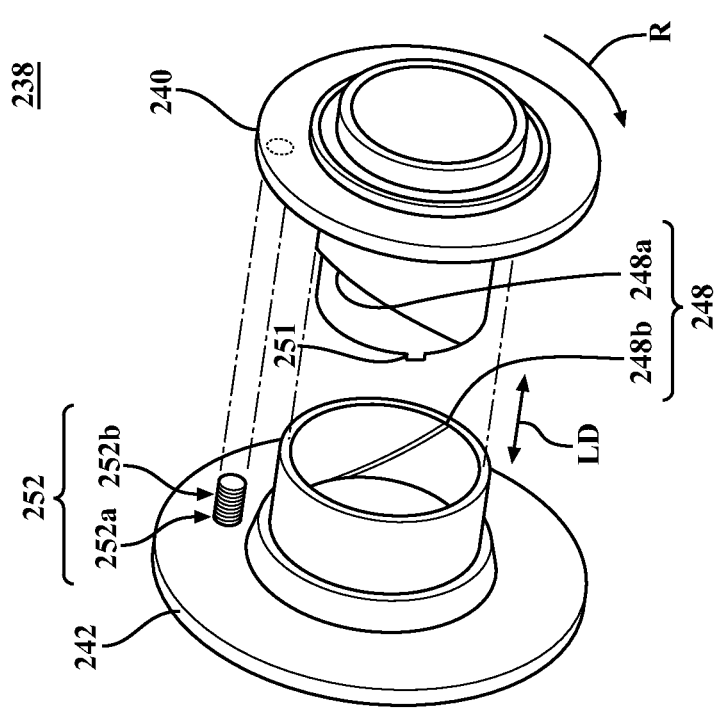
FIG. 4B schematically represents details of embodiments of a torque sensor system.
Figure 4D:
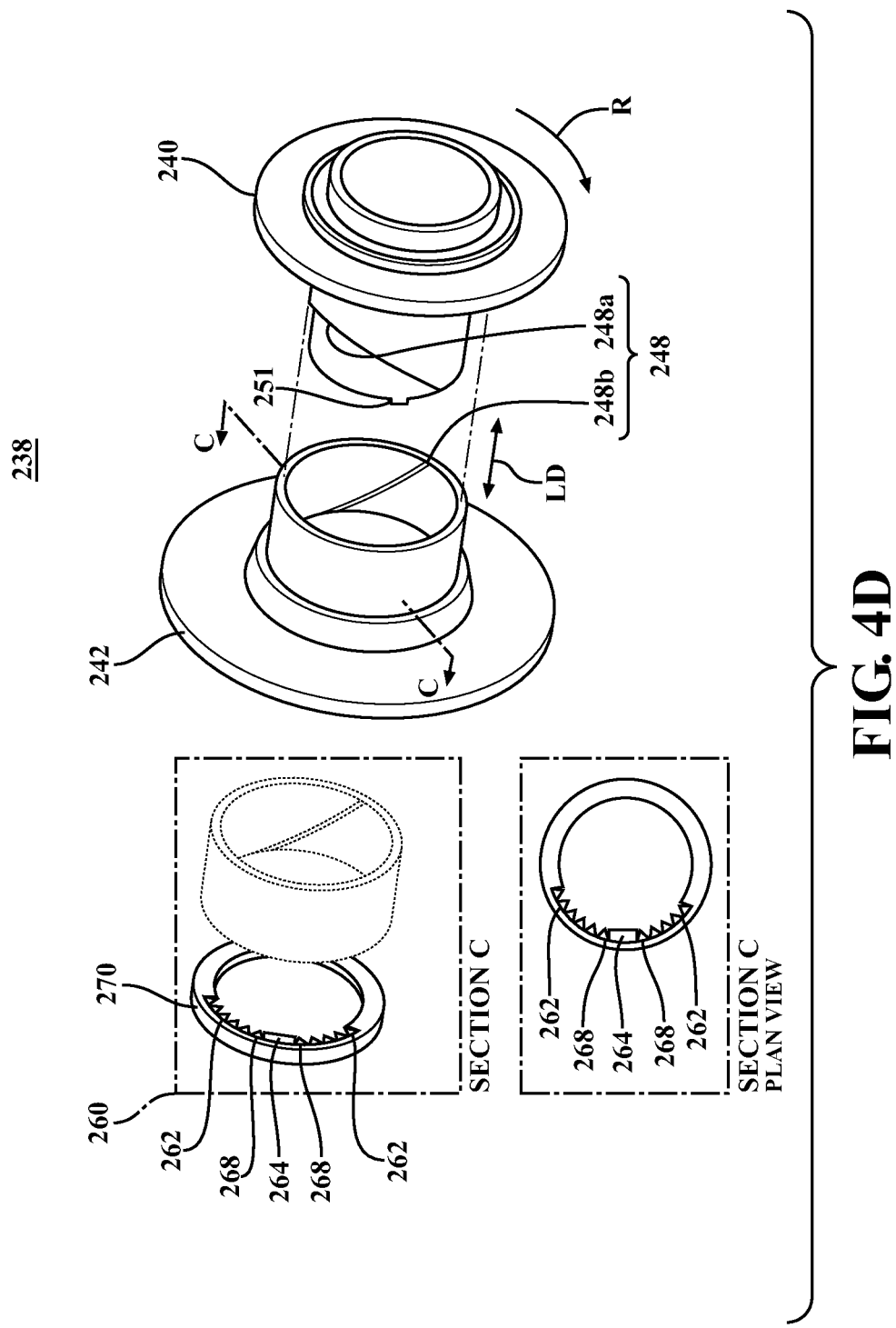
FIG. 4D schematically represents details of embodiments of a torque sensor system.

The inner sleeve 240 can be provided with a notch 251 that can interface with a spring/elastomer mechanism 260 (FIG. 4D). The spring/elastomer mechanism 260 applies a known force (i.e., by way of a known spring constant) on the inner sleeve 240 via the notch 251 of the inner sleeve 240. Accordingly, a torque applied to one of the inner and outer sleeves 240, 242 can be calculated from a combination of a measured lateral displacement LD and a known force applied to the notch of the inner sleeve 240.

The torque sensor system 238 illustrated in FIG. 4B operates in a similar manner as the torque sensor system 238 illustrated in FIG. 4A; however, the proximity sensor 244 of the torque sensor system 238 illustrated in FIG. 4A is replaced with a displacement sensor 252 with a spring/elastomer 252a and pressure sensor 252b, or other technologies for measuring distance such as resistive, capacitive, or other types of distance measurement technologies.

With reference to FIG. 4C, a torque sensor system 238 can alternatively or additionally include a velocity sensor system including one or more Hall Effect sensors and a plurality of magnets 258. In embodiments, the magnets 258 are provided in an alternating configuration on an outer surface of the inner sleeve 240, and spaced apart by a predetermined distance dl. That is, the magnets 258 provided on the outer surface of the inner sleeve alternate magnetic poles (e.g., N-S-N-S-N-S). In this manner, a velocity measurement can be calculated based using a variety of methods such as, number of magnetic poles measured per unit time, or time elapsed between magnetic poles, and other principles using a time-distance relationship.

With reference to FIG. 4D the spring/elastomer mechanism 260 of a torque sensor system 150 can include first and second springs/elastomers 262 and pressure sensors 268. The first and springs/elastomers 262 are provided in a cylindrical housing 270 of the outer sleeve 242, and are configured to provide a gap region 264 so that the notch 251 of the inner sleeve 240 can provided in the gap region 264. As described above, the spring/elastomer mechanism 260 can apply a known force (i.e., by way of a known spring constant) on the inner sleeve 240 via the notch 251.

The electrically motorized wheel 100 described above in connection with FIGS. 1A, 2A and 2B may be used to assist in powering a variety of human-powered wheeled vehicles such as bicycles, tricycles, wagons, trailers, wheel barrows, push carts (e.g., medical carts, carts used in food preparation, food service and others, delivery carts, carts use to move goods around warehouses and industrial facilities, etc.), carts used in moving (e.g., to move furniture, pianos, appliances, and large items), riding toys, wheeled stretchers, rolling furniture, wheeled appliances, wheelchairs, strollers, baby carriages, shopping carts and others.

In embodiments, such as for bicycles and tricycles, the electrically motorized wheel 100 may be readily installed by a customer for converting a vehicle to an electrically motorized vehicle via installation of the electrically motorized wheel. In these embodiments the electrically motorized wheel 100 may be attached to a vehicle using the existing attachment mechanisms. Embodiments may include a hardware developer kit for adapting the electrically motorized wheel 100 to the hardware environment of a specific non-electric vehicle such as a wheelchair, wheelbarrow, wagon and others.

The hardware developer kit facilitates attachment of sensor/peripheral devices to an open serial port of the electrically motorized wheel 100. This data can then be transmitted to the mobile device and subsequently to the server for access by the API. Since the API is accessible, developers may take readings from the sensor/peripheral devices to thereby expand the sensing/functionality/features of the electrically motorized wheel 100. Power for the sensor/peripheral devices may be their own power source or supplied by the electrically motorized wheel 100 either through a power connection internal to the electrically motorized wheel 100 or though the power port that permits power to flow in either direction—in from a charger or out to an external device if desired.

The electrically motorized wheel 100 may be used to provide additional motive force and braking to various types of otherwise human only powered vehicles. Thus, an entire vehicle may be sold as an integrated product, including an appropriately designed electrically motorized wheel 100.

Figure 5:
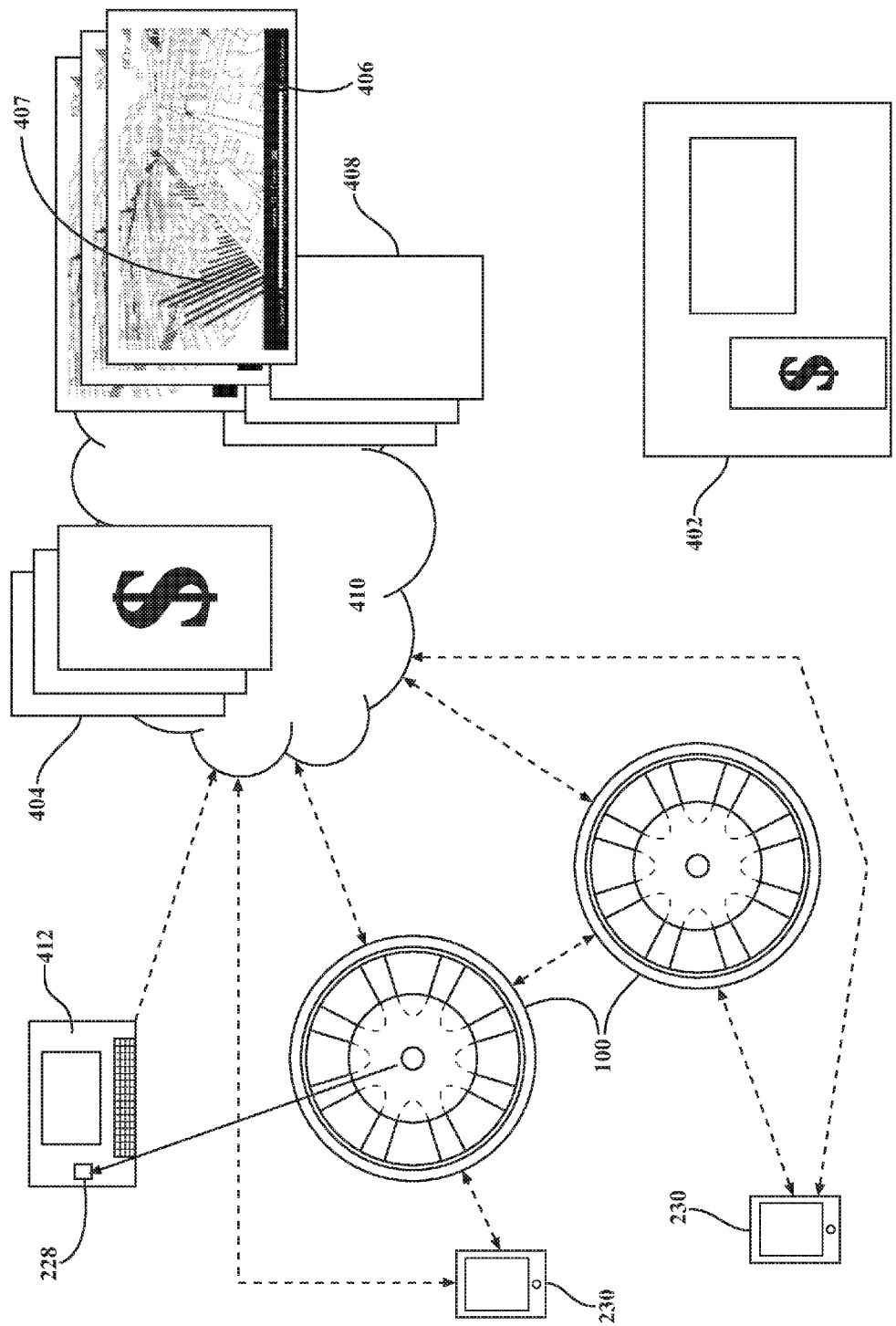
FIG. 5 schematically represents the environment of the mobile device.

With reference to FIG. 5 the electrically motorized wheel 100 may be purchased and serviced at a traditional brick and mortar store 402 such as a bicycle store, a hardware store, a store specializing in the vehicle to which electrically motorized wheel 100 is attached and others, or by electronic commerce. Thus, an electrically motorized wheel 100 may be provided as an individual element that can be attached to any generic vehicle, or it may be adapted for use with a wheel of a particular vehicle. For example, many bicycles have unique design features, colors, branding elements, or the like that can be matched, or complemented, by providing a electrically motorized wheel 100 that has appropriately related aesthetic features.

In embodiments, additional hardware and software accessories, applications, and other features may be purchased either at traditional brick and mortar stores 402, online stores 404, mobile app stores, and others. For example, a electrically motorized wheel 100 may be provided with a unique identifier, such as a serial number stored in memory, which can be used as an identifier of the electrically motorized wheel 100, the user, or the vehicle on which the electrically motorized wheel 100 is installed, for purposes of various applications, including navigation applications, applications measuring exercise, traffic reporting applications, pollution-sensing applications, and others. Such applications may be provided, for example, on a mobile device that presents user interface elements that include, or that are derived from, data inputs from electrically motorized wheel.

In embodiments, data from the electrically motorized wheel may be uploaded to one or more application data servers 408 on the server 410 via a wireless telecommunications system 318 in the motorized wheel hub 110. The communication may include a relatively short-range wireless system 1221 to transmit the data to the mobile device 230 and thence from the mobile device 230 to the server 410 via the wireless telecommunications system 318. Data may alternatively or additionally be physically transferred from the electrically motorized wheel 100 to a local computer 412 via the removable storage device 228 and from the local computer 412 to the one or more application data servers 408.

In embodiments, standard interfaces may be provided for both the software and hardware systems. An accessory port 218 (FIG. 2B) may support standard protocols such as USB, USB 2.0, Thunderbolt, Dicom, PCI Express and others. These interfaces may facilitate the support of accessory devices and peripherals such as environmental sensors, gyroscopes, supplemental memory and others by providing power to operate the accessory device and an interface for data transfer between the accessory device and data storage in the motorized wheel hub 110.

In embodiments, data exchange may occur using a short-range wireless system 1221 such as wireless USB, Bluetooth, IEEE 802.11 and others. Data exchange may alternatively or additionally be performed over long-range wireless or telecommunications system 222 such as 2G, 3G, and 4G networks.

In embodiments an API and/or software development kit facilitates access to data storage and transfer of data over a wireless network to a computer on a network, integration of sensor data with other data collected simultaneously, use of processing and reporting functions of the sensor-enabled wheel (e.g., reporting energy used, charge status, miles traveled, data from environmental sensors, user-entered data, or other data), and others.

In embodiments, the API and/or software development kit facilitates software and/or hardware access to the motor control system 208 of the electrically motorized wheel 100 such as when power is applied to electrically motorized wheel, when resistance is applied to electrically motorized wheel, energy regeneration, power management, access to the sensor data collected, and others.

In embodiments, the electrically motorized wheel 100 may be purchased through a variety of channels including online, specialty bicycle shops, and others. Further, online stores 404 may provide for purchase of "applications" or "behaviors" that leverage the hardware and software APIs to provide unique user experiences. These behaviors may be purchased online and downloaded to the electrically motorized wheel 100 through a short-range wireless connection 220 or via a standard hardware interface such as a cable that plugs into an appropriate port. Applications may include gaming, fleet management, rental management, environmental sensing and management, fitness, traffic management, navigation and mapping, social interface, health management, and others.

Many vehicles, either individually or those within a common fleet, may employ the electrically motorized wheel. As the vehicles are moving around various locations, the electrically motorized wheel may be utilized to sample the environment. The data collected can thus be utilized to provide a spatial and temporal indication of various parameters that are sampled.

In one example, current temperature data is sampled over the area covered by the vehicles at the location of each of the vehicles. As the vehicles move from location to location, a collection of such data is a representation at different locations over time. This may be expanded to numerous parameters sampled by numerous vehicles over time to monitor multi-dimensional phenomena to facilitate the generation of models that contain multivariate data, and other scientific uses such as for predicting future environmental conditions.

In another example, data may be collected and processed to profile the user. That is, as the vehicles move from location to location, a collection of data is generated to indicate how specific users operate the vehicle. Such data may facilitate generation of a feedback loop that may be utilized to improve infrastructure development, (e.g., traffic lights and municipal networks). The data may also be utilized to indicate to the user, for example, more efficient operations of the vehicle, e.g., recommended mode utilization.

The data may also be utilized to interact with a transportation to alert other vehicles such as smart cars to the presence of the vehicle with the electrically motorized wheel 100 as well as alert the user of the electrically motorized wheel 100 to the presence of the other vehicles.

The electrically motorized wheel 100 may additionally support a plurality of sensors that collect and process attributes related to the vehicle and the electrically motorized wheel 100 itself such as force applied, torque applied, velocity, "steadiness" of the vehicle, acceleration of the vehicle, usage of vehicle including time, distance, and terrain travelled, motorized assistance provided, available battery power, motor temperature, etc.

The electrically motorized wheel 100 may also include a data collection platform for integrating and analyzing the data collected by the plurality of sensors. In embodiments, the collected data may be integrated with data from a plurality of other electrically motorized wheels 100 as well as data from $3^{rd}$ party sources such as traffic data systems, geographical information systems (GIS) databases, traffic cameras, road sensors, air quality monitoring systems, emergency response systems, mapping systems, aerial mapping data, satellite systems, weather systems, and many others.

This combined data may then be integrated and analyzed onboard the electrically motorized wheel 100, off board the electrically motorized wheel 100, or a combination thereof. Such combined data leverages the sensor data collected by the plurality of vehicles traversing a relatively large geographic area and correlates the terrain traversed to time. This readily facilitates determination of a variety of insights as the plurality of electrically motorized wheels 100 essentially operate as distributed sensor network to provide sensor data for aggregation and interpretation. For example, the plurality of wheels, or a specific subset thereof, may be viewed in the aggregate to determine the best bicycling routes through a city, to promote the collective health of users (such as by routing away from areas with low air quality), and the like.

In embodiments, the telecommunications system and the global positional system may transmit data and/or communicate with infrastructure, other vehicles, or non-infrastructure entities in the surrounding environment. This data transfer or communication can alert the vehicles of a potential collision, cause traffic lights to switch, etc.

The data collected from the plurality of electrically motorized wheels 100 and viewed in the aggregate may facilitate the generation of detailed analyses and maps 406. The maps 406 may be utilized to depict, for example, environmental phenomena that vary over space and time. This data can be overlaid on existing street patterns, land use maps, topographical maps, population density maps and open space maps creating layered maps which may be accessed through mobile devices or a webpage and which provide an overview of environmental conditions in real time, as well as historical data detailing past conditions or predictions of future conditions.

These layered maps may be used as a tool with which cities, businesses, and/or individuals may, for example, monitor environmental conditions; facilitate determination of future environmental and traffic policy decisions such as the planning of new roads and paths; planning of commercial real-estate development; positioning of new cell towers and network repeaters; real time traffic analysis; the study of phenomena like urban heat islands; emergency preparedness; noise and environmental pollution; and when planning the least polluted routes through cities.

For example, data collected relative to wind speed and direction may be used to understand airflow through a city and used to map the impact of a dirty bomb and how it might disperse through a city. Data collected relative to signal strength and traffic patterns may be utilized to facilitate wireless companies in decisions regarding the placement of new cell towers. Temperature data collected over time may lead to the creation of urban gardens to ameliorate urban heat islands. Data related to global position and elevation may be used to provide ground truth for existing maps. Data related to traffic patterns may be used in planning of new commercial locations and store layouts. For example, bar graphs 407 may be overlaid onto a street map 406 to indicate high traffic areas, slow commute areas, high pollutant conditions, etc.

Aggregated data may also be used to facilitate improved real-time navigation, adjust real-time traffic patterns, divert bicycle traffic to other areas of the city, etc.

In embodiments, a multi-user game system permits users of vehicles having one or more electrically motorized wheels 100 to exchange data such as location, distance, torque applied, effort expended, distance travelled, total change in elevation, calories burned, heart rate elevation, environmental data collected and others.

In one example, a remote racing game may leverage the control systems of the individual electrically motorized wheels 100 and the local environmental data to modify the electrically motorized wheel 100 behavior in conjunction with the local terrain in such a way that players in different locations experienced a common effort of attempting to bicycle up a hill while riding across terrain that varied among players based on location. In embodiments the ability to modify the electrically motorized wheel 100 behaviors might be used to handicap users of difference skill levels.

Embodiments may include achievements, which may be unlocked after users surpass certain thresholds. For instance, a user could get a medal after riding 1000 miles. Achievements may include other distance thresholds, calorie thresholds, number of trips, number of cities, number of friends, power generated, and others.

Embodiments may include a system for targeting commercial opportunities to users wherein the offer is partially based on the location of the electrically motorized wheel 100. Embodiments may include a variant on geo-caching where the users visit specified geographic locations. The data collection system would be collecting data location and time and users would be able to compare locations visited and when.

In embodiments, profiling a user of the electrically motorized wheel may include assessing a user's current physical capabilities and monitoring the user's physical capabilities over time to facilitate identification of trends. Data collected may include torque applied, distance traversed over time, stability of electrically motorized wheel 100 and others. It should be understood that various sensors including heart rate sensors may be utilized to profile a user operating the electrically motorized wheel.

Analysis may be performed to sense changes in mobility patterns such as frequency, force applied, distance travelled, steadiness, times of day system accessed and others. Small changes in these measurements may be used to sense long-term, slowly developing diseases, such as Parkinson's syndrome, which are typically difficult to sense because the change in user capabilities is gradual over an extended period of time. This data may be provided directly from this system into an electronic medical record, EMR, or associated with an individual's healthcare data. The data may be aggregated with data from a plurality of other electrically motorized wheels 100 to provide data sets for public health analysis.

An example, data gathered from the electrically motorized wheel that facilitates physical therapy is the direct power the person's legs can output as compared to conventional sensors which may only measure steps taken and heart rate. The data gathered from the electrically motorized wheel may thereby be utilized to detect how the person's leg muscles are changing over time because torque is directly detected through the torque sensor.

In embodiments techniques such as collaborative filtering may be used to sort through different options, then suggest to one user options used by other users that are determined to be most similar to that user. Statistical techniques for sensing similarity may be performed, based on correlations, e.g., based on matrices of the "distances" between users with respect to various defined attributes that can be measured or derived based on the data collected by electrically motorized wheel or entered by the user. Thus, users who are similar to each other may be presented with similar applications, user interfaces, drive modes, navigation options, and others. For example, two users who regularly ride similar routes may be utilized to identify that one route is substantially faster given similar exertion/less hilly/fewer stops/intersections, etc. Such route comparison may be utilized to suggest a different route to the user of the slower route In an embodiment, data may be collected from a fleet of vehicles such as delivery vehicles, messenger services and others. Data collected may be analyzed and synthesized to facilitate a dispatcher in optimizing routes, schedules, estimating deliver times and others based on user fitness levels, terrain covered during current excursion including mileage, elevation change, level of assistance already provided, remaining battery life, current location, and terrain along proposed routes and others.

Data aggregated from public or private fleets may be analyzed to determine when bicycles need to be taken in for service, where bike racks should be located, where charging stations should be located, how many bicycles are in service at any given time, and other useful scenarios.

In embodiments, the electrically motorized wheel 100 may be installed on store shopping carts. The electrically motorized wheel 100 may assistance shopper shoppers needing additional assistance, for specialized large, heavier carts such as those adapted for shopping with children, as the cart increases in weight, and others. The data collected may include aisles traversed, time spent in which aisles, where along the aisle vehicle stop, and other such data. This data may be used to map the traffic flow through a store to facilitate planning for product placement, improved store layout and others.

In embodiments, the hardware API may facilitate hardware plug-ins to further modify the performance of the vehicle on which the electrically motorized wheel 100 is mounted. That is, the hardware plug-ins may include options, upgrades or other selectable accessory devices that each particular user may select and readily install, i.e., "plug-in" to their electrically motorized wheel 100.

In embodiments, the hardware plug-in may be a gyroscopic sensor that plugs into an electrically motorized wheel 100 on a bicycle to facilitate the performance of "wheelies" or other tricks. The gyroscopic sensor may be used to determine the orientation of electrically motorized wheeled vehicle. Several gyroscopic sensors may be used to determine the orientation of the vehicle in several dimensions. If these are monitored over a period of time, the stability of the vehicle may be determined.

Data from the hardware interface may be processed by the mobile device 230 (FIG. 3), and/or transmitted via the mobile device 230 to a server for processing. Data from the hardware interface may alternatively or additionally communicate directly from the electrically motorized wheel to a server using long-range wireless or telecommunications system such as 2G, 3G, and 4G networks. Further, the processed data may be communicated back to the electrically motorized wheeled vehicle to form a feedback loop to facilitate operation of the electrically motorized wheeled vehicle, each vehicle within a fleet, and/or other electrically motorized wheeled vehicles that may benefit from the collected data.

The accessory port 218 may support one or more sensors that are operable to measure environmental attributes such as temperature, humidity, wind speed and direction, barometric pressure, elevation, air quality, the presence of chemicals such as carbon dioxide, nitrogen, ozone, sulfur and others, radiation levels, noise levels, GPS signal strength, wireless network signal levels and others. The data collected by the sensors may be stored locally on the electrically motorized wheel or transmitted wirelessly to a remote system such as a network computer. Data stored locally on the electrically motorized wheel may later be transmitted wirelessly or otherwise transferred from the electrically motorized wheel to one or more application data servers 408. The data collected by the sensors may be stored in conjunction with additional contextual data such as the date and time data was collected, the GPS location associated with particular data, other data collected at the same time, date, location and others.

In embodiments the electrically motorized wheel 100 may be equipped with a system to alert users of objects in close proximity, thus enhancing user safety. In embodiments, the system may utilize the accessory port 218 to support a proximity sensor such as an optical sensor, an electromagnetic proximity-sensing detector, or the like. The proximity sensors facilitate detection of objects that approach the vehicle on which the electrically motorized wheel 100 is mounted, such as from behind or from the side, then display data or warnings on the mobile device 230.

The proximity of an object which is detected by the proximity sensor may be used to trigger automated actions as well, including decreasing speed, electronic braking, increasing speed, or triggering actions to connected peripheral devices, such as headlights, blinkers, hazard lights, personal electronic devices, bells, alarms, protective equipment, and others.

Proximity sensors may be mounted within the motorized wheel hub 110 adjacent to a window that allows an optical beam, an electromagnetic beam, or such transmission to pass through a static portion of the hub shell assembly 111. Alternatively, RADAR, SONAR or other beams may pass directly through the hub shell assembly 111.

The proximity sensors may communicate with the mobile device 230 to provide an alert to the user when an object is detected within a certain threshold distance. This alert may be conveyed using one or more of audible, visible, and tactile methods. This alert may be incorporated into the electrically motorized wheel 100 such as by shaking the vehicle or communicated to another device mounted elsewhere on the vehicle such as the mobile device 230, a GPS unit, a smart mobile device, tablet or the like. The proximity data may be transmitted using short-range wireless technologies such as wireless USB, Bluetooth, IEEE 802.11 and others.

Figure 6A:
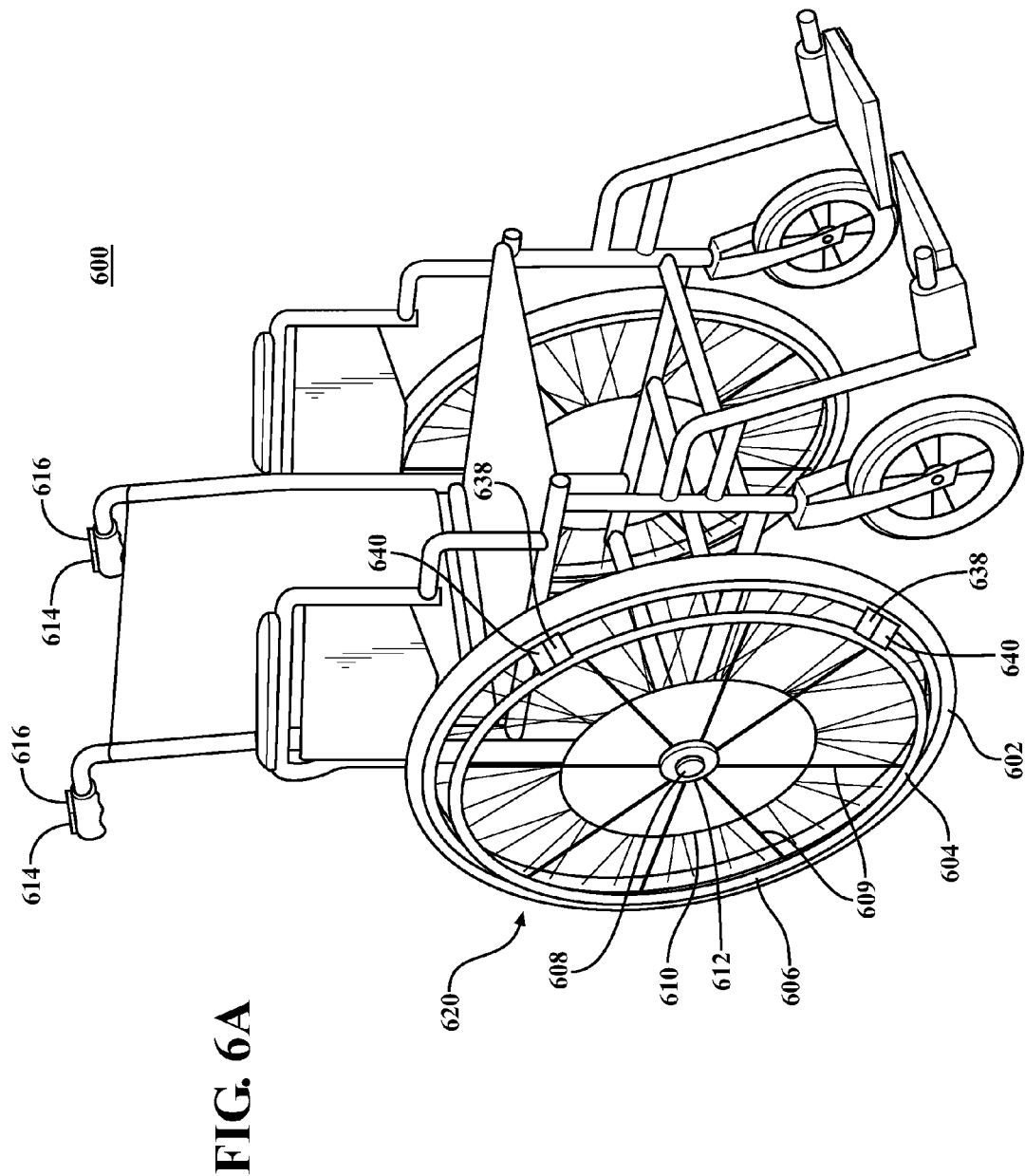
FIG. 6A schematically represents embodiments of the electrically motorized wheel installed on a wheelchair.

With reference to FIG. 6A, another disclosed embodiment of an electrically motorized wheel is illustrated herein as a wheelchair 600 retrofitted with at least two electrically motorized wheels 620 that are daisy chained one to another. Although this embodiment has specific illustrated components in a wheelchair embodiment, the embodiments of this disclosure are not limited to those particular combinations and it is possible to use some of the components or features from any of the embodiments in combination with features or components from any of the other embodiments.

The electrically motorized wheel 620 includes a multiple of motorized wheel hubs 610 comparable to those described above but these electrically motorized wheels 620 are daisy changed together. "Daisy chained," as described herein, indicates operation of the plurality of electrically motorized wheel 620 in concert, serial, parallel or other coordination. That is, the multiple of motorized wheel hubs 610 may communicate one to another in a "daisy chain" or other distributed interparty communication, and/or may be individually controlled directly but with regard to others.

A plurality of electrically motorized wheels 620 may be daisy changed together via a daisy chain protocol operable on the control system 214. The daisy chain protocol may be software resident on the control system 214 or may be effectuated via a hardware device that plugs into each of the plurality of electrically motorized wheels 620 to coordinate operation of the plurality of electrically motorized wheels and thereby facilitate operation of the vehicle. For example, should a user input be communicated to one electrically motorized wheel 620 the other electrically motorized wheel 620 daisy chained thereto may rotate in an opposite direction to perform a pivot-in-place of the vehicle to which the daisy chained wheels are installed. It should be understood that although a wheelchair is illustrated, various other vehicles may utilize daisy chained electrically motorized wheels.

For example, power can be shared between daisy chained wheels through a wired interconnection. Adjustments may be performed locally on each wheel but may be compensated appropriately and smoothly in another daisy chained wheel. Alternatively, adjustments could also be made in parallel.

For example, wheels may be daisy chained by different firmware and a cable that ties all the CAN interfaces together. The firmware could have one of the wheels be a central controller communicating with all the other wheels. Alternatively, control could be distributed, each wheel determining its own command but in-part based on the commands of the other wheels. It is also possible to add an external controller that performs coordination of the wheel command. For example, a plug may be connected to an accessory port in each of the wheels to be daisy chained.

Power may flow either in or out of the power port. The direction of flow is based upon what is connected, e.g., a charger will push current in, and a load will draw current out. The battery management system controls when the power port is open. For example, the power port opens when it detects a charge or when directed by the main wheel electronics, which thereby permits an external device to be powered. For example, a rider may connect an external device that needs power, and use an app to command the power port to turn on.

Figure 6B:
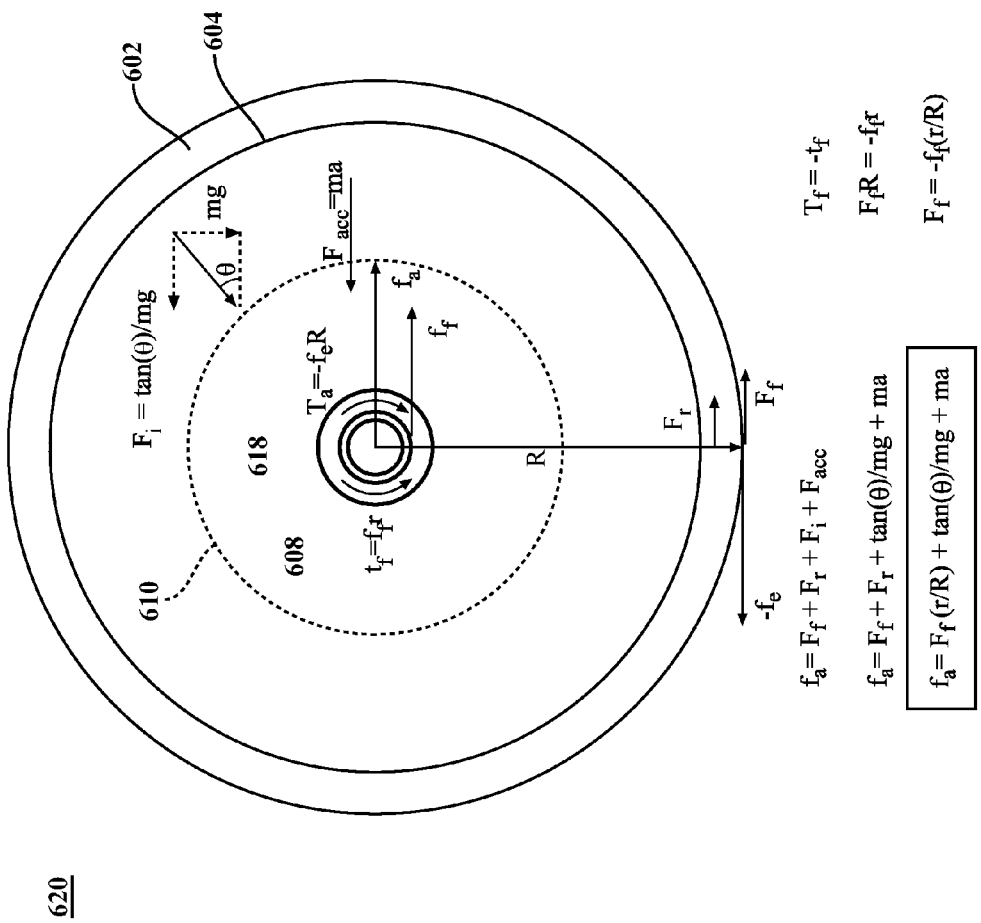
FIG. 6B schematically represents forces and torques associated with the electrically motorized vehicle.

With reference to FIG. 6B, one or more forces are applied ($f_a$) to electrically motorized wheeled vehicle that pass through the rigid body to a axles 608 upon which the electrically motorized wheels 620 are mounted. The forces provided to the vehicle ($f_a$) should be absorbed into the translational motion of the vehicle and the rotational motion of the electrically motorized wheel 620.

For force analyses purposes, the electrically motorized wheelchair 600 is assumed to be a rigid body. The force of earth ($f_e$) presents an equal and opposite reactionary force where the tire 602 meets the ground. This reactionary force is exerted onto electrically motorized wheel tangentially at a distance R equal to the radius of the electrically motorized wheel 620 from the axle 608 causing a rotational applied torque ($T_a$) on electrically motorized wheel in a forward rotational direction equal to $T_a=f_e R$. There is a frictional force ($f_f$) exerted between the axle 608 and bearings 618 that resists motion. (This represents the frictional force for all wheels on the vehicle.) The frictional force ($f_f$) at the bearings 618 causes a frictional torque of $t_f=f_f r$ resisting rotation. This torque ($t_f$) can be replaced by an equivalent torque of a force ($F_f$) applied at a radius R. Therefore, $F_f=-f_f(r/R)$. Electrically motorized wheels rotate when the force provided by the user $f_a$ exceeds the frictional, gravitational (incline) forces, and aerodynamic forces, which are often negligible at wheel chair speeds.

The rolling force $F_r$ resisting rotation of the tire 602 is small and may be ignored for these calculations, (as are other small forces).

$F_i$ is the amount of force required to push the vehicle up an inclined angle q.

The excess force over and above those described above, is expressed in acceleration of the vehicle, a. The force causing acceleration of the vehicle is described by the mass of the vehicle multiplied by the acceleration of the vehicle.

$$F_{acc}=ma.$$

Therefore, the total force applied to the vehicle fa is used to overcome the force of friction $F_f$, the force required to rolling of the tires $F_r$, the force to move up an incline $F_i$ and the force for acceleration $F_{acc}$.

$$f_a=F_f+F_r+F_i+F_{acc}$$

$$f_a=F_f+F_r+\tan(q)/mg+ma$$

(where q is the angle of incline.)

Since the force required to roll the tires is assumed negligible, this term drops out.

$$f_a=-f_f(r/R)+\tan(q)/mg+ma$$

When the applied force ($f_a$) exceeds the force of friction ($F_f$), the force of tire rotation ($F_r$) the force due to moving up an incline ($F_i$) it causes acceleration of the electrically motorized wheel 620 in a forward direction. Therefore, by knowing the force of friction $f_f$ due to electrically motorized wheel bearings, the radius r of the bearings, the radius R of electrically motorized wheel, the mass m of the vehicle and sensing the angle of incline q and the acceleration a, one may approximate the user input force $f_a$. This may then be used as an input to determine electric power to be provided to the electric motor in embodiments. Therefore, sensors are required to measure acceleration, and incline of the vehicle. An estimate is required for the frictional force and possibly the tire rolling force (to be more exact). Weight (and therefore mass) could be an initial given parameter, or it can be a measured parameter.

The electrically motorized wheel 620 is accelerated when the user force $f_a$ is applied to the axle 608. This force is applied to the ends of the axle as the electrically motorized wheel is mounted between the ends of the axles. If the axle is accelerated in a forward direction, the translational inertia of electrically motorized wheel causes electrically motorized wheel to resist a change in velocity, causing a force on the axle between the ends opposite the direction of acceleration. This may cause a slight flexing, bending or displacement of the axle 608 proportional to the force being exerted upon the axle 608. Pressure may be measured between the axle and the electrically motorized wheel 620 as an input. A forward acceleration on the ends of the axle 608 causes electrically motorized wheel to exert a rearward force of the middle of the axle 608 causing it to flex or bend slightly to cause the spacing between the axle 608 and electrically motorized wheel structures to change. Sensing these changes will assist the motorized wheel hub 610 in sensing that a user intends to move electrically motorized wheelchair 600 forward. This may be used in embodiments for sensing input force applied to the vehicle $f_a$. Similarly, stopping the electrically motorized wheelchair 600 moving at a given speed causes the opposite forces on the axle 608 indicating that the user intends to slow or stop electrically motorized wheelchair 600.

The friction of the bearings ($f_f$) of a rotating wheel causes torsion of the axle 608. This torsion may be measured and used to signal that the user is trying to accelerate forward. A reduction in this torque, or an opposite torque sensed at the axle 608 would cause the indication that a moving wheelchair 600 should be slowed or stopped. If the force on electrically motorized wheelchair 600 is sensed to be in a reverse direction and electrically motorized wheelchair 600 is moving in a reverse direction (determined by sensors) then the motorized wheel hub 610 determines that the user intends to accelerate in the reverse direction. Therefore, the force applied to the vehicle may be determined.

By monitoring various motion and acceleration parameters and the forces/torque applied, outside forces applied to the vehicle (both positive and negative) may be estimated. The estimated outside forces are then used to power the electric motor in a direction in which the vehicle is moving or in a direction opposite the direction the vehicle is moving, causing a braking effect or acceleration in a reverse direction. In embodiments, the user may also operate the electrically motorized wheelchair 600 by rotating the electrically motorized wheels. A ring handle 606 is attached to the motorized wheel hub 610. Typically, a user rotates ring handle 606 to cause electrically motorized wheelchair to move in one direction or rotates the ring handle 606 of each wheel in an opposite direction to cause the electrically motorized wheelchair 600 to pivot. It should be understood that in this vehicle embodiment, the ring handle 606 is the user input and, in contrast to a bicycle embodiment, is typically rotationally fixed rather than mounted via a freewheel typical of a bicycle. That is, the ring handle 606 is the mechanical drive system 612 for the electrically motorized wheel 620. Further, the input includes both rotation of the ring handle 606 as well as the wheelchair 600 being pushed, which is a linear input.

In embodiments, the torque sensors 638 are attached between the electrically motorized wheel 620 and the ring handle 606 to measure the user input such as a rotation, torque or other input. Since the ring handle 606 does not freewheel, the user input may be related to an applied torque. For example, a rim torque transceiver 640 transmits the sensed torque to the motorized wheel hub 610. The motorized wheel hub 610 then determines which direction the user is attempting to move and assists in that direction. If the torque sensors 638 sense that the user is attempting to slow using the ring handle 606, the motorized wheel hub 610 determines that a braking force is necessary.

By causing power to be provided urging the electrically motorized wheel 620 to drive in a direction opposite that of the direction currently moving, a braking effect is effectuated. Various other types of vehicles may provide power in a manner similar to a wheelchair, such as various types of push carts used in medical, food service, moving, warehouse and similar applications, various riding toys, and other applications where wheeled devices or vehicles are pushed or pulled by human power.

Figure 7B:
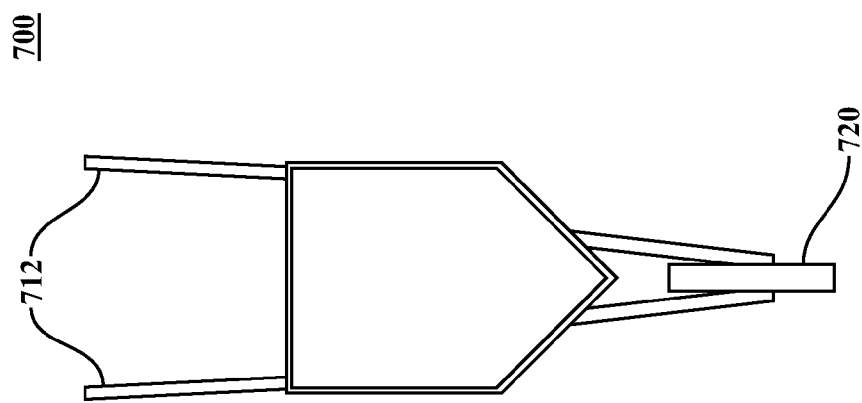
FIG. 7B schematically represents a top down view of electrically motorized wheelbarrow of FIG. 7A.
Figure 7A:
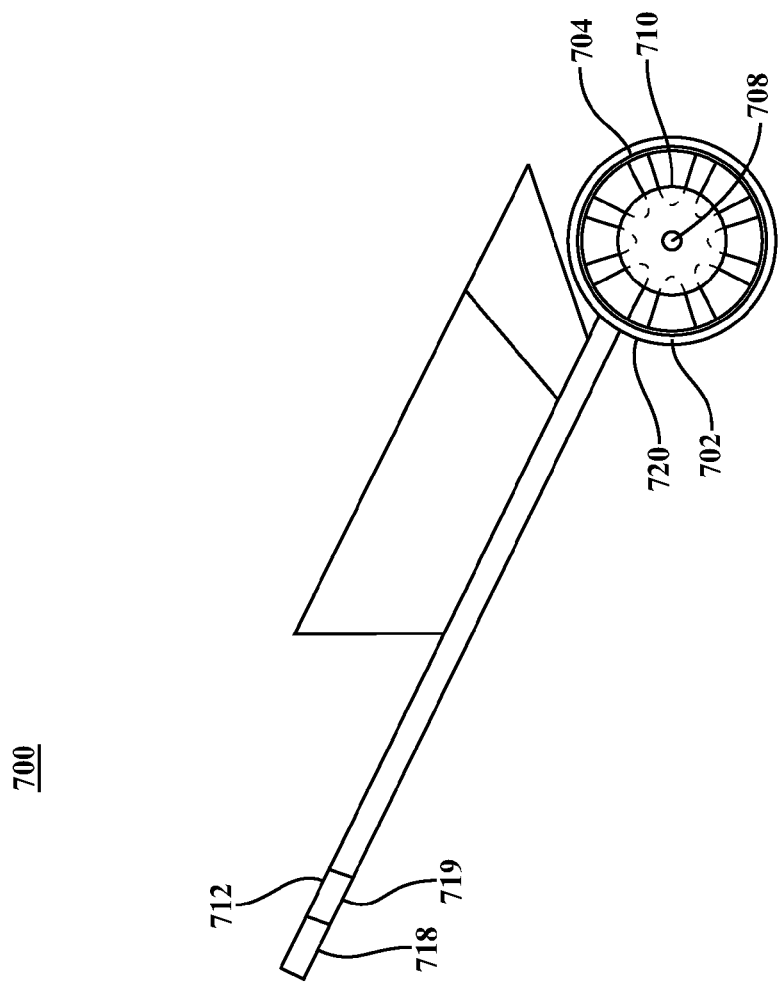
FIG. 7A schematically represents a side view of a wheelbarrow retrofitted with the electrically motorized wheel of FIG. 1A.

With reference to FIGS. 7A and 7B, an example wheelbarrow 700 is retrofitted with an electrically motorized wheel 720. Although this embodiment has specific illustrated components in for a wheelbarrow, the embodiments of this disclosure are not limited to those particular combinations and it is possible to use some of the components or features from any of the embodiments in combination with features or components from any of the other embodiments.

Figure 7C:
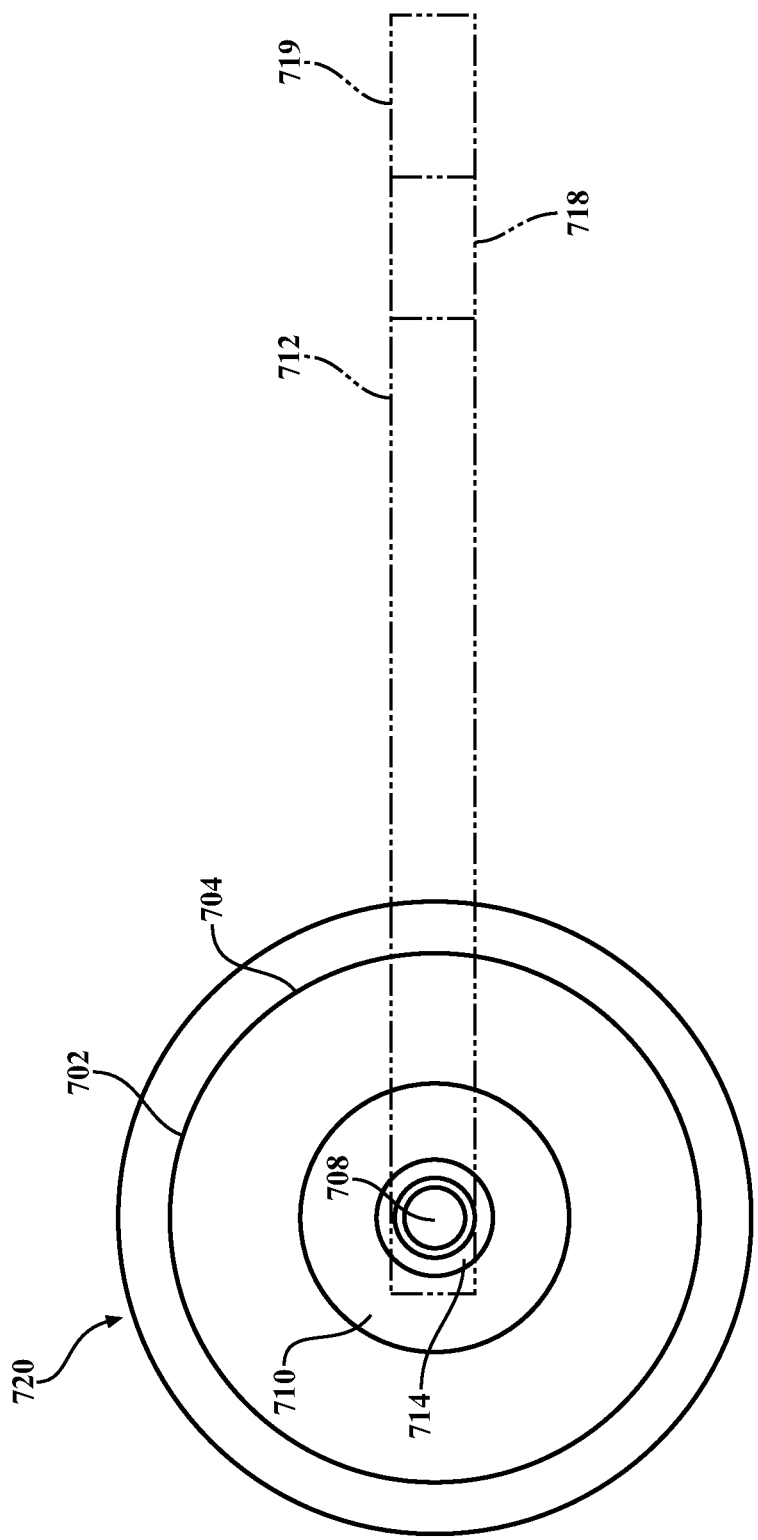
FIG. 7C schematically represents details of the force sensing connection between the electrically motorized wheel and electrically motorized wheelbarrow.

The electrically motorized wheel 720 includes a multiple of motorized wheel hubs 710 comparable to those described above but that are daisy changed together. That is, the plurality of electrically motorized wheels 720 operate in concert. The motorized wheel hub 710 rotates around an axle 708 that is fixed relative to a handle 712 (FIG. 7C).

The electrically motorized wheelbarrow 700 may have comparable functionality to that described above with the exception that the attitude may be determined differently as the electrically motorized wheelbarrow is typically designed to be tilted when in operation and level when not being used. Therefore, additional sensors may be used to determine the tilt relative to the ground and the inclination of the ground relative to a vertical line (representing direction of gravity). This can be done by measuring the distance from the front of the hub to the ground and the back of the hub to the ground and sensing a difference in distance between these. The vertical line may be determined by various known means, such as using gravity. Together these can be used to determine the incline angle of a hill up which electrically motorized wheelbarrow is travelling.

In embodiments, an axle transceiver 715 is utilized to transmit data from the handle 712 via axle force sensors 714 in communication with the control system 214. The handle 712 may alternatively include handle sensors 718 adjacent to the handles 712 to facilitate differentiating whether differential forces between the axle 708 and wheel hubs 710 is the result of force applied to one or both handles 712, or, for example, a change in terrain elevation. Data sensed by handle sensors 718 may be transmitted via a handle transceiver 719 to the control system 214 which may then determine which direction the user is trying to move and assistance in that direction.

For example, were the electrically motorized wheelbarrow 700 be moving while the input from the axle force sensors 714 and the handle sensors 718 are interpreted to be an attempt to slow the electrically motorized wheelbarrow 700, the control system 214 may determine that a braking force is required. Power is then provided to the motorized wheel hub 710 urging the motorized wheel hub 710 to drive in a direction opposite the direction of movement to cause a braking effect. This braking effect will facilitate stopping of the electrically motorized wheelbarrow 700.

Figure 8:
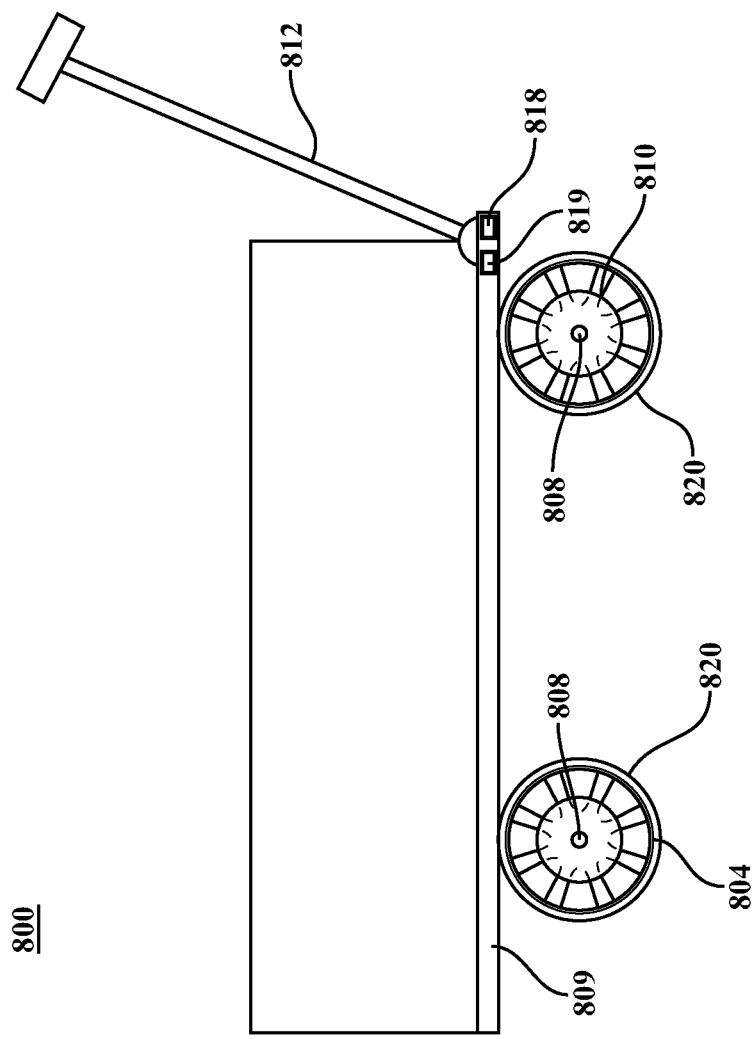
FIG. 8 schematically represents a side view of a wagon retrofitted with the electrically motorized wheel of FIG. 1A.

With reference to FIG. 8, in embodiments, a wagon 800 has installed thereon one or more electrically motorized wheels 820 with a motorized wheel hub 810 comparable to those described above. Although this embodiment has specific illustrated components in a wagon embodiment, the embodiments of this disclosure are not limited to those particular combinations and it is possible to use some of the components or features from any of the embodiments in combination with features or components from any of the other embodiments.

A user pulls a handle 812 of the wagon 800, which transmits the pulling force to an undercarriage 809 of the wagon 800 to which the electrically motorized wheels 820 are mounted.

Again, the wagon 800 is assumed to be a rigid body, such that the pulling force applied to the handle 812 is also applied through the wagon 800 and to axles 808. Each axle 808 and electrically motorized wheel 820 mounted thereto interact in a manner comparable to that of the electrically motorized wheelbarrow 700. As indicated, the determination of the force being applied on the wagon is based upon one or more inputs provided to the control system of the motorized hub.

In embodiments, a handle sensor 818 that measures magnitude, applied direction and applied force at the juncture of the handle 812 and the undercarriage 809. A transceiver 819 coupled to the handle sensor 818 transmits the force data to a control system 214 of the electrically motorized wheel 820. Based on the received data, the control system 214 operates to assist, for example, application of a positive force in the directions of motion, a braking force applied opposite the direction of motion, and relative motion such as to facilitate turning.

Even though the electrically motorized wheel has been described in connection with retrofitting a wagon, other vehicles such as a trailer or other wheeled vehicle that are pulled may be retrofitted in a comparable manner.

Figure 9A:
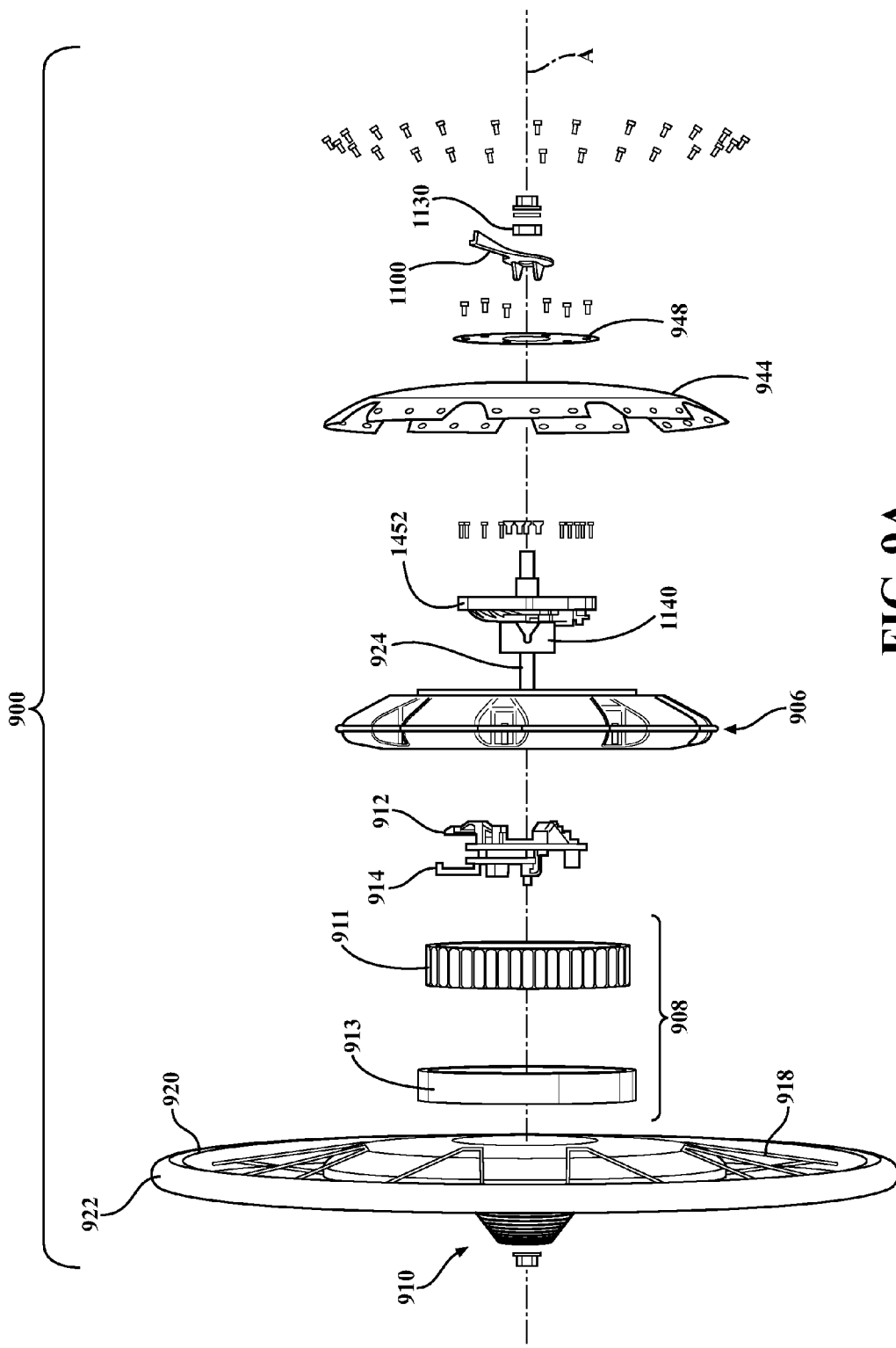
FIG. 9A is an exploded view of a single speed electrically motorized wheel.
Figure 9B:
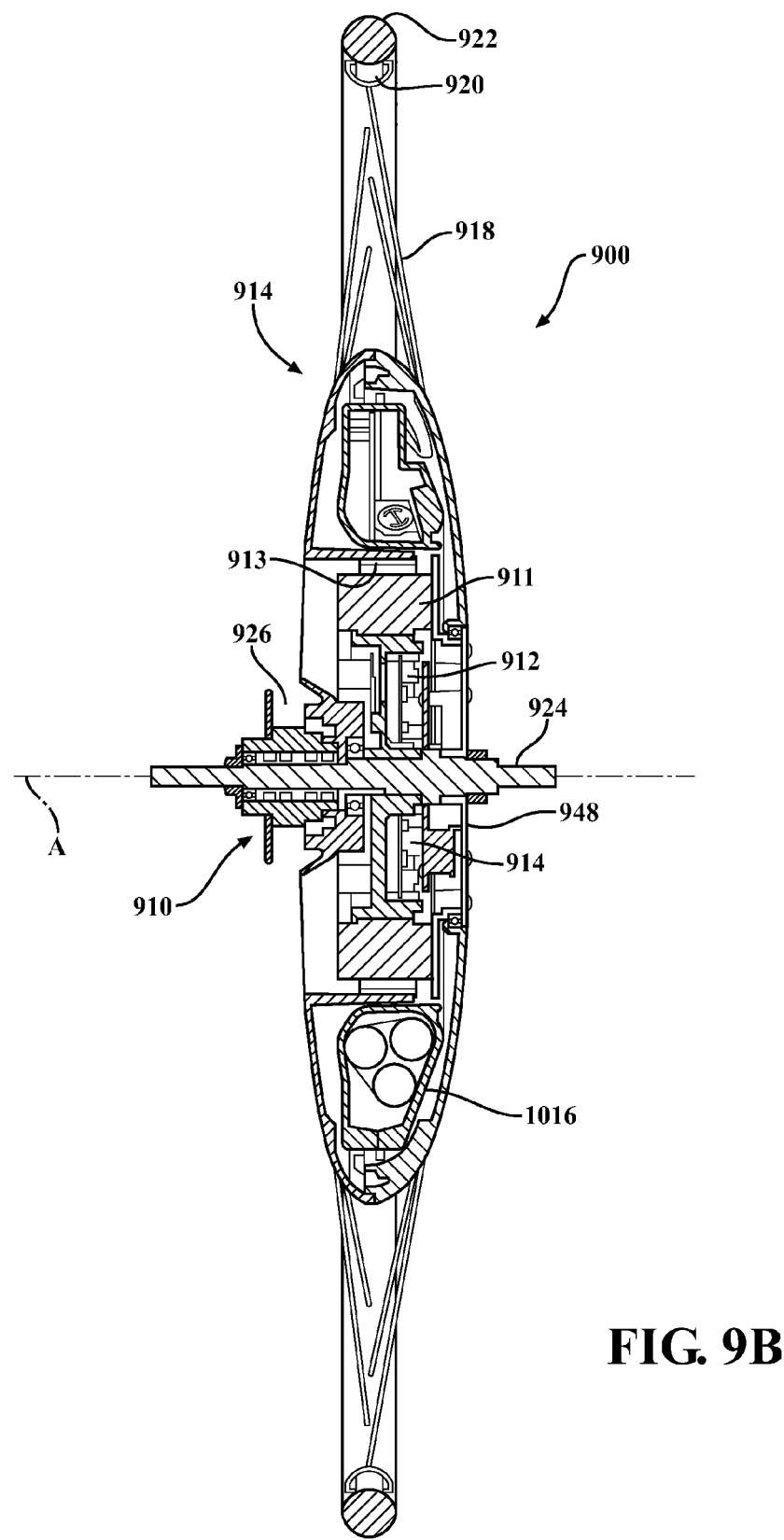
FIG. 9B is a sectional view of a single speed electrically motorized wheel.
Figure 9C:
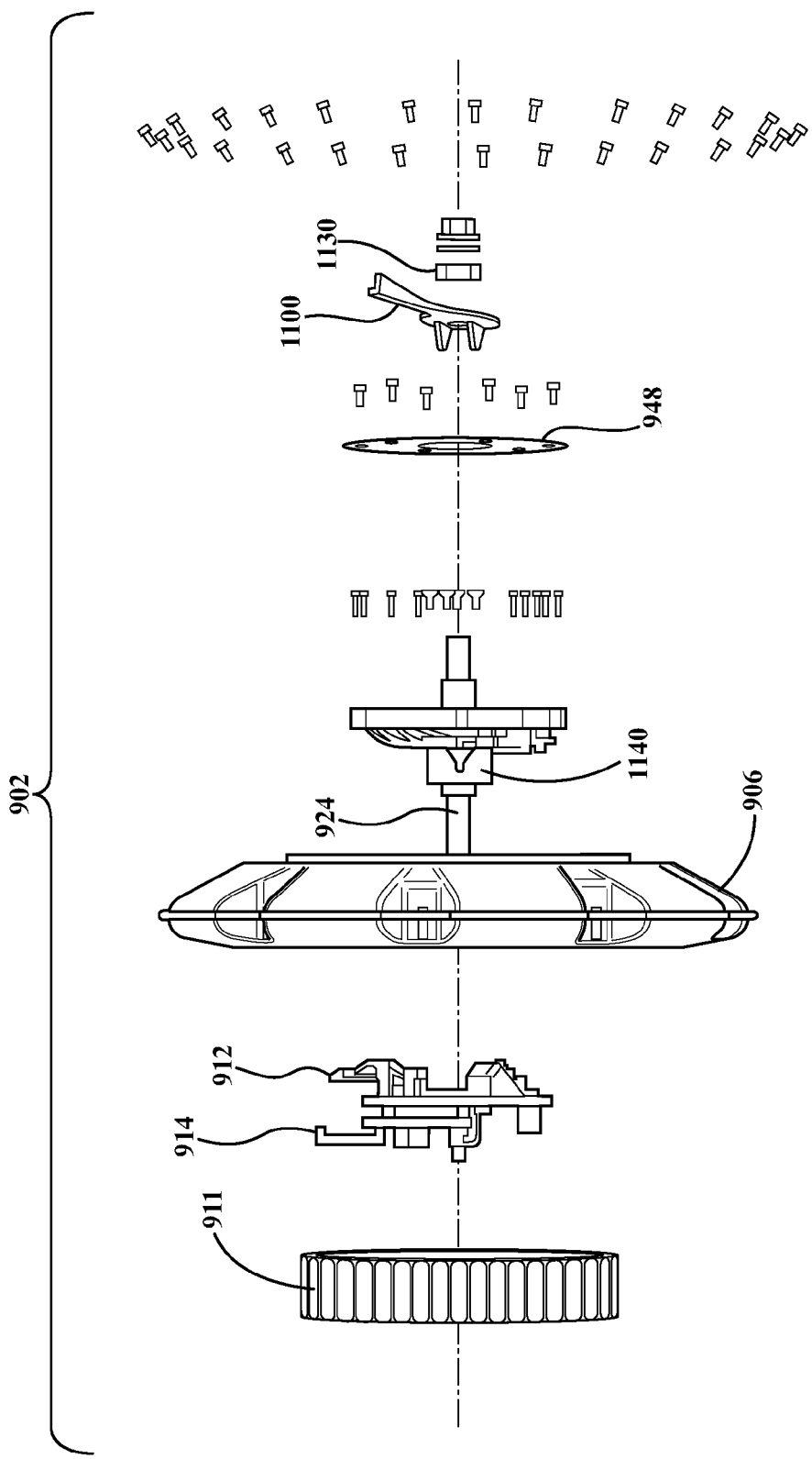
FIG. 9C is an exploded view of a static system of the electrically motorized wheel.
Figure 9D:
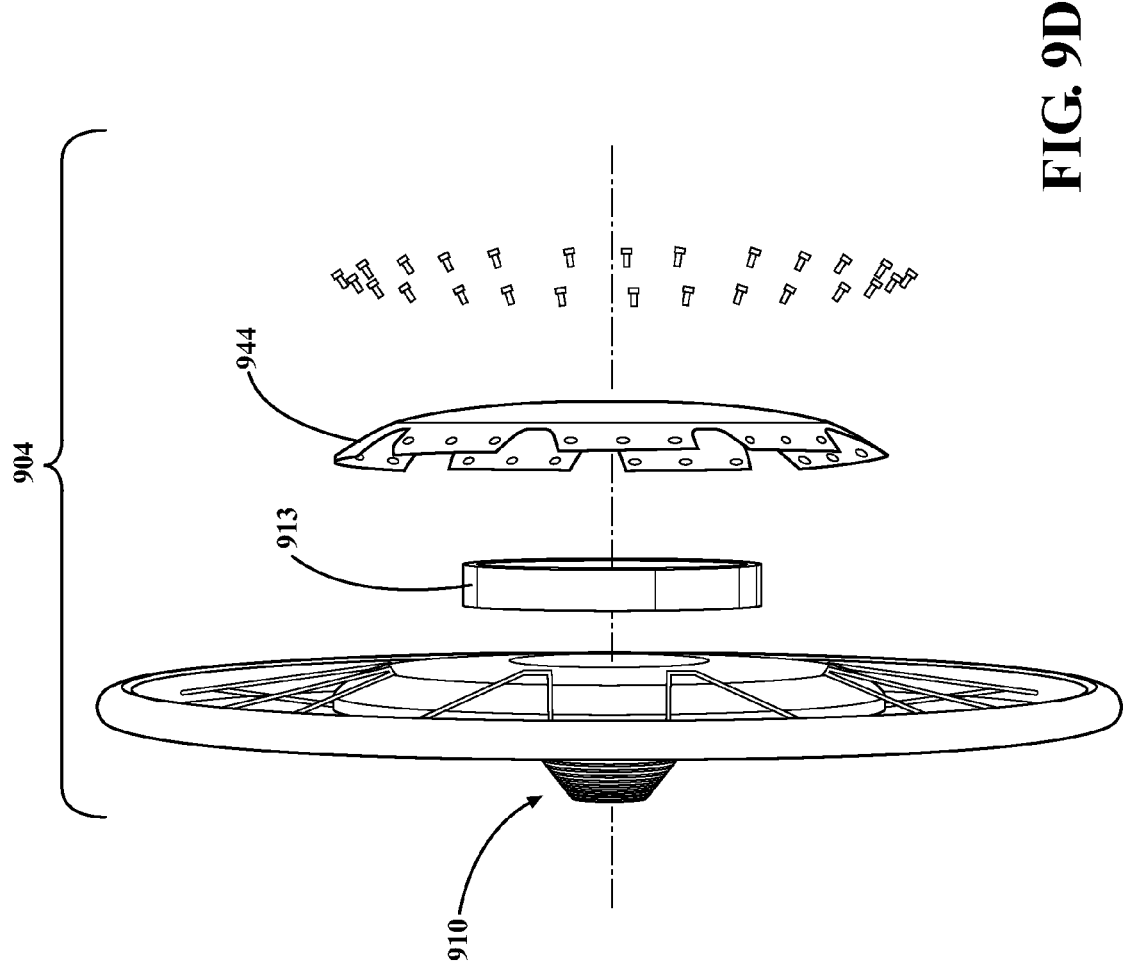
FIG. 9D is an exploded view of a rotational system of the electrically motorized wheel.
Figure 9E:
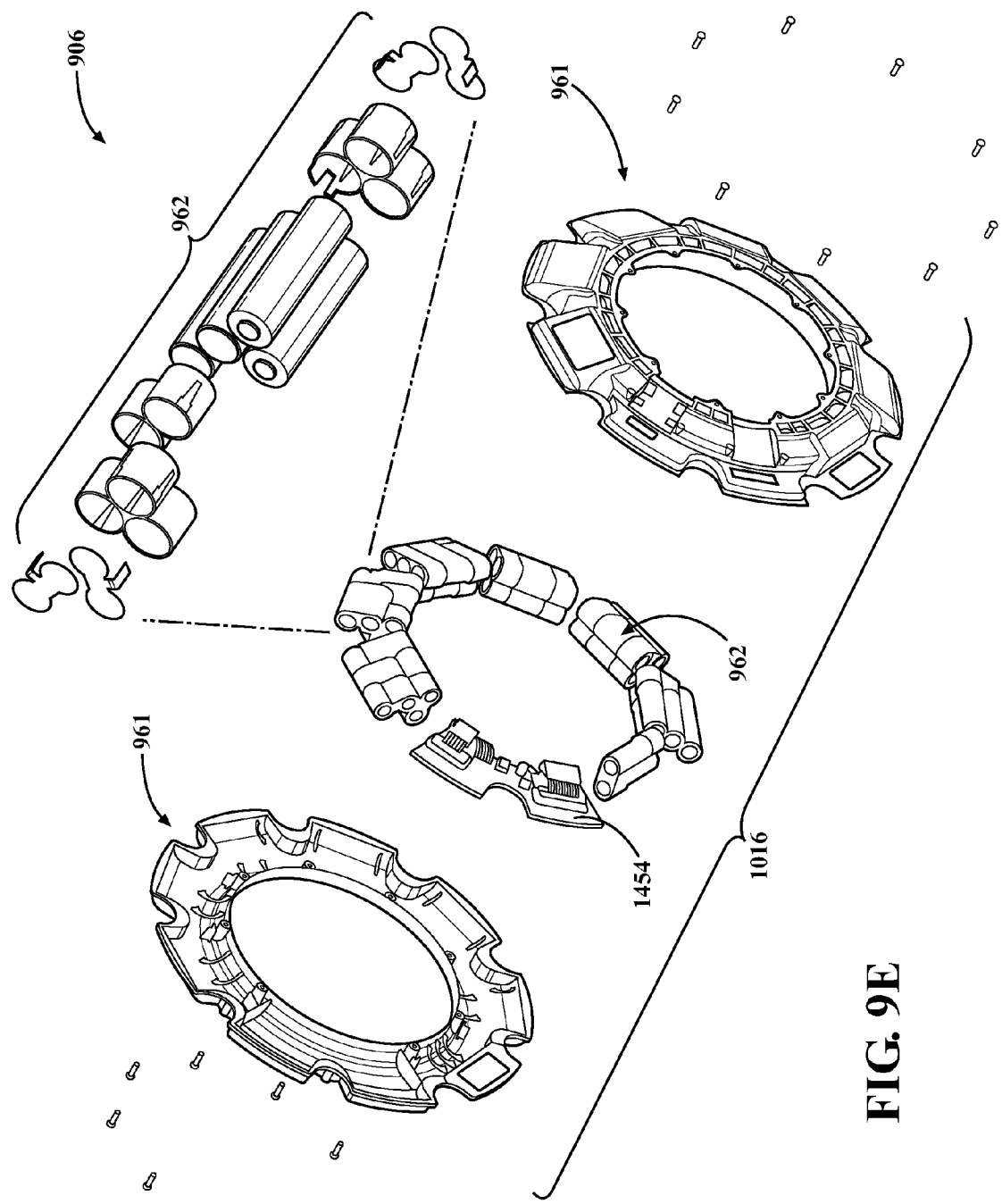
FIG. 9E is an exploded view of a system of the electrically motorized wheel.
Figure 9F:
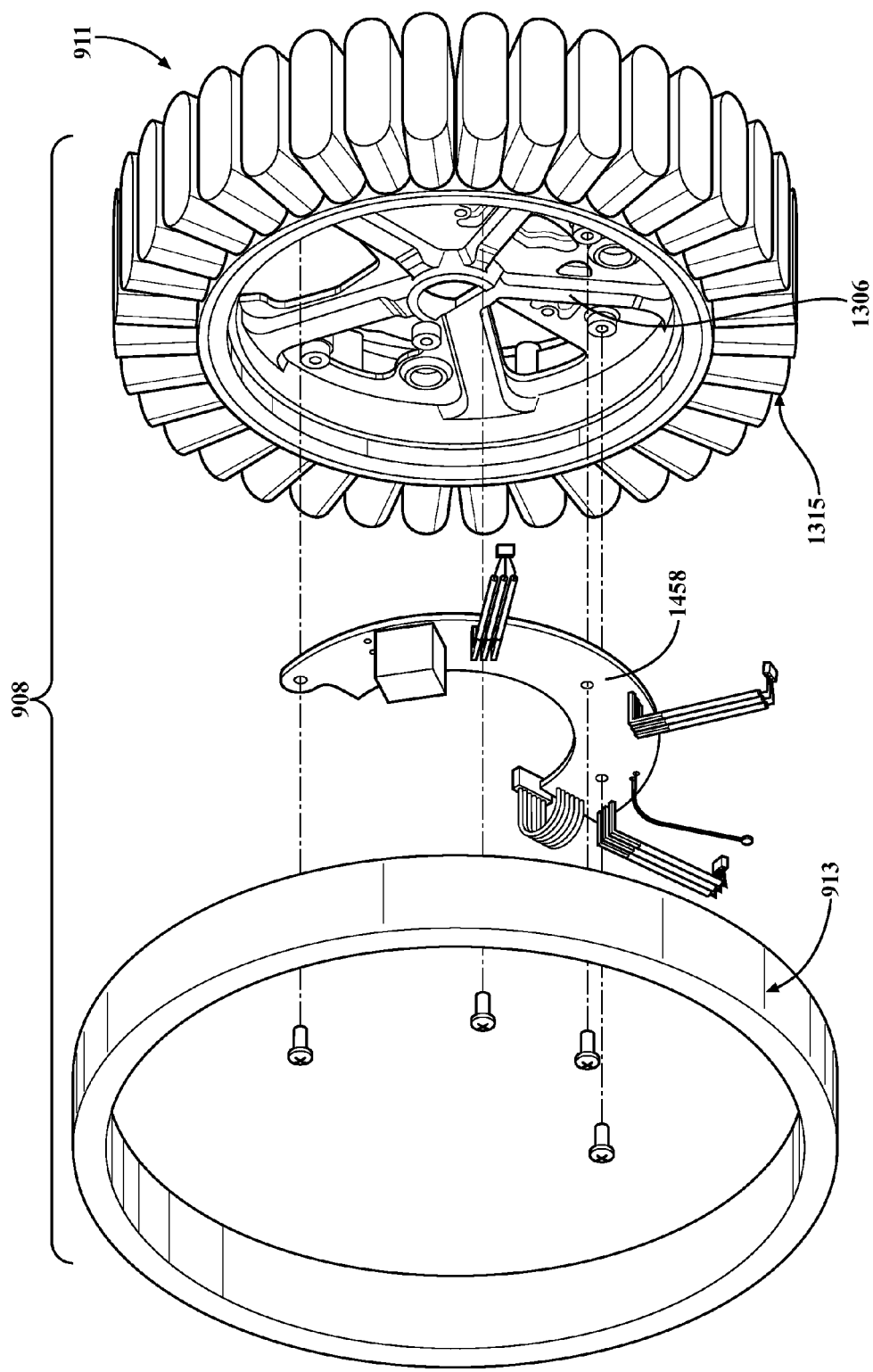
FIG. 9F is an exploded view of an electric motor of the electrically motorized wheel.
Figure 9G:
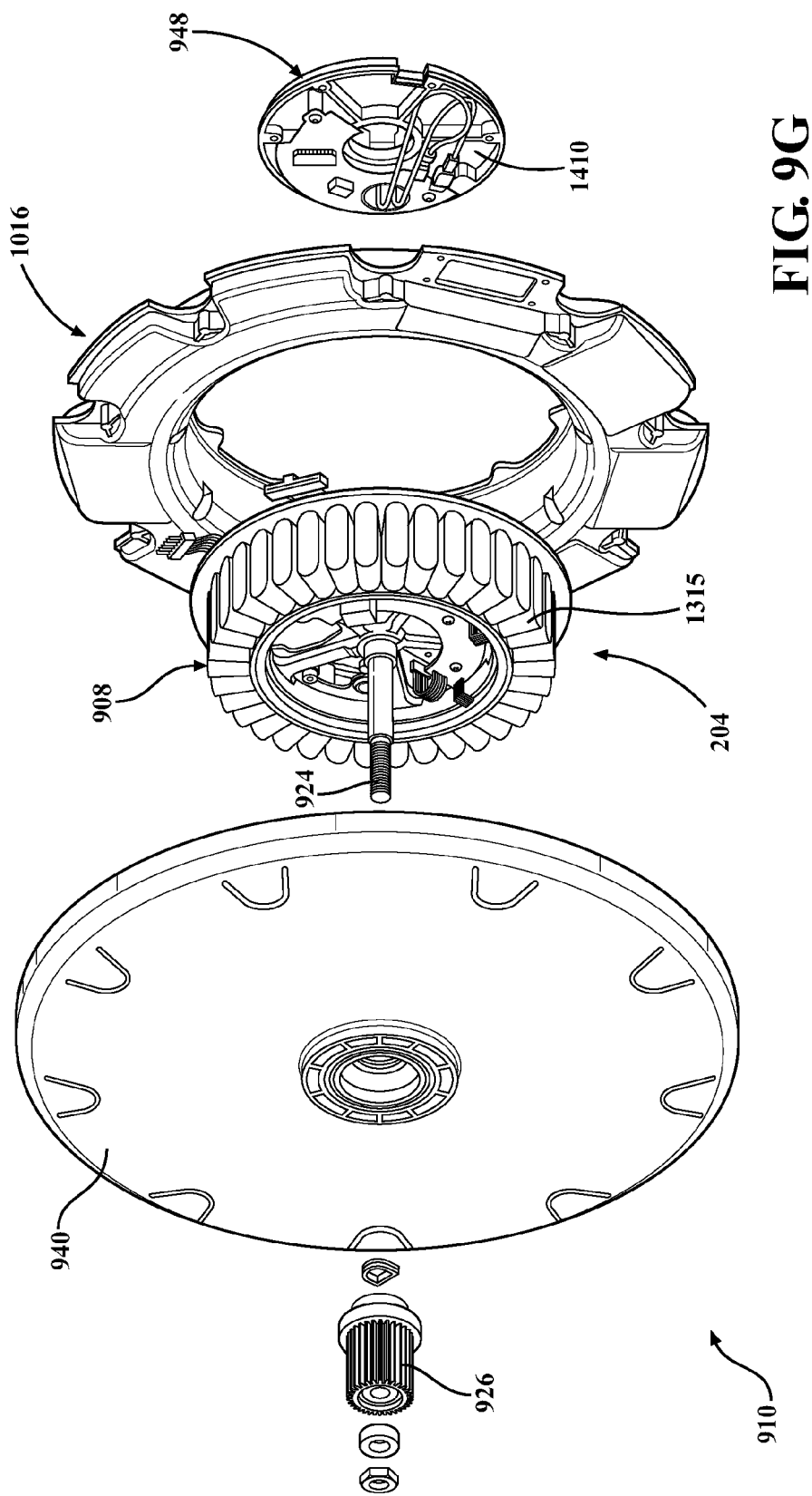
FIG. 9G is an exploded view of a mechanical drive system of the electrically motorized wheel.

With reference to FIGS. 9A-9J, embodiments of another electrically motorized wheel 900 (FIGS. 9A-9B) generally include a static system 902 (FIG. 9C), a rotating system 904 (FIG. 9D), a battery system 906 (FIG. 9E), an electric motor 908 (FIG. 9F), a mechanical drive system 910 (FIG. 9G), a sensor system 912 (FIG. 9H), a control system 914 (FIG. 9H), a hub shell assembly 916 (FIG. 9I), a multiple of spokes 918, a rim 920, a tire 922, a shaft 924, and a free hub torque assembly 926 (FIG. 9G). It should be appreciated that, although particular systems and components are separately defined, each, or any, may be otherwise combined or separated via hardware and/or software except where context indicates otherwise. Further, although this embodiment has specific illustrated components in a bicycle embodiment, the embodiments of this disclosure are not limited to those particular combinations and it is possible to use some of the components or features from any of the embodiments in combination with features or components from any of the other embodiments.

The static system 902 and the rotating system 904 are arranged around an axis of rotation A of the electrically motorized wheel 900, and the static system 902 is coupled to the non-motorized wheeled vehicle via a torque arm assembly that generally includes a torque arm 1100, a lock nut 1130, and a support block 1140 (FIG. 11A) such that the static system 902 is fixed to the vehicle frame. Alternatively, torque-transmitting features may be emplaced in the axle or other interface between the rotating system 904 and the static system 902. The electric motor 908 is selectively operable to rotate the rotating system 904 relative to the static system 902 to drive the spokes 918, the rim 920, and tire 922 thereof.

The mechanical drive system 910 is coupled to the rotational system 904 to rotate the rotational system 904 in response to an input applied by the user such as a pedaling input, ring handle of a wheelchair, pushing of a handle, pulling of a handle, etc. In one bicycle embodiment, the mechanical drive system 910 may include a multiple of sprockets for a multi-speed wheel 900A (FIG. 9A, 9B, 10A), often referred to as a "cassette," or a single sprocket for a single speed wheel 900B (FIG. 10B) that receive a rotational input from a pedaling input via a chain or belt.

The electric motor 908 (FIG. 9F) may include a motor interface board 1458, a magnetic ring rotor 913, and the stator 911 including motor windings 1315 and a hub 1306.

The sensor system 912 (FIG. 9H) may be operable to identify parameters indicative of the rotational input, such that the control system 914 in communication with a plurality of sensors is operable to continuously control the electric motor 908 in response to the input, such as that induced by a user pedaling. That is, the control system 914 is in communication with the sensor system 912 to continuously control the electric motor 908 even if the control momentarily results in no power being exerted by the electric motor 908. The battery system 906 is electrically connected to the control system 914 and the electric motor 908.

Figure 9H:
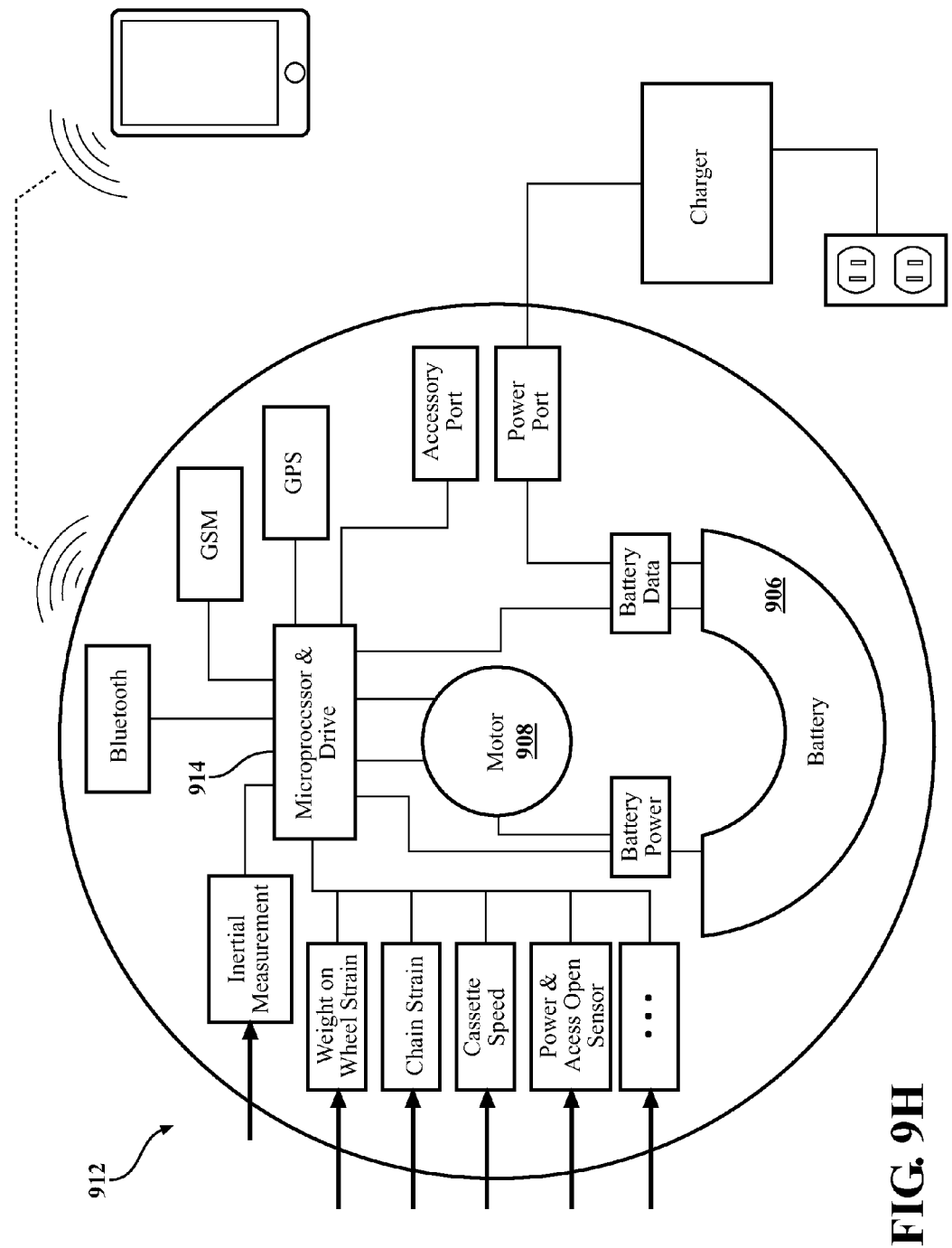
FIG. 9H is a schematic view of a system of the electrically motorized vehicle.
Figure 9I:
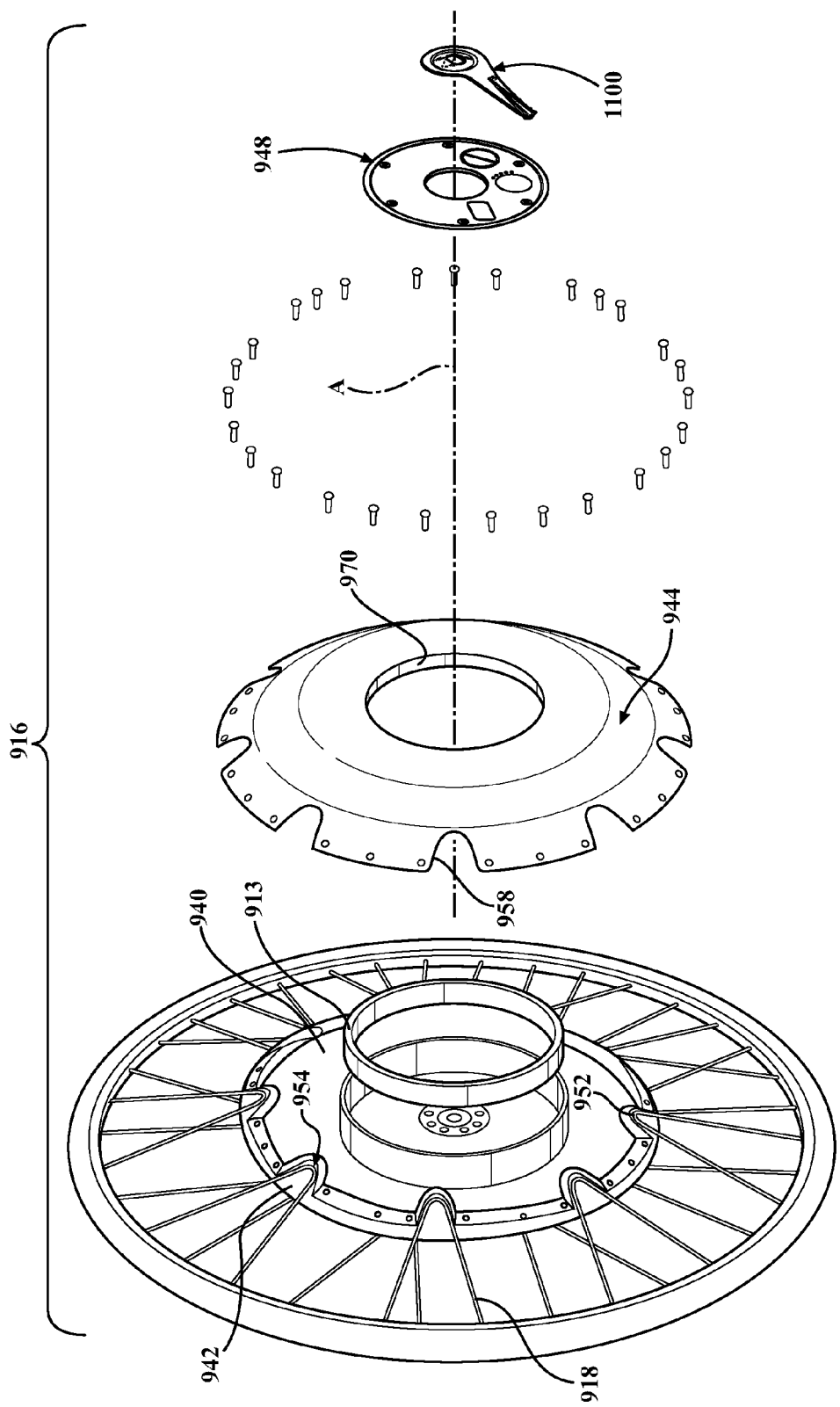
FIG. 9I is an exploded view of a system of the electrically motorized wheel.

In embodiments, the battery system 906, the electric motor 908, the mechanical drive system 910, the sensor system 912, and the control system 914, are enclosed with the hub shell assembly 916 (FIG. 9I). The hub shell assembly 916 may thereby be readily installed into a non-motorized wheeled vehicle through, for example, installation onto the spokes or rim of the electrically motorized wheel to provide an electrically motorized wheeled vehicle. Alternatively, the hub shell assembly 916 with the enclosed battery system 906, electric motor 908, mechanical drive system 910, sensor system 912, and control system 914 may be preinstalled on the electrically motorized wheel 900 to provide a self-contained device inclusive of the spokes 918, the rim 920, and the tire 922, such that an entire wheel of the vehicle is replaced by the electrically motorized wheel 900. That is, all operable componentry is on the electrically motorized wheel 900 itself and is installed as a self-contained device that does not require further modification of the vehicle. Alternatively, other, relatively minor components may be mountable on the vehicle itself rather than on the electrically motorized wheel 900 itself and still be considered a "self-contained" device as defined herein. For example a front wheel driven type vehicle may have an external controller, external throttle, a torque sensor, a speed sensor, a pedal sensor, and/or a pressure sensor mounted to the fork/trike/scooter/skateboard/back wheel etc., yet still communicate, such as in a wireless manner, with control system 914 and thus may still be considered a "self-contained" device as otherwise defined herein. In one example, such off wheel components may be readily easily installed components or sensors that are themselves self-contained.

With reference to FIG. 9I, the hub shell assembly 916, according to embodiments, generally includes a drive side shell 940, a non-drive side ring 942, a removable access door 944, and a user interface system 948. The hub shell assembly 916 is defined around the axis of rotation "A" defined by a shaft 924 (FIG. 9A).

Figure 12A:
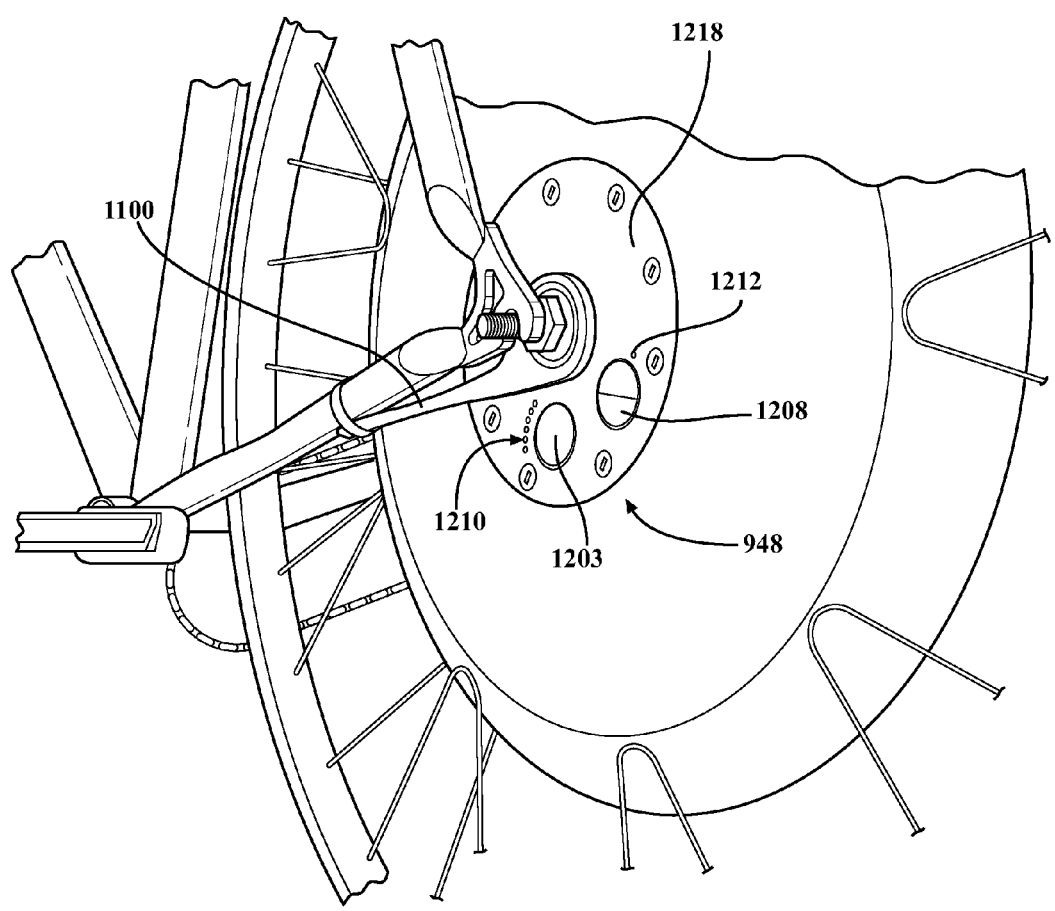
FIG. 12A is a perspective view of a user interface for the electrically motorized vehicle.
Figure 12B:
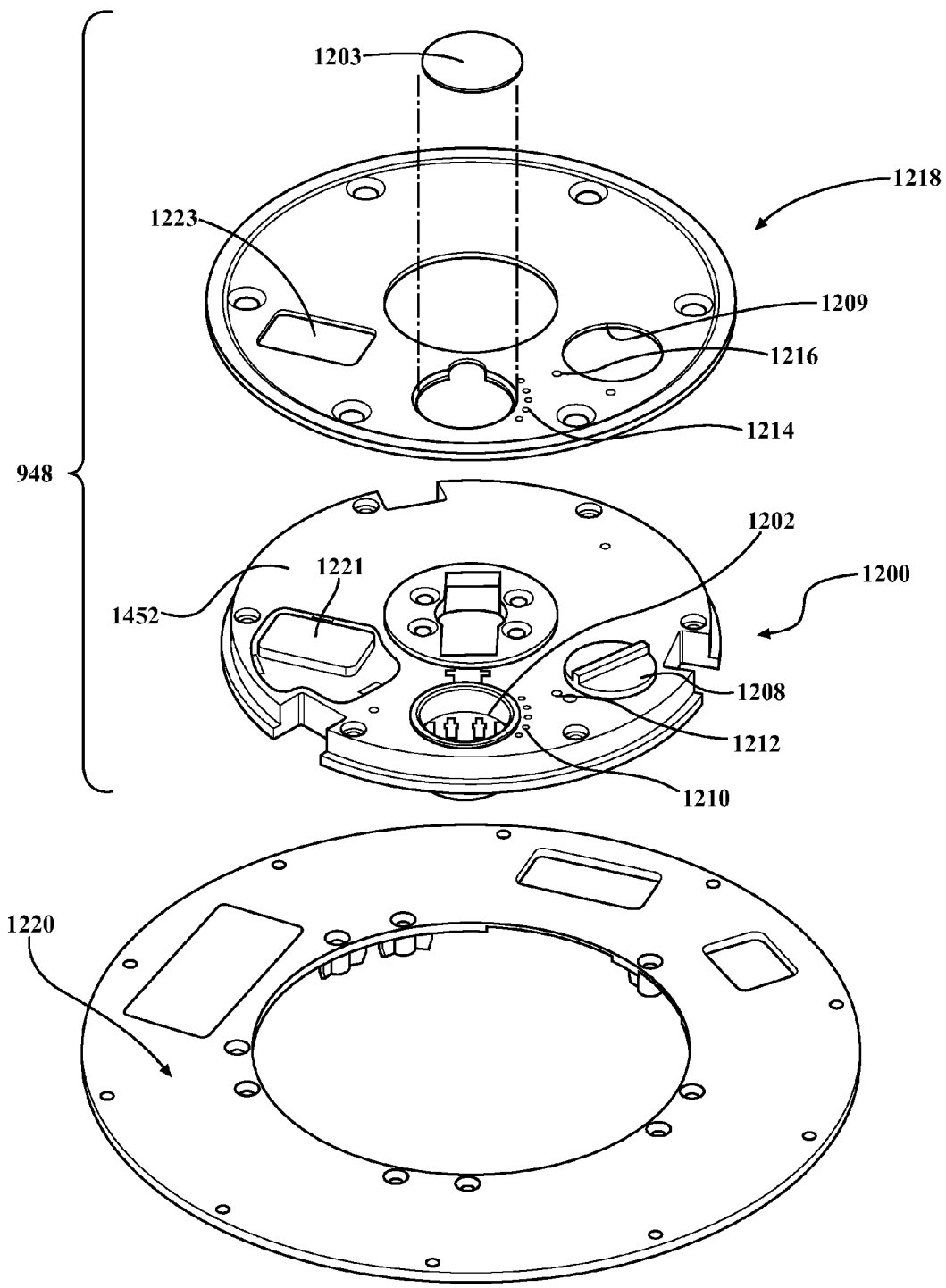
FIG. 12B is a perspective view of the user interface and user interface cover plate for the electrically motorized vehicle.

In embodiments, the hub shell assembly 916 contains the battery system 906 that, in turn, includes a Battery Management System (BMS) board 1454 (FIG. 12B), a multiple of battery packs 962 (FIGS. 9A and 9E) enclosed in a contoured battery housing 961 generally arranged the axis "A" and that is mounted to a battery mount plate 1220 (FIG. 12B). The contoured battery housing 961 together with the multiple of enclosed battery packs 962 may be referred to jointly herein as the contoured battery 1016. The battery system 906, in embodiments, may be rotationally stationary, however, the battery system 906 may, alternatively, rotate within the hub shell assembly 916. It should be understood that various shaped battery packs, e.g., linear, arced, circular, cylindrical, "L," "T," etc., formed from two, three, four, or more battery clusters, may be combined or otherwise assembled to achieve a desired configuration. The essentially scallop-shaped contoured battery 1016 is passable through a contoured inner periphery 954 of the non-drive side ring 942 with minimal effect upon other components.

The drive side shell 940 is a generally circular, lens-shaped chassis that supports the mechanical drive system 910 (FIG. 9A). The mechanical drive system 910 may include a free hub torque assembly 926 and the free hub sensor. The convex contour of the drive side shell 940 may be defined to specifically accommodate the mechanical drive system 910. For example, the multi-speed hub 940A may be relatively flatter, less convex, than the single speed hub 940B (FIGS. 10A, 10B).

Illustrative Clauses

In some implementations, a method of battery maintenance without delacing the spokes may be facilitated as described in the following clauses and illustrated by FIGS. 9E and 9I.

1. A method of battery maintenance for an electrically motorized wheel, the method comprising:
accessing a contoured battery within the electrically motorized wheel while each of a multiple of spokes of the electrically motorized wheel remains laced.

2. The method as recited in clause 1, further comprising:
accessing the contoured battery via a removable access door, the removable access door removably attachable to a non-drive side ring mounted to a drive side shell.

3. The method as recited in clause 2, further comprising removing a user interface panel cover plate mounted to the drive side shell prior to accessing the contoured battery via the removable access door.

4. The method as recited in clause 3, further comprising:
accessing the contoured battery from around a user interface panel subsequent to removal of the user interface panel cover plate.

5. The method as recited in clause 4, further comprising:
accessing the contoured battery without removal of a bearing mounted to the user interface panel.

6. The method as recited in clause 1, further comprising:
accessing the contoured battery without disassembly of an electric motor and a control system therefor.

7. A hub casing assembly of an electrically motorized wheel, comprising:
a drive side casing defined about an axis;
a non-drive side ring mounted to the drive side casing, the non-drive side ring defines a non-circular contour; and a contoured battery housing that is passable through the non-circular contour of the non-drive side ring.

8. The assembly as recited in clause 7, further comprising a removable access door removably attachable to the non-drive side ring.

9. The assembly as recited in clause 7, wherein the non-circular contour includes a multiple of arcuate sections.

10. The assembly as recited in clause 7, wherein the non-circular contour includes a multiple of scallops.

11. The assembly as recited in clause 7, wherein contoured battery housing contains a multiple of batteries of a battery system.

12. The assembly as recited in clause 7, wherein at least one of the multiple of batteries includes a 2-battery cluster.

13. The assembly as recited in clause 7, wherein at least one of the multiple of batteries includes a 4-battery cluster.

14. The assembly as recited in clause 13, wherein the 4-battery cluster is arranged in an L-configuration.

15. The assembly as recited in clause 7, further comprising a user interface panel cover plate mounted to the drive side shell, the user interface panel cover plate removable prior to accessing the contoured battery via the removable access door.

16. The assembly as recited in clause 15, wherein the contoured battery is contoured to permit removal/replacement from around a user interface panel subsequent to removal of the user interface panel cover plate.

17. The assembly as recited in clause 13, further comprising a multiple of spokes mounted to the non-drive side ring and the drive side casing such that a removable access door is removable from the non-drive side ring without delacing any of the multiple of spokes.

18. A hub shell assembly for an electrically motorized wheel, comprising:
a drive side shell defined about an axis;
a non-drive side ring mounted to the drive side shell;
a removable access door removably attachable to the non-drive side ring; and
a multiple of spokes mounted to the non-drive side ring and the drive side casing such that a removable access door is removable from the non-drive side ring without delacing any of the multiple of spokes 19. The assembly as recited in clause 18, further comprising a contoured battery housing that is passable through the non-circular contour of the non-drive side ring.

20. A method of maintenance for an electrically motorized wheel, the method comprising:
accessing at least one component of the electrically motorized wheel while each of a multiple of spokes of the electrically motorized wheel remain laced, the at least one component located within a hub shell assembly of the electrically motorized wheel.

With continued reference to FIG. 9I, the non-drive side ring 942 typically includes a multiple of spoke interfaces 952 such as arcuate grooves to receive the spokes 918. The non-drive side ring 942 is held in contact with the drive side shell 940 via the tension of the spokes 918, fasteners, or a combination thereof. A magnetic ring rotor 913 is fixed to, and rotates with, the drive side shell 940. A contoured inner periphery 954 of the non-drive side ring 942 matches an outer contoured periphery 958 of the removable access door 944 such that the removable access door 944 is readily removed without despoking or delacing to access the contoured battery 1016 that contains the multiple of batteries packs 962 and contoured battery housing 961 of the battery system 906 (FIG. 9E). Alternatively, or in addition, other components including the ones described herein may be accessed through the removable access door 944 without despoking or delacing the wheel.

In one example, the contoured inner periphery 954 may be scalloped and/or the contoured battery 1016 may be formed of a multiple of circumferential segments (FIG. 9E) to facilitate removal. An inner periphery 970 of the removable access door 944 may be circular to receive the user interface system 948. As will be further described, the user interface system 948 is rotationally static and may include, for example, a power port, on/off switch, status lights, etc., that are readily accessible to a user.

The contoured battery 1016 may be arranged circumferentially around the motor 204 and the control system 914 on a control system board 1410 underlying the user interface system 948 (FIG. 9G). The contoured battery 1016 may be mounted to the hub 1306 of the stator 911 such that there is no relative rotation between these components (FIG. 9G). In one embodiment, the contoured battery 1016 may be readily removable from the electrically motorized wheel 900 without extensively disassembling, despoking, or delacing. In this embodiment, battery removal may be accomplished by: a) removing the user interface cover plate 1218 (FIG. 12B) thereby uncovering the user interface panel 1200, b) unscrewing and removing the removable access door 944 (FIG. 9I), c) disconnecting the contoured battery 1016 from internal components, such as by unplugging from the control system 1410, then d) unscrewing the battery mount plate 1220 (FIG. 12B) from the contoured battery 1016 to remove the contoured battery 1016 out from, and around, the internal electronic components, motor assembly, bearings, and/or other components which otherwise remain undisturbed. Alternatively, or in addition, one or more of the multiple of battery packs 962 (FIG. 9E) may be separately removed then replaced from the contoured battery housing 961 by disassembly thereof.

With reference to FIGS. 10A-10B, sectional views of two embodiments of the electrically motorized wheel are shown. FIG. 10A shows a multi-speed electrically motorized wheel 900A having a mechanical drive system 910A which may include a multiple of sprockets. The multi-speed drive side shell 940A may be relatively flatter, less convex, than the single speed drive side shell 940B of a single speed wheel 900B. FIG. 10B shows a single speed wheel 900B having a mechanical drive system 910B which may include a single sprocket. The single speed drive side shell 940B may be relatively more convex than the multi-speed drive side shell 940A.

Illustrative Clauses

In some implementations, a torque arm and support block may facilitate the transfer of torque to the frame of a vehicle as described in the following clauses and illustrated by FIGS. 11A-11I.

1. A support block for a torque arm on a vehicle comprising:
a first indentation and a second indentation each having an opening adapted to accept a portion of a torque arm, the first indentation and the second indentation each having a relief cut opposite the opening into which a portion of a torque arm can fit.

2. The support block as recited in clause 1, wherein the first indentation and the second indentation are each V-shaped.

3. The support block as recited in clause 2, wherein the relief cut is located at the apex of the V-shape.

4. The support block as recited in clause 1, wherein the first indentation and the second indentation are located through a sidewall of the block.

5. The support block as recited in clause 1, wherein the block has a substantially circular cross section.

6. The support block as recited in clause 1, wherein the block includes an aperture to receive a shaft.

7. The support block as recited in clause 1, wherein the block includes a multiple of fastener apertures therethrough.

8. A torque arm assembly for a wheel of a vehicle, the torque arm assembly comprising:
a block with a first indentation and a second indentation, the first indentation including a relief cut and the second indentation including a relief cut; and
a torque arm with a first hinge portion engageable with the first indentation and extending partially into the relief cut on the first indentation, and a second hinge portion engageable with the second indentation and extending partially into the relief cut on the second hinge portion.

9. The assembly as recited in clause 8, wherein the torque arm includes a non-circular opening.

10. The assembly as recited in clause 9, wherein the non-circular opening rotationally keys the torque arm to a shaft.

11. The assembly as recited in clause 10, wherein the non-circular opening permits the torque arm to pivot about a hinge that defines a pivot for the torque arm such that an arm portion may interface with a frame member of the vehicle.

12. The assembly as recited in clause 11, wherein the arm portion interfaces below a frame member to transfer torque to the frame member of the vehicle.

13. The assembly as recited in clause 8, wherein the hinge portions are substantially V-shaped.

14. The assembly as recited in clause 13, wherein an apex of each of the two hinge portions interface with a respective relief cut to provide a two line contacts for each of the respective first indentation and the second indentation.

15. The assembly as recited in clause 14, wherein an apex of each of the two hinge portions is arcuate.

16. The assembly as recited in clause 8, further comprising a clamp to retain the arm portion below a frame member.

17. The assembly as recited in clause 10, wherein the torque arm comprises a substantially semi-spherical surface comprising the non-circular opening.

18. The assembly as recited in clause 17, further comprising a lock nut that interfaces with the semi-spherical portion.

19. The assembly as recited in clause 18, wherein the lock nut includes a non-planar interface that interfaces with the semi-spherical portion.

20. The assembly as recited in clause 19, wherein the lock nut mounts to the shaft to lock the torque arm at a desired angle to accommodate a multiple of vehicle frame arrangements.

Figure 11A:
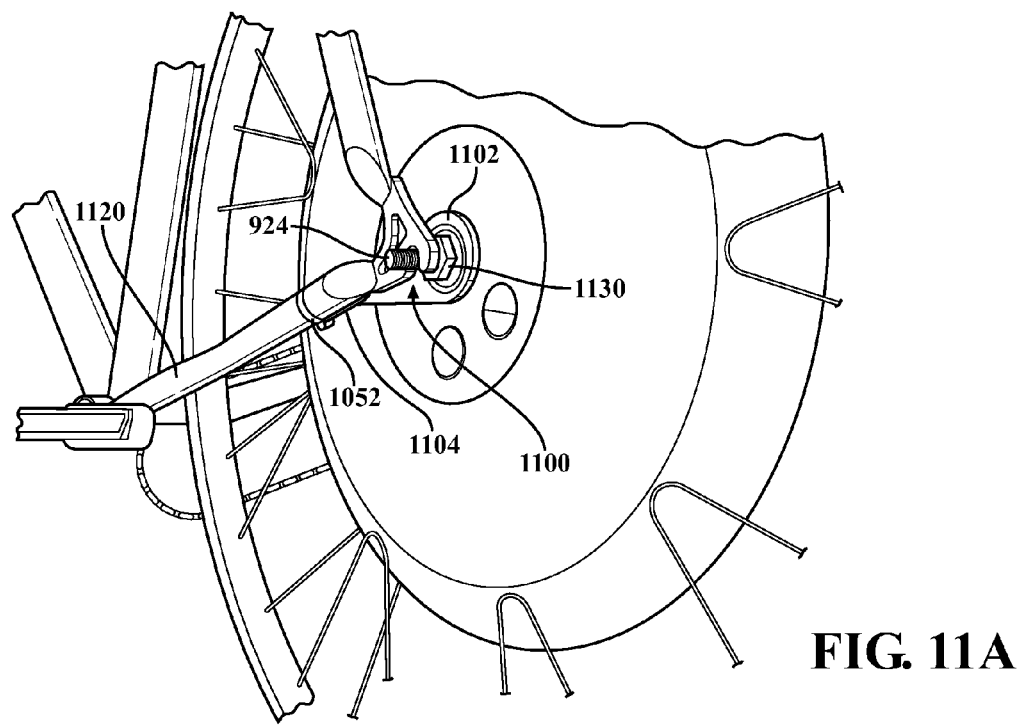
FIG. 11A is a perspective view of a torque arm assembly.
Figure 11B:
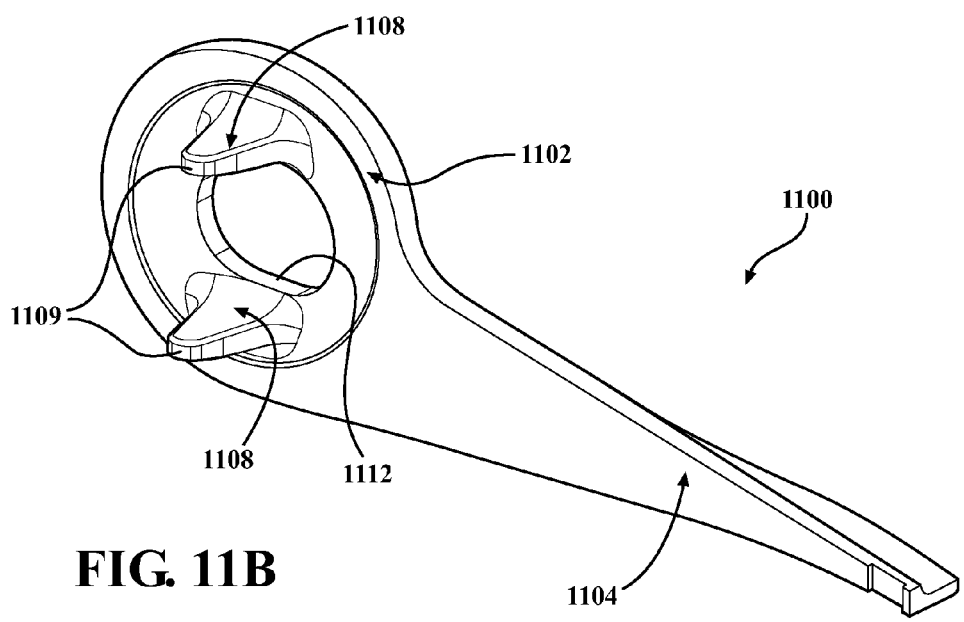
FIG. 11B is a perspective view of a torque arm for the electrically motorized wheel.
Figure 11E:
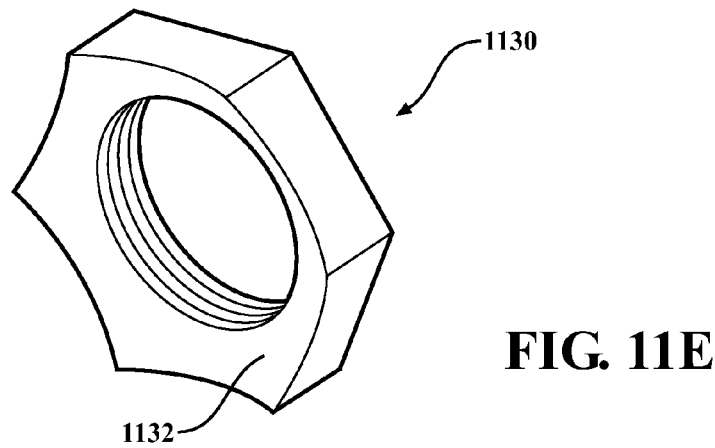
FIG. 11E is a perspective view of a nut for the torque arm for the electrically motorized wheel.
Figure 11F:
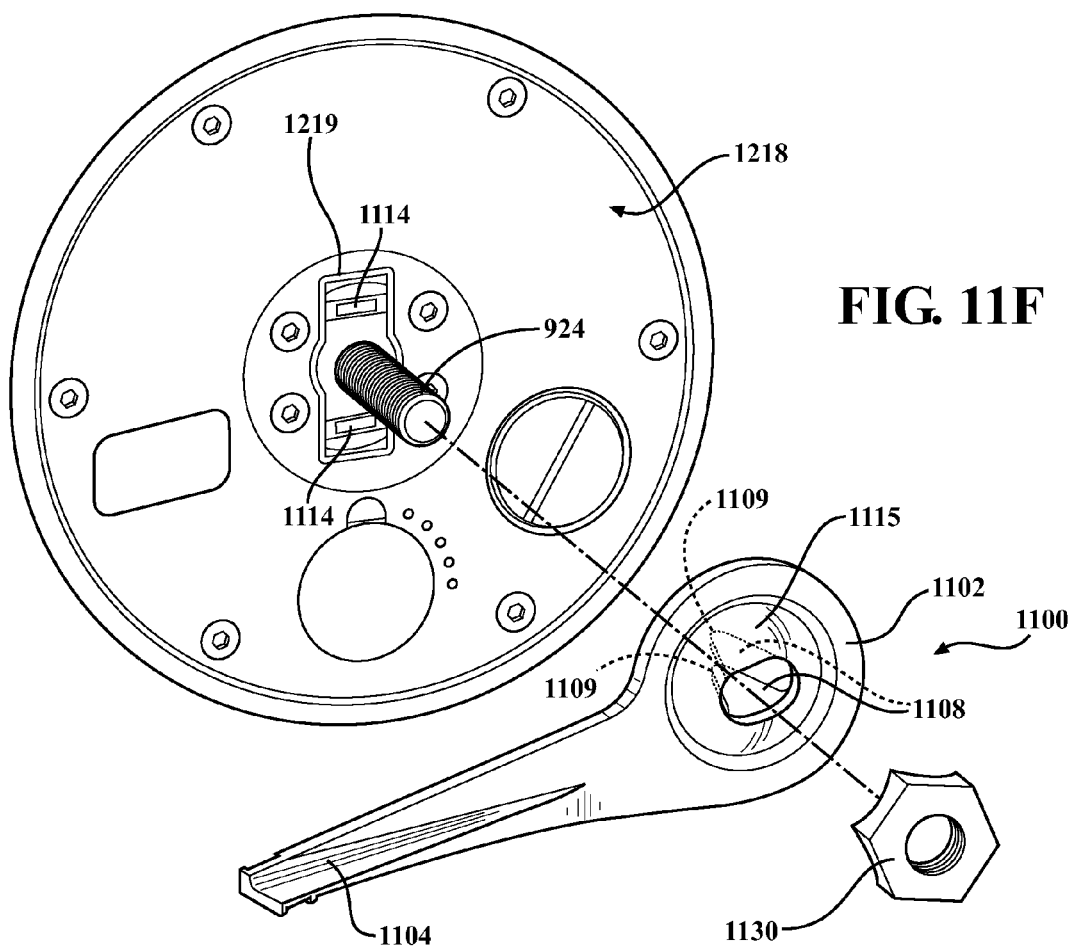
FIGS. 11F-11I are perspective views of the interface of the torque arm and the support block.

With reference to FIG. 11A, a torque arm 1100 provides a substantially rigid mechanical connection between the stationary portion of the hub assembly and a frame member 1120 of the vehicle on which the electrically motorized wheel is mounted, thereby maintaining the stationary portion in a fixed position relative to the frame of the vehicle. As various frames have various rear drop-outs (i.e., where the axle interfaces the frame) an essentially universal interface is required to maintain the stationary portion of the hub in a fixed position relative to the frame of the vehicle With reference to FIGS. 11B-11C, the torque arm 1100 generally includes a ring portion 1102, an arm portion 1104, and a hinge portion 1108 (FIG. 11B) that extends from the ring portion 1102. An inner periphery 1112 (FIG. 11C) of the ring portion 1102, and an increased diameter non-circular shaft section, e.g., oval, polygonal or of another shape that rotationally keys the torque arm 1100 to the shaft 924, yet permits the torque arm 1100 to pivot relative thereto. In one disclosed non-limiting embodiment, the hinge portions 1108 are generally V-shaped with an arcuate apex 1109 (FIG. 11B) that extends from the ring portion 1102 to interface with respective indentations 1114 in the support block 1140 (FIGS. 11D-1-11D-2). The side of the ring portion 1102 on the side opposed to the hinges 1108 may be a convex, conical, arcuate, or semi-spherical surface 1115 (FIG. 11C) to interface with lock nut 1130 (FIG. 11E).

Figure 11G:
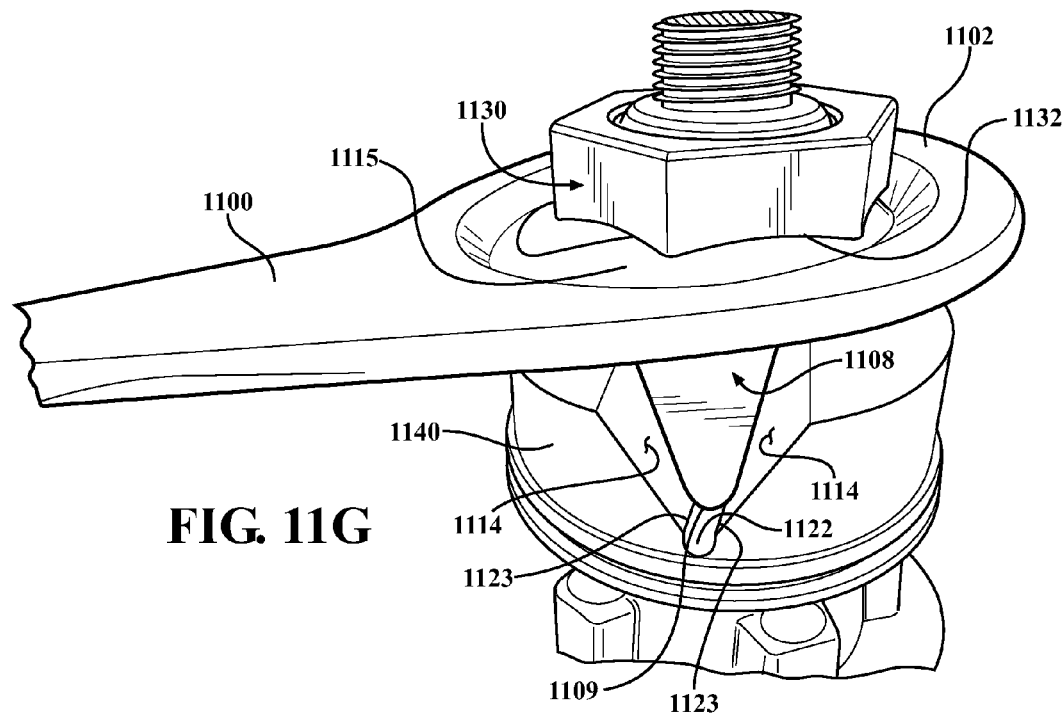
Figure 11I:
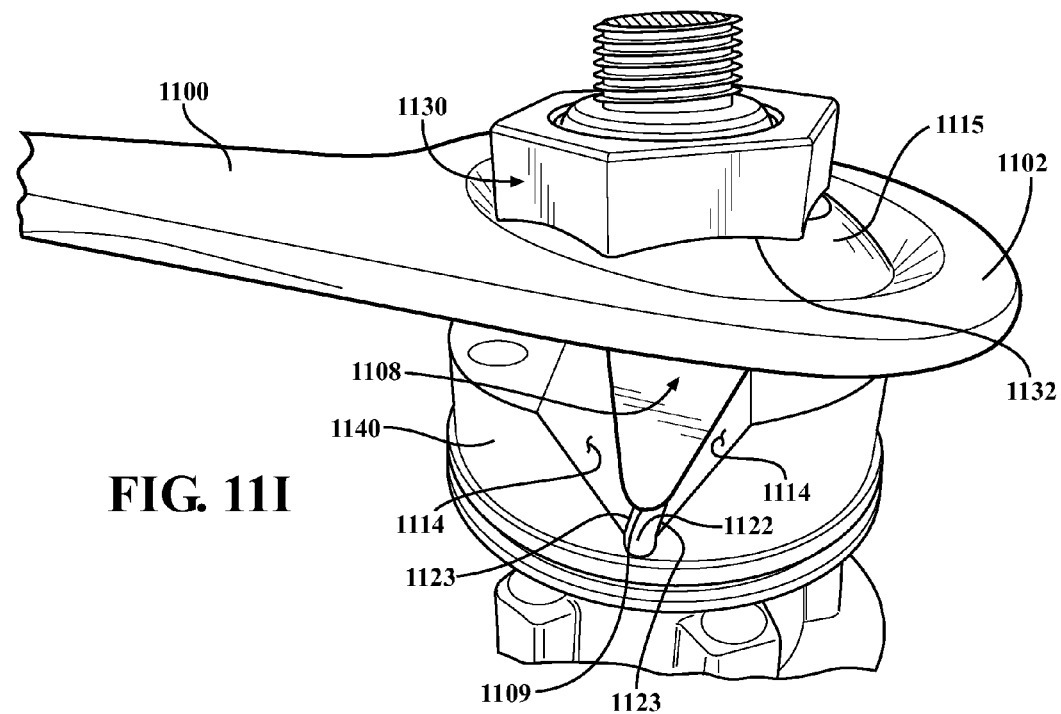
Figure 11H:
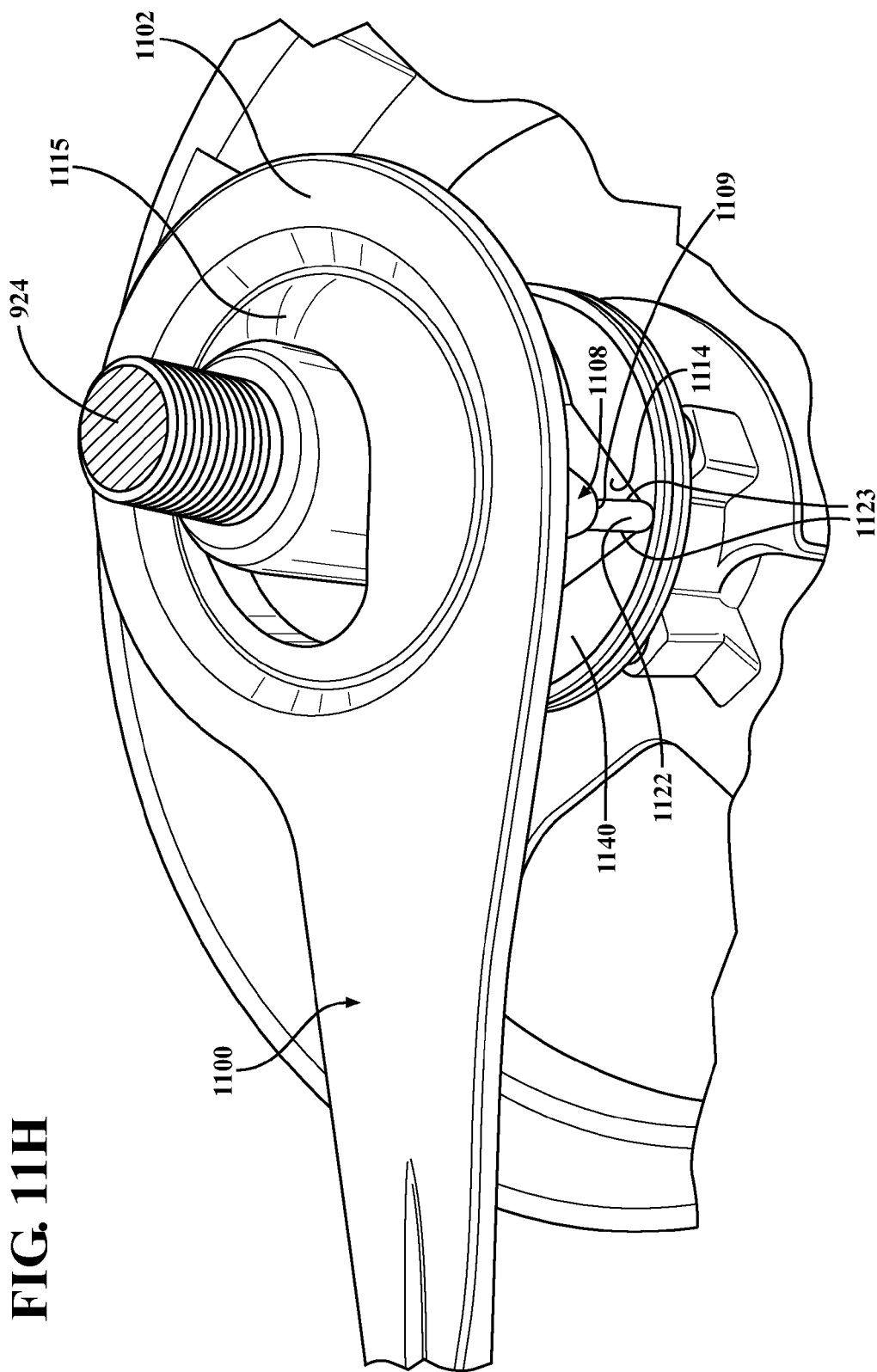

Referring to FIGS. 11D-1-11D-2, the support block 1140 may be generally annular and have a substantially circular cross-section 1143 to be received around the shaft 924. The support block 1140 may be secured to the shaft 924 via a set of splines, with apertures 1141 to receive fasteners, or any other suitable attachment method. The removable support block 1140 facilitates replacement should the interface with the hinge portion 1108 wear over time. The support block 1140 may include two opposed indentations 1114 in the sidewall thereof. That is, the indentations 1114 are opposed on the support block 1140 on either side of the circular cross-section 1143. In one embodiment, the indentations 1114 are generally V-shaped with a relief cut 1122 at the apex of each. The relief cut 1122 in each of the indentations 1114 serves to define line contacts 1123 as an interface for the respective hinge portions 1108. The indentations 1114 increase the flexibility and fit to a multiple of vehicle frames (FIGS. 11G-11H).

The hinge portions 1108 extend to provide support for the torque arm 1100 within the respective indentations 1114 such that the arcuate apex 1109 of the hinge portion 1108 partially fits into the relief cut 1122. The relief cut 1122 permits the hinge portion 1108 of the torque arm 1100 to be supported on the essentially two line contacts 1123 (FIGS. 11D-1, 11G, 11I) as defined by each edge of each relief cut 1122 (FIGS. 11G-11I).

A lock nut 1130 may include a non-planar surface 1132 (FIG. 11E) such as a concave, conical, arcuate, or semi-spherical surface to interface with a related convex, conical, arcuate, or semi-spherical surface 1115 (FIG. 11C) on the torque arm 1100 to accommodate any angle of the torque arm 1100 with respect to the shaft 924 to interface with the frame member 1120 (FIG. 11A). That is, the non-planar surface 1132 and the semi-spherical surface 1115 operate essentially as a ball joint such that the torque arm 1100 may be positioned at a desired angle to accommodate a multiple of vehicle frame arrangements.

In one disclosed non-limiting embodiment (FIG. 11F), a support block 1140 is operable to support the torque arm 1100. The support block 1140 may be positioned behind the user interface cover plate 1218 and at least partially through the user interface panel 1200. The user interface cover plate 1218 may include apertures 1219 such that the indentations 1114 may be accessed to receive the hinge portions 1108 at least partially therethrough. The user interface cover plate 1218 and user interface panel 1200 may also be fastened to the support block 1140 to ensure that the mating features for the torque arm 1100 and the support block 1140 remain stable and properly oriented relative to one another.

The hinge portion 1108 defines a pivot for the torque arm 1100. The non-planar surface 1132 and the semi-spherical surface 1115 accommodates the pivoting such that the arm portion 1104 may interface with a frame member 1120, and additionally, may be secured thereto via a clamp 1052 (FIG. 11A). It should be understood that various clamps and other interfaces may be utilized to secure the arm to the frame member 1120 as well as positional relationships that do not require a clamp such as that which locates the arm portion 1104 to rotationally ground the static system to the frame member 1120.

The hinge portions 1108 further permits the design of other torque resisting interfaces other than the illustrated torque arm 1100 design that couples the non-rotating parts to a vehicle frame such as that of a bike. For example, a manufacturing tester might have a complete differently shaped reaction torque mount that utilizes the same mating features.

Referring to FIGS. 11G-11I, various views of the torque arm 1100 interface with the support block 1140 are shown. The torque arm 1100 facilitates accommodation of different vehicle frames, is rotatable when aligning the electrically motorized wheel to the vehicle frame during install, then may be pivoted outwards (FIG. 11I) or inwards (FIG. 11G) with respect to the electrically motorized wheel, such that the torque arm 1100 may be positioned directly under the frame member 1120 onto which the electrically motorized wheel is installed. This facilitates effective torque transfer and straightforward installation of the electrically motorized wheel. Further, although this torque arm embodiment has specific illustrated components in a bicycle embodiment, the embodiments of this disclosure are not limited to those particular combinations and it is possible to use some of the components or features from any of the embodiments in combination with features or components from any of the other embodiments.

Illustrative Clauses

In some implementations, a user interface panel for interaction with a motorized wheel may be facilitated as described in the following clauses and illustrated by FIGS. 12A-12B. 1. A user interface for an electrically motorized wheel with a hub shell assembly, the user interface comprising:

a user interface cover plate for a user interface panel that provides for operation of the electrically motorized wheel, the user interface cover plate rotationally stationary relative to a rotatable portion of the hub shell assembly, the user interface cover plate including an antenna aperture for an antenna of a wireless system.

2. The user interface as recited in clause 1, wherein the hub shell assembly comprises:

a drive side shell defined about an axis;

a non-drive side ring mounted to the drive side shell; and a removable access door removably attachable to the non-drive side ring, the user interface cover plate is generally circular and rotationally fixed within the rotatable removable access door.

3. The user interface as recited in clause 1, further comprising a switch aperture within the user interface cover plate for an on/off switch mounted to the user interface panel to operate the electrically motorized wheel.

4. The user interface as recited in clause 3, wherein the switch aperture is circular.

5. The user interface as recited in clause 3, wherein the switch is low profile. 6. The user interface as recited in clause 1, further comprising a port aperture within the user interface cover plate for a port mounted to the user interface panel to provide communication with the electrically motorized wheel.

7. The user interface as recited in clause 1, further comprising a port aperture within the user interface cover plate for a power port to charge the electrically motorized wheel, the power port mounted to the user interface panel.

8. The user interface as recited in clause 7, further comprising a removable cover mountable over the port aperture.

9. The user interface as recited in clause 7, further comprising an arrangement of status lights to at least partially surround the port.

10. The user interface as recited in clause 1, wherein the wireless system is located behind and protected by the user interface cover plate.

11. The user interface as recited in clause 1, wherein the antenna of the wireless system is flush with the user interface cover plate.

12. The user interface as recited in clause 1, wherein the user interface cover plate includes a central shaft aperture. 13. The user interface as recited in clause 12, wherein the central shaft aperture is rectilinear.

14. A method of mounting an antenna to an electrically motorized wheel with a hub shell assembly comprising:

locating an antenna aperture for an antenna of a wireless system in a user interface cover plate for a user interface panel that provides for operation of the electrically motorized wheel, the wireless system mounted to the user interface panel, the user interface cover plate and the user interface panel rotationally stationary relative to a rotatable portion of the hub shell assembly.

15. The method of clause 14, further comprising mounting the antenna to be flush with the user interface cover plate.

16. The method of clause 14, further comprising mounting the antenna to the user interface panel behind and protected by the user interface cover plate.

17. The method of clause 14, further comprising mounting the antenna to the user interface panel to avoid formation of a Faraday cage.

18. A user interface for an electrically motorized wheel, the user interface comprising:

a user interface cover plate for a user interface panel that provides for operation of the electrically motorized wheel, the user interface cover plate rotationally stationary relative to a rotatable portion of a hub shell assembly, the user interface cover plate including a port aperture within the user interface cover plate for communication access with the user interface panel of the electrically motorized wheel.

19. The user interface as recited in clause 18, wherein the user interface cover plate is mounted to the user interface panel and the user interface cover plate and user interface panel are generally circular and form a stationary portion of a hub shell assembly.

20. The user interface as recited in clause 18, further comprising a switch aperture within the user interface cover plate for an on/off switch to operate the electrically motorized wheel.

21. The user interface as recited in clause 20, wherein the switch aperture is circular.

22. The user interface as recited in clause 21, wherein the switch is low profile.

23. The user interface as recited in clause 18, wherein the port provides access to a power port to charge the electrically motorized wheel, the power port mounted to the user interface panel.

24. The user interface as recited in clause 23, further comprising a removable cover mountable over the port aperture.

25. A user interface for an electrically motorized wheel, the user interface comprising:

a user interface cover plate for a user interface panel that provides for operation of the electrically motorized wheel, the user interface cover plate rotationally stationary relative to a rotatable portion of the hub shell assembly, the user interface cover plate including a switch aperture within the user interface cover plate for an on/off switch mounted to the user interface panel to operate the electrically motorized wheel.

26. The user interface as recited in clause 25, wherein the user interface cover plate is generally circular.

27. The user interface as recited in clause 25, wherein the switch aperture is circular.

28. The user interface as recited in clause 25, wherein the switch is low profile.

29. A hub for an electrically motorized wheel, the hub comprising:

a rotating element;

a stationary element mounted relative to the rotating element, the stationary element configured to support a user interface;

a charge port mounted to the stationary element, the charge port having an electrical connection to at least one component located within the hub; and a switch mounted to the stationary element.

With reference to FIG. 12A, the user interface system 948 includes a user interface panel covered by a user interface cover plate 1218 that is located on the non-drive side of the wheel to remain clear of the mechanical drive system, chain, sprocket, etc. that may be located on the drive-side. This permits easy access for a user to interface with the wheel as well as a rotationally stationary area to which the torque arm 1100 (FIG. 11A) may be located with respect to the frame of the vehicle. Although the example describes a drive and non-drive side of the wheel, this is intended to describe features such as the user interface panel, charge port, switch and the like being located on a stationary element of an electrically motorized wheel.

The user interface panel 1200 (FIG. 12B) may include a User Interface board 1452, a power port 1202 such as a Rosenberger connection under a removable cover 1203 in the user interface cover plate 1218, an on/off switch 1208, an arrangement of battery power status lights 1210, and a power indicator light 1212. In one example, the arrangement of battery power status lights 1210 is arcuate to at least partially surround the removable cover 1203, and the power indicator light 1212 may be located adjacent to the on/off switch 1208. The battery power status lights 1210 and the power indicator light 1212 are visible through respective windows 1214, 1216 in the user interface cover plate 1218. In this example, the on/off switch 1208 is generally flush with the user interface cover plate 1218 to facilitate, for example minimal aerodynamic resistance. In other embodiments, the user interface panel 1200 may include a display screen.

With reference to FIG. 12B, the user interface panel 1200 may also include a short-range wireless system 1221 and the user interface cover plate 1218 may include a corresponding aperture 1223 for the short-range wireless system 1221. This configuration locates the short-range wireless system 1221 flush with, rather than within, the user interface cover plate 1218 of the hub shell assembly 916 (FIG. 9I). Such a configuration prevents the hub shell assembly and the user interface cover plate 1218 from operating as a Faraday cage and thereby potentially interfering with the connection between the short-range wireless system 1221 and the mobile device 230 (FIG. 2A).

The short-range wireless system 1221 may be located on the user interface panel 1200 such that, when the electrically motorized wheel 900 is installed, the short-range wireless system 1221 is shielded from physical damage or inadvertent user interaction. For example, the short-range wireless system 1221 may be located at least partially behind, and thereby be protected by another element of the electrically motorized wheel 900 or the frame of the vehicle to which the electrically motorized wheel 900 is installed. Such a configuration may also obscure the short-range wireless system 1221 from direct view, thereby preserving the aesthetic design of the electrically motorized wheel 900. It should be understood that various ports, hardware interfaces, and other user interfaces may alternatively or additionally be provided.

The user interface system 948 may be mounted to a battery mount plate 1220 (FIG. 12B) that supports the battery system 906 in a rotationally static manner. That is, the user interface system 948 is a portion of the static system (also referred to as a stationary element) 902 (FIG. 9C) that is at least partially supported by the battery mount plate 1220 about which the rotating system 904 (FIG. 9D) rotates.

Normal operations of the electrically motorized wheel may result in the heating of various components, including motor components, various electrical components, mechanical components, and energy storage components. The generated heat may eventually affect performance of such components; impose stress as a result of thermal expansion and contraction of materials; affect the stability or working lifetime of components; or the like. For example, semiconductor components in processors can be sensitive to heat, batteries can be rendered inoperable, and motors can provide reduced output or be damaged when overheated.

Illustrative Clauses

In some implementations, passive thermal management may be facilitated as described in the following clauses and illustrated by FIGS. 13A-13G.

1. A method of thermal management for an electrically motorized wheel, the method comprising:

defining a thermally conductive path from at least one component, said at least one component becoming heated during operation of the electrically motorized wheel, providing the path with a thermally conductive material and further defining the path such that the path contacts the at least one component, further defining the path such that the path contacts a hub shell assembly of the electrically motorized wheel thereby conducting heat from the at least one component to the hub shell assembly.

2. The method as recited in clause 1, further comprising arranging the hub shell assembly in proximity to the at least one component to facilitate a short thermally conductive path therebetween.

3. The method as recited in clause 2, further comprising locating a plurality of fins on the hub shell assembly that extend from the hub shell assembly.

4. The method as recited in clause 1, further comprising defining the thermally conductive path from the at least one component to a shaft of the electrically motorized wheel.

5. The method as recited in clause 4, further comprising further defining the thermally conductive path from the at least one component through the shaft of the electrically motorized wheel to a frame of a wheeled vehicle upon which the electrically motorized wheel is installed.

6. The method as recited in clause 1, further comprising defining the thermally conductive path through the hub shell assembly by selecting a thickness of the hub shell assembly wherein the thickness is between about 2-4 mm.

7. The method as recited in clause 1, further comprising defining the thermally conductive path through the hub shell assembly by selecting a material of the hub shell assembly from one of an aluminum, magnesium, steel and titanium alloy.

8. The method as recited in clause 1, further comprising defining the thermally conductive path through a plurality of fins of the hub shell assembly.

9. The method as recited in clause 8, further comprising agitating airflow within the hub shell assembly with the plurality of fins.

10. The method as recited in clause 9, further comprising further defining the thermally conductive path from the at least one component through the shaft of the electrically motorized wheel to a frame of a wheeled vehicle upon which the electrically motorized wheel is installed.

11. The method as recited in clause 1, wherein the hub shell assembly in proximity to the at least one component to facilitate a short thermally conductive path therebetween.

12. The method as recited in clause 2, further comprising a plurality of fins extending from the hub shell assembly.

13. A method of thermal management for an electrically motorized wheel having a hub shell assembly containing at least one component that becomes heated during operation of the electrically motorized wheel, the method comprising:

agitating airflow within the hub shell assembly via a plurality of fins that extend within the hub shell assembly; and forming a thermal path from the at least one component that becomes heated during operation of the electrically motorized wheel to the hub shell assembly 14. The method as recited in clause 13, further comprising defining the thermal path through the hub shell assembly by selecting a thickness of the hub shell assembly wherein the thickness is between about 2-4 mm.

15. The method as recited in clause 13, further comprising defining the thermal path through the hub shell assembly by selecting a material of the hub shell assembly from one of an aluminum, magnesium, steel and titanium alloy.

16. The method as recited in clause 13, further comprising defining the thermal path from the hub shell assembly to a shaft of the electrically motorized wheel.

17. The method as recited in clause 16, further comprising defining the thermal path from the at least one component that becomes heated through the shaft of the electrically motorized wheel to a frame of a non-motorized wheeled vehicle upon which the electrically motorized wheel is installed.

18. A hub shell assembly for an electrically motorized wheel, comprising:

a drive side shell defined about an axis;

a non-drive side ring mounted to the drive side shell; and a removable access door removably attachable to the non-drive side ring, wherein at least one of the drive side shell, the non-drive side ring and the removable access door forms a portion of a thermal path defined from at least one component that becomes heated during operation of the electrically motorized wheel.

19. The assembly as recited in clause 18, wherein at least one of the drive side shell, the non-drive side ring and the removable access door includes at least one fin to agitate an airflow within the hub shell assembly.

20. The assembly as recited in clause 19, wherein at least one of the drive side shell, the non-drive side ring and the removable access door is about 2-4 mm thick.

21. The assembly as recited in clause 18, wherein at least one of the drive side shell, the non-drive side ring and the removable access door is manufactured of at least one of an aluminum, magnesium, or titanium alloy.

22. The assembly as recited in clause 18, wherein at least one of the drive side shell, the non-drive side ring and the removable access door is manufactured of a material for heat transfer without air exchange.

23. A device of an electrically motorized wheel to convert a non-motorized wheeled vehicle to an electrically motorized wheeled vehicle via installation of the device to a wheel of the non-motorized wheeled vehicle, the device comprising:

a static unit and a rotating unit around a rotor shaft that defines an axis of rotation, the static unit coupled to the non-motorized wheeled vehicle;

an electric motor selectively operable to rotate the rotating unit relative to the static unit;

a mechanical drive unit operable to rotate the rotational unit in response to a input from the user;

a sensing system adapted to identify parameters indicative of input; and a control unit mounted to the electrically motorized wheel, the control unit in communication with the sensing system to continuously control the electric motor in response to input; and wherein at least one component of the electrically motorized wheel becomes heated during operation of the electrically motorized wheel and the at least one component is positioned on a conductive thermal path from the at least one component to the shaft of the wheel.

24. The device as recited in clause 23, wherein the input is mechanical.

25. The device as recited in clause 23, wherein the input is electrical.

26. The device as recited in clause 23, wherein the electric motor is at least partially enclosed in a hub shell assembly.

27. The device as recited in clause 26, wherein the hub shell assembly comprises:

a drive side shell defined about an axis;

a non-drive side ring mounted to the drive side shell; and a removable access door removably attachable to the non-drive side ring.

28. The device as recited in clause 27, wherein at least one of the drive side shell, the non-drive side ring, and the removable access door includes at least one fin.

29. The device as recited in clause 27, wherein at least one of the drive side shell, the non-drive side ring, and the removable access door is manufactured of magnesium.

30. The device as recited in clause 27, wherein at least one of the drive side shell, the non-drive side ring, and the removable access door is between about 2-4 mm thick.

31. The device as recited in clause 27, further comprising defining the thermal path from the at least one component to a shaft of the electrically motorized wheel.

32. A thermal management system for an electrically motorized wheel, the system comprising:

a thermally conductive path from at least one component, the at least one component becoming heated during operation of the electrically motorized wheel, wherein the path comprises thermally conductive material and contacts at least one component; and a hub shell assembly of the electrically motorized wheel in contact with the path.

Figure 13A:
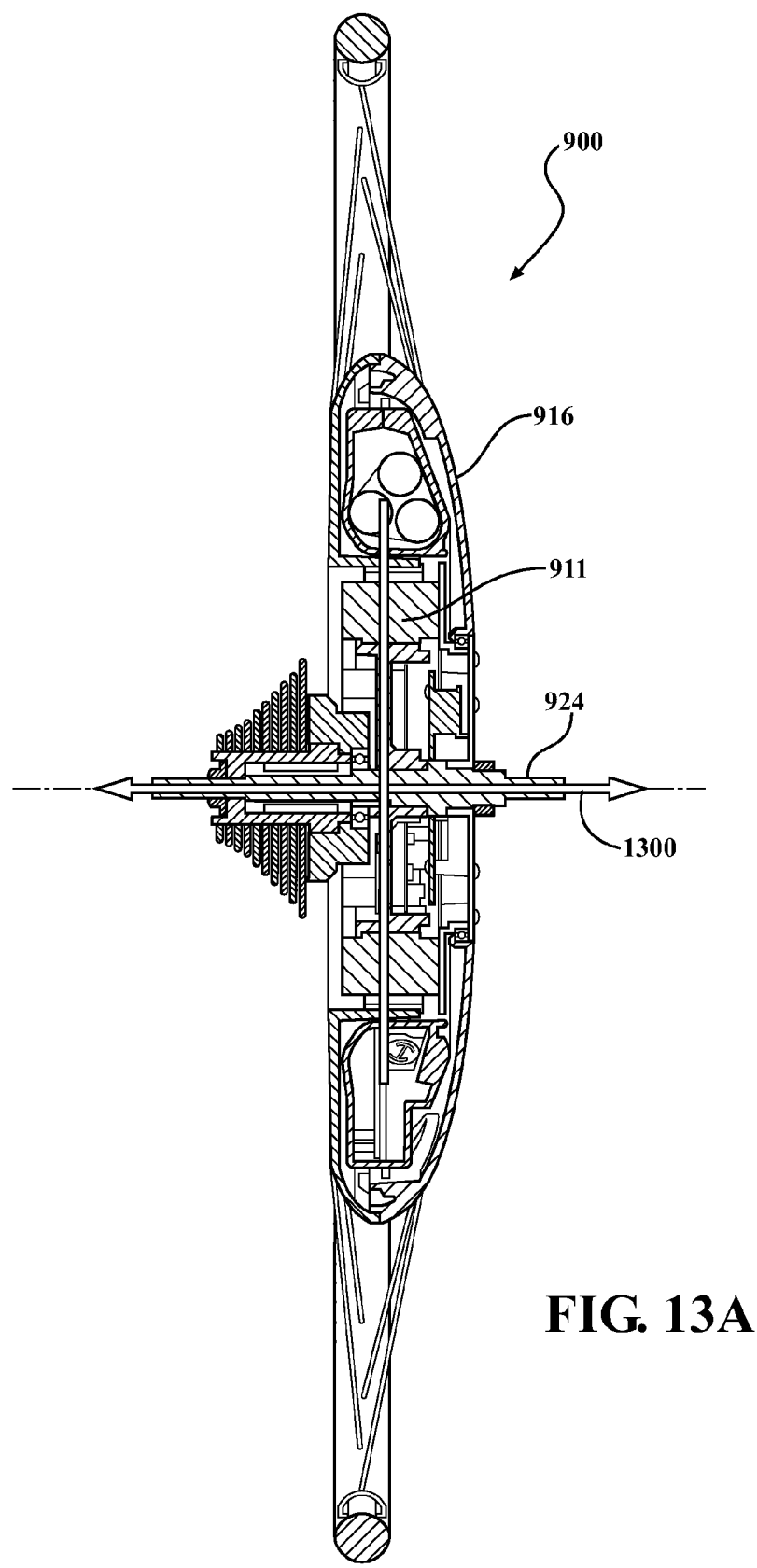
FIG. 13A is a sectional view for a thermal path within the electrically motorized wheel.
Figure 13B:
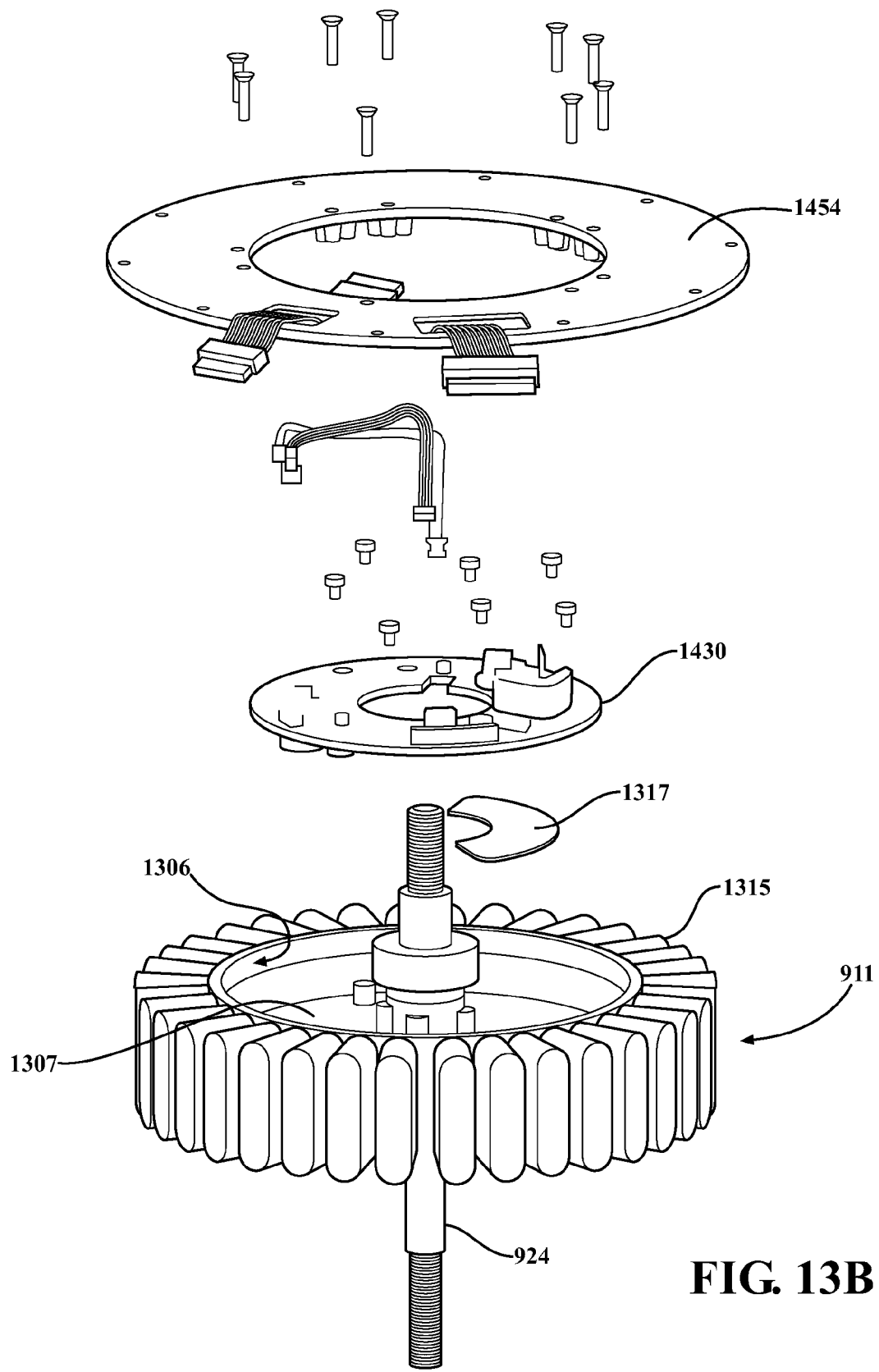
FIG. 13B is a perspective view for a thermal path within the electrically motorized wheel.
Figures 1, 13C:
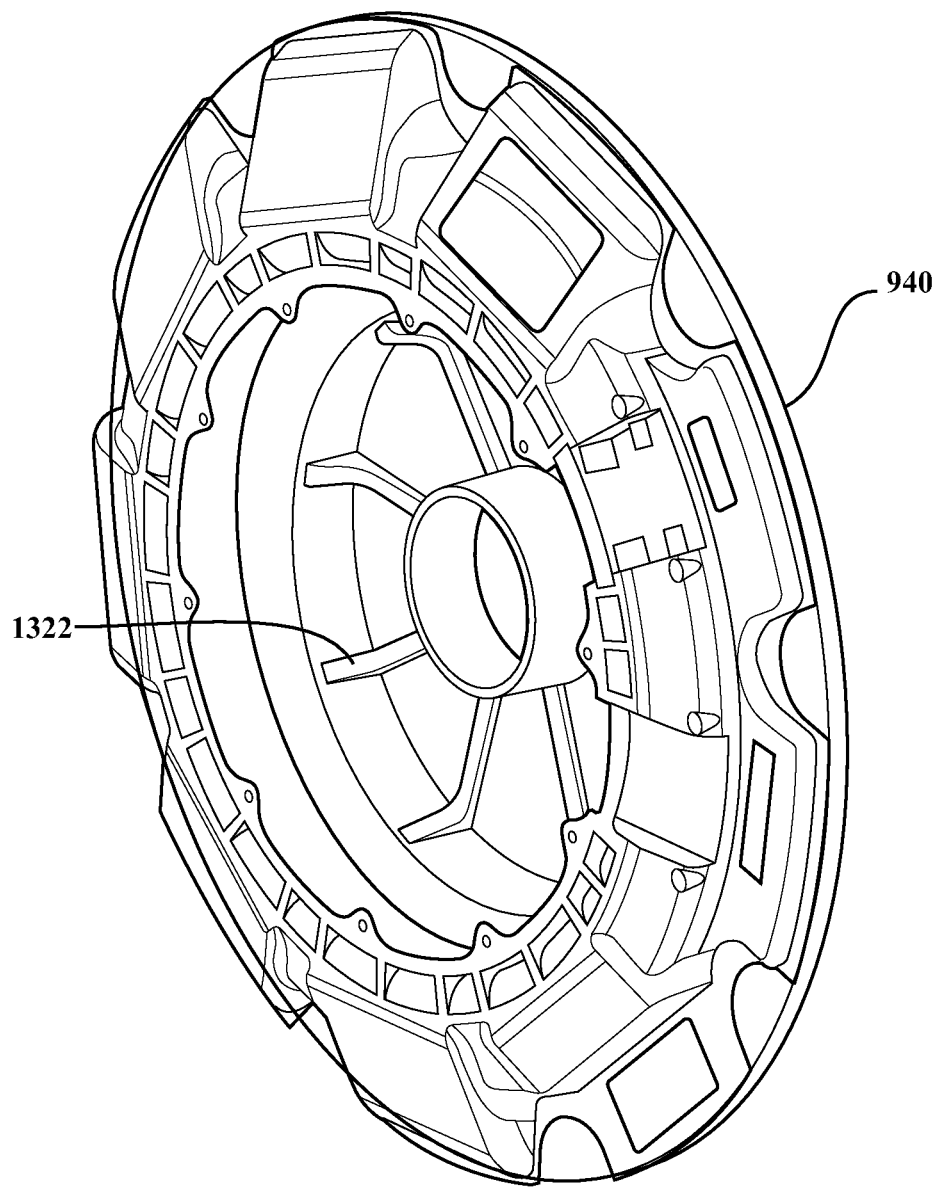
Figures 2, 13C:
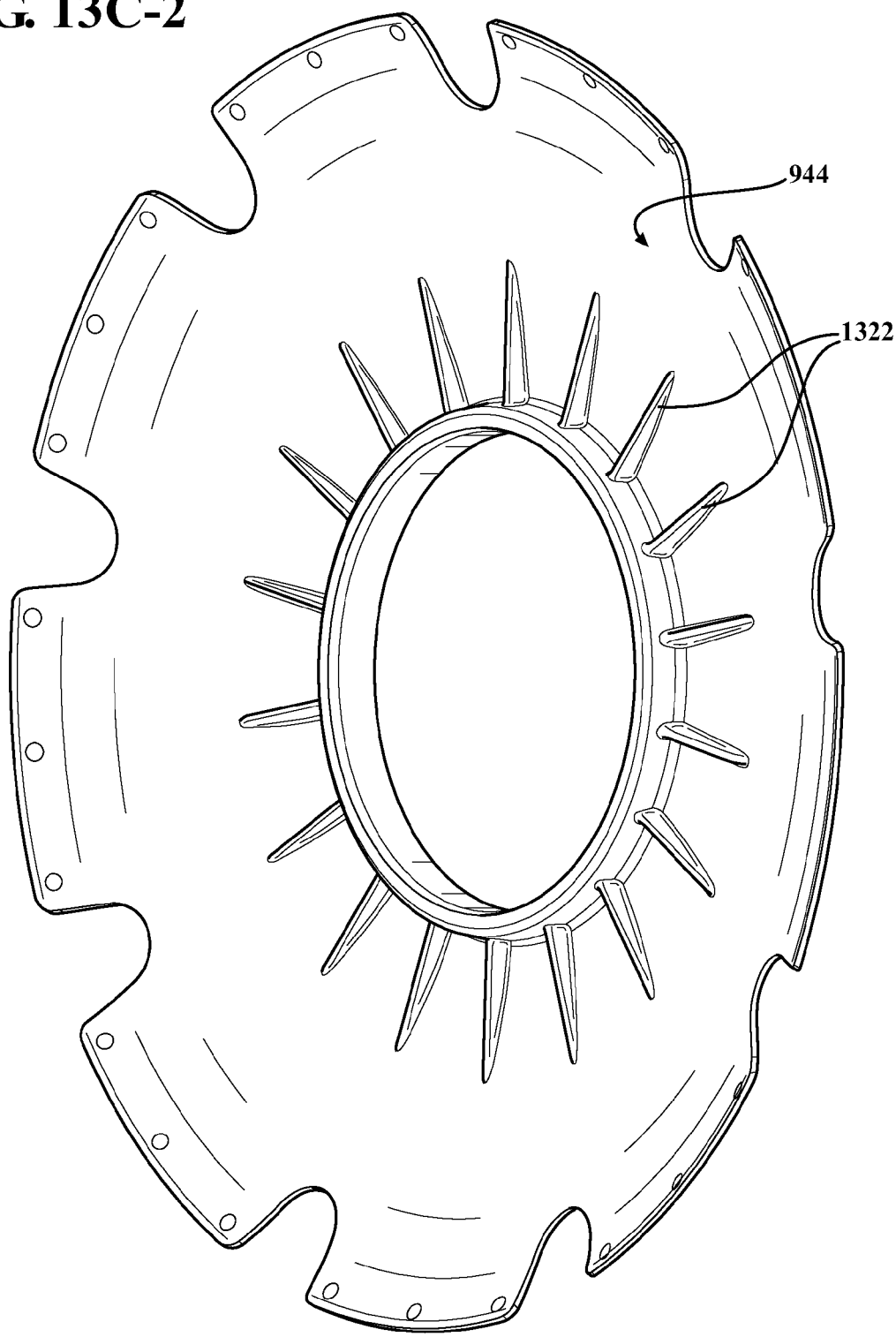

With reference to FIGS. 13A and 13B, passive thermal management is performed through the conduction of heat along a thermally conductive path 1300 to the shaft 924, thence into and/or through the hub shell assembly 916 and/or into and through the vehicle frame to which the shaft 924 is mounted. Both the electric motor windings 1315 of the stator 911, and the main control board 1430 of the control system are rotationally static in embodiments.

Referring to FIG. 13B, in embodiments, the motor windings 1315 surround a hub 1306 of the stator 911, while a heat generating electronic board, such as the main control board 1430 is mounted directly to the hub 1306. The control system thus utilizes a web 1307 of the stator 911 as a heat sink for the main control board 1430. A thermally conductive, yet electronically insulated pad 1317 may also be utilized between the main control board 1430 and the stator 911.

The thermally conductive path 1300 may be defined from the motor windings 1315 to the hub 1306 and thence from the hub 1306 to the shaft 924 on which the electrically motorized wheel 900 is mounted. The thermally conductive path 1300 thereby extends into the vehicle frame to which the shaft 924 is mounted as the stator 911 is mounted to the shaft 924 that is attached to the frame of the vehicle. Some of the heat from, for example, the control board 1430 and the motor windings 1315, thus ultimately flows through the stator 911 to the shaft 924, thence to the frame along the thermally conductive path 1300. The frame, such as that of a bicycle or a wheelchair, thus operates as a heat sink of significant volume.

To further facilitate thermal dispersion, the hub 1306 may be manufactured of a thermally conductive material such as Aluminum, Steel, and other pure metals or alloys.

With reference to FIGS. 13C-1-13C-2, the hub shell assembly 916 may form a portion of the thermally conductive path 1300. To still further facilitate thermal dispersion, a drive side shell 940 may include a multiple of convection elements 1322. The removable access door 944 may alternatively or additionally include convection elements 1322 (FIG. 13C-2). The convection elements 1322 may be fins of various thermally radiative shapes that are located, for example, on the interior surface of the drive side shell 940, and/or the interior surface of the removable access door 944 to maximize airflow such as within and/or along gaps through which air may inherently flow. The convection elements 1322 may be otherwise positioned to facilitate a direction of airflow and/or furthers locate the hub shell assembly 916 in proximity to the heat generating component to facilitate a short thermally conductive path 1300 therebetween. That is, the convection elements 1322 may guide free stream airflow as well as that airflow which is generated from the rotation of the rotating hub shell assembly 916.

The drive side shell 940, removable access door 944, and/or other shell components of the hub shell assembly 916 may also be involved in heat exchange with the environment surrounding the electrically motorized wheel 900. The hub shell assembly 916 may be manufactured of a relatively thin (e.g., about 2-4 mm thick), lightweight material such as aluminum, magnesium, titanium, or another alloy for heat transfer without air exchange. For example, thermal energy from heat-generating components such as the motor windings 1315 and/or the control board 1430 may be transferred to the hub shell assembly 916 without following the conductive heat transfer path described above via convection, agitation, and/or radiation. The thermal energy may then be conducted through the drive side shell 940 and/or the removable access door 944 and thence be transferred to the ambient environment, thereby cooling the electrically motorized wheel 900. In some configurations, the drive side shell 940 and/or the removable access door 944 may not even need be made of an efficient thermal conductor, but this conduction may still be facilitated by the relatively thin structure of the hub shell assembly 916.

It should be appreciated that other cooling schemes such as internal air channels, convection cooling, impingement cooling, effusion, pin film cooling, transpiration cooling, boundary layer cooling, and thermal barrier coatings may alternatively or additionally be utilized.

Some of the heat from, for example, the battery system 906, the main control board 1430, and/or the motor stator 911, heats the air inside the spinning hub shell assembly 916 and the air transfers the heat to the full internal surface area of the spinning hub shell assembly 916 which, in turn, transfer the heat through conduction to the external surface and through convection to the ambient air around the exterior of these hub shell assembly components. The convection elements 1322 may also operate as heat sinks to facilitate the collection of heat from within the hub shell assembly 916 and transmission thereof through the exterior thereof. The convection elements 1322 may also be utilized to direct the heat from one side of the hub shell assembly 916 toward the other.

Figure 13D:
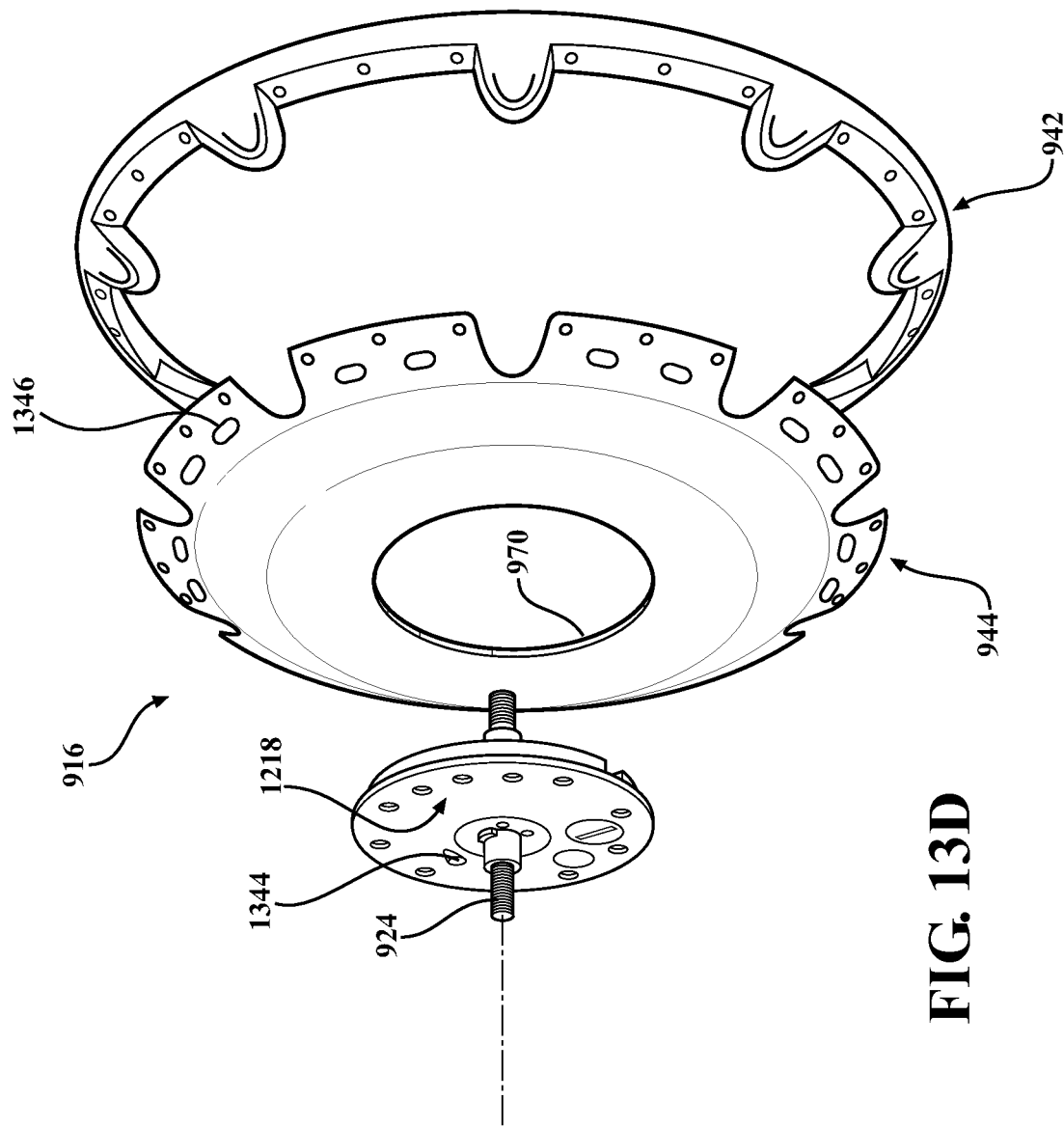
FIG. 13D is an inner side view of an airflow path through the electrically motorized wheel.

Referring to FIG. 13D, in other embodiments, an active cooling system communicates air through or over the heat generating components to conduct heat therefrom. The air may be introduced to the interior of the spinning hub shell assembly 916 through an air intake 1344 (illustrated schematically) such as a vent, valve, scoop and/or pump which may be actively controlled to open and close so as to initiate, moderate, and control, the airflow.

In one example, airflow may be selectively induced by opening the air intake 1344 on the user interface cover plate 1218 to the ambient environment to provide passive cooling. Alternatively, one or more heat exchangers within the hub shell assembly 916 may be utilized to actively cool the airflow. For example, a vent, valve and/or pump may induce airflow in response to a sensor that identifies a temperature above a predetermined or calculated threshold. Such selective operation may be performed so as to minimize aerodynamic interference. That is, drag is typically greater when the air intake 1344 is open than when closed. Alternatively, the air intake 1344 may be operated by centripetal force, opening under the force of rotation and closing when the wheel is stopped. This would facilitate water resistance yet provide ventilation. Air intakes 1344, which may be located in the rotationally fixed user interface cover plate 1218, intake air which is then circulated through the interior of the spinning hub shell assembly 916 and essentially flung radially outward through outlets 1346 in the removable access door 944.

In embodiments, another fluid such as a gas, vapor, or liquid, may be used. The fluid cooling system may include one or more pumps, valves, or the like, as well as sealed fluid channels that pass the fluid over parts that benefit from conductive cooling. For example, a fluid may be passed over or through one or more of the heat generating components. Alternatively, the fluid may be passed over or through the hub shell assembly 916 to provide a chilled environment for the components therein. The fluid system may be under control of the control system, which may be responsive to inputs, such as from a user or based on a temperature sensor.

Figure 13E:
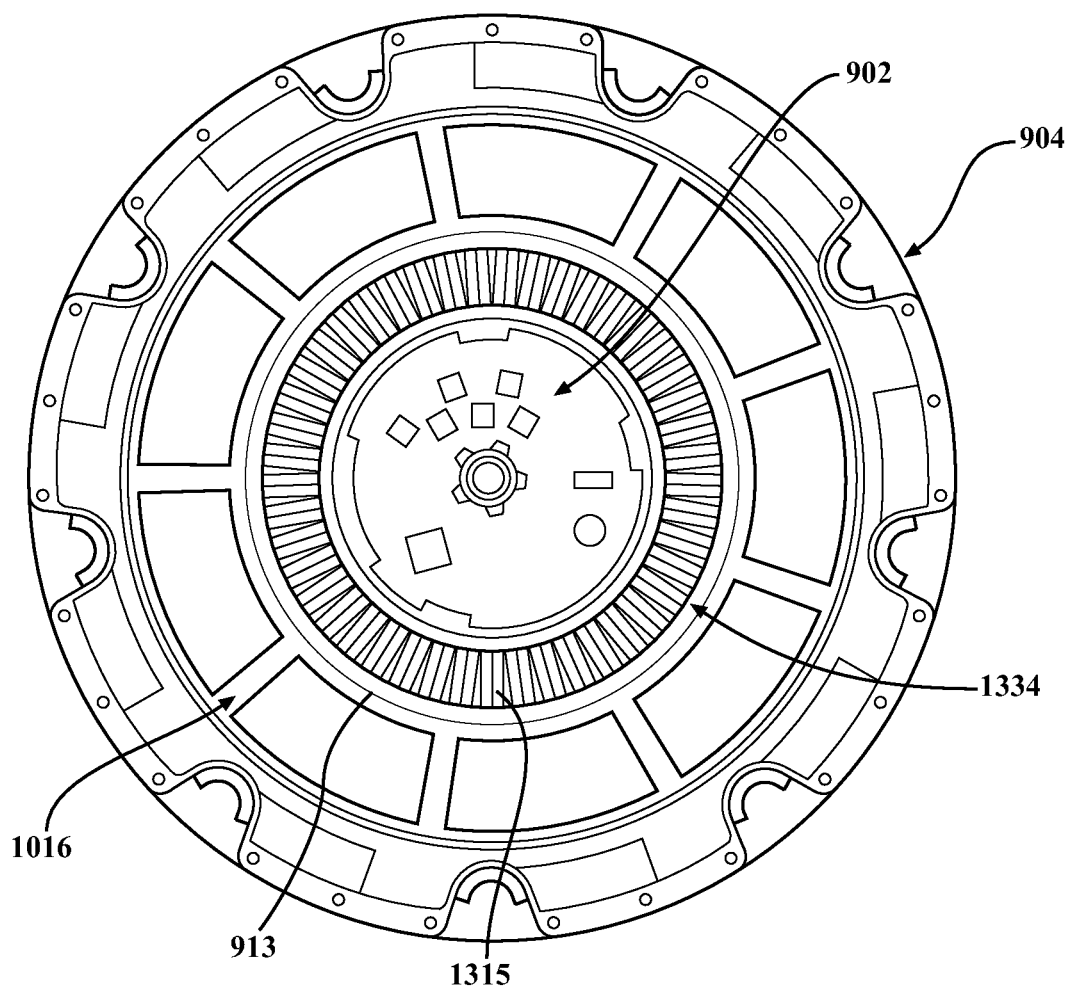
FIG. 13E is a side view of an airflow path through the electrically motorized wheel.

With reference to FIG. 13E, the rotating system 904 and the static system 902 may form a gap 1334 of, for example, about 2 mm between a stationary motor winding 1315 and a magnetic ring rotor 913 that is fixed to, and rotates with, the shell 940. When power is supplied to the motor winding 1315, a magnetic current is induced from the electrical wires wound on the stator 911 causing the magnetic ring rotor 913 and the shell 940 to rotate. In embodiments, the magnetic ring rotor 913 is arranged between the contoured battery 1016 and the motor windings 1315—both of which are stationary—but are organized such that the magnetic ring rotor 913, located therebetween, rotates with the shell 940.

A gap may also be located between the drive side shell 940 and the contoured battery 1016 as the drive side shell 940 rotates relative to the rotationally stationary contoured battery 1016. These gaps operate as a thermal insulator. To avoid this insulation effect and induce airflow for cooling, the gap widths may be optimized for passive thermal cooling, mechanical operation, and combinations thereof. To further facilitate airflow direction such as within and/or along gaps, convection elements 1322 may be placed to facilitate such passive thermal cooling.

Figure 13F:
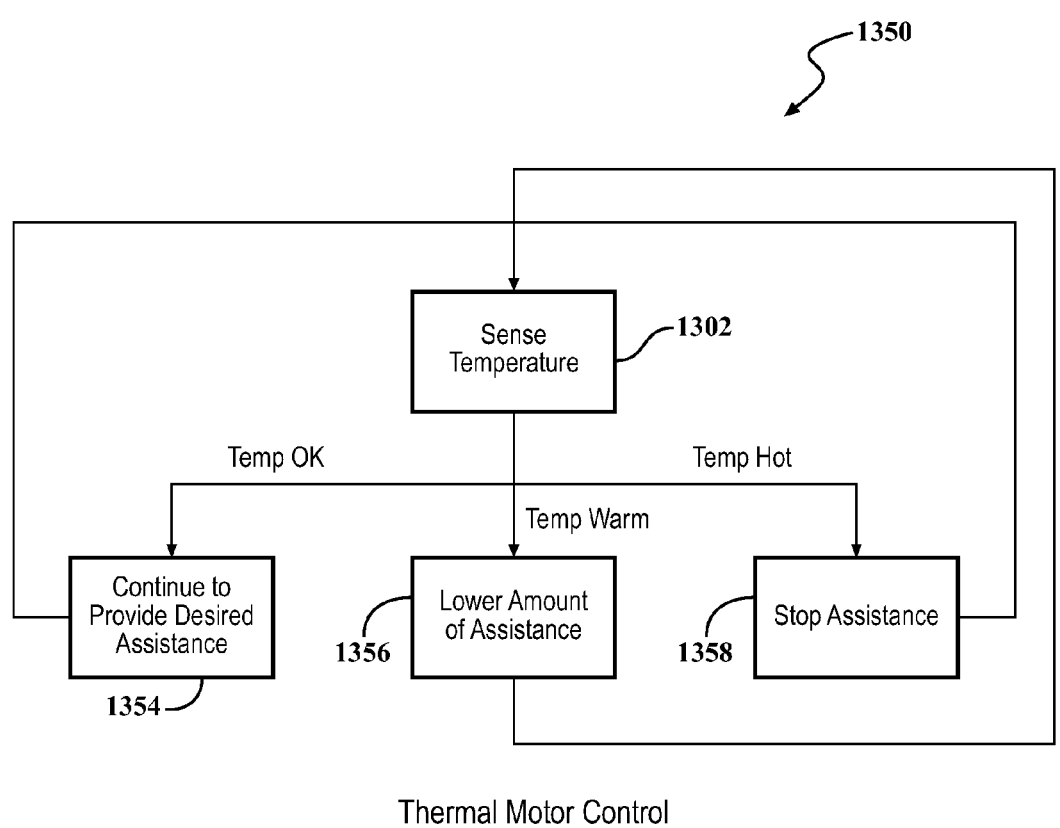
FIG. 13F is a schematic view of a power system for the electrically motorized vehicle.
Figure 13G:
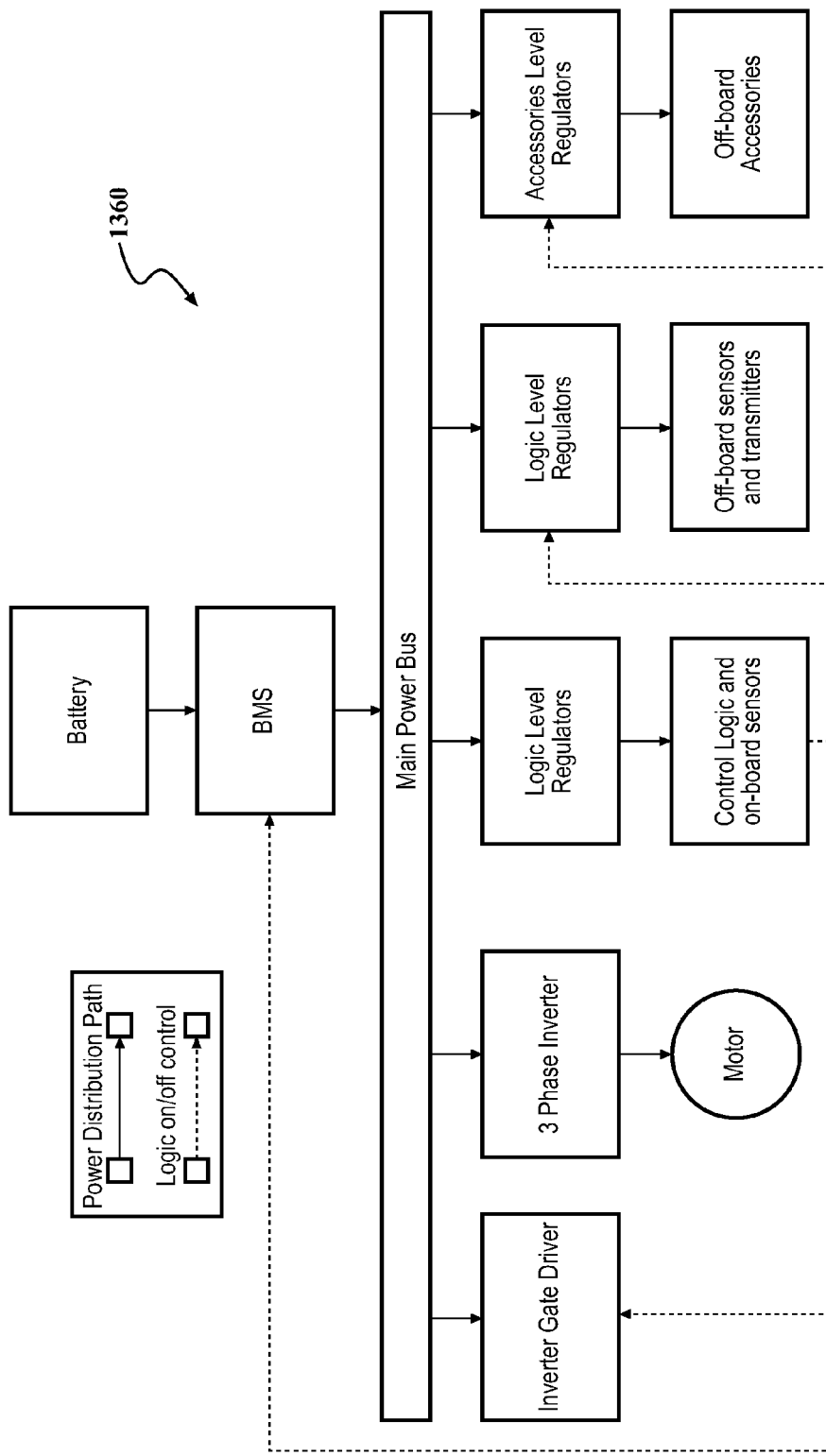
FIG. 13G is a schematic view of a power system for the electrically motorized vehicle.

With reference to FIG. 13F-13G, active thermal management according to embodiments, is performed through control of the electric motor to limit temperatures below a desired maximum. Such active thermal management may be performed through control of power usage within the power distribution system 1360 of the electrically motorized wheel (FIG. 13G).

In embodiments, active thermal control algorithms 1350 generally include sensing temperatures 1302 of the electric motor, the main control board and energy stage components, electronic controllers, battery, or other heat sensitive components then attenuating operation of the electric motor, the primary heat source, to limit these sensed temperatures below a desired maximums by selectively attenuating an assistance/resistance 1354, 1356, 1358.

Figure 14A:
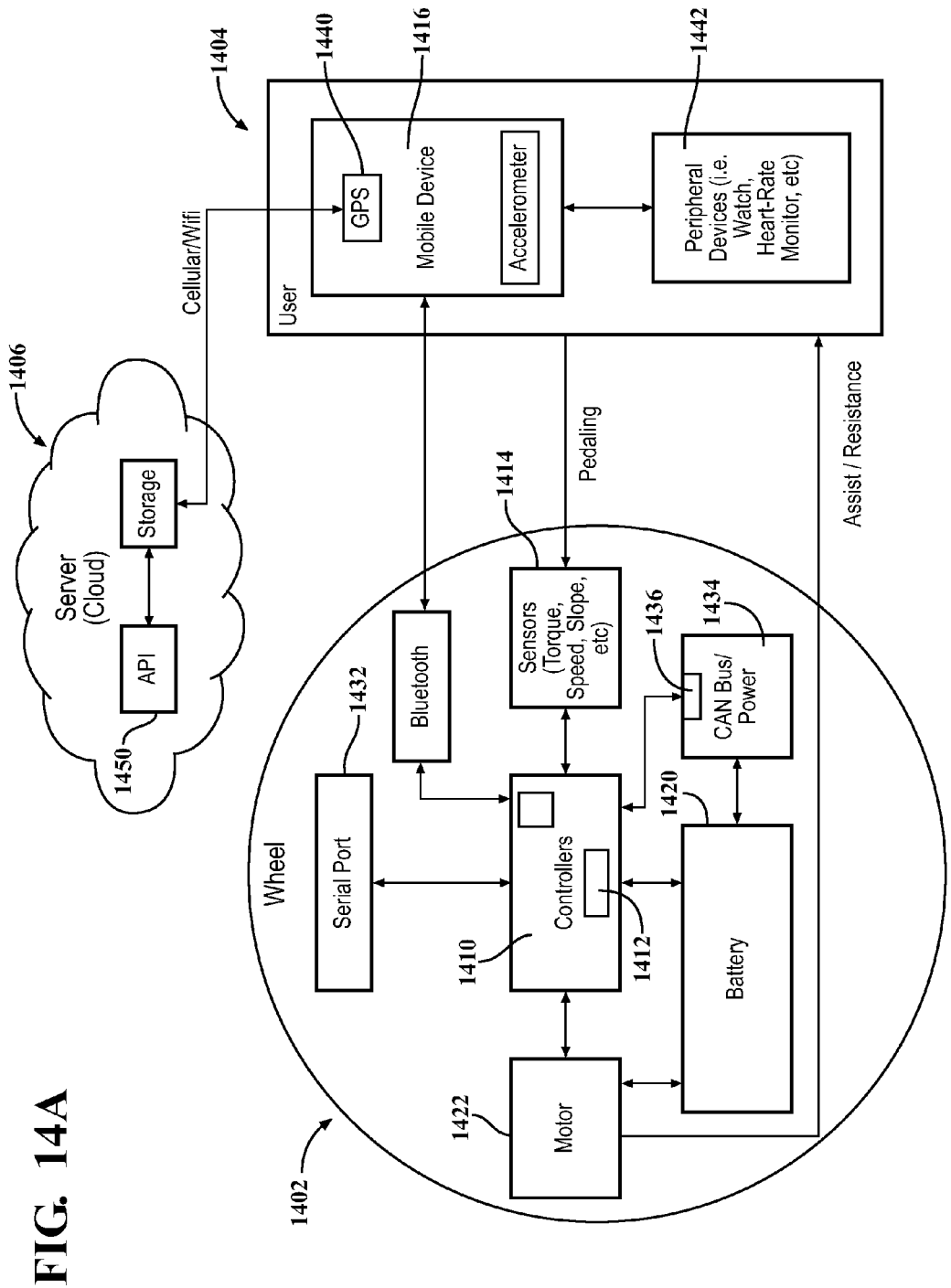
FIG. 14A is a schematic view of a system for the electrically motorized vehicle.

With reference to FIG. 14A, a data flow 1400 can be provided between the electrically motorized wheel 1402, the user 1404, and a server 1406 such as a cloud-based server/ API or other remote server, module, or system. Various communication and data links may be provided between the electrically motorized wheel 1402, the user 1404, and the server 1406 such as a mobile device 1416 which serves as an interface therebetween for relatively long-range cellular and satellite type communication. That is, a smart phone of the user associated with the electrically motorized wheel 1402 operates as a data link between the electrically motorized wheel 1402 and the server 1406. The electrically motorized wheel 1402 is operable to calculate the assistance and resistance required at any given time, i.e., essentially instantaneously.

The control system 1410 utilizes an algorithm 1412 that applies data from a sensor system 1414 and, if available, the mobile device 1416, to determine an essentially instantaneous energy transfers between a battery system 1420 and an electric motor 1422. The control system 1410 may also regulate and monitor the sensors 1414 and connected components for faults and hazards for communication to the mobile device 1416.

Figure 14B:
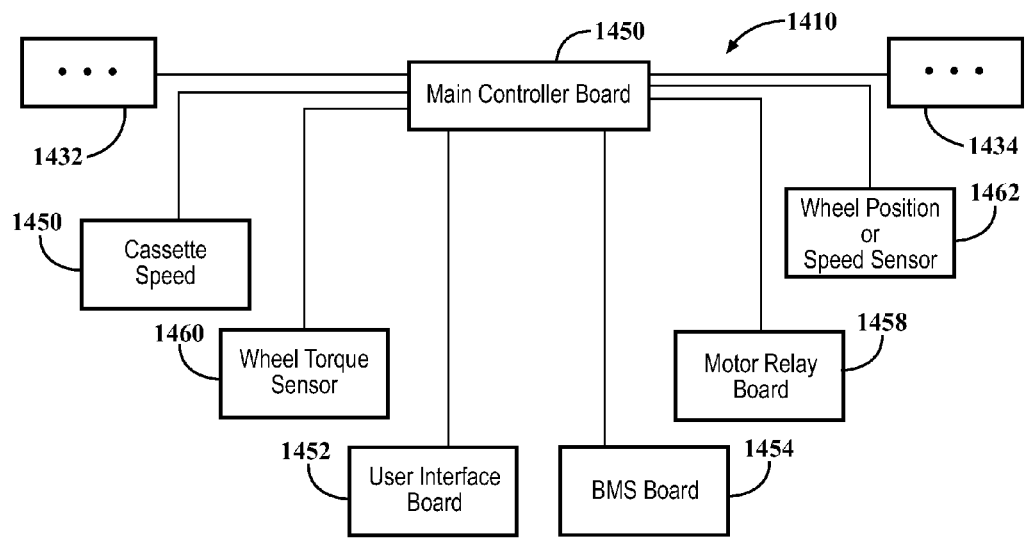
FIG. 14B is a schematic view of a system for the electrically motorized vehicle.

With reference to FIG. 14B, the control system 1410 may include a multiple of printed circuit boards to distribute control, facilitate maintenance, and thermal management thereof. In this example, the control system 1410 includes a main control board 1450, a User Interface board 1452, a Battery Management System (BMS) board 1454 (FIG. 12B), a motor interface board 1458, and a sensor system, here disclosed as a wheel torque sensor 1460, and a wheel speed sensor 1462. It should be understood that the boards may be otherwise combined or distributed. It should also be understood that other sensors such as a GSM, GPS, inertial measurement sensors, weight on wheel strain sensors, chain strain sensors, cassette speed sensors, environmental sensors, and other sensors may be provided and integrated into the one or more of the boards. Further, various ports and hardware interface may additionally be provided, to include, but not be limited to, a diagnostic connector, a charger connector, and/or others.

The User Interface board 1452, in one example, may include relatively short-range wireless systems such as Bluetooth, IEEE 802.11, etc., for communication with various mobile devices.

The motor interface board 1458 may be mounted to the motor hub 1306 and hosts the motor relay, the motor commutation hall sensors, the motor temperature sensor, and/or other motor related sensors. The motor interface board 1458 collects those signals to one connector for connection to the main control board 1450.

The Battery Management System (BMS) board 1454 (FIG. 9E) may, in one example, be mounted to the contoured battery 1016. The motor interface board 1458 may be mounted to the stator 911 (FIG. 9F) such that the stator 911 operates as a heat sink.

The control system 1410 may further include a hardware interface 1432, e.g. input ports, data ports, charging ports, device slots, and other interfaces, that permit the plug in of other sensors, hardware devices, and/or peripherals to provide communication with the main control board 1450 and associated boards. Alternatively or in addition, each board may have one or more hardware interface 1432 such as a power port for the Battery Management System (BMS) board 1454.

Additionally, a charging port 1434 that, similar to a USB connector, provides not only power, but also data transfer. This may be performed through, for example, a controller area network (CAN bus) interface 1436 integrated into the connection. Between the hardware interface 1432 and CAN bus interface implementation of additional sensors or external plugin hardware components is readily enabled, e.g., extended battery, lights, humidity sensors, proximity sensors, speakers, anti-theft devices, charging racks, etc.

Data from the hardware interface 1432 may be communicated to the mobile device 1416 via short-range wireless systems. The data may be processed by the mobile device 1416, and/or further transmitted via the mobile device 1416 to a server for processing. Data may be communicated directly from the electrically motorized wheel to the server using relatively long-range wireless communications systems such as cellular, satellite, etc.

Feedback to the user, alterations to control parameters, and/or other data may be communicated to the electrically motorized wheel on the basis of the processed data. In one example, distance sensor data, e.g. RADAR, SONAR, LIDAR, imagery, etc., that provide for identification of an approaching object, may feedback such identification to the user in the form of an audible, visual or tactile sensation. For example, a rear directed camera might communicate imagery to the mobile device 1416 so that a user may be readily apprised of traffic approaching from the rear. Alternatively, identification of an approaching object by the rear directed camera may result in a tactile output from the electrically motorized wheel, e.g., a shaking or jitter, to gain the attention of the user.

In another example, environmental data indicating high humidity levels, altitude, and/or other environmental factors may be utilized to adjust the control parameters for a given mode such that additional motor assistance is provided under such conditions. For example, as the vehicle traverses a mountain, additional assistance may be provided at higher altitudes.

The mobile device 1416 may collect data at a rate of, for example, about 1 data point per second. Each data point may include time and location data stamps from, for example, a GPS module 1440 or the inertia navigation system. Applications to interface with the electrically motorized wheel 1402 may thus perform minimal calculations. Other peripheral devices 1442 such as a wearable health monitor may also be utilized with, or as a replacement for, the mobile device 1416 to provide data collection and/or communication with the electrically motorized wheel.

The electrically motorized wheel may also communicate with a server via the mobile device 1416. The server enables reception and/or streaming of data collected by one or more electrically motorized wheels for communication and display essentially in real time from the mobile device 1416 to the electrically motorized wheel, another electrically motorized wheel, and/or a fleet of electrically motorized wheels such as a delivery service, shopping cart fleet of a store, etc.

The collected data may include direction of travel, faults associated with the fleet vehicle, and other data. Aggregated data collected from a single electrically motorized wheel, or multiple electrically motorized wheels, may then be utilized to, for example, analyze routes and modes, provide different analyses of the data, customize a user experience, and/or generate suggestions for a more efficient commute.

In embodiments, the hardware interface 1432 may be utilized to charge devices such as a mobile device 1502. That is, the mobile device 1502 such as a smart phone may be utilized as a user interface to the electrically motorized wheel as well as being charged therefrom.

With reference to FIG. 15A, a mobile device user interface 1500 for a mobile device 1502 may provide selection among various operational modes 1504. The mobile device user interface 1500 may be a downloadable application or other software interface to provide, for example, selection among the operational modes 1504, data communication, and/or data transfer to and from the electrically motorized wheel. In alternative embodiments, the operational mode may be selected for the user, such as based on user inputs, a user profile, information about user history, environmental factors, information about a route, inputs of third parties (e.g., a doctor or trainer) or many other factors disclosed throughout this disclosure. Selection of an operational mode may occur at the wheel 100, on the user mobile device, or remotely, such as on a server or other external system.

In embodiments, an algorithm 1508 that governs a control regime for a device of the wheel 100 such as to control operation of the electrically motorized wheel or device thereof typically includes a set of parameters in which each parameter is a placeholder for a multiplier, or gain, in the algorithm 1508. The selected mode 1504 provides values for the set of parameters, one of which may optionally select which algorithm or control regime to use. These values may be input into the selected algorithm 1508 to provide an associated level of assistance or resistance the user will experience in response to inputs, such as from the sensor data from the sensor system 1510, data from external systems (e.g., information systems containing terrain information, weather systems, traffic systems, and the like), and further input from the user. It should be understood that each parameter, multiplier, and/or term may correlate to some control relationship such as exponential, a linear function, a step function, or a separate calculation, that relates a control input to a specified level of motor control output.

The system may transition among various operational modes, such as based on user selection or other determination of the appropriate operational mode. Alternatively, in embodiments where the wheel itself does not automatically select an operational mode based on sensor or similar inputs, if no mobile device 1502 or other selection facility is in present communication with the control system 1512, a standard mode may be automatically set as a default operational mode, or the wheel may use the most recently used past mode, if a mobile device or other selection facility was previously connected. Generally, in bicycle embodiments, the user need only ride the bicycle, and the wheel sensor system 1510 will sense various input data such as torque, slope, speed, etc., that is then communicated to the control system 1512 that employs the algorithm 1508. The operational mode selected by the user via the mobile device, or otherwise selected, essentially provides values for the parameters in the algorithm 1508. When the parameters, having the appropriate values for the selected operational model, are applied to the present set of inputs (such as sensed by the sensor system 1510 or otherwise obtained, such as by a data collection facility of the wheel 100), the algorithm produces an output. The output determines the current control command for the wheel, which in embodiments is essentially a specification of the nature and extent of the energy exchange between a battery system 1514 and an electric motor 1518. The output of the electric motor 1518 is the level of assistance or resistance that the user experiences when operating the wheel 100, which varies for a particular situation, based on the selected mode.

For some operational modes, the value for a single parameter may be supplied to the algorithm 1508. This value may represent an overall gain for the assistance provided. For example, a standard mode may provide an overall gain value of one (1) to the algorithm 1508, in contrast to a "turbo" mode that may result in an overall gain value greater than one (>1) being supplied to the algorithm 1508. Conversely, a selection of an "economy" mode may result in an overall gain value less than one (<1) being supplied to the algorithm 1508. Alternatively, the overall gain may be used to adjust the algorithm based upon the total payload weight the wheel is propelling, compensate other environmental conditions such as a head wind, or other conditions.

For some operational modes, a plurality of parameter values may be supplied to the algorithm 1508. These values may be associated with parameters representing multipliers or gains for different portions of the algorithm 1508 to control various components that contribute to the overall ride, such as wheel data, user input data (such as torque or cadence), environmental factors (such as slope or wind resistance), "gestures" or command motions, such as sensed at the user inputs (such as backpedaling to control braking), etc. The parameters may alternatively or additionally represent multipliers for different sensor values and/or calculated values representative of various components that contribute to the overall ride.

In embodiments, the algorithm 1508 can have a general form that relates control inputs to outputs. The control inputs may fall generally into a set of categories such as inputs that relate to inputs from the rider or another individual, either sensed (e.g., as rider torque) or entered data (e.g., as a riders weight or age, a training goal entered by a physical therapist for the rider, a work constraint entered by a physician of a rider, or the like); inputs that relate to the operational state of the electrically motorized wheel (e.g., wheel speed); inputs that relate to the conditions of the environment or operational context of the wheel (e.g., slope, temperature, wind, etc.); and inputs collected from various data sources (e.g., other vehicles, other wheels, traffic networks, infrastructure elements, and many others). These inputs may be combined with other parameters such as gains, or passed through other conditioning functions such as a filter. The output of these combinations of inputs may be the "terms" of the algorithm 1508. These terms may be linear, non-linear, discrete, continuous, time-dependent, or time-invariant.

These terms may then be summed, multiplied, divided, or otherwise combined (such as taking the maximum or minimum of some or all of the terms) to provide one or more outputs. In some embodiments, it may be advantageous to provide a multitude of terms in the control system that isolate or separate conditions under which a user would receive assistance or resistance. For example it may be advantageous to be able to have a separate terms for the amount of effort that a rider puts in and for aerodynamic forces such as riding against the wind.

This beneficially allows each term to have a form that is suited to the input and underlying phenomenon. For example in the case of the rider effort, it may be a linear or proportional response, and in the case of aerodynamic forces it may be proportional to the square of the wheel or vehicle speed at lower speeds and a cube or other function at higher speeds. The rider, or one specifying the response of the wheel to inputs, such as a provider of wheels, may thereby readily adjust the gains independently to customize the response of the control to the conditions that they care about, e.g. hills, wind, power, or the like.

Additionally, multipliers on some or all of the terms allow the gains for each term to be scaled together in response to another input. For example, increasing the overall responsiveness to rider inputs with environmental temperature could provide the rider with more assistance when operating in high temperatures and thus prevent a user from excessive exertion or perspiration.

In embodiments, the algorithm 1508 uses a combination of terms (or types of terms). For example, a mechanical drive unit input torque and a wheel operational state (such as wheel speed) may be summed to construct a motor command with the sum including a term proportional to rider input torque and a term proportional to wheel speed. In other examples, terms such as ones based on environmental inputs or data collected by the wheel may similarly be combined with any of the other input types noted in this disclosure.

In another example, the algorithm 1508 use a summation of a series of input terms, each multiplied by gains (which may be adjusted as noted above based on the selected operational mode of the wheel) to yield a command, such as a current command for the motor.

In embodiments, given the various inputs (e.g. rider inputs such as: mechanical drive unit input torque; mechanical drive unit input speed; and rider weight; various wheel operational states, such as wheel speed and angle of the device with respect to gravity; data inputs such as safety information from a traffic system or other vehicle; and environmental inputs such as ambient temperature) a motor command equation may be constructed such as by creating terms proportional to various inputs. For example, the equation may include a term proportional to rider input torque; a term proportional to the square of wheel speed; a term proportional to the angle of the device with respect to gravity; a multiplier that is proportional to ambient temperature; a multiplier that is zero when input speed in zero and increases as input speed approaches wheel speed; and a multiplier that is proportional to the rider's weight (optionally normalized to a base weight). The terms may then be summed, and where applicable the sum may be multiplied by a multiplier.

In an embodiment, the gains may be independent and variable over time. This allows the rider, provider, or other user to adjust the response to a desired preference. Additionally, multipliers may allow some overall multiplication of the response to factors that in general may warrant an overall increase in assistance, such as a hot ambient temperature.

Alternatively, or in addition, the algorithm 1508 can be constructed in a manner that allows switching between different forms, such as among the examples given above. In this case, one parameter of the equation may be an identifier for which form of equation to use (i.e., which terms, gain parameters and multipliers are to be used, such as for a selected operational mode).

Figures 15B, 15C:
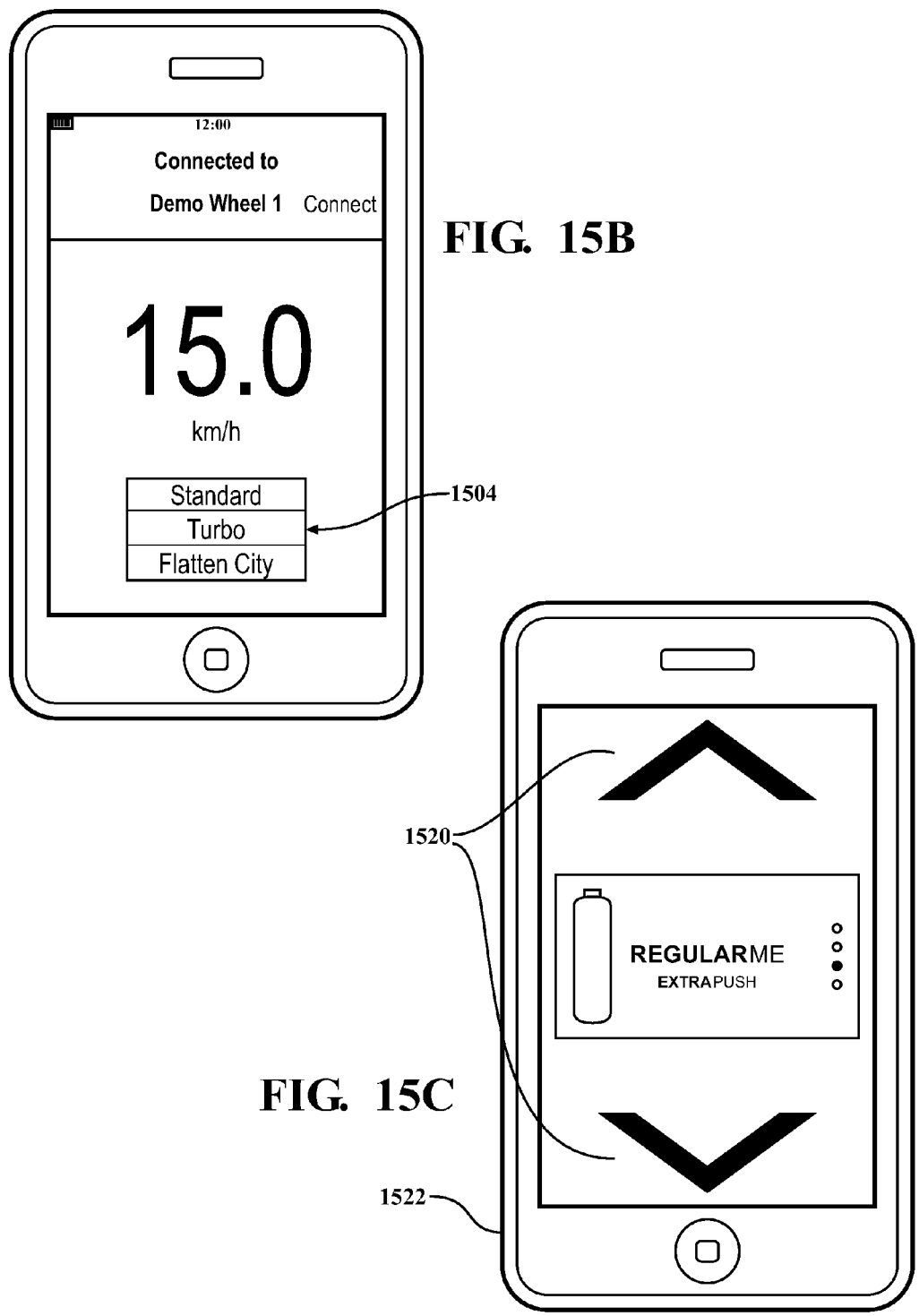
FIG. 15B is a page of a mobile device in communication with the electrically motorized vehicle.
FIG. 15C is a page of a mobile device in communication with the electrically motorized vehicle.

With reference to FIG. 15B, the user may select an operational mode from a multiple of operational modes that alters the behavior of the electrically motorized wheel. Each mode may include one or more parameter settings, and/or combinations thereof to change the operational behavior of the electrically motorized wheel. Example operational modes 1504, as will be further described, may include a "turbo" mode for maximum assistance; a "flatten city" mode; "fitness challenge" mode; a "maximum power storage" mode a "standard" mode; a "exercise" mode; a "rehabilitation" mode; a "training" mode, a "commuter" mode, a "maximum help" mode etc. The "flatten city" mode may provide motor assistance on ascents and hill climbs, with braking on descents to thereby "flatten" the terrain. The "commuter" mode may allow a user to enter a "not-to-be-exceeded" torque or exertion level to modulate the assistance. The exercise mode may allow a user to enter a total number of Calories to be burned, a desired rate of Calorie burn, a maximum level of exertion or torque, etc. Each mode may also include adjustable parameters to automatically modulate the assistance provided over the duration of the ride by the electrically motorized wheel such as a minimum time that the assistance must be available, maximum speed, and/or others.

The mobile device user interface 1500 may present the multiple of operational modes 1504 in an order that allows a user to browse different control parameters, such as Eco-Mode; Maximum Assistance Mode; Target Energy Mode, Maximum Energy Storage, etc. That is, a user can essentially scroll through a multiple of operational modes.

Alternatively, the mobile device user interface 1500 may provide an "automatic mode" that selects the desired mode automatically without user input. That is, the automatic mode may be speed based to select between modes during a trip so that the vehicle obtains the most efficient trip. Alternately, the automatic mode may be time based to select between modes during a trip so that the vehicle reaches a destination at a desired time. Such selections may be made based completely on sensor data determined by the electrically motorized wheel, or alternatively or in addition with data from a server or from other data devices that a user may be using such as a health monitoring device such as a heart rate monitor.

The "flatten city" mode provides assistance or resistance on non-level terrain. Adjustable parameters may include data about the level of assistance, minimum incline of the hill before rendering assistance, and others. That is, the amount of assistance while travelling uphill and the amount of resistance while traveling downhill may be controlled to require user input about equivalent to a user input required on a level surface.

The "maximum speed control" mode introduces braking on hills to limit the maximum speed of the vehicle. Such a "maximum speed control" may also determine the maximum permitted speed to particular legal jurisdictions as determined by a global Positioning Unit.

The "maximum energy storage" mode maximizes the power storage achieved. Such "maximum energy storage" mode may also be related to energy conservation or energy recovery.

The "fitness challenge" mode might include applying resistance to the electrically motorized wheel to require additional effort by the user and thus provide a work-out to the user.

The "fitness challenge" mode may provide parameter assistance and resistance to, for example, simulate intermittent uphill climbs, an uphill climb of a desired duration, height or other parameter. Such parameter assistance and resistance may be associated with a user's performance or preset conditions, work-outs, heart rate, etc. The "fitness challenge" mode may also provide visual/audible encouragement to user via a mobile device. The encouragement may indicate up coming challenges and an expected output by the user and may be presented on the mobile device user interface 1500.

Adjustable parameters for each mode may include data about the desired destination, a maximum desired exertion for the user, the maximum desired speed, current location, and others. Data such as destination may be used together with data on current geospatial location, possible routes to a destination and associated road modes, traffic data, user preferences, user capability/fitness level, together with data related to wheel capacity such as energy storage data and others. The combination of data may be used to suggest possible routes, manage power utilization over the selected or anticipated commute route, estimate remaining battery life based on available energy, user fitness level, topography of proposed route, etc.

With reference to FIG. 15C, the user interface may include relatively large buttons 1520 and/or icons for navigation functions such as scrolling through the different modes as well as other actions which may be performed while the vehicle is in motion, or idle during a trip (e.g. at a stop light). The use of the large buttons 1520 facilitates visibility and selection while riding. The large button 1520 may occupy a significant portion of the available screen area so as to enable easy selection by a user, for example, the buttons 1520 on the mobile device 1522 may each occupy a minimum of 1 inch by 1 inch of display space.

Figure 15E:
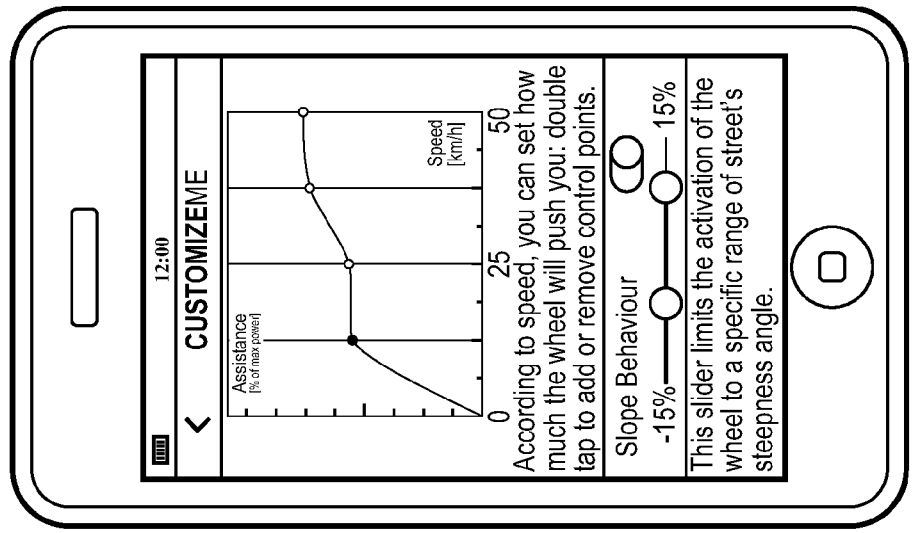
FIG. 15E is a page of a mobile device in communication with the electrically motorized vehicle.
Figure 15D:
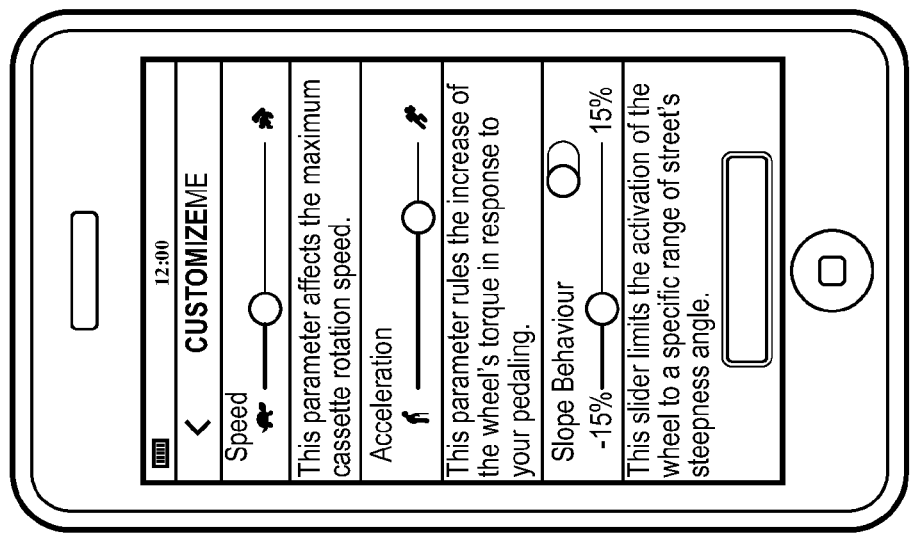
FIG. 15D is a page of a mobile device in communication with the electrically motorized vehicle.

Similar to creating custom sound settings with an equalizer, the user can create custom assistance modes from within the mobile application, or by logging into their account online. With reference to FIG. 15D, upon selection of an operational mode, the mobile user interface may permit the input of parameters 1530 such as a maximum speed of the cassette, an acceleration in response to pedaling, slope behavior and/or other inputs. In one example, the inputs may be provided via a slider. Once the parameters have been entered, the user mobile interface may transition to a progress screen 1538 (FIG. 15E) that highlights progress to the goal such as the destination and specified calorie burn.

Figure 16D:
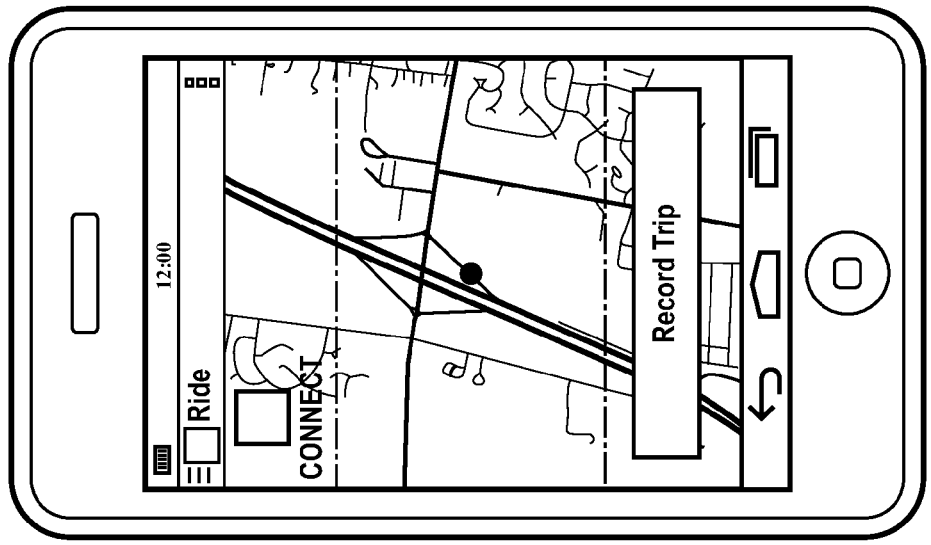
FIG. 16D is a mobile device page of a system for the electrically motorized vehicle.

With reference to FIG. 16A, a trip 1600 may be represented as, a line 1602 with one or more events 1604 there-along. The mobile device or other application may calculate the trip 1600. A directional arrow 1606 may also be provided for guidance along a calculated route 1608 to navigate without a map, and without turn-by-turn directions. Instead, the directional arrow 1606 points in the direction of the destination which may be advantageous as bicycles need not be necessarily restricted to motor roadways.

The route 1608 may be accompanied by other symbology such as, for example, distance notation 1616 to indicate how far to the next turn. Further, the view may be presented to account for the vehicle direction of travel such that the current direction is, for example, straight up to facilitate orientation. Other symbology such as an elevation graph 1618 may be provided to indicate upcoming hills, a time such as ETA 1620, and other such navigation and trip related data.

In embodiments, the route 1608 may be enhanced for a particular user through a slight alternation 1614 in the route 1608 (FIG. 16B). For example, various third party data sources such as demographic data of an area may be utilized to determine the route 1608 so as to avoid areas based on various parameters in response to a user selection.

The data from each trip 1600 may be communicated either directly to a server 1610 using a wireless or cellular technology, or from the control system of the electrically motorized wheel to the connected mobile device 1612 thence to the server or stored on the mobile device to be communicated to the server at a later time according to a set of rules that may include, for example, battery charge on the mobile device, signal strength, the presence of a Wi-Fi connection, and others.

Alternatively, aggregated data from a multiple of other electrically motorized wheels may be searched to select, for example, a more efficient, faster, or more scenic route. Data from the server may be associated with the specific electrically motorized wheel that generated the trip data then aggregated with trip data from other electrically motorized wheels. The aggregated data may then be subjected to statistical techniques for sensing similarity, based on correlations, e.g., based on common segments of the trip data, destinations, origins, etc. The aggregated data may then be provided to the user to, for example, make recommendations for routes, mode selection, and other guidance that will benefit the user.

The electrically motorized wheel and the mobile device 1502 may be utilized to catalogue potholes, road conditions, and other obstacles from, for example, GPS data and accelerometer data along the route. The GPS data and/or other sensors, can be utilize to facilitate such cataloging in an automated manner. For example, start/stops, uneven terrain, and other obstacles can be identified by the electrically motorized wheel via interpretation of data from the speed sensor, the torque sensor, and/or the inertial sensors such as the accelerometers and gyroscopes, of the sensor system. The torque sensor also directly measures power output from the user for association and catalogue with the route location and conditions.

In embodiments, obstacle detection may be catalogued in response to sudden changes in elevation or acceleration that are detected by the sensor system. That is, the cataloging is essentially automatic. For example, a sudden swerve, detection that the user is standing on the pedal, or other such indices may be utilized to catalog a pothole to a particular GPS position.

Figure 16C:
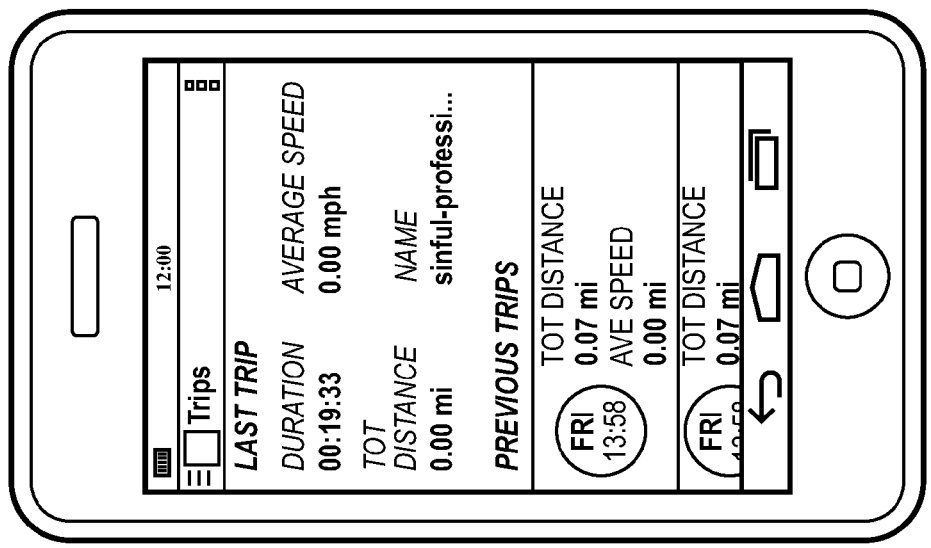
FIG. 16C is a mobile device page of a system for the electrically motorized vehicle.

Alternately, or in addition, the mobile device 1502 may be utilized to accept user input, such as pothole detection, along a route. That is, the cataloging is essentially manual. For example, should the user identify a pothole, the user may touch a button on the mobile device 1502 which is then catalogued via GPS. Other represented pages may include last trip (FIG. 16C), record trip (FIG. 16D), user settings (FIG. 16E), support (FIG. 16F), and others (FIG. 16G). It should be understood that the illustrated pages are merely representative, and various other pages may be alternatively or additionally provided.

Figure 17A:
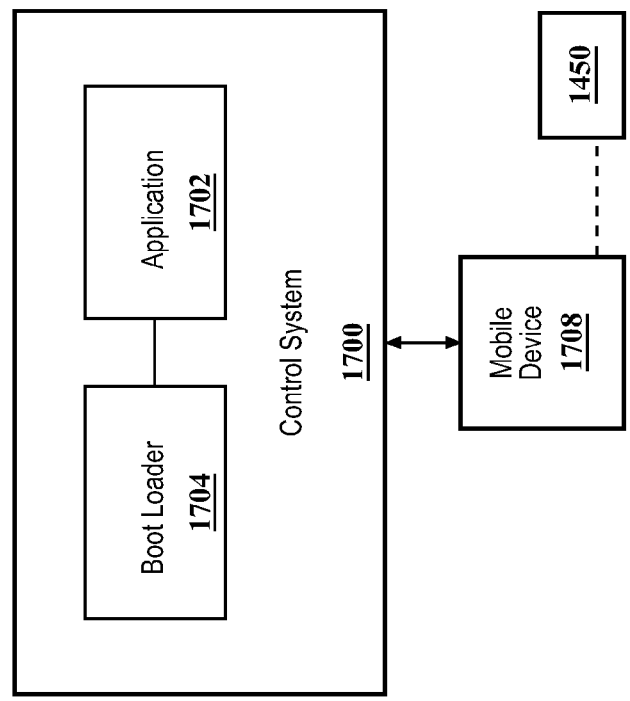
FIG. 17A is a schematic view of a system for the electrically motorized vehicle.

With reference to FIG. 17A, the control system 1700 of the electrically motorized wheel may include an application module 1702 that executes various functions, to include, for example, operation of control algorithms that manage the operation of the electrically motorized wheel. A boot loader module 1704 is in communication with the application module 1702 to facilitate loading and updating thereof. It should be understood that various hardware, software, and combinations thereof may be used to implement the modules.

In embodiments, upon start-up of the control system 1700, the electrically motorized wheel verifies that the version of the application module 1702 currently installed on the control system 1700 is valid and current. It should be understood that 'start-up" may include connection by various user interfaces that communicate with the electrically motorized wheel as well as various security and other communications. If, for example, the application module 1702 is valid and up to date, system initialization occurs. If the application module 1702 is not valid, the control system 1700 may initiate the boot loader module 1704 to update the application module 1702.

In embodiments, when a mobile device 1708 connects with the control system 1700, the control system 1700 may upload firmware version numbers for the application module 1702, the boot loader module 1704, and other elements, such as a Bluetooth (BT) radio and the battery management system. The mobile device 1708 may check with a source, such as a server operating such an application program interface (API) of a cloud-based server, to determine whether the uploaded version number of the application module 1702 is the most recent version.

In embodiments, non-mobile devices such as a desktop computer may connect locally with the control system 1700 such as via a Bluetooth connection.

If a newer version is available, the user may, based on a rule set, be prompted via the mobile device 1708 to update the electrically motorized wheel. That is, updated firmware for updated operation of the electrically motorized wheel. If the user elects to update the electrically motorized wheel, the mobile device 1708 may direct the control system 1700 to enter the boot loader module 1704. The rule set for updates may permit updates only under certain defined conditions such as when there is at least a minimum battery life on the electrically motorized wheel, a minimum battery life on the mobile device 1708, a minimum signal strength for the mobile device 1708, availability of direct power for electrically motorized wheel and mobile device, and others.

Upon downloading the updated version of the application module 1702, the mobile device 1708 may command the boot loader module 1704 to download the new version of the application module 1702 and, if download is successful, to erase the current application module 1702 from the control system 1700. Alternatively, the new version of the application module 1702 may be downloaded and stored on the mobile device 1708 for later update of the of the electrically motorized wheel such as via a Bluetooth connection.

The new version of the application module 1702 may be sent from the mobile device 1708 to the boot loader module 1704 via a wireless connection. The boot loader module 1704 may confirm the transfer of the individual packets and the total transfer of the new application module 1702 onto the control system 1700. If the boot loader module 1704 confirms that the new application module 1702 was loaded successfully, the mobile device 1708 may initiate a restart of the electrically motorized wheel and control system 1700. Alternatively the boot loader module 1704 may proceed with updates though a hard-wired interface such as a CAN bus that is made externally available at the User Interface panel or power port.

Figure 17B:
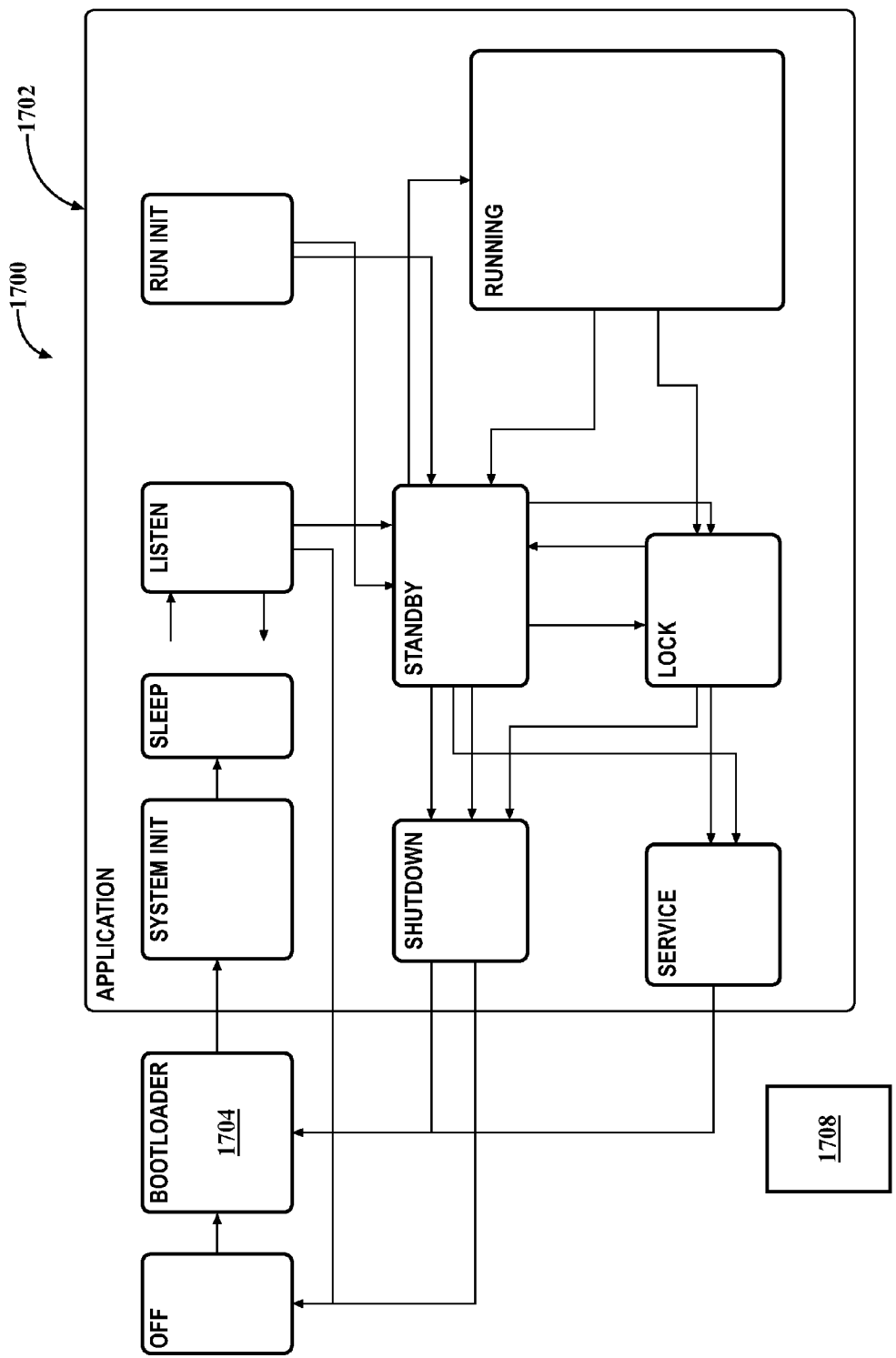
FIG. 17B is a schematic view of a system for the electrically motorized vehicle.

With reference to FIG. 17B, the application module 1702 of the control system 1700 may utilize various control techniques, including algorithms that govern, manage, and/or change operational parameters of the electrically motorized wheel. That is, the operational parameter of the electrically motorized wheel may be changed via the control system that, for example, changes a parameter based on various factors, such as the maximum speed of the vehicle on which the electrically motorized wheel is installed, the conditions of the environment (e.g., terrain, weather, and others), input from the user including the force sensed from pedaling effort, data input to the electrically motorized wheel, etc., and parameters that are based on multiple factors (referred to herein in some cases as blended parameters), the energy used (such as by the user, by a battery associated with the electrically motorized wheel, or the like), and/or other control systems that provide various other modes.

In embodiments, levels of gain (such as the level of assistance and/or resistance provided by the electrically motorized wheel in relation to a given user input such as pedaling effort) can be managed in connection with the electrically motorized wheel. In some embodiments, a progression of gains may be utilized to smooth the transition from one operational regime to another regime (e.g., a change in terrain from uphill to downhill conditions, a change in speed of the vehicle on which the electrically motorized wheel is installed, environmental conditions such as wind direction and temperature, etc.) Other embodiments may include a step-wise change between an initial gain one or more new levels of gain. Normally a step-wise change in operational mode of the electrically motorized wheel (e.g., between differing levels of assistance or from assistance to resistance) or a change in gains may result in a discontinuity in the response of the electrically motorized wheel to torque command. Such discontinuities may be smoothed by:

1. recognizing that a change in gains has occurred;

2 taking and optionally storing the value of the command immediately prior to the change;

3. creating an offset that is at least a portion of the difference between the prior command and the new command;

4. subtracting the offset from the new command (this results in a new command that has a value of or in the range of the old command to the new command); and 5. reducing the offset over a period of time until it is zero, at which point the transition to the new command is completed.

This smoothing process beneficially effectuates gain changes and control regime changes because it preserves a degree of continuity in the user experience. The process can handle repeated transitions, as new offsets are generated with each change (e.g., in regime and condition) that results in a new command. This may include offsets from prior transitions, and there may be a variety of ways to reduce the command to give the transition different characteristics (e.g., a finite transition time, a fixed rate of command change, a maximum level of change, etc.)

Figure 18A:
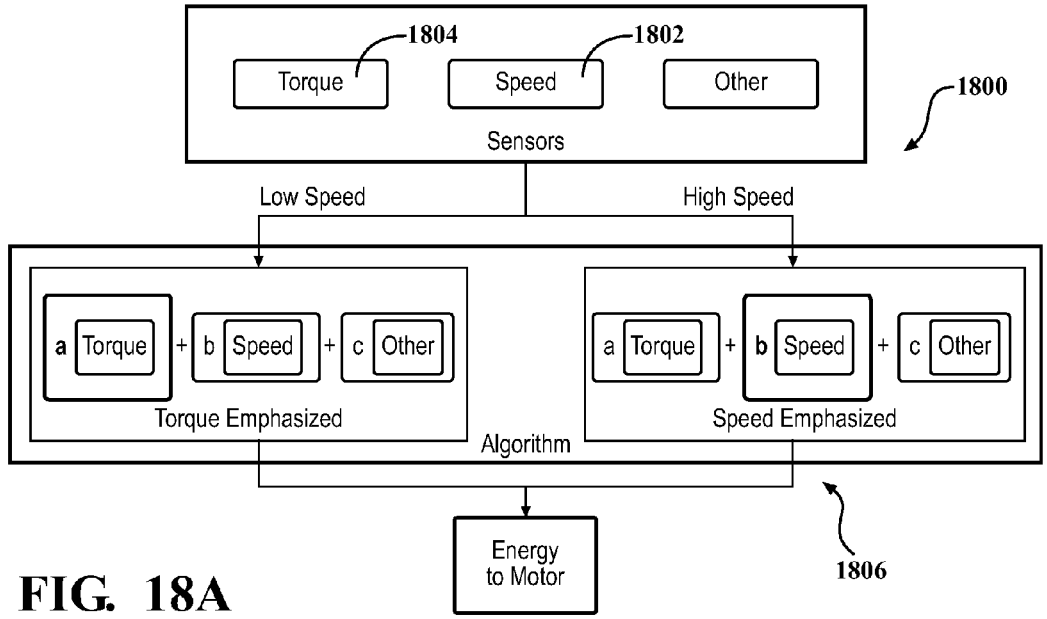
FIG. 18A is an algorithm for operation of the electrically motorized vehicle.

With reference to FIG. 18A, a blending algorithm 1800 for operation of the electrically motorized wheel may also be controlled by blending 1806 inputs relating to different factors that may be sensed in connection with the operation of the electrically motorized wheel. For example, sensor inputs may be considered from both a speed sensor 1802 that senses the speed of rotation of the electrically motorized wheel or displacement of the vehicle, and as a torque sensor 1804 that senses the amount of torque on the electrically motorized wheel.

The control parameters of relevance to the user experience can vary significantly depending on, for example, the speed of the vehicle. In considering a bicycle pedaling example, at low speeds, responding to pedal torque may be relatively more important to ride quality, as significant effort is required to initiate movement of the vehicle. At higher speeds, maintenance of a consistent cadence or speed may be relatively more important to ride quality. As such, the amount of assistance in response to each user input (in this example torque and cadence) may vary based on the speed of the vehicle. Thus, data from the torque sensor may be used as a primary factor in a control regime at low speeds, while the data from the speed sensor may be used as the primary factor in the control regime at higher speeds. As a result, control may be managed by delivering high responsiveness to the torque sensor at low speeds and by using less responsiveness to the torque sensor at high speeds. Components related to the torque and the speed can be factored into the control algorithm that ultimately determines the quantity of energy, or rate of energy delivery from the battery system to the electric motor.

The blending algorithm 1800 is thereby operable to provide a fluid control scheme that scales the importance of each sensor as a factor in the control scheme based on speed.

Figure 19A:
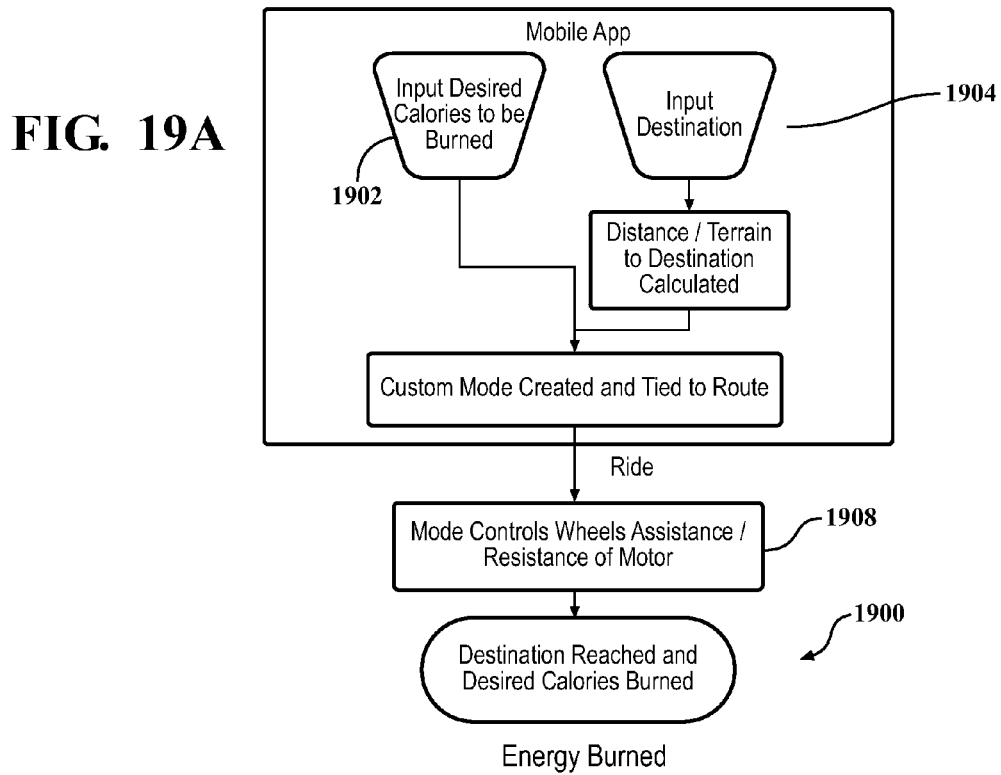
FIG. 19A is an algorithm for operation of the electrically motorized vehicle.

With reference to FIG. 19A, an energy burn control algorithm 1900 permits a user to input the amount of energy (step 1902) the user would like to burn on a particular ride (e.g., how many calories to burn between home and work). The energy burned by the user relates to the amount of work performed in order to move the vehicle from a first point to a second point. This work may be modeled based on various physical factors, including the terrain, friction, the weight of the user such as measured by a sensor of the vehicle or entered by the user, the weight of the bicycle including any accessories and additional loads, e.g., camping equipment, the distance traveled, and others.

A portion of the work may be performed by the user, such as by pedaling, while the remainder may be provided by the electrically motorized wheel. The portion of energy expended by the user may be modeled as the difference between the total work required to move a user of a given weight over the terrain (which may be known based on a GPS model of the terrain or based on measurements (such as altimeter measurements) from past trips) and the amount of assistance provided to the user by the electrically motorized wheel. Thus, as the user indicates an amount of energy desired to be burned, the control system 1700 may control the electrically motorized wheel to provide assistance, such as on hills of the route, to make up any difference between the desired work and the actual work required to cover the distance. If the desired portion of the work performed by the user is higher, the electrically motorized wheel may provide resistance to the user, re-route the user to a longer route, etc. Thus, the algorithm 1900 may utilizes the user input 1902 and data about the route/terrain 1904 to adjust the assistance/resistance of the electric motor 908 so that the user burns the desired amount of calories over the course of the route. Once the goal has been identified, the ride may be previewed and, as the ride progresses, the user interface may transition to a progress screen that highlights progress to the goal such as the destination and specified calorie burn.

Figure 19B:
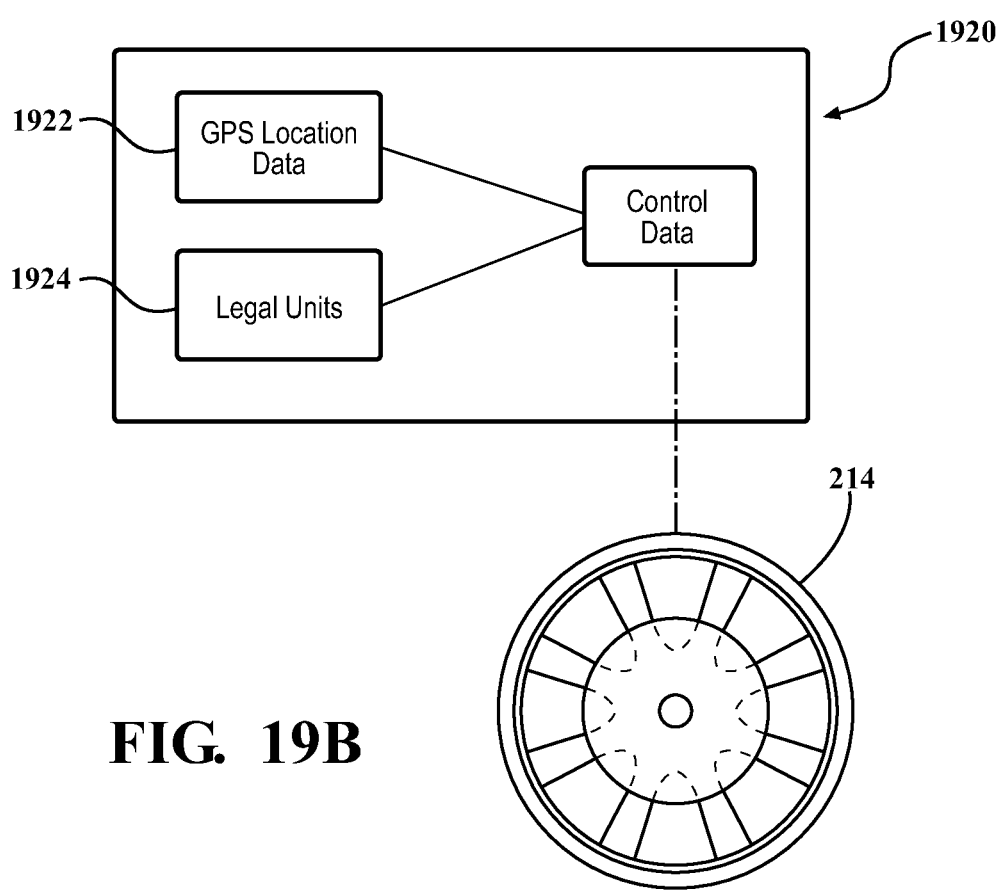
FIG. 19B is an algorithm for operation of the electrically motorized vehicle.

With respect to FIG. 19B, the mobile application 1920 may utilize available GPS location data 1922 and a stored database of data to determine legal limits 1924 as regulations vary geographically with respect to various factors that govern operation of electrically driven or assisted vehicles. These may include regulations of assisted speeds, level of assistance provided, and/or motor output. The mobile application 1920 or other control system may use this data to create a custom mode or set of control parameters that can be sent to electrically motorized wheel, such as to govern maximum assistance, speed, or the like. The mobile device or other control system may recalculate control parameters when the legal limits change and send updated control parameters to the electrically motorized wheel.

In one example, the EU may have a standard regulation of a top-assisted speed of 25 km/h and 250 W of motor assistance, while the US may have a top assisted speed of 32 km/h and 750 W of motor assistance. By using the GPS data available at any given location, it is possible to regulate the assistance cutoff within the electrically motorized wheel to comply automatically with the local regulations, without further intervention.

Further, many of the laws only apply to bicycles when they are riding on roads with other motor vehicles and pedestrians. If the GPS indicates the bicycle to be sufficiently far away from the road, the bicycle may be assumed to be on a trail in which case the local regulations may be different, or nonexistent, in which case limitations on the assistance provided may be removed. In embodiments, a user may be permitted, such as through the mobile application, to override the controls, such as to allow more assistance in an emergency situation.

In embodiments the mobile application 1920 may also utilize available GPS location data 1922 to facilitate control while in operational modes. For example, extremely hilly terrain will result in different battery regeneration calculations than flat terrain.

Figure 20A:
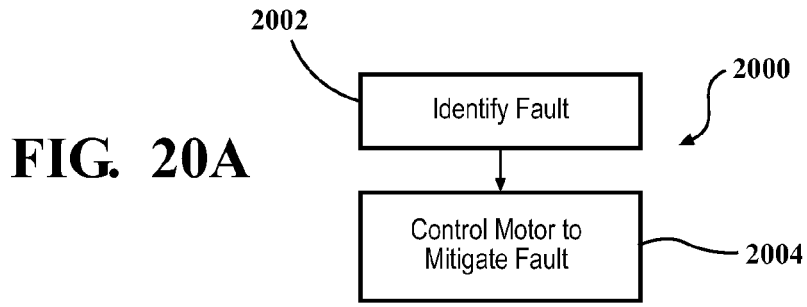
FIG. 20A is an algorithm for operation of the electrically motorized vehicle.

With reference to FIG. 20A, a fault detection and prediction system, referred to herein as a "faultless algorithm" 2000 is operable to sense conditions that have the potential to damage wheel hardware or subsystems as they occur in essentially real time (step 2002) then respond by performing mitigating actions based on the detection of same (step 2004). For example, if the electric motor approaches a predetermined maximum temperature, beyond which damage may occur to the electric motor, the amount of assistance or resistance generated by the electrically motorized wheel to the user of a vehicle on which the electrically motorized wheel is disposed can be reduced to prevent a further rise in temperature of the motor.

Figure 21A:
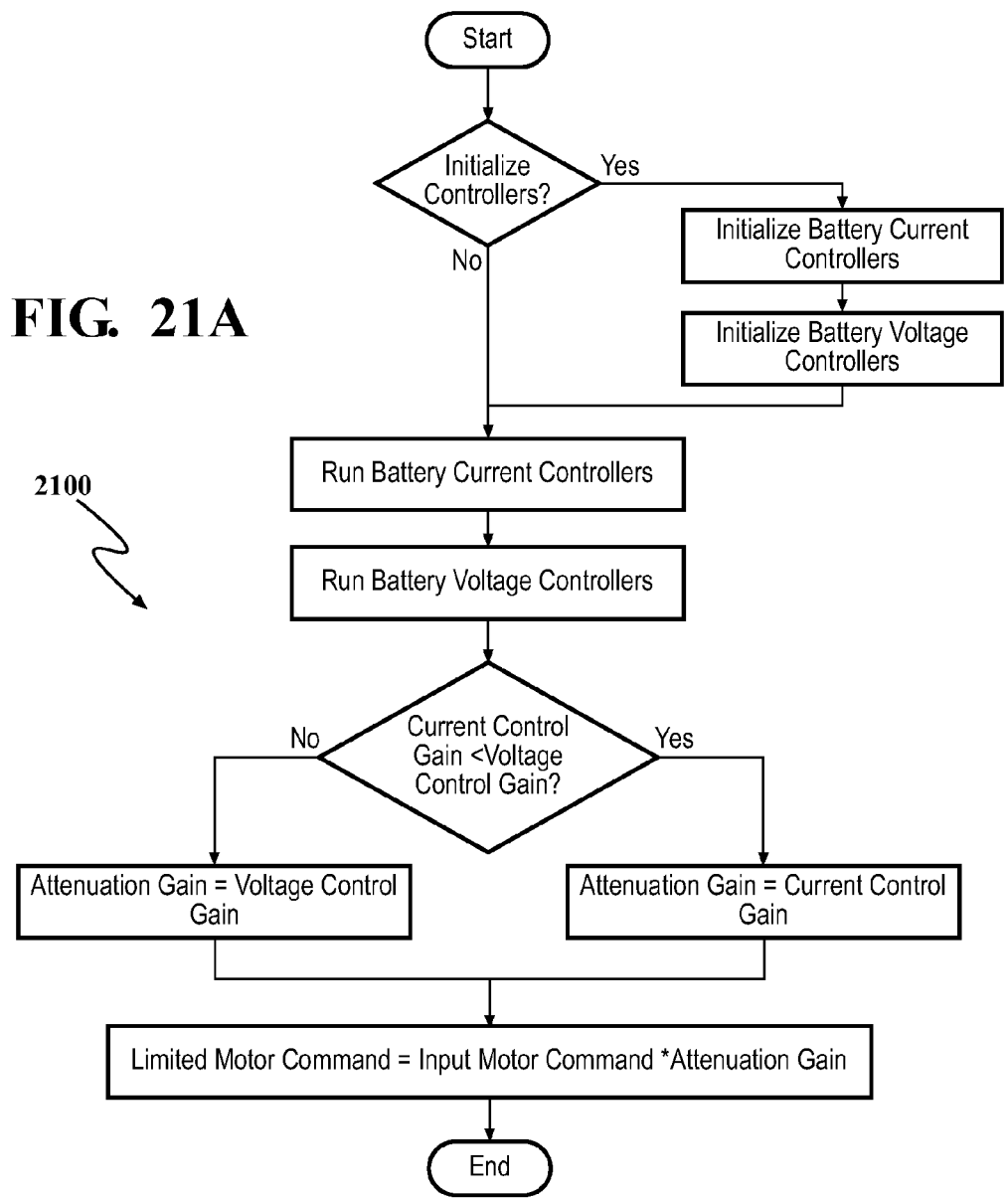
FIG. 21A is an algorithm for operation of the electrically motorized vehicle.

With reference to FIG. 21A, a battery protection algorithm 2100 may provide different and optionally independent command attenuators, including, but not limited to:

1. Protecting the battery from high discharge currents;
2. Protecting the battery from high regeneration currents;
3. Protecting the battery from high voltages that may result from regeneration;
4. Protecting the battery from low voltages that may result from motoring;
5. Protecting the battery from high temperatures due to high loads or heat from other components like the motor; and/or
6. Protecting the battery from regeneration currents at low temperatures.

Each of these command attenuators can utilize automatic controls such as a single-sided, closed loop proportional-integral (PI) control system to generate an attenuated gain ranging from 1.0 (no attenuation) to 0.0 (full attenuation). Alternatively, command limiters may be utilized instead of the command attenuators. The command attenuators provide an immediate and linear smooth response, as command limiters are inherently non-linear in nature and can present control challenges, but are nonetheless a valid controllers.

In embodiments, the gain from relevant attenuators can be determined, combined, and applied to the motor command. The algorithm may be based on the minimum gain among all control systems, the maximum gain among all control systems, the sum of gains from all control systems, and various other ways for combining the gains, multiplying them, conditionally selecting, limiting the assistance provided by the motor to the user, etc.

Under some conditions, the electric motor may be driven by the battery system, while under other conditions the battery system may store energy from the motor such as when the motor is used to slow the vehicle in downhill operation. In situations with significant energy generation capability, the battery system may be subjected beyond its normal operational limits for temperature, voltage and/or current. As such, there are limits that may need to be enforced for operation of the battery system. There are at least three general sets of battery limits, i.e., current, voltage, and temperature. As to limits relating to current, there may be maximum discharge current and maximum battery regeneration current. As to voltage limits, there may be a maximum voltage limit and a minimum voltage limit. As to temperature, there may be a maximum temperature limit and a minimum temperature limit.

The battery protection algorithm 2100 may operate to manage the motor drive operation, such as to maintain battery parameters within acceptable operational values for voltage, current and temperature. This may address the electric motor contribution to the load on the battery system. Other sources of load on the battery system may also be managed separately.

In embodiments, single-sided proportional-integral (PI) closed loop limiters, e.g., one for each limit, may be deployed in connection with limiting various operational conditions, such as: battery motoring current; battery regeneration current; battery over voltage; battery under voltage, etc.

The output of each PI closed loop limiter may be an attenuation gain. Each PI closed loop limiter may have its own control system, with its own separate gains, as the dynamics of each limiter may require individual tuning.

The minimum gain of all the limiters may be taken and applied to the motor current control command. As a particular limit is approached, the motor command may be attenuated, such as to reduce the demand on the battery. The voltage limiters may selectively apply the attenuation gain. For the over voltage limiter, the attenuation gain for over voltage may be applied only when commanding regeneration of the battery. This allows motoring to then alleviate or avoid the over voltage condition. For the under voltage limiter the attenuation gain may be applied only when commanding motoring/assistance which allows regeneration to then alleviate or avoid the low voltage condition.

In embodiments, battery power control systems may run at the motor control system frequency, as the battery control systems may need to have similar or higher bandwidth to keep limit excursions short in duration. In other embodiments, battery power control systems may run just prior to the motor control current loop and after motor drive analog data has been collected, such that the battery control systems attenuate the command for the motor control current loop. This sequence may reduce delay in the control response that would occur if the data collection and attenuation occurred at different times.

The control system may be initialized each time the motor drive is enabled, as the motor drive can be enabled and disabled during normal operation. The battery control systems may have data items, such as integrators, that can be reset with every instance of enablement of the motor drive.

The control system can provide dynamic limits, because limits of the battery system may not be static over time and may vary, for example, with state of charge, temperature, etc. Dynamic control system limits may be bounded by predetermined maximum and minimum values, as this provides some protection against potential errors in measuring time-varying gains. Battery current and battery voltage may need to be sampled at the same data rate as other motor control feedback, as these control systems are part of the motor drive control, and because they run at motor control update rates, the sensor data may need to have the same frequency of sampling as other motor control data.

The control system may be single sided, closed loop, PI limiters that attenuate the motor current control loop command as PI limiters beneficially provide steady-state limiting with good bandwidth. An attenuator output, as compared to a limit output, may provide immediate intervention.

Over voltage attenuation gains may be only applied when the sign of the motor current command is negative (e.g. the motor is being commanded to oppose forward momentum, i.e., regenerate), because this allows motoring to alleviate high voltage conditions. Under voltage attenuation gain may be applied only when the sign of the motor current command is positive (e.g., the motor is being commanded to assistance in driving the vehicle), because this allows regeneration to alleviate low voltage conditions.

The PI control systems may have enough control authority to attenuate the motor current control system command to zero, because attenuating the command to zero is the maximum control authority possible, and maintain the battery system within operational limits may have priority over providing assistance to the user.

Sensors used in hardware protection algorithms may include sensing of battery voltage, battery current, motor voltage, motor current, battery temperature, ambient temperature or humidity, etc. Limits may be set statically in accordance with component design specifications or updated over time to account for factors such as component age or environment of usage as determined by GPS or weather data.

Pedal cadence is useful for a user to maintain a desired pace over the course of a ride. Typically, a cyclist may desire to pedal at a specific cadence to make the most efficient use of their effort and provide the most benefit from an exercise physiology standpoint.

In typical bicycle cadence sensors, measurements are performed directly at the crank, however, such direct measurements are not possible, nor desired, if the sensor system is to be contained within the electrically motorized wheel that is separated from the pedals by a drivetrain. Although this embodiment has specific illustrated components in a bicycle embodiment, the embodiments of this disclosure are not limited to those particular combinations and it is possible to use some of the components or features from any of the embodiments in combination with features or components from any of the other embodiments.

Figure 22A:
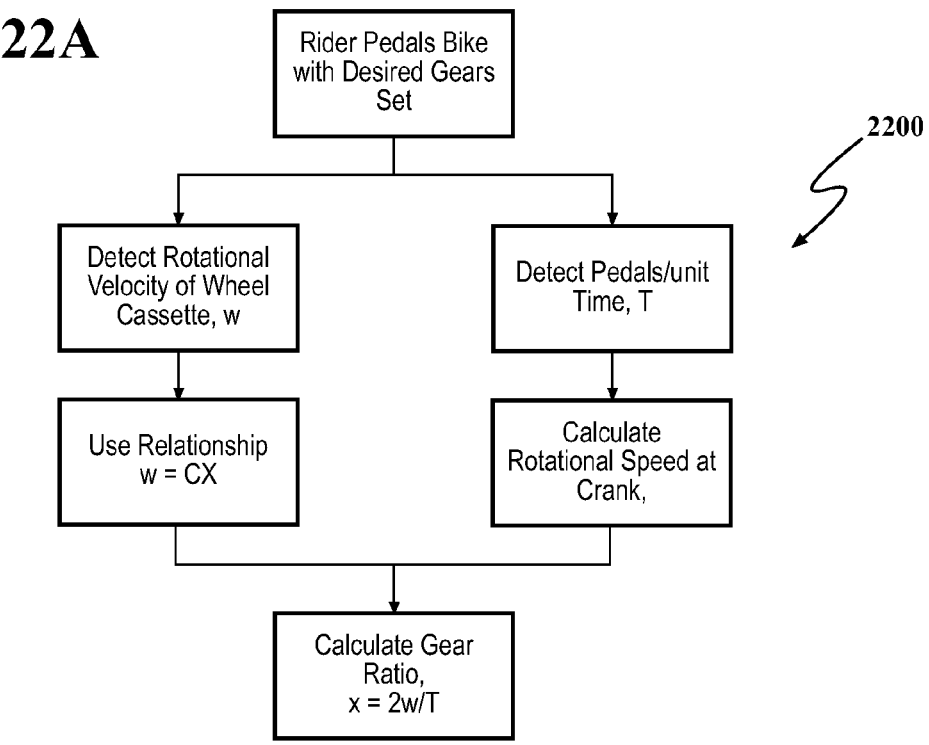
FIG. 22A is an algorithm for operation of the electrically motorized vehicle.

With reference to FIG. 22A, a pedal cadence estimation algorithm 2200 operates to estimate the pedal cadence from the torque input frequency which will have frequency content that is directly related to pedal cadence. Each time the user provides a rotational input, i.e., pushes on the pedal, the user is generating a torque into the system that is detectable. That is, the pedal rotational frequency (or cadence) is detected by the torque sensor system and can be communicated to the control system for use by a gear estimation algorithm 2200. The gear estimation algorithm 2200 is operable to calculate the gear ratio because the rotational velocity of the cassette is known from, for example, a cassette speed sensor, and the pedal cadence is known by estimation. The gear ratio may be determined by a ratio of these two speeds.

In embodiments, there are two speed sensors: one for the electrically motorized wheel and one for the cassette of the mechanical drive system. With knowledge of a rotational velocity of the cassette, and the torque frequency, both pedal cadence (pedal speed), and the gear ratio are readily determined by the gear estimation algorithm 2200. That is, how the pedal frequency relates to the rotational velocity of the electrically motorized wheel is known even if the number of speeds on a particular bicycle, or which gears are set on the rear cassette and the crank, are not known.

For example, the rotational velocity w is known from the cassette speed sensor. The torque frequency, t, is related to cadence, C: C=t/2. C is equal to the number of revolutions of the crank per second. Therefore, ω=CX, or ω=(t/2)X, where X is the gear ratio. Thus in simple forms, X=2 ω/t. Additional sophistication may exist in the estimator to update estimates under conditions where input signals may be small, such as at low speed or low torques. This sophistication may include closed-loop state estimation algorithms for example.

Figure 23A:
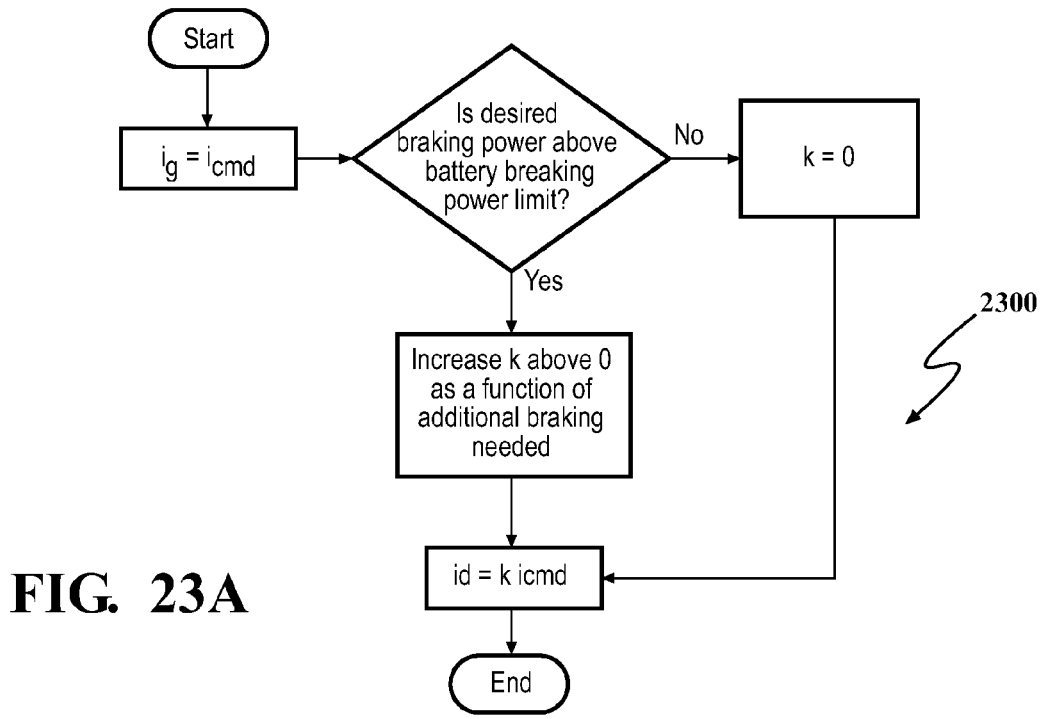
FIG. 23A is an algorithm for operation of the electrically motorized vehicle.

With reference to FIG. 23A, a braking dissipation algorithm 2300 accommodates an architecture in which the battery system 906 may be relatively limited in the amount of energy that can be absorbed during braking (in which energy can be directed to recharge the battery) without damage occurring to the battery. In embodiments, the motor control system of the electrically motorized wheel is field-oriented and controls the magnetic flux generated in the stator 911 as a vector that is precisely aligned with the rotor 913. This vector may be controlled to rotate through the stator 911 in synchronization with the rotor 913 of the motor by segregating the applied current vector into two orthogonal components. One component, Iq, the quadrature component, is at a right angle to the back electromagnetic field (back-EMF) vector generated by the motor. The other, Id, the direct component, is directly aligned with the back-EMF vector.

Maintaining the direct component (which produces no torque in certain embodiments) at zero (Id=0) and the quadrature component at a commanded level (Iq=Icmd) is how a field-oriented control system normally ensures the most efficient use of battery power to produce motor torque. Allowing Id to stray from zero is less efficient and thus dissipates more energy in the motor, which, while normally inefficient in regimes in which the desire is to maximize efficiency of power generation to propel a vehicle, creates an opportunity when other objectives are in play, such as involving braking and/or reducing current flow into the battery during regeneration, to degrade efficiency of motor in transferring power to the battery.

The battery protection algorithm 2100 maintains regenerative charging currents within limits that will not damage the battery, for example, below about 5.5 A of regeneration in certain embodiments. Since the battery protection algorithm limits the quantity of power that can be delivered back into the battery, the braking dissipation algorithm provides another place to send braking power in lieu of the battery without the addition of another dissipative load such as a traditional shunt resistor, thus allowing or causing more braking than would otherwise be allowed. This is effectuated by reducing motor current (used to control power) as needed to maintain the regeneration current directed to the battery in check. Also the braking torque is reduced, in some cases significantly, at higher speeds.

This speed dependence is because at higher speeds, the same amount of braking torque generates proportionally higher power levels. That is, at the battery system 906, since voltage is essentially constant, higher regeneration power translates directly to higher current into the battery system. Since current is limited, capacity for braking thus goes down as speed goes up.

The electric motor 908 in embodiments may have windings with a relatively high resistance. One consequence of this is that during hard braking, when the braking torque is high and thus the motor current is high, the power dissipated in the electric motor 908 is quite high, so the motor absorbs significant braking energy. As the speed drops, the braking power drops and the proportion of the braking power absorbed by the motor increases until it reaches the point where the motor is absorbing all of the braking power. At this point regeneration of power back into the battery system 906 ceases and the available braking torque is at a maximum. This threshold can be reached fairly quickly when slowing down and can cause the braking experienced by the user to rise abruptly. This behavior is likely unexpected by the user and thus is potentially undesirable.

In embodiments, the dynamic braking algorithm 2300 is activated by backpedaling so the user can use just one method of control, i.e., pedaling forward is a control that signals acceleration/assist while pedaling backwards is a control that signals braking—in either case the user need utilize only a single user input that is typical of the vehicle, i.e., pedaling in this example. The relative lack of desired braking at high speed, and the abrupt increase in braking at lower speeds is addressed such that the user mode of control, e.g. pedaling in this example, is seamless. That is, the braking that this technique provides at higher speeds also provides a partial solution to braking abruptness problem when slowing down by narrowing the difference in braking capability at high and low speeds.

In embodiments, the motor control system is field-oriented and controls the magnetic flux generated in the stator 911 as a vector that is precisely aligned with the rotor 913 for generating maximum torque. This vector is controlled to rotate through the stator 911 in synchronization with the rotor 913 of the motor by segregating the applied current vector into two orthogonal components. The quadrature component is thus at a right angle to the back-EMF vector generated by the motor, while the direct component is directly aligned with the back-EMF vector such that each of these components has a control system therefor.

The quadrature component produces torque, while the direct component produces no torque. Thus, for maximum efficiency, a control system is commanded to maintain the direct component at zero (Id=0) while the quadrature component is controlled at the commanded current level (Iq=Icmd). If the control system were to allow the direct component to grow, the overall motor current would increase, but no additional torque would be produced, and energy would be wasted in the resistance of the stator 911 windings.

Embodiments for braking set Iq=Id=Icmd. This locates the current vector out of alignment with the back-EMF vector by 45 degrees. As Icmd increases, both Iq and Id would increase and vice-versa. This has the benefit of allowing higher overall Iq values than when holding Id to zero, because Id is dissipating at least some of the energy regenerated by Iq, rather than it returning it all to the battery. If the motor current is to be attenuated to protect the battery, motor, or electronics, both are attenuated equally. It should be understood, however, that ratios of Id to Iq other than one may alternatively be provided, with different ratios affecting the level of regeneration relative to wasting of mechanical power, and such ratios may be varied, such as accounting for factors like vehicle speed, the level of stored energy in the battery, sensed state (e.g., temperature) of motor components, and others.

In one example, when the motor gets hot, such as while braking during downhill travel in hot weather, the motor may not have the capacity to accept the added power and the supplied braking may fade. Damage to the motor is avoided by having the control systems limit the motor current, which is where the sensation of fading brakes originates. In embodiments, this may prompt other actions, such as activating supplemental braking systems, prompting to the user via the mobile device to use manual braking, etc.

In embodiments, a directly connected electric motor is of the permanent magnet type, such that the rotor rotates with the electrically motorized wheel. When the motor drive applies a voltage higher than the generated voltage of the electric motor, the motor assists the user. The faster the electrically motorized wheel rotates, the higher the voltage generated. If the speed is high enough to generate a voltage that is higher than an allowed voltage, the electrically motorized wheel is in an "over-speed" condition. The allowed voltage may be specified for safety, hardware protection, and/or other reasons such as protection from high-back EMF due to high wheel speeds. EMF is present, however, EMF may become a problem when wheel speed is high enough for it to exceed battery voltage.

An inherent function of the power bridge that drives the motor is full wave rectification of the back-EMF voltage from the rotation of the electrically motorized wheel onto the DC bus. Thus, it is possible for the user to pedal the bicycle to speeds that can generate this over-speed condition, especially downhill. In embodiments such as ones involving direct drive motors, the voltage that can be generated is limited only by how fast the vehicle is moving and thus has the potential to damage embedded system electronics.

Electronic braking through regeneration can be used to facilitate automatic control of maximum vehicle speed. However, the battery can only absorb so much energy before its voltage reaches its maximum limit such that a battery protection algorithm may automatically protect itself by disconnecting the battery from the DC bus if the voltage reaches a predetermined value. True, power is related to current, but at lower battery voltages the power limit will be lower (P=1*V) while the current limit is the same.

Further, even when the battery state of charge is low enough to accept regeneration energy, the rate at which the battery can accept the energy is bounded by its charging current limit. At higher speeds, this charging current limit may severely reduce the braking capability of the electrically motorized wheel, making it more likely for the user to overcome any automatic speed regulation the electrically motorized wheel may try to enforce, especially on a steep downhill. To address this condition, a warning may be provided to the user via the mobile device.

Reasonable speeds are allowed, and mitigation of potential damage to the hardware may be provided, such as by placement of a relay to isolate and protect the power-electronics bridge and all other electronics connected to the DC bus from the high voltage generated by back-EMF generated when the motor is mechanically driven to an over-speed condition.

Figure 23B:
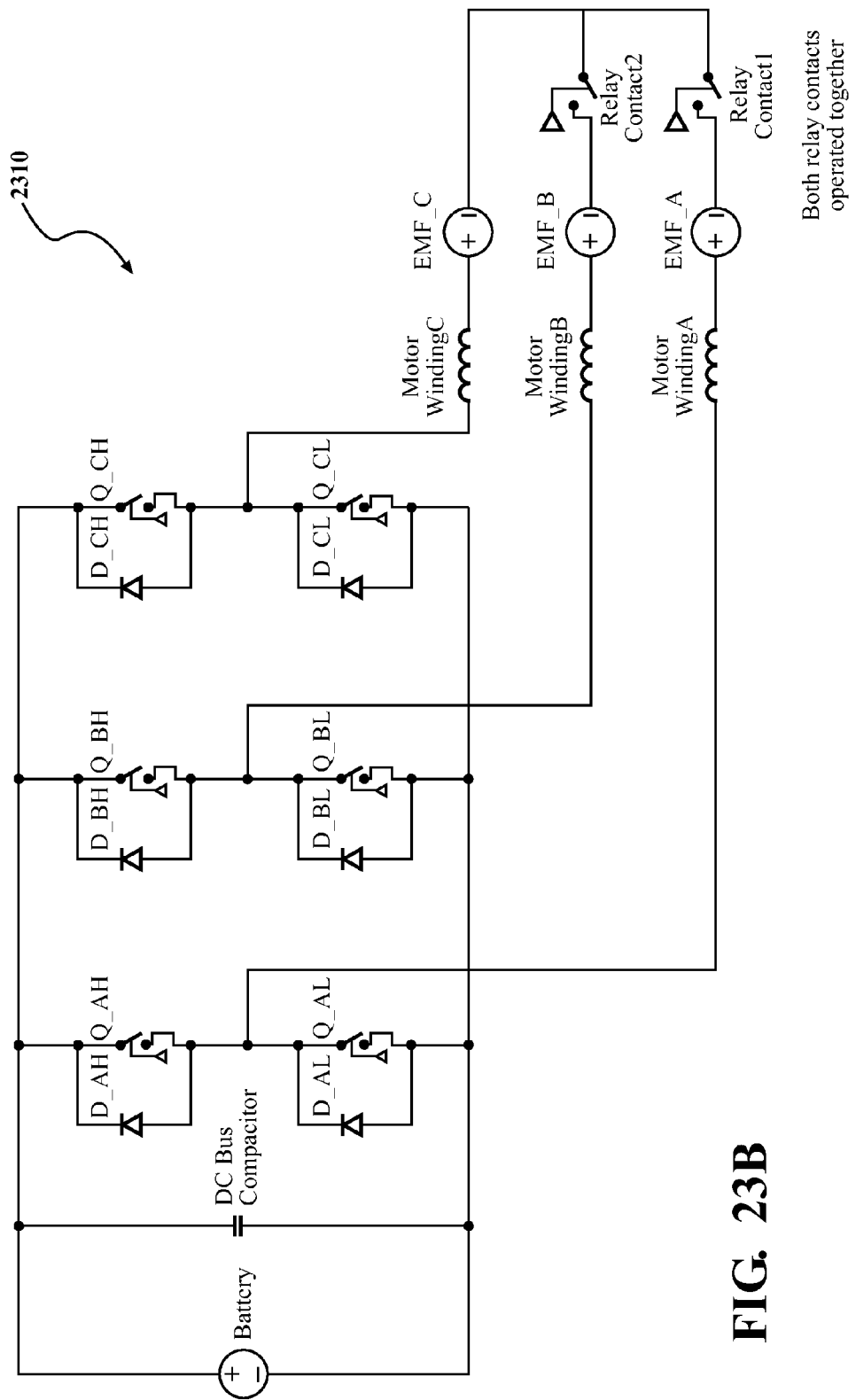
FIG. 23B is a schematic view of a wiring diagram for of the electrically motorized vehicle.

In embodiments, diodes in the bridge 2310 operate as rectifiers if the back-EMF voltage exceeds the DC bus voltage (FIG. 23B). As motor over-speed increases, back-EMF potentially pushes the DC bus voltage to uncontrolled levels. To avoid such an over-voltage condition, relay contacts are opened based upon measured or estimated back-EMF appearing at motor terminals approaching the DC bus voltage. In one embodiment Back-EMF is estimated in accordance with:

$$VEMF = Ke * SpdMot$$

Where:
VEMF is the terminal-to-terminal EMF voltage [V].
Ke is the motor back EMF constant [V/(rad/s)].
SpdMot is the motor speed [rad/s].
SI units are used here with voltages measured line-to-line (vs. line-to-neutral), and 0-to-peak of sine (vs. RMS). So the units on Vemf are [V], on SpdMot are [rad/s], and on Ke are [V/(rad/s)].

Figure 23C:
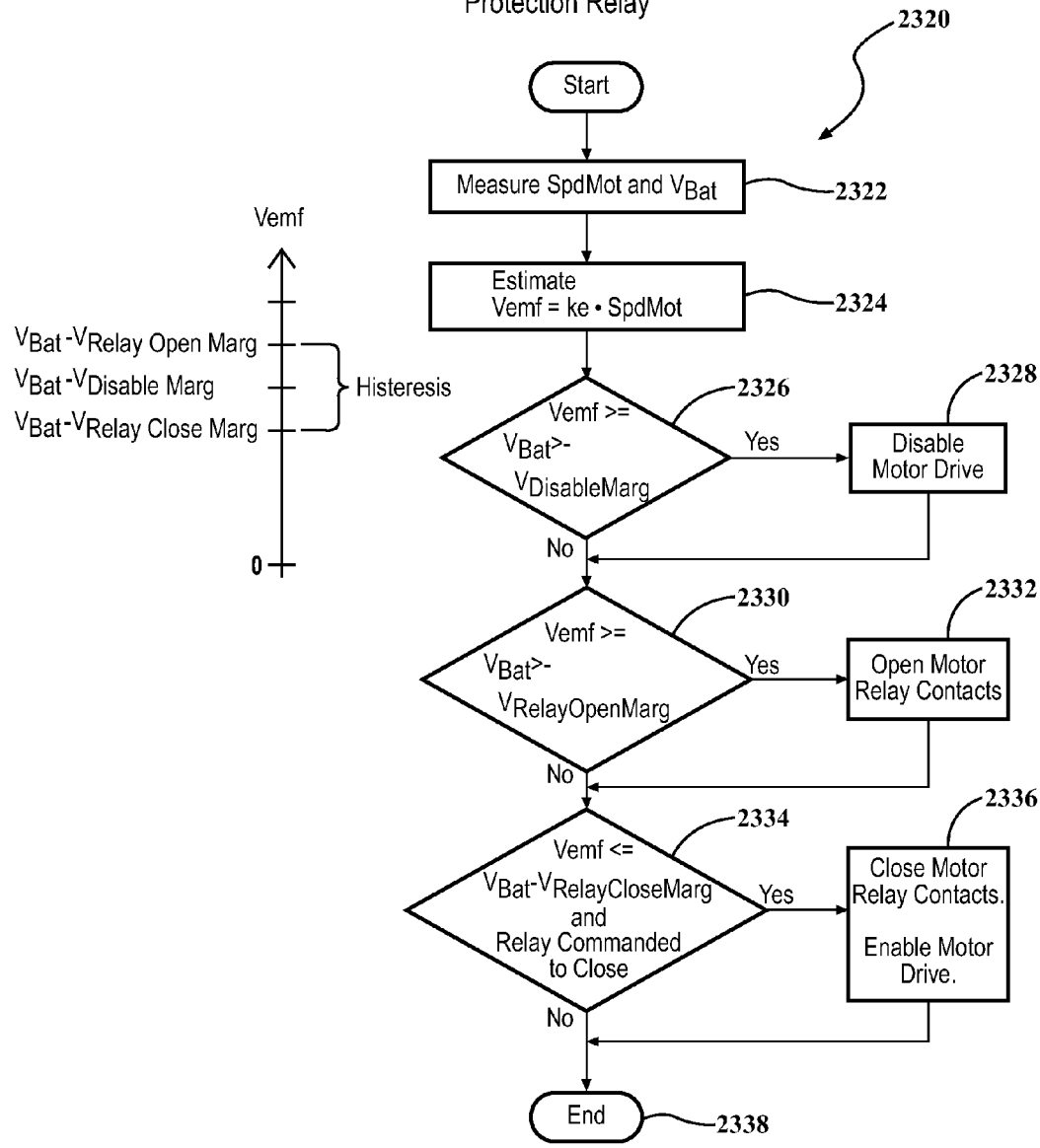
FIG. 23C is a flow chart for operation of the electrically motorized vehicle.

With reference to FIG. 23C, a method 2320 of motor over-speed protection includes:
Measuring SpdMot and Vbatt (step 2322);
Estimating the VEMF as Ke*SpdMot (step 2324); and
Sensing if VEMF>=to Vbatt−VDisableMargin (step 2326).
If Yes, the Motor Drive is disabled (step 2328).
If No, sensing if VEMF>=to Vbatt−VrelayOpeningMargin (step 2330);
If Yes, the Motor relay contacts are opened (step 2332).
If No, determine if VEMF<=to Vbatt−VrelayCloseMargin (step 2334)
If Yes, close the motor relay contacts and enable the Motor Drive (step 2336).
If No, END (step 2338).

That is, the motor relay contacts are opened as the estimated back EMF of the motor, based for example, on the back EMF constant and the speed of the motor, approaches the measured bus voltage which varies with battery state of charge.

With reference to FIG. 23D, an example thermal model schematic for the motor utilize capacitors to represent heat-sinking characteristic of the various thermal generating components in the hub shell assembly. They are responsible for the fact that it takes some time for these components to heat up, thus allowing the wheel to have higher performance until those thermal generating components are hot. The resistors represent the paths for heat to spread inside of, then ultimately escape the hub shell assembly.

Figure 23E:
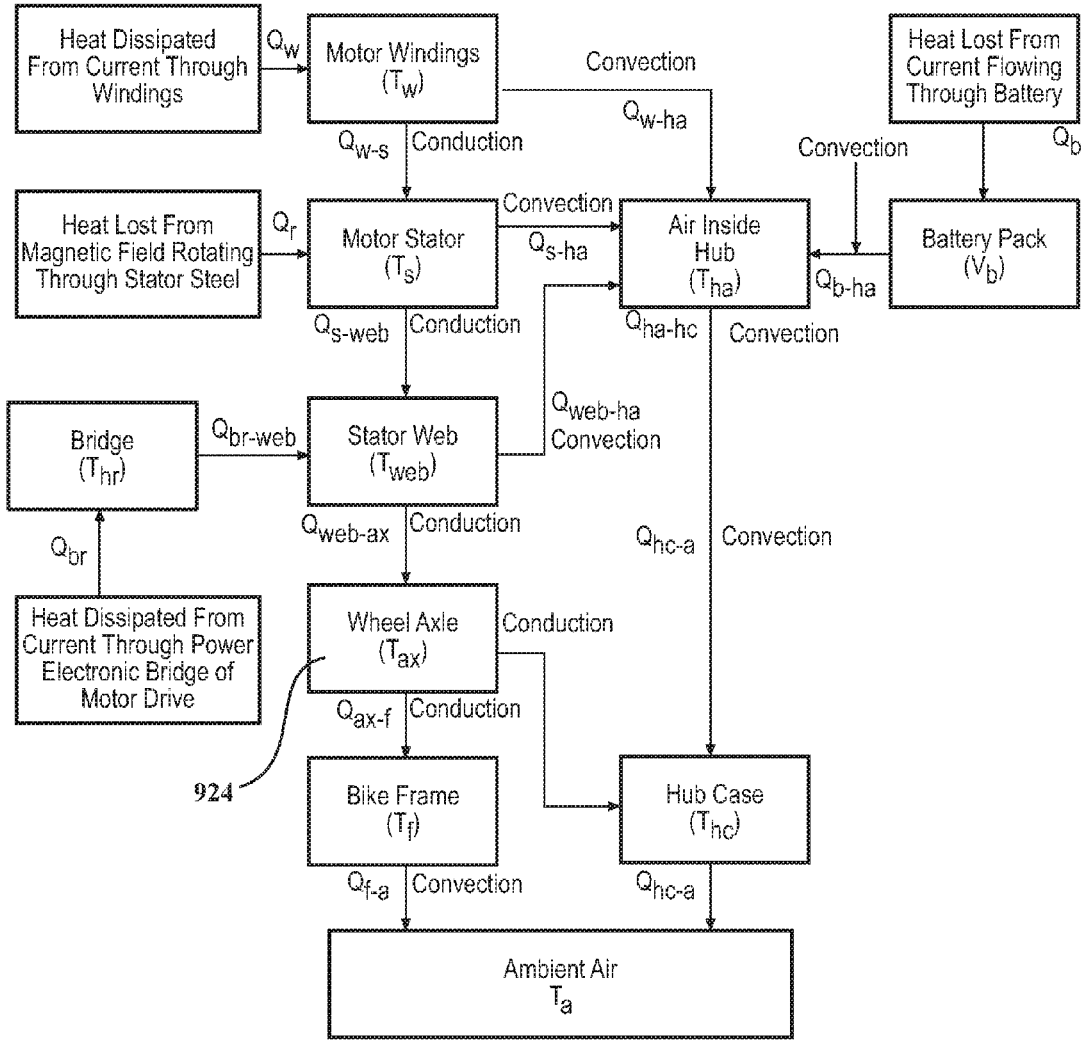
FIG. 23E is a thermal schematic for the electrically motorized vehicle.

With reference to FIG. 23E, a thermal schematic for the electrically motorized wheel includes four major heat sources: winding losses in the motor windings, rotational losses in the motor stator steel, losses in the power electronic bridge of the motor drive, and losses in the battery pack. The heat sources are ultimately communicated to the shaft 924, thence to the bicycle frame along mechanical thermally conductive paths. The bicycle frame thus ultimately operates as a heat sink of significant volume.

With reference to FIG. 24A, a torque sensing algorithm 2400 may be provided to measure different process parameters related to torque. The torque sensing algorithm 2400 may include non-contact sensor technology that utilizes fundamental mechanical and magnetic properties of the material to measure different process parameters such as magnetoelastic materials. The process involves measuring changes in the properties of remnant magnetic fields as the mechanical characteristics change, such as shear stress, as external forces are applied onto the sensor host (step 2402).

The torque sensor 1204 may include highly sensitive fluxgate sensors located in close proximity to a magnetized member to sense the change in the magnetic-field characteristics that are proportional to the applied force. The mechanical member may be directly magnetized instead of attaching additional elements, such as a ring. The change in the magnetic-field characteristics are linear and repeatable within the elastic limit of the material, and are accurate under normal and extended operating conditions such that an applied force can be readily determined (step 2404).

For example, when the shaft is subjected to a mechanical stress, such as torque from pedaling, the magnetic susceptibility of the magnetoelastic material changes and is detected by the surrounding sensor. The torque sensor 1204 produces a signal proportional to the torque applied by the user, which is then communicated to the control system 914.

With reference to FIG. 24B, a vertical load sensing algorithm 2450 may be provided to measure different process parameters such as vertical load. The vertical load sensing algorithm 2450 may communicate with a magnetic field flux sensor measuring change in magnetic field (step 2452) resulting from an initial mechanical stress applied such as, for example, when the user mounts the bicycle. The change in magnetic field may be generated by the shaft, shell, or other wheel component manufactured or including a magnetoelastic material that is deformed when a load is applied on electrically motorized wheel. The change in the magnetic-field characteristics are linear and repeatable within the elastic limit of the material, and are accurate under normal and extended operating conditions such that an applied force can be readily determined (step 2454).

The measured vertical load may be used as a modifier by the control algorithms. For example, the measured vertical load may contribute to calculations controlling for calories burned due to a weight of the user, identification of a user to unlock the electrically motorized wheel, etc.

In embodiments, various components of the shell, such as the drive side shell 940, the non-drive side ring 942, the removable access door 944, and the like may include a magnetoelastic material. Alternately, a thin coating of magnetoelastic material may be applied to a component. The coating may be applied overall or in a directional pattern and in various thicknesses. Magnetic flux sensors situated in close proximity to the magnetoelastic material enable the detection of changes in the magnetic flux created by the deformation of the component during operation. Insight into the deformation of a component, such as the shell, may be used to understand electrically motorized wheel environment and inform future design modifications.

Figure 25A:
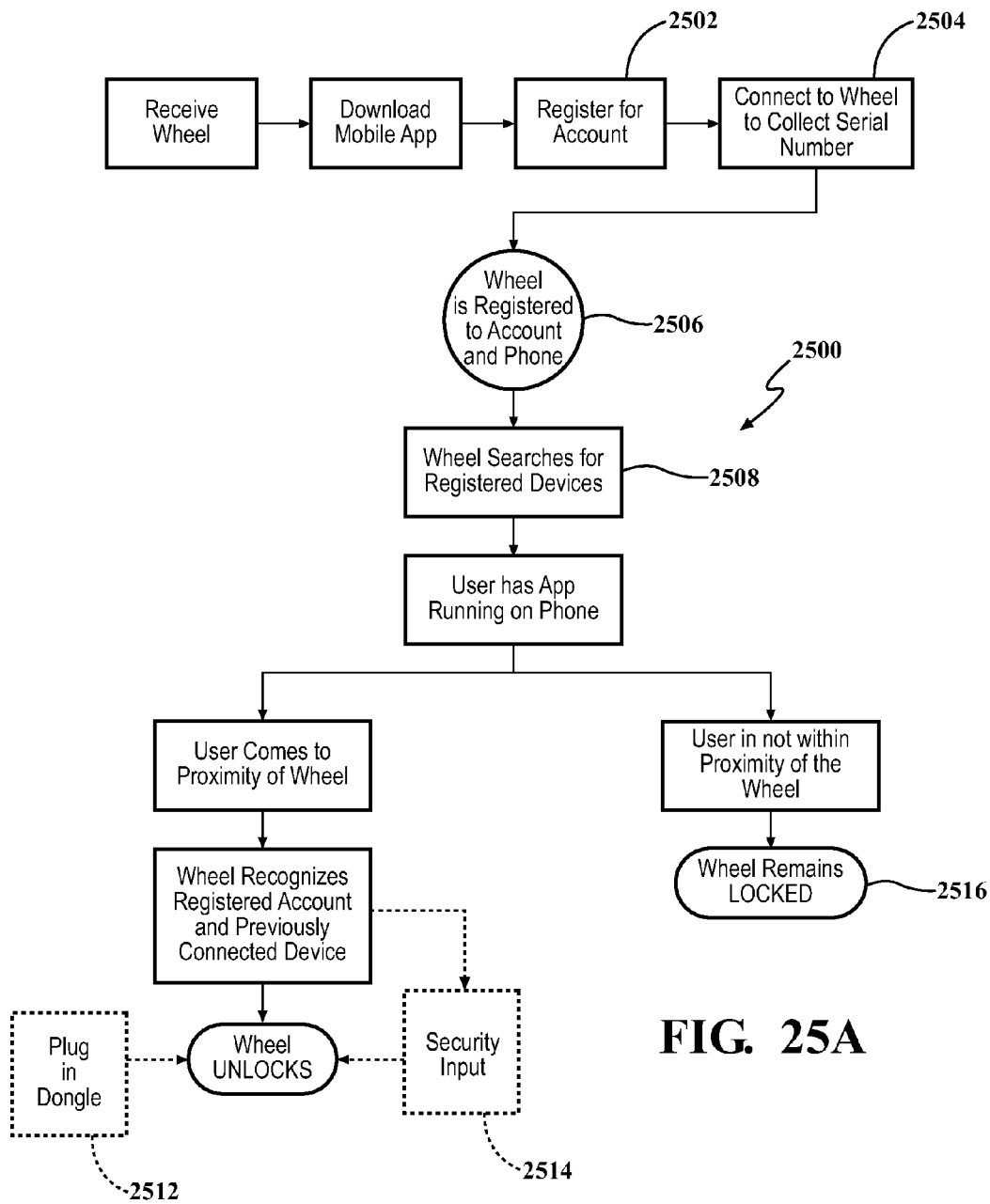
FIG. 25A is an algorithm for operation of the electrically motorized vehicle.

With reference to FIG. 25A, a security algorithm 2500, may be provided for security of the electrically motorized wheel until authentication is performed in an exchange between a mobile device and the electrically motorized wheel. This may be automatic once an initial authentication is performed (step 2502). Initial authentication may be performed when first connecting to the electrically motorized wheel to collect the serial number (step 2504).

Once the electrically motorized wheel is registered to the account and mobile device (step 2506), the electrically motorized wheel will search for registered mobile devices via a relatively short-range wireless connection, for example, Bluetooth (BT) (step 2508). The electrically motorized wheel may store previously authenticated mobile devices and reconnect to them automatically when within a predetermined proximity (step 2510). Alternatively, another key such as a wireless car key, or other key is utilized to unlock the electrically motorized wheel (step 2512).

Alternatively, or in addition, a dongle plugs into the electrically motorized wheel to unlock the electrically motorized wheel (step 2512).

When locked, the main control board 1450 can configure motor controller to resist or prevent rotation of the electrically motorized wheel. Alternatively, the lock function could prevent the use of the electrically motorized wheel to provide assist while letting the wheel spin freely. In one example, identification of the authenticated mobile device being within a predetermined proximity is sufficient to unlock the electrically motorized wheel. Alternatively, or in addition, a security input (step 2514) to the mobile device, or directly to the electrically motorized wheel such as entry of a code, entry of a password, facial recognition, fingerprint scan, unlock plug, and others may be utilized to unlock the electrically motorized wheel.

The electrically motorized wheel may be triggered to lock (step 2516) by a combination of criteria, such as the electrically motorized wheel no longer being connected to the mobile device, the mobile device being beyond a predetermined proximity from the vehicle, a user not being seated on the vehicle, the electrically motorized wheel not moving for a prescribed time period, the vehicle not moving for a prescribed time period, a timeout, etc. Further, the electrically motorized wheel may be selectively locked from the mobile device.

The electrically motorized wheel may receive input from various sensors and other data sources for interface with the control system 1700. The support and/or ports provided for additional sensors and other hardware (FIG. 14A) may be used to enhance user safety in a variety of ways such as alerting the user to a danger, alerting other's to the user's presence, enhancing user visibility and others. Data from one or more sensors may be transferred to the main control board and from there to the user's mobile device or to a remote location. In some examples, data may be sent to the user's mobile device and commands sent back to the electrically motorized wheel in response. In some examples, data may be sent to a server then commands sent back to the electrically motorized wheel in response. In other examples, data may be processed directly at the mobile device for the electrically motorized wheel. For example, a proximity sensor may send data to the user's mobile device causing the mobile device to provide an alert to the user using one or more of an audio alert, a visual alert, and a tactile alert. A tactile alert may be delivered by providing commands to the electrically motorized wheel so as to cause a small perturbation in performance of the electrically motorized wheel, such as a vibration, a change in speed, a change in the amount of assistance provided to a pedaling user, a change in resistance and others, which may be felt by a user and understood as a signal indicating a change in performance or the approach to an operational limit of the wheel, such as maximum motor temperature, or maximum regeneration current.

Figure 14C:
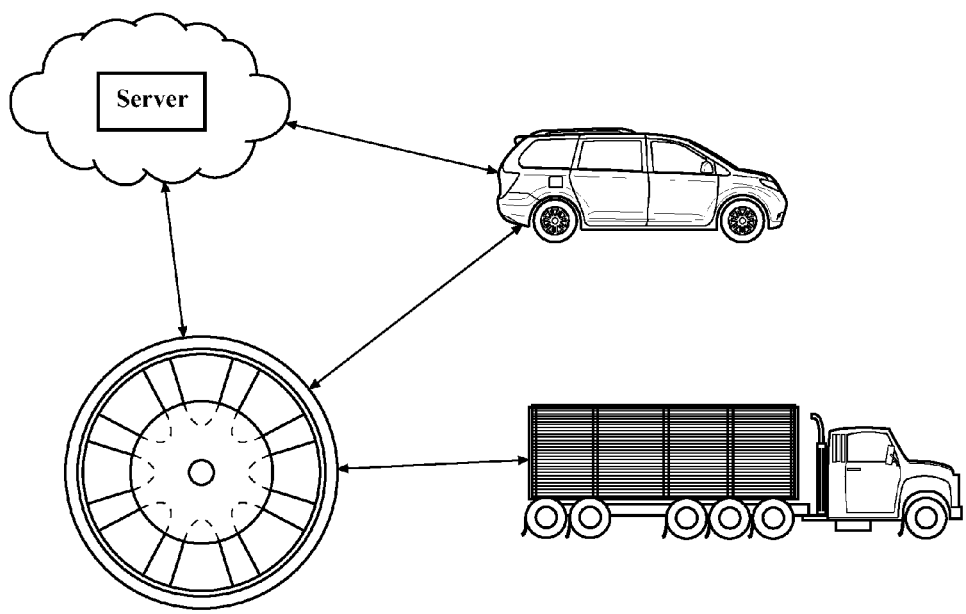
FIG. 14C is a schematic view of an ad hoc local traffic net system for the electrically motorized vehicle.

In embodiments, a proximity sensor may provide data regarding the user's location, such as via a traffic network, for alerting drivers of other vehicles (automobiles, trucks, buses, other electrically motorized vehicles, or the like) of the user's presence. A proximity sensor may be GPS or other global location sensor (or set of sensors, such as used in triangulation to locations of infrastructure elements, such as satellites, cellular towers, or the like), a sensor or sensors associated with a network (e.g., a cellular, Bluetooth, NFS, or other local wireless network), a sensor associated with a transportation infrastructure (e.g., located at a road sign, traffic signal, crossing, or the like), a sensor associated with a mobile device (e.g., a camera of a mobile device), or any other sensor that would provide data about the location of vehicle enabled with an electrically motorized wheel. For example, the electrically motorized wheel may communicate directly with other vehicles, (e.g., a cellular, Bluetooth, NFS, or other wireless network) to form an ad hoc local traffic network (FIG. 14C) that provides relative positional information of the adjacent vehicles to, for example, alert a vehicle to the presence and relative position of the electrically motorized wheel. Alternatively, the electrically motorized wheel may communicate globally with a local server (FIG. 14D), such as that located at an intersection, or a city wide server that then communicates with adjacent vehicles on the traffic net to provide relative positional information of the adjacent vehicles.

In another example, an illumination level sensor may provide data to an application that would cause the bicycle lights to turn on when illumination falls below a set level. Alternatively a data source may provide daylight data based on geological clock, which may be associated with proximity data, such that the electrically motorized wheel sends a signal to turn on illumination when in use at night at the current location of the electrically motorized wheel.

With reference to FIG. 25B, a remote diagnostics algorithm 2500, may be provided for the electrically motorized wheel. The remote diagnostics algorithm 2500 operates to collect operational data from, for example, the various sensors in the sensory system of the electrically motorized wheel (step 2552).

The operational data may include software and hardware version numbers as well as an application state of the electrically motorized wheel to include, but not be limited to, system initialization, sleeping, listening, stand by initiated, standing by, running initiated, running, locked, service mode, shutdown, default, boot loading, and others. The operational data may also include hazard indicators, both critical hazard indicators, which require the cessation of assist functions, such as motor overheated and transient hazard indicators, which allow continued use but with restricted performance, such as motor temperature being close to a limit but not over it.

The operational data may include system response data such as a reduction in motor assistance in response to a motor warm hazard indicator, regenerative braking turned off in response to the battery being full, results of a self test run in response to a torque sensor fault, and others. The operational data may also include any system fault errors generated by the different subsystems such as battery, motor drive, sensors, communications, processing board, peripheral, system, and others. The operational data may further include sensor data that is used for controlling the vehicle such as bicycle velocity, pedal speed, cassette torque, cassette speed, and others.

The operational data may be communicated on a predetermined frequency basis for analysis (step 2554). The data may be communicated either directly to a server via, for example, wireless or cellular technology such as 3G/4G, or to the connected mobile device via a wired connection, Bluetooth, or other wireless technologies. Data communicated to the mobile device may then be sent directly to a server or stored on the mobile device to be communicated to the server at a later time according to a set of rules that may include, for example, battery charge on the mobile device, signal strength, the presence of a Wi-Fi connection, and others. Data may also be stored locally on the wheel and sent to the server at a later time, either automatically once a mobile device connects to the wheel, or when connected to service tool through a wireless or a wired connection port 218. Data sent to the server may be associated with the specific wheel that generated the data. This association enables a service representative to view and analyze the operational data when responding to a trouble call, thus facilitating resolution of the issue (step 2556).

The operational data may be analyzed for internal consistency and error detection. For example, if a positive torque is measured at the cassette but there a negative speed measured at the cassette, there is a problem either with the torque or speed measurement. This is because in a bicycle with a freewheel positive torques cannot be sustained with negative pedal speed.

In another example, data, such as cassette speed, may be checked for errors using a variety of sensors such as the speed sensor, the torque frequency measured at the cassette torque sensor. Because the pedals cannot spin faster than the measured wheel speed, if the pedal speed exceeds the motor speed there is a problem either with the cassette or wheel speed measurements.

Additionally, operational data may be collected for understanding the context of usage. For example, temperature data may be reviewed to determine the temperature at which the batteries were charged and discharged and/or accelerometer data may be used to sense crashes, falls, drops and others. The operational data may thus be used to determine the occurrence of user actions and events outside the "normal wear and tear," that might void the warranty (step 2558).

Extensive testing may be performed during manufacturing to verify the robustness of various components prior to final assembly. For example, the shell 940 and the magnetic ring rotor 913 may be assembled then torque applied to check for slippage of the magnetic ring rotor 913 relative to the shell 940 prior to full assembly. In another example, torque may be applied to the torque sensor until destruction. In another example, accelerated life testing may be performed and may include environmental and performance testing.

Figure 26A:
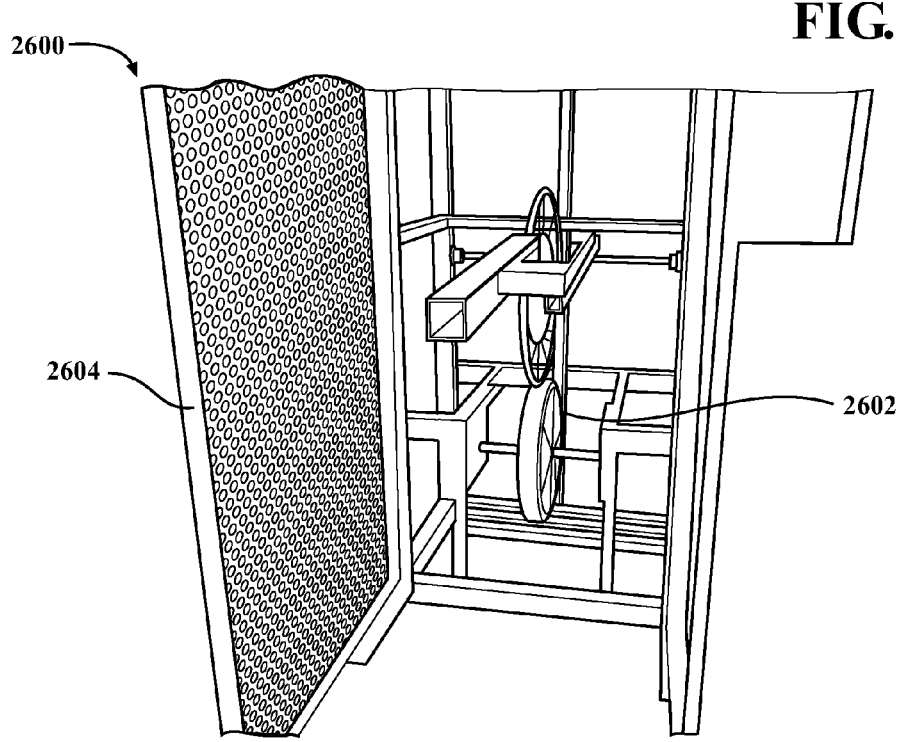
FIG. 26A is a perspective view of a test cell for the electrically motorized vehicle.

With reference to FIG. 26A, an electrically motorized wheel testing apparatus 2600 positions a drive wheel 2602 with a number of "bumps" fixed onto the circumference thereof into driving contact with the electrically motorized wheel to be tested. The bumps may be removable or otherwise configurable to represent various road conditions.

The electrically motorized wheel to be tested rotates the drive wheel 2602 and an outer cage 2604 protects personnel. The electrically motorized wheel may be supplied with external power to run for extended periods. Alternatively, the drive wheel 2602 may be powered to drive the electrically motorized wheel. As the drive wheel 2602 rotates, the electrically motorized wheel is thus subjected to a "bumpy" road. The electrically motorized wheel testing apparatus 2600 thus provides a compact extended life test cell to facilitate testing.

The ability to alter the amount of assistance or resistance provided by the electrically motorized wheel together with the reporting of data therefrom supports the use of electrically motorized wheel in remote rehabilitation therapies. Rehabilitation from an injury or recovery from a surgery may involve a progressive increase in usage time, an increase in resistance weight, and others for the recovering body part. For example, rehabilitation of a knee may involve weight training with the weight increasing a given percentage per week or biking with the distance increasing a given percentage a week.

Figure 27A:
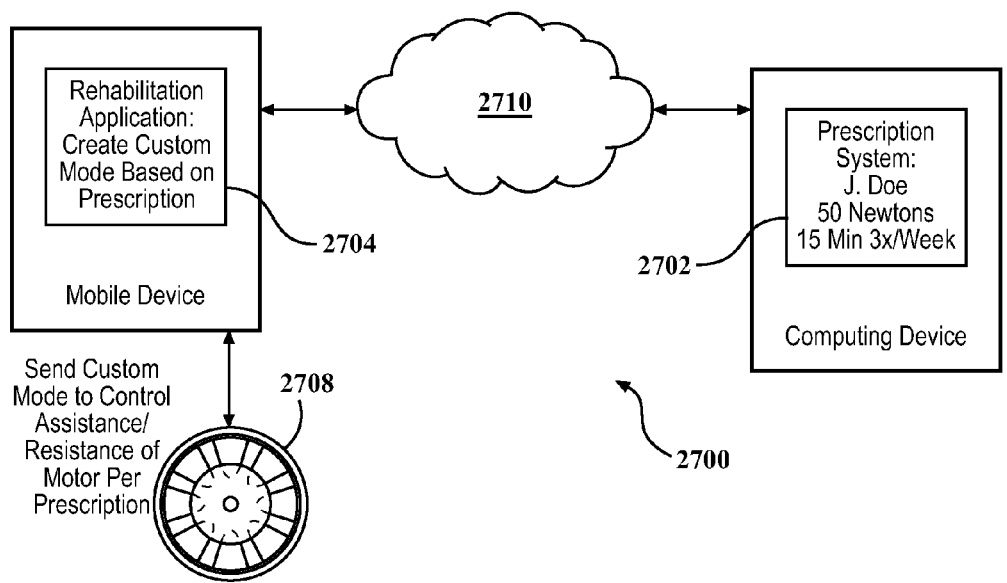
FIG. 27A is a schematic view of a server for the electrically motorized vehicle.

With reference to FIG. 27A, a rehabilitation system 2700 is disclosed in which a rehabilitation provider may prescribe an exercise regime for a patient. The prescription may include a desired level of exertion, resistance, torque, length of time, frequency and other factors using a prescription system 2702 on a computing device accessible to the rehabilitation provider. The prescription may be communicated via a server 2710 to a corresponding rehabilitation application 2704 resident on a patient's mobile device.

The rehabilitation application 2704 may be utilized to generate a custom mode such that the control parameters sent to the patient's electrically motorized wheel 2708 provides the prescribed assistance and resistance to the user. Alternatively, the rehabilitation application 2704 may calculate the appropriate assistance and resistance to effectuate the prescription. The rehabilitation application 2704 may additionally encourage the patient to use the electrically motorized wheel for the desired time and frequency.

The rehabilitation application 2704, together with the server 2710, provides compliance data and wheel performance data such as speed, distance, time, torque, energy used and others, to the prescription system 2702 where a rehabilitation provider may review patient compliance relative to the prescription, actual torque provided by patient, leg to leg non-uniformity of applied torque, and others. This data may then be used to modify the patient prescription such as altering the level of assistance and resistance, altering recommend training time, notifying the patient of unexpected results, and others.

In embodiments, the mobile device 1502 may be in communication with a wearable sensor such as a heart rate monitor to selectively adjust the operational mode of the wheel in response thereto. Such selection may be utilized in concert with a training mode to maintain a desired heart rate or in rehabilitation mode to assure the user's heart rate does not exceed a predetermined value.

In embodiments, the mobile device 1502 can be utilized to measure a force on the user such as a force applied to a user's knees via one or more sensors in communication therewith. The rehabilitation application 2704 may then be utilized to provide compliance and goal related data during performance of the physical therapy program. This data may then be used to modify the patient prescription such as altering the level of assistance and resistance, so that user may experience optimized levels of assistance and resistance in essentially real time. A feedback loop is thus provided to control the level of assistance and resistance in based on a training or rehabilitation regimen.

Figure 28A:
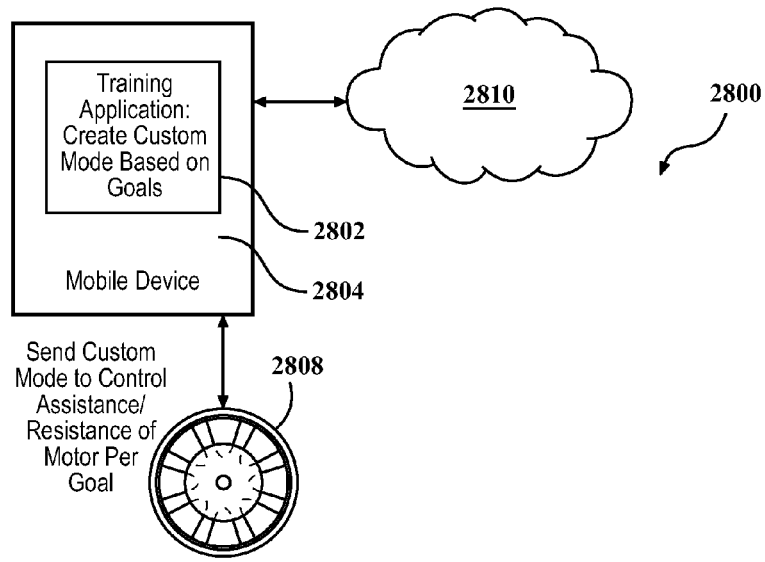
FIG. 28A is a schematic view of a server for the electrically motorized vehicle.

With reference to FIG. 28A, a training system 2800 is disclosed in which a training application 2802 on a mobile device 2804 is in communication with an electrically motorized wheel 2808. The training application 2802 permits the user to specify training goals such as a level of exertion, level of resistance, rate of Calorie expenditure, maximum heart rate, desired Calorie expenditure, percent increase over previous performance, fitness goals (e.g. complete the tour de France).

The training application 2802 may then convert the specified goals to a custom set of control parameters to be transmitted to the electrically motorized wheel and provide the appropriate assistance and resistance to meet the specified goals. The electrically motorized wheel may provide performance data such as levels of assistance and resistance provided, total calories burned, rate of calories burned, torque applied by the user and others to the training application 2802 for review by the user or a trainer.

Bicycle stands for stationary indoor training may be used with the electrically motorized wheel, however, when the electrically motorized wheel provides resistance for the user, electricity is generated. Such generated electricity may be used to drive peripheral devices such as a fan, power or charge mobile devices, and others. The power generated may used to heat the room, stored to an external battery, or uploaded to the electrical grid. Alternatively, the power generated may simply be dissipated via a resistor or other energy conversion device that for example, plugs into the electrically motorized wheel when operated on a bicycle stand.

In embodiments, the bicycle stands for stationary indoor training may also be particularly tailored to the electrically motorized wheel to provide power output connections, docking for accessory devices, peripheral devices, battery charging stations, etc.

Figure 29A:
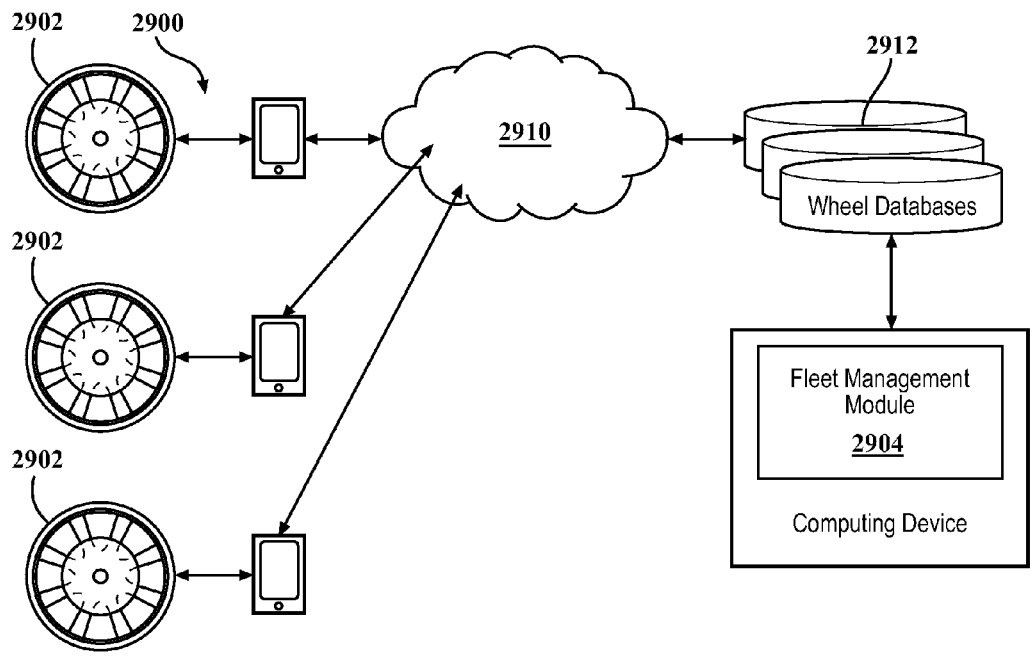
FIG. 29A is a schematic view of a server for the electrically motorized vehicle.

With respect to FIG. 29A, a fleet management system 2900 includes a plurality of electrically motorized wheels 2902 that may be in communication with a server 2910 to receive data for interchange with one or more wheel databases 2912. The data received may include user data such as user mode selections, user route selections and annotations, calories burned during current ride, time riding and others. The plurality of electrically motorized wheels 2902 may belong to a common owner such as a delivery service, a multiple of wheel chairs in a hospital, or a multiple of shopping carts in a store. The data received may also include operating versions, wheel performance data such as speed over time, control parameters, available battery life, accelerations, motor assistance and others. The data received may also include environmental data such as elevation changes, ambient temperature, humidity, and others.

A fleet management module 2904 may utilize the data in the electrically motorized wheel databases 2912 to facilitate coordination of a fleet such as assuring that all vehicles in the fleet have the same software version, have proper battery conditioning and maintenance performed, coordinating routing based on wheel location, meta-analysis of fleet data and other aggregation and correlation of data such that issues with specific electrically motorized wheels may be readily identified.

For example, data regarding current location, routes, available battery life, motor assistance/resistance provided during current ride, Calories burned during current ride, user's average ride statistics such as speed, and others might be used to determine new routings and selection of users for new destinations being added.

In another example, data regarding wheel speed over time, accelerations, motor assistance and resistance provided, wheel sensor data, temperature data over different routes may be used to optimize future routes. In yet another example, data such as speed over time, accelerations motor assistance and resistance, route, and others may be used as input when evaluating overall user performance.

In still another example, the fleet management system 2900 may be utilized to confirm driver activity and metrics to facilitate payment, improved performance, route coordination, etc.

Figure 30A:
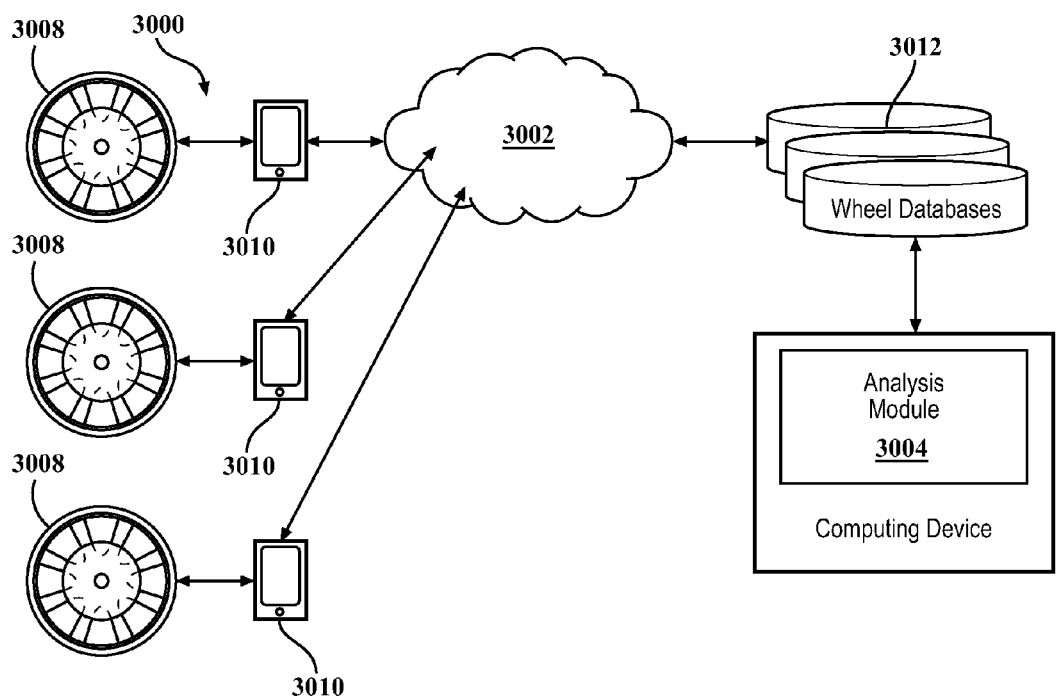
FIG. 30A is a schematic view of a server for the electrically motorized vehicle.

With reference to FIG. 30A, a server 3002 such as cloud-based server/API may receive user data, wheel performance data, environmental data, and geographic data, is in communication with a multiple electrically motorized wheels 3008 to interchange data. The data may originate with the electrically motorized wheel 3008 via the associated mobile device 3010. The data may then be transmitted to the server 3002 from each of the electrically motorized wheels 3008. The data received may include user data such as user mode selections, user route selections, annotations, travelled routes, available battery mode over a trip, and instantaneous battery life at a given location, energy supplied by the user, time required to travel a route, average speed over route, and others. The data received may also include wheel performance data such as speed over time, control parameters, accelerations, motor assistance and others. The data received may still further include location of mobile device 3010.

A computer-based analysis module 3004 may access an electrically motorized wheel database 3012 and analyze the combined wheel data from multiple rides reported by an individual wheel to identify trends in that user's health, fitness level, user preferences, and other such data. The computer-based analysis module 3004 may also analyze the combined data from different users to identify patterns and sense trends in public health and fitness levels, frequently used routes and others.

User annotations may alternatively or additionally be used to rate links in the road network and facilitate identification of where to locate new bicycle paths. The data regarding the differences between location where an electrically motorized wheel stopped and the final location may be used to optimize bicycle paths and bicycle parking.

Alternatively or in addition, aggregated data over common routes may be used for pothole detection, identification of road conditions/road type, whether a street is closed, average number of starts and stops on a route, average energy consumed over links in the road network, elevation gains over links in the road network, and others. This data may be used to optimize control algorithms along a particular route or recommend safer routes to a user, as starts and stops may be indicative of energy consumption and/or user safety. More frequent starts and stops may increase energy consumption. Also, starts and stops may be seen as indicative of intersections and a user's risk of injury typically increases with each intersection.

Alternatively or in addition, aggregated data over may be used to facilitate multi-player games such as geo-caching where the user visits specified geographic locations. The data collection system thereby collects data location and time such that users with access to the computer-based analysis module 3004 can compare locations visited.

The methods and systems described herein may be deployed in part or in whole through a machine that executes computer software, program codes, and/or instructions on a processor. The processor may be part of a server, application data server, client, network infrastructure, mobile computing platform, stationary computing platform, or other computing platform. A processor may be any kind of computational or processing device capable of executing program instructions, codes, binary instructions and others. The processor may be or include a signal processor, digital processor, embedded processor, microprocessor or any variant such as a co-processor (math co-processor, graphic co-processor, communication co-processor and others) and others that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and others described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and others.

A processor may include one or more cores that may enhance speed and performance of a multiprocessor. In embodiments, the process may be a dual core processor, quad core processors, other chip-level multiprocessor and others that combine two or more independent cores (called a die).

The methods and systems described herein may be deployed in part or in whole through a machine that executes computer software on a server, application data server, client, firewall, gateway, hub, router, or other such computer and/or networking hardware. The software program may be associated with a server that may include a file server, print server, domain server, internet server, intranet server and other variants such as secondary server, host server, distributed server and others. The server may include one or more of memories, processors, computer readable media, storage media, ports (physical and virtual), communication devices, and interfaces capable of accessing other servers, clients, machines, and devices through a wired or a wireless medium, and others. The server, as described herein and elsewhere may execute the methods, programs, or codes. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and others. Additionally, this coupling and/or connection may facilitate remote execution of program across the network. The networking of some or all of these devices may facilitate parallel processing of a program or method at one or more location without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and others. The client may include one or more of memories, processors, computer readable media, storage media, ports (physical and virtual), communication devices, and interfaces capable of accessing other clients, servers, machines, and devices through a wired or a wireless medium, and others. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and others. Additionally, this coupling and/or connection may facilitate remote execution of program across the network. The networking of some or all of these devices may facilitate parallel processing of a program or method at one or more location without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and others. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and others. The cell network may be a GSM, GPRS, 3G, EVDO, mesh, or other networks types.

The methods, programs codes, and instructions described herein and elsewhere may be implemented on or through mobile devices. The mobile devices may include navigation devices, cell mobile devices, mobile devices, mobile personal digital assistants, laptops, palmtops, netbooks, pagers, electronic books readers, music players and others. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and others; other computer memory such as dynamic memory, static memory, read/write storage, mutable storage, read only, random access, sequential access, location addressable, file addressable, content addressable, network attached storage, storage area network, bar codes, magnetic ink, and others.

The methods and systems described herein may transform physical and/or or intangible items from one state to another. The methods and systems described herein may also transform data representing physical and/or intangible items from one state to another, such as from usage data to a normalized usage dataset.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile devices, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and others. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be understood that the various steps identified and described above may be varied, and that the order of steps may be operable to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontroller systems, embedded microcontroller systems, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be understood that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the other embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

All documents referenced herein are hereby incorporated by reference.

It should be understood that relative positional terms such as "forward," "aft," "upper," "lower," "above," "below," "bottom", "top", and others are with reference to the normal operational attitude and should not be considered otherwise limiting.

It should be understood that like reference numerals identify corresponding or similar elements throughout the several drawings. It should also be understood that although a particular component arrangement is disclosed in the illustrated embodiment, other arrangements will benefit herefrom.

Although the different embodiments have specific illustrated components, the embodiments of this disclosure are not limited to those particular combinations. It is possible to use some of the components or features from any of the embodiments in combination with features or components from any of the other embodiments.

Although particular step sequences are shown, described, and claimed, it should be understood that steps may be performed in any order, separated or combined unless otherwise indicated and will still benefit from the present disclosure.

The foregoing description is exemplary rather than defined by the limitations within. Various embodiments are disclosed herein, however, one of ordinary skill in the art would recognize that various modifications and variations in light of the above teachings will fall within the scope of the appended claims. It is therefore to be understood that within the scope of the appended claims, the disclosure may be practiced other than as specifically described. For that reason the appended claims should be studied to determine true scope and content.

What is claimed:

1. A support block for a torque arm on a vehicle comprising:
   a first indentation and a second indentation each having an opening adapted to accept a first and second portion of the torque arm, the first indentation and the second indentation each having a relief cut opposite the opening into which the respective first and second portions of the torque arm fit.

2. The support block as recited in claim 1, wherein the first indentation and the second indentation are each V-shaped.

3. The support block as recited in claim 2, wherein the relief cut is located at an apex of the V-shape of each of the first indentation and the second indentation.

4. The support block as recited in claim 1, wherein the first indentation and the second indentation are located through a sidewall of the support block.

5. The support block as recited in claim 1, wherein the support block has a substantially circular cross section.

6. The support block as recited in claim 1, wherein the support block includes an aperture to receive a shaft.

7. The support block as recited in claim 1, wherein the support block includes a multiple of fastener apertures therethrough.

8. A torque arm assembly for a wheel of a vehicle, the torque arm assembly comprising:
   a block with a first indentation and a second indentation, the first indentation including a relief cut and the second indentation including a relief cut; and
   a torque arm with a first hinge portion engageable with the first indentation and extending partially into the relief cut on the first indentation, and a second hinge portion engageable with the second indentation and extending partially into the relief cut on the second indentation.

9. The torque arm assembly as recited in claim 8, wherein the torque arm includes a non-circular opening.

10. The torque arm assembly as recited in claim 9, wherein the non-circular opening rotationally keys the torque arm to a shaft.

11. The torque arm assembly as recited in claim 10, wherein the non-circular opening permits the torque arm to pivot about a hinge that defines a pivot for the torque arm such that an arm portion may interface with a frame member of the vehicle.

12. The torque arm assembly as recited in claim 11, wherein the arm portion interfaces below a frame member to transfer torque to the frame member of the vehicle.

13. The torque arm assembly as recited in claim 8, wherein the first and second hinge portions are substantially V-shaped.

14. The torque arm assembly as recited in claim 13, wherein an apex of each of the two hinge portions interfaces with the respective relief cuts on the first and the second indentations to provide two line contacts between each of the two hinge portion interfaces and each of the respective first and second indentations.

15. The torque arm assembly as recited in claim 14, wherein the apex of each of the two hinge portions is arcuate.

16. The torque arm assembly as recited in claim 11, further comprising a clamp to retain the arm portion below a frame member.

17. The torque arm assembly as recited in claim 10, wherein the torque arm comprises a substantially semi-spherical surface comprising the non-circular opening.

18. The torque arm assembly as recited in claim 17, further comprising a lock nut that interfaces with the semi-spherical surface.

19. The torque arm assembly as recited in claim 18, wherein the lock nut includes a non-planar interface that interfaces with the semi-spherical surface.

20. The torque arm assembly as recited in claim 19, wherein the lock nut mounts to the shaft to lock the torque arm at a desired angle.

* * * * *

UNITED STATES PATENT AND TRADEMARK OFFICE
CERTIFICATE OF CORRECTION

| | | |
|---|---|---|
| PATENT NO. | : 9,884,548 B2 | Page 1 of 2 |
| APPLICATION NO. | : 14/951165 | |
| DATED | : February 6, 2018 | |
| INVENTOR(S) | : Assaf Biderman et al. | |

It is certified that error appears in the above-identified patent and that said Letters Patent is hereby corrected as shown below:

In the Drawings

On sheet 27 of 67, in Figure 9H, Line 11, delete "Acess" and insert -- Access --, therefor.

Figure 16F:
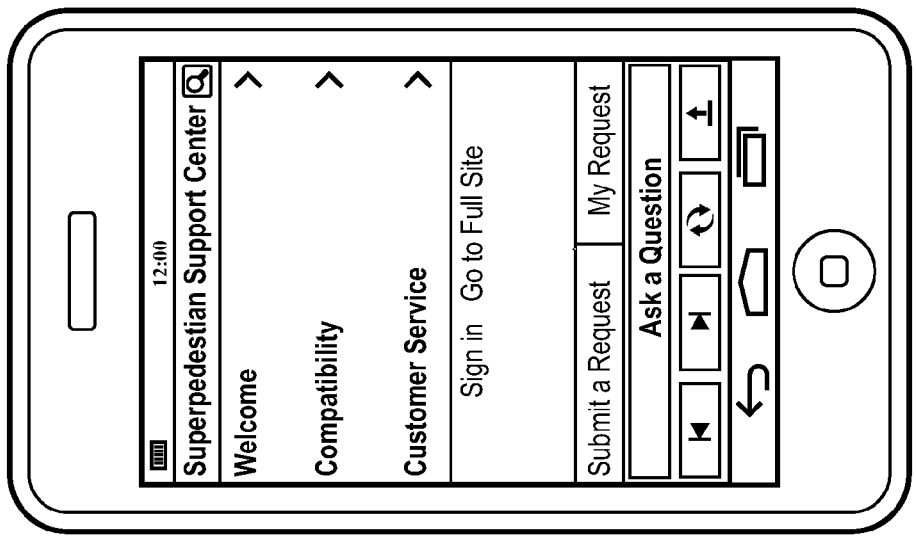
FIG. 16F is a mobile device page of a system for the electrically motorized vehicle.
Figure 16E:
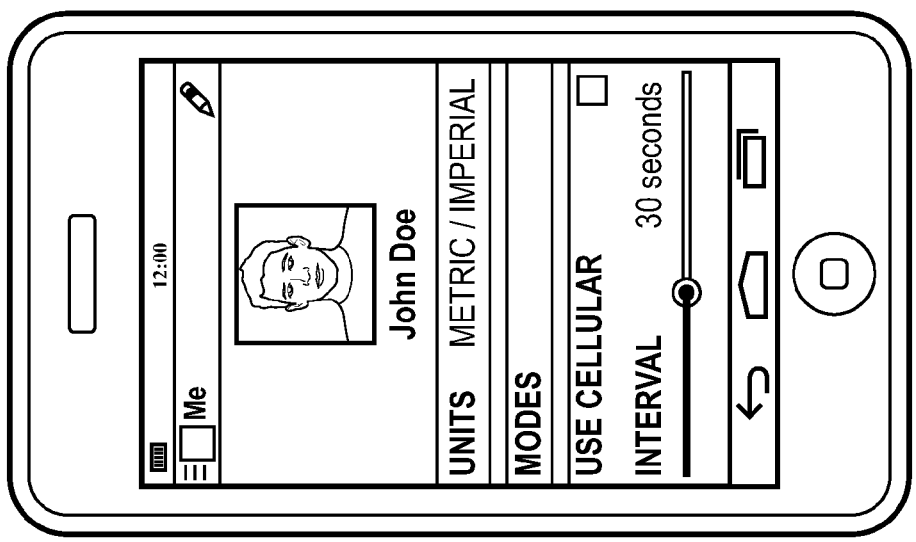
FIG. 16E is a mobile device page of a system for the electrically motorized vehicle.
Figure 16G:
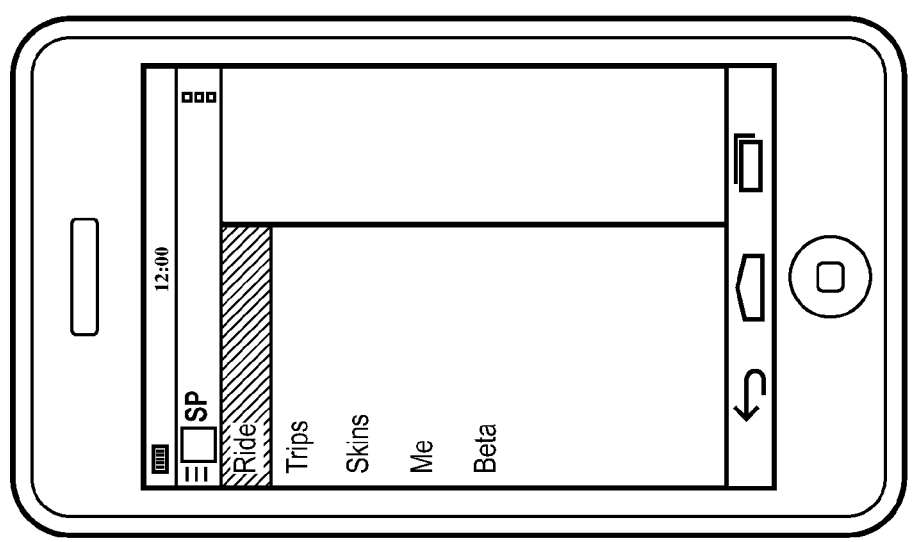
FIG. 16G is a mobile device page of a system for the electrically motorized vehicle.

On sheet 52 of 67, in Figure 16F, Line 2, delete "Superpedestian" and insert -- Superpedestrian --, therefor.

On sheet 59 of 67, in Figure 23B, Line 3, delete "Compacitor" and insert -- Capacitor --, therefor.

In the Specification

In Column 14, Line 42, delete "on/of" and insert -- on/off --, therefor.

In Column 17, Line 53, delete "therebeween" and insert -- therebetween --, therefor.

In Column 19, Line 29, delete "to transmit a transmit" and insert -- to transmit --, therefor.

In Column 30, Line 22, delete "route" and insert -- route. --, therefor.

In Column 33, Line 39, delete "-f$_t$(r/R)" and insert -- -f$_f$(r/R) --, therefor.

In Column 36, Line 66, delete "FIG." and insert -- FIGS. --, therefor.

In Column 39, Line 24, delete "spokes" and insert -- spokes. --, therefor.

In Column 41, Line 44, delete "vehicle" and insert -- vehicle. --, therefor.

In Column 47, Line 12, delete "assembly" and insert -- assembly. --, therefor.

In Column 50, Line 65, delete "FIG." and insert -- FIGS. --, therefor.

Signed and Sealed this
Twenty-fourth Day of July, 2018

Andrei Iancu
*Director of the United States Patent and Trademark Office*

In Column 59, Line 1, delete "'start-up'" and insert -- 'start-up' --, therefor.

In Column 59, Line 42, delete "of the of the" and insert -- of the --, therefor.

In Column 60, Line 26, delete "2" and insert -- 2. --, therefor.